(12) United States Patent
Hangauer, Jr. et al.

(10) Patent No.: US 7,772,216 B2
(45) Date of Patent: *Aug. 10, 2010

(54) PROTEIN KINASE AND PHOSPHATASE INHIBITORS AND METHODS FOR DESIGNING THEM

(75) Inventors: David G. Hangauer, Jr., Amherst, NY (US); Moustafa E. El-Araby, Plainsboro, NJ (US); Karen L. Milkiewicz, Exton, PA (US)

(73) Assignee: The Research Foundation of State University of New York, Amherst, NY (US)

( * ) Notice: Subject to any disclaimer, the term of this patent is extended or adjusted under 35 U.S.C. 154(b) by 563 days.

This patent is subject to a terminal disclaimer.

(21) Appl. No.: 11/206,115

(22) Filed: Aug. 16, 2005

(65) Prior Publication Data

US 2006/0030544 A1    Feb. 9, 2006

Related U.S. Application Data

(63) Continuation of application No. 10/277,217, filed on Oct. 19, 2002, now Pat. No. 7,005,445.

(60) Provisional application No. 60/336,191, filed on Oct. 22, 2001.

(51) Int. Cl.
  *A61K 31/405*   (2006.01)
  *A61K 31/675*   (2006.01)
  *C07F 9/547*    (2006.01)

(52) U.S. Cl. .................. 514/80; 514/419; 548/414; 548/493

(58) Field of Classification Search .............. None
See application file for complete search history.

(56) References Cited

U.S. PATENT DOCUMENTS

| | | | |
|---|---|---|---|
| 5,464,861 A | 11/1995 | Dobrusin et al. | |
| 5,532,167 A | 7/1996 | Cantley et al. | |
| 5,552,534 A | 9/1996 | Hirschmann et al. | |
| 5,648,378 A | 7/1997 | Huang | |
| 5,705,585 A | 1/1998 | Hogan, Jr. | |
| 5,736,412 A | 4/1998 | Zambias et al. | |
| 6,011,175 A | 1/2000 | Sebti et al. | |
| 6,420,338 B1 | 7/2002 | Schneider et al. | 514/12 |
| 6,552,066 B1 | 4/2003 | Sharpe et al. | 514/419 |
| 6,747,053 B2 | 6/2004 | Gabriel et al. | |
| 7,005,445 B2 | 2/2006 | Hangauer, Jr. et al. | 514/419 |
| 7,070,936 B1 | 7/2006 | Hangauer, Jr. et al. | 435/7.1 |
| 7,129,225 B2 | 10/2006 | Nicotera et al. | 514/64 |
| 7,141,596 B2 | 11/2006 | Combs et al. | |
| 2003/0016615 A1 | 1/2003 | Lee et al. | 369/112.24 |
| 2004/0019015 A1 | 1/2004 | Nicotera et al. | 514/64 |
| 2005/0256159 A1 | 11/2005 | Barton et al. | |
| 2006/0089401 A1 | 4/2006 | Hangauer et al. | 514/419 |
| 2006/0122197 A1 | 6/2006 | Yao et al. | |
| 2006/0172971 A1 | 8/2006 | Nicotera et al. | 514/64 |
| 2008/0004241 A1 | 1/2008 | Hangauer | 514/80 |

FOREIGN PATENT DOCUMENTS

| | | |
|---|---|---|
| CA | 2264020 A1 | 3/1998 |
| CA | 2360581 A1 | 7/2000 |
| CA | 2392866 A1 | 7/2001 |
| CA | 2407677 A1 | 10/2002 |
| DE | 43 07 883 A1 | 9/1993 |
| EP | 0 370 381 A2 | 5/1990 |
| EP | 0 463 638 A1 | 1/1992 |
| EP | 0 846 464 A2 | 6/1998 |
| EP | 0974584 A1 | 1/2000 |
| JP | S45-39538 | 12/1970 |
| JP | 01132579 A | 5/1989 |
| WO | WO 91/09849 | 7/1991 |
| WO | WO 96/35805 | 11/1996 |
| WO | WO 96/39384 | 12/1996 |
| WO | WO 96/39385 | 12/1996 |
| WO | 97/29091 | 8/1997 |
| WO | WO 98/07695 | 2/1998 |
| WO | WO 98/27108 | 6/1998 |

(Continued)

OTHER PUBLICATIONS

Huang et al., "Polyhydroxylated 3-(N-Phenyl) Carbamoyl-2-Iminochromene Derivatives as Potent Inhibitors of Tyrosine Kinase $p60^{c-src}$," *Bioorganic & Medicinal Chemistry Letters*, 5(20):2423-2428(1995).

Levitzki et al., "Tyrosine Kinase Inhibition: An Approach to Drug Development," *Science*, 267:1782-1788 (1995).

Lawrence et al., "Protein Kinase Inhibitors: The Tyrosine-Specific Protein Kinases," *Pharmacol. Ther.*, 77(2):81-114 (1998).

Lai, et al., "The Design, Synthesis and Activity of Pentapeptide $pp60^{c-src}$ Inhibitors Containing L-phosphotyrosine Mimics," *J. Peptide Res.*, 51:271-281 (1998).

Kennedy, "Role of Protein Tyrosine Phosphatase-1B in Diabetes and Obesity," *Biomedicine & Pharmacotherapyy*, 53(10):466-470 (1999) (Abstract).

(Continued)

*Primary Examiner*—Kamal A Saeed
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The present invention provides a method for identifying inhibitors of protein kinases and/or protein phosphatases. Methods are also provided for inhibiting protein kinase and/or protein phosphatase activity. Specific non-peptide protein tyrosine kinase and/or protein phosphatase inhibitors are provided. The protein kinase or protein phosphatase inhibitors of the present invention may be used to treat a number of conditions in patients, including cancer, psoriasis, arthrosclerosis, immune system activity, Type II diabetes, and obesity.

14 Claims, 17 Drawing Sheets

FOREIGN PATENT DOCUMENTS

| WO | WO-9915500 A1 | 4/1999 |
|---|---|---|
| WO | 99/34018 | 7/1999 |
| WO | WO 99/48868 | 9/1999 |
| WO | WO-9954309 A1 | 10/1999 |
| WO | WO-9959973 A1 | 11/1999 |
| WO | WO 00/42213 | 7/2000 |
| WO | WO-0042213 A1 | 7/2000 |
| WO | WO-0116097 A1 | 3/2001 |
| WO | WO 01/53274 A1 | 7/2001 |
| WO | WO 01/55111 | 8/2001 |
| WO | WO-0160814 A2 | 8/2001 |
| WO | WO 01/85726 A1 | 11/2001 |
| WO | WO 01/98290 A2 | 12/2001 |
| WO | 02/04459 | 1/2002 |
| WO | WO 02/00661 A1 | 1/2002 |
| WO | WO 02/04459 A1 | 1/2002 |
| WO | WO 02/072548 A2 | 9/2002 |
| WO | 02/80926 A1 | 10/2002 |
| WO | WO 02/080926 A1 | 10/2002 |
| WO | WO-03086385 | 10/2003 |
| WO | WO 03/093297 A2 | 11/2003 |
| WO | WO-2004022525 A1 | 3/2004 |
| WO | 2004/056774 A2 | 7/2004 |
| WO | 2005/032493 A2 | 4/2005 |
| WO | 2007/026920 A2 | 3/2007 |

OTHER PUBLICATIONS

Biscardi, et al., "c—Src, Receptor Tyrosine Kinases and Human Cancer," *Advances in Cancer Research*, 61-119 (1999).

"Amersham Pharmacia Biotech to Market and Distribute BioFocus' SoftFocus(TM) Kinase Libraries in North America," News release: Nov. 23, 1999.

Ripka, "Chapter 21. Protein Tyrosine Phosphatase Inhibition," *Annual Reports in Medicinal Chemistry*, 35:231-250 (2000) (Abstract).

Pestell, et al., "Small Molecule Inhibitors of Dual Specificity Protein Phosphatases," *Oncogene*, 19(56):6607-6612 (2000) (Abstract).

Moller, et al, "Protein Tyrosine Phosphatases (PTPs) as Drug Targets: Inhibitors of PTP-1B for the Treatment of Diabetes," *Current Opinion in Drug Discovery & Development*, 3(5):527-540 (2000) (Abstract).

Irby et al., "Role of Src Expression and Activation in Human Cancer," *Oncogene*, 19:5636-5642 (2000).

Garcia-Echeverria, et al., "ATP Site-Directed Competitive and Irreversible Inhibitors of Protein Kinases," *Med. Res. Rev.*, 20(1):28-57 (2000).

Abram, et al., "Src Family Tyrosine Kinases and Growth Factor Signaling," *Experimental Cell Research*, 254:1-13 (2000).

Marsilje, et al., "The Design, Synthesis and Activity of Non-ATP Competitive Inhibitors of pp60$^{c-src}$ Tyrosine Kinase. Part 1: Hydroxynaphtalene Derivatives," *Bioorg. Med. Chem Lett.*, 10:477-481 (2000).

Milkiewicz et al., "The Design, Synthesis and Activity of Non-ATP Competitive Inhibitors of pp60$^{c-src}$ Tyrosine Kinase. Part 2: Hydroxyindole Derivatives," *Bioorg. Med. Chem. Lett.*, 10:483-486 (2000).

Schelssinger, "New Roles for Src Kinases in Control of Cell Survival and Angiogenesis," *Cell*, 100:293-296 (2000).

Sedlacek, "Kinase Inhibitors in Cancer Therapy," *Drugs*, 59(3):435-476 (2000).

Susa et al., "Tyrosine Kinase Src Inhibitors: Potential Therapeutic Applications," *Drug News Perspect.*, 13(3):169-175 (2000).

Sridhar et al., "Protein Kinases as Therapeutic Targets," *Pharmaceutical Research*, 17(11):1345-1353 (2000).

Biscardi, et al., "Tyrosine Kinase Signaling in Breast Cancer: Epidermal Growth Factor Receptor and c-Src Interactions in Breast Cancer," *Breast Cancer Res.*, 2:203-210 (2000).

Susa et al., "Src Inhibitors: Drugs for the Treatment of Osteoporosis, Cancer or Both?," *TiPS*, 21:489-495 (2000).

Hubbard et al., "Protein Tyrosine Kinase Structure and Function," *Annu. Rev. Biochem.*, 69:373-398 (2000).

Fretz et al., "Structure-based Design of Compounds Inhibiting Grb2-SH2 Mediated Protein-Protein Interactions in Signal Transduction Pathways," *Current Pharmaceutical Design*, 6(18):1777-1796 (2000) (Abstract).

Vu, "Recent Advances in the Design and Synthesis of SH2 Inhibitors of Src, Grb2 and ZAP-70," *Current Medicinal Chemistry*, 7(10):1081-1100 (2000) (Abstract).

Haskell, et al., "c-Src Tyrosine Phosphorylation of Epidermal Growth Factor Receptor, P190 RhoGAP, and Focal Adhesion Kinase Regulates Diverse Cellular Processes," *Chemical Reviews*, 101(8):2425-2440 (2001).

McCluskey et al., "Small Molecule Inhibitors of Serine/Threonine Protein Phosphatases," *Mini-Reviews in Medicinal Chemistry*, 1(1):43-55 (2001) (Abstract).

Zhang, "Protein Tyrosine Phosphatases: Prospects for Therapeutics," *Current Opinion in Chemical Biology*, 5(4):416-423 (2001) (Abstract).

Bridges, "Chemical Inhibitors of Protein Kinases," *Chemical Reviews*, 101(8):2541-2571 (2001).

Park et at., "Metabolism of Fluorine-Containing Drugs," *Annu. Rev. Pharmacol, Toxicol.*, 41:443-470 (2001).

Sawyer et al., "Src Inhibitors: Genomics to Therapeutics," *Expert Opin. Investg. Drugs*, 10(7):1327-1344 (2001).

Blume-Jensen et al., "Oncogenic Kinase Signaling," *Nature*, 411:355-365 (2001).

Martin, "Timeline: The Hunting of the Src," *Nat. Rev. Mol. Cell Biol.*, 2:467-475 (2001).

Garcia-Echeverria, "Antagonists of the Src Homology 2 (SH2) Domains of Grb2, Src, Lck and ZAP-70," *Current Medicinal Research*, 8(13):1589-1604 (2001) (Abstract).

Muller, "Peptidomimetic SH2 Domain Antagonists for Targeting Signal Transduction," *Topics in Current Chemistry*, 211:17-59 (2001) (Abstract).

Zhang, "Protein Tyrosine Phosphatases: Structure and Function, Substrate Specificity, and Inhibitor Development," *Annual Review of Pharmacology and Toxicology*, 42:209-234 (2002) (Abstract).

McCluskey et al., "Serine-Threonine Protein Phosphatase Inhibitors: Development of Potential Therapeutic Strategies," *Journal of Medicinal Chemistry*, 45(6):1151-1175 (2002) (Abstract).

Johnson et al., "Protein Tyrosine Phosphatase 1B Inhibitors for Diabetes," *Nat. Rev. Drg Discov.*, 1(9):696-709 (2002) (Abstract).

Frame, "Src in Cancer: Deregulation and Consequences for Cell Behavior," *Biochemica et Biophysica Acta*, 1602:114-130 (2002).

Druker, "STI571 (Gleevec) as a Paradigm for Cancer Therapy," *Trends in Molecular Medicine*, 8(4 Suppl):S14-18 (2002) (Abstract).

Bakhtiar et al., "Quantification of the Anti-Leukemia Drug STI1571 (Gleevec) and its Metabolite (CGP 74588) in Monkey Plasma Using a Semi-Automated Solid Phase Extraction Procedure and Liquid Chromatography-Tandem Mass Spectrometry," *Journal of Pharmaceutical & Biomedical Analysis*, 28(6):1183-1194 (2002) (Abstract).

Burke et al., "Phosphotyrosyl Mimetics in the Development of Signal Transduction Inhibitors," *Acc. Chem. Res.*, 36:426-433 (2003).

Levitzki, "Protein Kinase Inhibitors as a Therapeutic Modality," *Acc. Chem. Res.*, 36(6):462-469 (2003).

Stein, "SH2 and SH3 Domains. Unraveling Signaling Networks with Peptide Antagonists," *Methods in Molecular Biology*, 88:187-195 (1998) (Abstract).

Sparks et al., "Identification and Characterization of Src SH3 Ligands from Phage-Displayed Random Peptide," *Journal of Biological Chemistry*, 269(39):23853-23856 (1994) (Abstract).

Milkiewicz, "Design Synthesis and Biological Testing of Non-ATP Competitive Inhibitors of the pp60$^{c-src}$ Protein Tyrosine Kinase," A dissertation submitted to the Faculty of the Graduate School of State University of New York at Buffalo in Partial Fulfillment of the Requirements for the Degree of Doctor of Philosophy, Department of Medicinal Chemistry (Sep. 5, 2001).

Stahura et al., "Molecular scaffold-based design and comparison of combinatorial libraries focused on the ATP-binding site of protein kinases", *J. Mol. Graphics Modelling*, 17:1-9 (1999).

Chemical Abstracts vol. 67, No. 1 (1967) abstract No. 1850x (Chi-Ting Chou) p. 166 & Yao Hsueh Ao, vol. 13, No. 6 (1966).

Hoover et al. *J. Med. Chem.*, 41(16):2934-2938 (1998).
Patent Abstracts of Japan vol. 013, No. 384 (1989) & JP 01 132579 A (SS Pharmaceut. Co. Ltd.) abstract only (1989).
Poulain et al. *J. Med. Chem.*, 44(21):3378-3390 (2001).
Romero et al. *J. Med. Chem.*, 37(7):999-1014 (1994).
Supplementary Partial European Search Report for EP 02 77 3833, mailed Sep. 29, 2005.
Alfaro-Lopez et al., "Discovery of a novel series of potent and selective substrate-based inhibitors of p60c-src protein tyrosine kinase: conformational and topographical constraints in peptide design", *J. Med. Chem.*, 41:2252-2260 (1998).
Al-Obeidi et al., "Protein Tyrosine Kinases: Structure, Substrate Specificity, and Drug Discovery", *Biopoly*, 47:197-223 (1998).
Bishop et al., "Screening a Hydroxystilbene Library for Selective Inhibition of the B Cell Antigen Receptor Kinase Cascade", *Tetrahedron*, 53(35)11995-12004 (1997).
Budde et al., "Discovery, Development, and Testing of Substrates and Inhibitors of PP60$^{C-SRC}$", *Int. J. Pharmacognosy*, 33:27-34 (1995).
Burke et al., "Bicyclic compounds as ring-constrained inhibitors of protein-tyrosine kinase p56lck", *J. Med. Chem.*, 36(4):425-432 (1993).
Burke, et al., "Phosphotyrosyl mimetics in the development of signal transduction inhibitors", *Acc. Chem. Res.*, 36:426-433 (2003).
Casnellie et al., "The Use of Synthetic Peptides for Defining the Specificity of Tyrosine Protein Kinases", *Adv. Enzyme Regul.*, 22:501-515 (1984).
Choi "Development of a Cellular Mimetic Protein Kinase Assay and a Novel Methodology for Determining the Mode of Inhibition for Multisubstrate" thesis, Bell & Howell Co., (1999).
Davidson et al., "Discovery and characterization of a substrate selective p38α inhibitor", *Biochemistry*, 43:11658-11671 (2004).
Dolle, R. E., "Discovery of enzyme inhibitors through combinatorial chemistry", *Mol. Diversity*, 2:223-236 (1996).
Duong, et al., "Inhibition of Osteoclast Function by Adenovirus Expressing Antisense Protein-tyrosine Kinase 2*", *J. Biol. Chem.* 276:7484-7492 (2001).
Engstrom et al., "Detection and Identification of Substrates for Protein Kinases: Use of Proteins and Synthetic Peptides", *Meth. Enzymol.*, 107:130-154 (1984).
Faltynek et al., "Damnacanthal is a highly potent, selective inhibitor of p56lck tyrosine kinase activity", *Biochem.*, 34:12404-12410 (1995).
Fry et al., "A specific inhibitor of the epidermal growth factor receptor tyrosine kinase", *Science*, 265:1093-1095 (1994).
Fukunaga et al., "Identifying protein kinase substrates by expression screening with solid-phase phosphorylation", *Protein Phosphorylation, Second Edition*, Chapter 13, pp. 291-313 (1999).
Guo, et al., "Tyrosine Phosphorylation of the NR2B Subunit of the NMDA Receptor in the Spinal Cord during the Development and Maintenance of Inflammatory Hyperalgesia" *J. Neurosci.* 22:6208-6217 (2002).
Hadjeri, et al., "Antimitotic Activity of 5-Hydroxy-7-methoxy-2-phenyl-4-quinolones", *J. Med. Chem.* 47:4964-4970 (2004).
Hanke et al., "Discovery of a novel, potent, and Src family-selective tyrosine kinase inhibitor. Study of Lck- and FynT-dependent T cell activation", *J. Biol. Chem.*, 271(2):695-701 (1996).
Hsiao et al., "A Facile Synthesis of tert-Butyl 2'[(Benzyloxycarbonyl)amino]-3-(4,4,5,5-tetramethyl-1,3,2-dioxaborolan-2-yl)propionate: An Orthogonally Protected Boronic Acid Analog of Aspartic Acid", *Synthesis*, 1043-1046 (1998).
Hubbard, "Crystal structure of the activated insulin receptor tyrosine kinase in complex with peptide substrate and ATP analog", *EMBO J.*, 16(18):5572-5581 (1997).
Johnson et al., "Protein Tyrosine Phosphatase 1B Inhibitors for Diabetes", *Nature Reviews*, 1:696-709 (2002).
Kemp et al., "Design and Use of Peptide Substrates for Protein Kinases", *Meth. Enzymol.*, 200:121-134 (1991).
Kemp et al., "Protein kinase recognition sequence motifs", *TIBS*, 15:342-346 (1990).
Kim et al., "Tetrapeptide tyrosine kinase inhibitors. Enantioselective synthesis of p-hydroxymethyl-L-phenylalanine, incorporation into a tetrapeptide, and subsequent elaboration into p-(R,S-hydroxyphosphonomethyl)-L-phenylalanine", *Int. J. Peptide Protein Res.*, 44:457-465 (1994).
Lai et al., "Synthesis of a Vicinal Tricarbonyl Amide Derivative of L-Phenylalanine", *J. Org. Chem.*, 61:1872-1874 (1996).
Levitzki, "Protein kinase inhibitors as a therapeutic modality", *Acc. Chem. Res.*, 36:462-469 (2003).
Lou et al., "Identification of GIYWHHY as a novel peptide substrate for human p60c-src protein tyrosine kinase", *Bioorg. Med. Chem.*, 4(5):677-682 (1996).
Martin, et al., "Discovery of a human liver glycogen phosphorylase inhibitor that lowers blood glucose *in vivo*" *Proc. Natl. Acad. Sci. USA*, 95:1776-1781 (1998).
Metcalf III et al., "Targeting Protein Kinases for Bone Disease: Discovery and Development of Src Inhibitors", *Cur. Pharm. Des.*, :2049-2075 (2002).
Miyazaki, et al., "Src Kinase Activity Is Essential for Osteoclast Function" *J. Biol. Chem.* 279:17660-17666 (2004).
Mohammadi et al., "Structures of the tyrosine kinase domain of fibroblast growth factor receptor in complex with inhibitors", *Science*, 276:955-960 (1997).
Nair et al., "Synthesis of Orthogonally Protected L-Homocysteine and L-2-Amino-4-phosphonobutanoic Acid From L-Homoserine", *Synthesis*, 810-814 (1995).
Nair et al.," Identification of efficient pentapeptide substrates for the tyrosine kinase pp60c-src", *J. Med. Chem.*, 38:4276-4283 (1995).
Norman et al., "A Structure-Based Library Approach to Kinase Inhibitors", *J. Am. Chem. Soc.*, 118:7430-7431 (1996).
Parang, et al., "Recent advances in the discovery of Src kinase inhibitors" *Expert Opin. Ther. Patents* 15:1183-1207 (2005).
Patrick et al., Protein kinase inhibitors for the treatment of cancer, *DDT*, 1(8):325-330 (1996).
Paul, et al., "Src deficiency or blockade of Src activity in mice provides cerebral protection following stroke" *Nat. Med.*, 7:222-227 (2001).
Pearson et al., "Protein Kinase Phosphorylation Site Sequences and Consensus Specificity Motifs: Tabulations", *Meth. Enzymol.*, 200:62-81 (1991).
Pestell, et al., "Small molecule inhibitors of dual specificity protein phosphatases", *Oncogene*, 19:6607-6612 (2000).
Ramdas et al., "A tyrphostin-derived inhibitor of protein tyrosine kinases: isolation and characterization", *Arch. Biochem. Biophys.*, 323(2):237-242 (1995).
Rewcastle et al.,"Tyrosine kinase inhibitors. 10. Isomeric 4-[(3-bromophenyl)amino]pyrido[d]-pyrimidines are potent ATP binding site inhibitors of the tyrosine kinase function of the epidermal growth factor receptor", *J. Med. Chem.*, 39:1823-1835 (1996).
Ruzzene et al., "Assay of protein kinases and phosphatases using specific peptide substrates", *Protein Phosphorylation, Second Edition*, Chapter 10, pp. 221-253 (1999).
Saperstein et al., "Design of a selective insulin receptor tyrosine kinase inhibitor and its effect on glucose uptake and metabolism in intact cells", *Biochem.*, 28:5694-5701 (1989).
Sawutz et al., "In vitro characterization of a novel series of platelet-derived growth factor receptor tyrosine kinase inhibitors", *Biochem. Pharmacol.*, 51:1631-1638 (1996).
Sawyer et al., "Cancer metastasis therapeutic targets and drug discovery: emerging small-molecule protein kinase inhibitors", *Exp. Opin. Investig. Drugs*, 13(1):1-19 (2004).
Sawyer et al., "Src inhibitors: genomics to therapeutics", *Exp. Opin. Investig. Drugs*, 10(7):1327-1344 (2001).
Shoichet, B.K., "Virtual screening of chemical libraries", *Nature*, 432:862-865 (2004).
Showalter et al., "Small molecule inhibitors of the platelet-derived growth factor receptor, the fibroblast growth factor receptor, and Src family tyrosine kinases", *Pharmacol. Ther.*, 76(1-3):55-71 (1997).
Songyang et al., "The Use of Peptide Library for the Determination of Kinase Peptide Substrates", *Meth. Mol. Biol.*, 87:87-98 (1998).
Sparks et al., "Molecular Basis for Substrate Specificity of Protein Kinases and Phosphatases", *Int. J. Biochem.*, 18(6):497-504 (1986).
Sun et al., "CombiDOCK: Structure-based combinatorial docking and library design", *J. Computer-Aided Mol. Des.*, 12:597-604 (1998).

Susa, et al., "Src inhibitors: drugs for the treatment of osteoporosis, cancer or both?", *TiPS*, 21:489-495 (2000).

Taylor et al., "Protein kinase inhibition: natural and synthetic variations on a theme", *Curr. Opin. Chem. Biol.*, 1:219-226 (1997).

Tegge et al., "Analysis of Protein Kinase Substrate Specificity by the Use of Peptide Libraries on Cellulose Paper (SPOT-Method)", *Meth. Mol. Chem.*, 87:99-106 (1998).

Thakkar et al., "Synthesis and protein-tyrosine kinase inhibitory activity of polyhydroxylated stilbene analogues of piceatannol", *J. Med. Chem.*, 36:2950-2955 (1993).

Xu et al., "Three-dimensional structure of the tyrosine kinase c-Src", *Nature*, 385:595-602 (1997).

Yu, et al., "Src, a molecular switch governing gain control of synaptic transmission mediated by N-methyl-D-aspartate receptors" *Proc. Natl. Acad. Sci USA*. 96:7697-7704 (1999).

Zheng et al., "Crystal structure of the catalytic subunit of cAMP-dependent protein kinase complexed with MgATP and peptide inhibitor", *Biochem.*, 32:2154-2161 (1993).

Prasit, Accession No. 2002:695723, Document No. 137:232908, "Preparation of N-cyanomethyl amides as cathepsin cystein protease inhibitors".

Strobel, Accession No. 2002:637636, Document No. 137:185515, "Preparation of acylated indanyl amines and their use as remedies in upregulation of endothelial nitric oxide synthase."

Takahashi, Accession No. 1999:271331, Document No. 130:311803, "Preparation of aminobutanoic acid derivatives as inhibitors of matrix metalloproteinases."

Wright, W.B. et al, Journal of Medicinal Chemistry, 1968, vol. 11, No. 6, p. 1164-67.

x-ray structure of (PKA):Mg$_2$ATP:pseudosubstrate Inhibitor (Distances in Å)

In Closed Conformation

General Module $M_1$ Design Features For Binding To The Conserved Protein Kinase Catalytic Region

SUBSTRATE BEHAVIOR FOR BORONIC ACID PKA INHIBITORS 21 & 22

Binding interactions of src substrate
Ac-Ile-Tyr-Gly-Glu-Phe-NH$_2$ in model src active site.

Design of naphthalene-based src inhibitor scaffold src:peptide substrate complex src:naphthalene-based
non-peptide inhibitor
binding mode Design of isoquinoline and indole-based src inhibitor scaffolds src:isoquinoline-based
non-peptide inhibitor
binding mode src:indole-based
non-peptide inhibitor
binding mode (Residues are from the IR1'K ternary structure and dotted bonds are H-bonds)

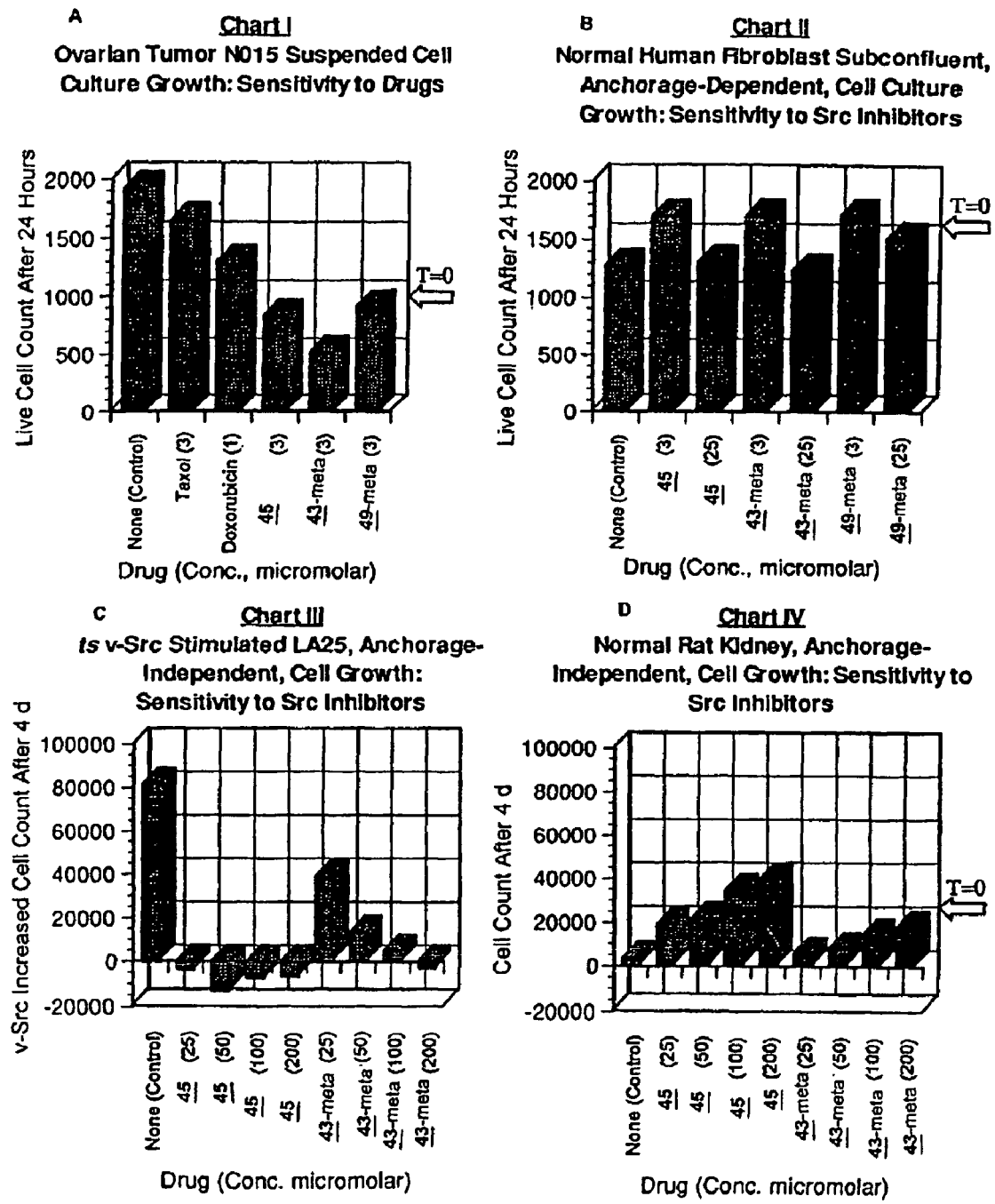

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: src
      substrate pentapeptide

<400> SEQUENCE: 1

Ile Tyr Gly Glu Phe
 1               5

<210> SEQ ID NO 2
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: Xaa in position 4 is modified Ala.
<220> FEATURE:
<223> OTHER INFORMATION: Description of Artificial Sequence: PKA
      pentapeptide scaffold

<400> SEQUENCE: 2

Arg Arg Gly Xaa Ile
 1               5

<210> SEQ ID NO 3
<211> LENGTH: 5
<212> TYPE: PRT
<213> ORGANISM: Artificial Sequence
<220> FEATURE:
<221> NAME/KEY: PEPTIDE
<222> LOCATION: (2)
<223> OTHER INFORMATION: Xaa in position 2 is modified Tyr.
<220> FEATURE:
<223> OTHER INFORMATION: Description of Artificial Sequence: src
      pentapeptide scaffold

<400> SEQUENCE: 3

Ile Xaa Gly Glu Phe
 1               5

<210> SEQ ID NO 4
<211> LENGTH: 5
<212> TYPE: PRT
<213> ORGANISM: Artificial Sequence
<220> FEATURE:
<221> NAME/KEY: PEPTIDE
<222> LOCATION: (4)
<223> OTHER INFORMATION: Xaa in position 4 is Ala or modified Ala.
<220> FEATURE:
<223> OTHER INFORMATION: Description of Artificial Sequence: Boronic
      acid-containing PKA inhibitor

<400> SEQUENCE: 4

Arg Arg Gly Xaa Ile
 1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence:  Kemptamide

```
<400> SEQUENCE: 5

Leu Arg Arg Ala Ser Leu Gly
1               5

<210> SEQ ID NO 6
<211> LENGTH: 7
<212> TYPE: PRT
<213> ORGANISM: Artificial Sequence
<220> FEATURE:
<221> NAME/KEY: MOD_RES
<222> LOCATION: (5)
<223> OTHER INFORMATION: Xaa in position 5 is ALA; PHOSPHORYLATION
<220> FEATURE:
<223> OTHER INFORMATION: Description of Artificial Sequence:
      Phosphorylated Kemptamide

<400> SEQUENCE: 6

Leu Arg Arg Ala Xaa Leu Gly
1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:  Peptide
      substrate for Src

<400> SEQUENCE: 7

Gly Ile Tyr Trp His His Tyr
1               5
```

PROTEIN KINASE AND PHOSPHATASE INHIBITORS AND METHODS FOR DESIGNING THEM

RELATED APPLICATIONS

This application is a continuation of U.S. Ser. No. 10/277,217, filed on Oct. 19, 2002, now U.S. Pat. No. 7,005,445 which claims the benefit of U.S. Provisional Patent Application Ser. No. 60/336,191, filed Oct. 22, 2001, the entire contents of each are hereby incorporated by reference.

BACKGROUND OF THE INVENTION

Protein kinases are a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation, and proliferation. There are estimated to be about 2,000 distinct protein kinases in the human body (Hunter, 1987, 1994, Hanks & Hunter, 1995), and although each of these phosphorylate particular protein/peptide substrates, they all bind the same second substrate ATP in a highly conserved pocket. Protein phosphatases catalyze the transfer of phosphate in the opposite direction.

Inhibitors of various known protein kinases or protein phosphatases could have a variety of therapeutic applications provided sufficient selectivity, and acceptable in vivo pharmacological properties, can be incorporated into such inhibitors (Levitzki, 1996a). Perhaps the most promising potential therapeutic use for protein kinase or protein phosphatase inhibitors is as anti-cancer agents. This potential application for protein tyrosine kinase ("PTK") inhibitors has been highlighted in many recent reviews (e.g. Lawrence & Hiu, 1998, Kolibaba & Druker, 1997, Showalter & Kraker, 1997, Patrick & Heimbrook, 1996, Groundwater et al., 1996, Levitzki, 1995). The foundation for this application is based partly upon the fact that about 50% of the known oncogene products are PTKs and their kinase activity has been shown to lead to cell transformation (Yamamoto, 1993).

The PTKs can be classified into two categories (Courtneidge, 1994), the membrane receptor PTKs (e.g. growth factor receptor PTKs) and the non-receptor PTKs (e.g. the Src family of proto-oncogene products). There are at least 9 members of the Src family of non-receptor PTK's with pp60$^{c\text{-}src}$ (hereafter referred to simply as "Src") being the prototype PTK of the family wherein the ca. 300 amino acid catalytic domains are highly conserved (Rudd et al., 1993, Courtneidge, 1994). The hyperactivation of Src has been reported in a number of human cancers, including those of the colon (Mao et al., 1997, Talamonti et al., 1993), breast (Luttrell et al., 1994), lung (Mazurenko et al, 1992), bladder (Fanning et al., 1992), and skin (Barnekow et al., 1987), as well as in gastric cancer (Takeshima et al., 1991), hairy cell leukemia (Lynch et al., 1993), and neuroblastoma (Bjelfman et al., 1990). Overstimulated cell proliferation signals from transmembrane receptors (e.g. EGFR and p185HER2/Neu) to the cell interior also appears to pass through Src (Mao et al., 1997, Parsons & Parsons, 1997, Bjorge et al., 1996, Taylor & Shalloway, 1996). Consequently, it has recently been proposed that Src is a universal target for cancer therapy (Levitzki, 1996), because its' hyperactivation (without mutation) is involved in tumor initiation, progression, and metastasis for many important human tumor types.

In view of the large, and growing, potential for inhibitors of various protein kinases and protein phosphatases, a variety of approaches to obtaining useful inhibitors is needed. The status of the discovery of PTK inhibitors (Lawrence & Niu, 1988, Showalter & Kraker, 1997, Patrick & Heimbrook, 1996, Groundwater et al., 1996, Budde et al., 1995, Levitzki & Gazit, 1995; Frame, 2002; Sawyer et al., 2001; Haskell et al., 2001, Martin, 2001; Bridges, 2001; Blume-Jensen et al., 2001; Biscardi et al., 2000; Susa & Teti, 2000; Susa et al., 2000; Irby et al., 2000; Schlessinger, 2000; Abram et al., 2000; Garcia-Echeverria et al., 2000; Sedlacek, 2000; Sridhar et al., 2000; Biscardi et al., 1999) has been extensively reviewed. Random screening efforts have been successful in identifying non-peptide protein kinase inhibitors but the vast majority of these bind in the highly conserved ATP binding site. A notable recent example of such non-peptide, ATP-competitive, inhibitors are the 4-anilinoquinazolines, and analogs, which were shown to be effective against the epidermal growth factor receptor PTK (EGFR PTK) (e.g. Rewcastle et al., 1996). Although this class of inhibitors was reported to be selective for the EGFR PTK vs. six other PTKs (including Src, Fry et al., 1994) it is unknown what their effect is on most of the remaining 2,000 protein kinases that all bind ATP as well as a large number of other ATP, ADP, GTP, GDP, etc. utilizing proteins in the body. Therefore, potential side effects from PTK inhibitor drugs that mimic ATP, which might only be discovered after expensive animal toxicity studies or human clinical trials, are still a serious concern. Also, although this class of compounds was a nice discovery and is undergoing further exploration, they do not provide a rational and general solution to obtaining non-peptide inhibitors for any desired PTK, e.g. in this case Src. The risk of insufficient specificity in vivo with ATP-competitive PTK inhibitors has also been noted by others, along with the inherent three order of magnitude reduction in potency these inhibitors display when competing with the mM levels of intracellular ATP rather than the μM levels used in the isolated enzyme assays (e.g. see Lawrence & Niu, 1998, Hanke et al., 1996, Kelloff et al., 1996).

An older, and more extensively studied, class of non-peptide PTK inhibitors is erbstatin and the related tyrphostins (see reviews). This class of inhibitors are active against the receptor PTKs and their mode of inhibition is complex but does not appear to involve binding in the peptide substrate specificity site regions of the active site (Hsu et al., 1992, Posner et al., 1994). Furthermore, they are inactive against the isolated PTK when the unnatural assay metal $Mn^{2+}$ is replaced with the natural $Mg^{2+}$ (Hsu et al., 1992), are chemically unstable (Budde et al., 1995, Ramdas et al., 1995 & 1994), and are known to be cytotoxic to normal and neoplastic cells by cross-linking proteins (Stanwell et al., 1995 & 1996) as well as inhibit cell growth by disrupting mitochondria rather than PTK inhibition (Burger et al., 1995).

An important contribution to the protein kinase field has been the x-ray structural work with the serine kinase cAMP-dependent protein kinase ("PKA") bound to the 20-residue peptide derived from the heat stable inhibitor protein, PKI(5-24), and $Mg_2ATP$ (Taylor et al., 1993). This structural work is particularly valuable because PKA is considered to be a prototype for the entire family of protein kinases since they have evolved from a single ancestral protein kinase. Sequence alignments of PKA with other serine and tyrosine kinases have identified a conserved catalytic core of about 260 residues and 11 highly conserved residues within this core (Taylor et al., 1993). Two highly conserved residues of particular note for the work proposed herein are the general base Asp-166 which is proposed to interact with the substrate OH and the positively charged residue, Lys-168 for serine kinases and an Arg for tyrosine kinases (Knighton et al., 1993), which is proposed to interact with the γ-phosphate of ATP to help catalyze transfer of this phosphate. Two additional important PKA crystal structures have been reported (Madhusudan et al., 1994), one for the ternary PKA:ADP:PKI(5-24) complex wherein the PKI Ala 21 has been replaced with Ser (thereby becoming a substrate), and one for the binary PKA:PKI(5-24) complex wherein the PKI Ala 21 has been replaced with phosphoserine (an end product inhibitor). The ternary complex shows the serine OH donating a H-bond to Asp-166 and accepting a H-bond from the side chain of Lys 168. The binary complex shows the phosphate group of phosphoserine forming a salt bridge with the Lys-168 side chain and within H-bonding distance of the Asp-166 carboxyl group. These structures support the earlier proposed roles for Asp-166 and Lys-168 in the catalytic mechanism.

The x-ray structures of PKA show that the enzyme consists of two lobes wherein the smaller lobe binds ATP and the larger lobe the peptide substrate. Catalysis occurs at the cleft between the lobes. The crystallographic and solution structural studies with PKA have indicated that the enzyme undergoes major conformational changes from an "open" form to the "closed" catalytically active form as it binds the substrates (Cox et al., 1994). These conformational changes are presumed to involve the closing of the cleft between the two lobes as the substrates bind bringing the γ-phosphate of ATP and the Ser OH in closer proximity for direct transfer of the phosphate.

However, many inhibitors of protein kinases and protein phosphatases still lack the specificity and potency desired for therapeutic use. Due to the key roles played by protein kinases and protein phosphatases in a number of different diseases, including cancer, psoriasis, arthrosclerosis, Type II diabetes, obesity, and their role in regulating immune system activity, inhibitors of specific protein kinases and protein phosphatases are needed. The present invention provides a novel approach for designing protein kinase and/or protein phosphatase inhibitors and the resulting protein kinase and/or protein phosphatase inhibitors, which may be more specific for the targeted pathways.

SUMMARY OF THE INVENTION

The invention provides a non-peptide protein tyrosine kinase inhibitor and/or protein phosphatase inhibitor having the formula:

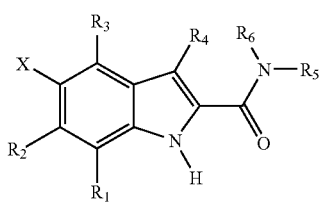

wherein X is a halogen, and $R_1$ through $R_6$ may be the same or different, and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl, or $R_5$ and $R_6$ together form a heterocyclic compound. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

In one embodiment, at least one of $R_5$ or $R_6$ is

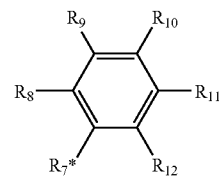

wherein $R_7^*$ is the point of attachment and is $(CH_2)_x$, wherein X is from 0 to 10, $CH_2CHOH$, $CH(CH_3)$(R-isomer), or $CH(CH_3)$(S-isomer), and each of $R_8$ through $R_{12}$ may be the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_8$ through $R_{12}$ can be substituted or unsubstituted.

In another embodiment, at least one of $R_5$ or $R_6$ is

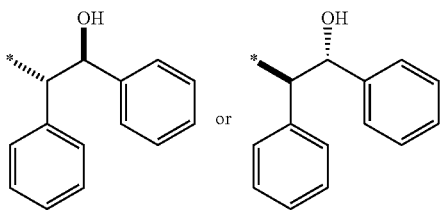

wherein the asterisk indicates the point of attachment to the nitrogen.

The present invention also provides a non-peptide protein tyrosine kinase inhibitor and/or protein phosphatase inhibitor having the formula:

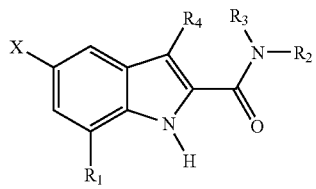

wherein X is a halogen, preferably, fluorine, and $R_1$ through $R_4$ are specificity side chain elements. In one embodiment, $R_1$ is H, $R_2$ is

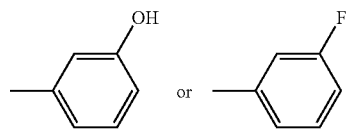

$R_3$ is H, and $R_4$ is H. The compound may also be substituted at any other position on the indole ring.

The present invention provides a method for identifying inhibitors of protein kinases. The method involves providing at least one first module having one or more functional groups each capable of covalently or non-covalently binding to catalytic residues of the protein kinase, wherein at least one of the one or more functional groups is a halogen, combining at least one first module with at least one second module which provides a non-peptide scaffold to form one or more combinations of the first and second modules, screening the one or more combinations of the first and second modules for protein kinase inhibition, and selecting combinations of the first and second modules which inhibit protein kinase activity. As used herein, a module is a single molecular entity or a collection of functional groups. As used herein, a non-peptide scaffold is a molecule which may include peptide bonds, so long as a part of the molecule is not a peptide.

The present invention also provides a method of inhibiting a protein kinase. The protein kinase is contacted by a compound comprising at least one first module having one or more functional groups each capable of covalently or non-covalently binding to catalytic residues of the protein kinase, wherein the one or more functional groups comprise a halogen, and a second module which provides a non-peptide scaffold. The combination of at least one first module and second module inhibits the protein kinase activity.

In yet another embodiment, the present invention provides a method of treating a condition, responsive to a protein kinase inhibitor, in a subject. A protein kinase inhibitor is administered to a subject. The protein kinase inhibitor has at least one first module having one or more functional groups each capable of covalently or non-covalently binding to catalytic residues of the protein kinase, wherein the one or more functional groups comprise a halogen, and a second module which provides a non-peptide scaffold. The combination of at least one first module and second module inhibits protein kinase activity in the subject.

In a further embodiment, the present invention provides a method for identifying inhibitors of protein phosphatases. The method involves providing at least one first module having one or more functional groups each capable of covalently or non-covalently binding to catalytic residues of the protein phosphatase, combining at least one first module with at least one second module which provides a non-peptide scaffold to form one or more combinations of the first and second modules, screening the one or more combinations of the first and second modules for phosphatase inhibition, and selecting combinations of the first and second modules which inhibit protein phosphatase activity.

Another aspect of the present invention is a method of inhibiting a protein phosphatase. The protein phosphatase is contacted by a compound comprising at least one first module having one or more functional groups each capable of covalently or non-covalently binding to catalytic residues of the protein phosphatase, and a second module which provides a non-peptide scaffold. The combination of at least one first module and second module inhibits the protein phosphatase activity.

In yet another embodiment, the present invention provides a method of treating a condition, responsive to a protein phosphatase inhibitor, in a subject. A protein phosphatase inhibitor is administered to a subject. The protein phosphatase inhibitor has at least one first module having one or more functional groups each capable of covalently or non-covalently binding to catalytic residues of the protein phosphatase, and a second module which provides a non-peptide scaffold. The combination of at least one first module and second module inhibits protein phosphatase activity in the subject.

BRIEF DESCRIPTION OF THE DRAWINGS

FIG. 16A shows a comparison of taxol and doxorubicin (they were more effective than etoposide and cisplatin in this tumor cell culture) with the three Src inhibitors (45, 43-meta, and 49-meta from Table V) utilizing ovarian tumor cells from tumor N015. FIG. 16B shows the results from tests of the Src inhibitors for inhibition of normal human fibroblast cell growth. No inhibition of normal cell growth (both subconfluent and confluent; some enhanced growth was observed instead) was found, indicating that these inhibitors are not toxic to normal cells even at a 10-fold higher concentration. FIG. 16C shows the results from tests of two of the Src inhibitors for inhibition of ts v-Src stimulated LA25 cell growth. FIG. 16D shows the results from tests of two of the Src inhibitors for inhibition of normal rat kidney cell growth.

DETAILED DESCRIPTION OF THE INVENTION

Figure 1:
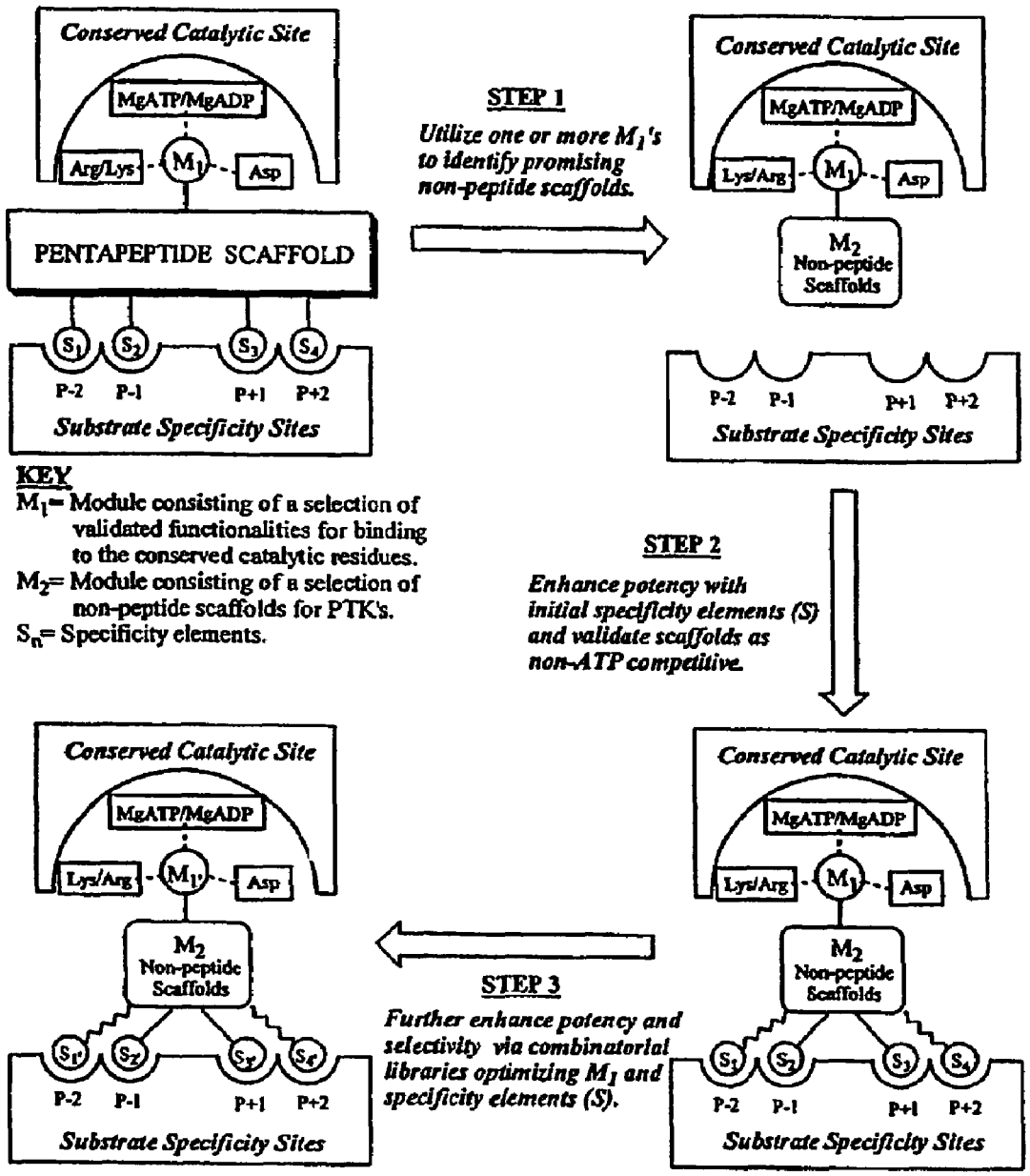
FIG. 1 depicts the modular strategy for developing non-peptide protein kinase inhibitors. Step 1 utilizes one or more first modules ("$M_1$'s") to identify promising non-peptide scaffolds. Step 2 enhances the potency by adding specificity elements. During this step the scaffolds are validated. Whether the inhibitor is non-ATP competitive can also be determined. In step 3, the potency and selectivity are further enhanced using combinatorial libraries to optimize $M_1$ and specificity elements.

The present invention provides inhibitors of protein kinases and/or protein phosphatases. In one embodiment, the protein kinase and/or protein phosphatase inhibitor is a non-peptide inhibitor having the following formula:

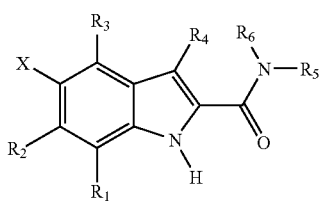

wherein X is a halogen, and $R_1$ through $R_6$ may be the same or different, and are selected from the group consisting of H, $C(O)R_a$, $C(O)NR_aR_b$, $C(O)OR_a$, $C(O)SR_a$, OH, $OR_a$, $OC(O)$ $R_a$, $OC(O)OR_a$, $NH_2$, $NR_aR_b$, $NR_aC(O)R_b$, $NR_aC(O)NR_b$ $R_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)$ $OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl, or $R_5$ and $R_6$ together form a heterocyclic compound. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions. Examples of suitable R groups are provided in Table VI, below.

In one embodiment, at least one of $R_5$ or $R_6$ is

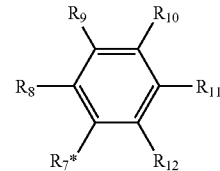

wherein $R_7^*$ is the point of attachment and is $(CH_2)_x$, wherein X is from 0 to 10, $CH_2CHOH$, $CH(CH_3)(R\text{-isomer})$, or $CH(CH_3)(S\text{-isomer})$, and each of $R_8$ through $R_{12}$ may be the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)$ $NR_bR_c$, $NR_aC(O)OR_b$, $NR_aC(O)SR_b$, $NR_aS(O)R_b$, $NR_aS$ $(O)_2 R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)$ $OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions. In a preferred embodiment, each of $R_8$ through $R_{12}$ is selected from the group consisting of $OCH_3$, $OCH_2CH_3$, H, $CH_3$, OH, $CH_2OH$, $CF_3$, $OCF_3$, CFO, $C_6H_5$, $OC_6H_5$, $OCH_2C_6H_5$, $OCH_2CH_2CH_3$, CHO, $CO_2H$, $CO_2CH_3$, $CH_2CO_2H$, $CH_2CO_2CH_3$, $NO_2$, and halogen.

In another embodiment, at least one of $R_5$ or $R_6$ is

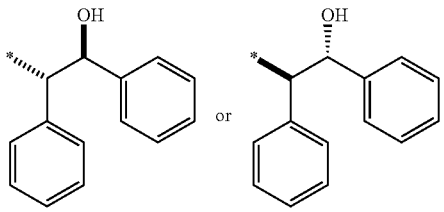

wherein the asterisk indicates the point of attachment to the nitrogen.

In a preferred embodiment, the non-peptide inhibitor inhibits the activity of $pp60^{c-src}$ tyrosine kinase, $pp56^{lck}$ tyrosine kinase, or $pp55^{fyn}$ tyrosine kinase.

In another preferred embodiment, the non-peptide inhibitor inhibits the activity of protein tyrosine phosphatase 1B (PTP-1B).

Another non-peptide protein tyrosine kinase and/or protein phosphatase inhibitor of the present invention has the following formula:

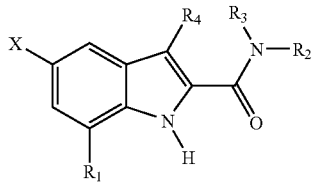

wherein X is a halogen, preferably, fluorine, and $R_1$ through $R_4$ are specificity elements. As used herein, specificity elements or specificity side chains are side chains which will bind in unique binding pockets for individual protein kinases. Thus, the side chains used will depend on the particular protein kinase or protein phosphatase to be inhibited. To identify suitable side chains, known peptide binding side chains may be used to identify analogues which are then used in combinatorial chemistry techniques to expand the library of possible side chains.

In one embodiment, $R_1$ is H, $R_2$ is

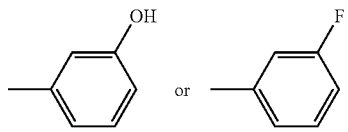

$R_3$ is H, and $R_4$ is H. The compound may also be substituted at any other position on the indole ring.

The compounds of the present invention provide activity against tyrosine kinases, such as $pp60^{c-src}$, and are expected to improve the ability of the compound to inhibit tyrosine kinases in vivo, since one easily metabolized OH group has been removed. In particular, an OH group at the 5-position on the indole ring has been substituted with a halogen. The halogen is a hydrogen bond acceptor, useful with catalytic residues which are hydrogen bond donors. In addition, the halogen is not metabolized in phase II metabolism and is electronegative, leading to in vivo benefits (see, e.g., Park et al., 2001). Some members of this class are also inhibitors of the opposing enzymes, i.e., phosphotyrosine phosphatases. These compounds are inhibitors of $pp60^{c-src}$, of highly metastatic prostate cancer cell growth, and are non-toxic in mice upon high dose acute i.p. administration, as described in Example 1, below. Some of these compounds may be found to have other biological activities upon broader testing (e.g., inhibit glycogen phosphorylase for Type II diabetes, HIV reverse transcriptase, or thromboxane synthase). Thus, these compounds may be used as tyrosine kinase inhibitors for therapeutic applications, such as cancer. Tyrosine kinase inhibitors have other potential therapeutic applications as well (e.g., immunosuppressants in the case of p56lck) and inhibitors of the tyrosine phosphatase PTP-1B may provide drugs for treating Type II diabetes or obesity.

The present invention also provides a method for identifying inhibitors of protein kinases. The general modular strategy for the development of non-peptide PTK inhibitors is outlined in FIG. 1. Basically, at least one first module having a one or more functional groups for binding to catalytic residues of the protein kinase (in a preferred embodiment, at least one of the functional groups is a halogen) is combined with at least one second module which provides a non-peptide scaffold. The functional group(s) of the at least one first module are each capable of covalently or non-covalently binding with catalytic residues of the protein kinase. Thus, each functional group of each first module is capable of reversible or irreversible bond formation, either covalently or non-covalently, to catalytic residues of the protein kinase when the protein kinase the first module are combined under conditions effective for such binding. Combinations of the first and second modules which inhibit protein kinase activity are then selected. Step 1 begins with protein kinase inhibitor information which was already generated, i.e. pentapeptide scaffolds which bind in the substrate specificity sites of PKA or Src have already been used to position various rationally designed functional groups (i.e. module "$M_1$" or "first module") to interact with the conserved catalytic residues, MgATP or MgADP. A selection of preferred functional groups have now been identified in this fashion to serve as the initial $M_1$ module for Step 1. These $M_1$ functional groups have been utilized to identify promising non-peptide scaffolds for Src inhibitors in Step 1. It was anticipated that these bare non-peptide scaffolds, with only an $M_1$ appendage, would have low binding affinity and be relatively non-selective among the protein tyrosine kinases (PTKs). A lack of selectivity at the level of Step 1 is viewed as an advantage for the development of a general strategy which can be reapplied to additional PTKs. Therefore, the suite of non-peptide scaffolds identified in Step 1 can be recycled for use against additional PTKs by re-screening them and carrying the better ones through Steps 2 and 3, all using the new PTK target. The potency of these bare scaffolds from Step 1 may be increased enough by the attachment of one or two initial specificity elements ($S_n$) to allow for the validation of the scaffold as non-ATP competitive and amenable to further potency enhancements using combinatorial chemistry in a rationally guided fashion. Promising Src non-peptide $M_2$ (second module) scaffolds identified in Step 1 have undergone Step 2 and displayed a one to two order-of-magnitude increase in potency against Src as well as non-competitive binding relative to ATP.

Validation of the scaffolds at the level of Step 2 before undertaking the resource intensive combinatorial library synthesis and testing of Step 3 is important for three reasons: 1) to develop the chemistry for appending the specificity element ($S_n$) side chains; 2) to determine that these inhibitors are not ATP-competitive; and 3) to determine that the potency is responding to the side chain $S_n$ properties and attachment points as would be expected based upon the working model for the Src:inhibitor complex (this provides some confidence that rationally guided choices can be made for the ranges of individual selectivity elements $S_n$ to include in the focused libraries of Step 3).

It is in Step 3 that high potency and specificity for a particular PTK is anticipated because numerous combinations of $M_1$ functional groups (and close analogs $M_1$') with selectivity elements ($S_n$) will be evaluated experimentally via combinatorial chemistry and high-throughput screening. Potency and selectivity may be further increased if necessary by appending additional specificity elements (see optional $S_n$'s in FIG. 1).

In each of the Steps 1-3, molecular modeling studies with the IRTK:peptide:AMP-PNP crystal structure, the model of the Src:peptide complex and the models for the Src complex with the individual families of inhibitors based upon a particular scaffold will be used as qualitative guides. These modeling studies have been remarkably helpful thus far in guiding the inhibitor design efforts as detailed later. Combining structure-based design and combinatorial chemistry technologies in this fashion provides a synergy wherein the major individual deficiencies of these technologies used in isolation are addressed by the strengths of the other. The major deficiency of structure-based design is the difficulty in quantitatively predicting ligand binding affinities, which is particularly challenging due to the complex effects of solvation and entropy (Ajay & Murcko, 1995). The major strength of structure-based design is its capability to predict what types of molecules are likely to be good ligands. Structure-based design can determine the rough boundaries (proteins have some flexibility which need to be taken into account) for molecular size and shape as well as indicate where hydrophobic, H-bonding, and ionic interactions are likely to occur. On the other hand, the major deficiency of combinatorial chemistry is that "molecular space" for drug-sized molecules (i.e. MW ca. 500 or less) is so large that one could not hope to sample all of this molecular space with a high density of coverage in a reasonable sized combinatorial library. A recent estimate (Bohacek et al., 1996) of the number of possible compounds containing up to 30 atoms chosen only from carbon, nitrogen, oxygen and sulfur (in addition to H's) is $10^{60}$ compounds. This is in the molecular weight range of typical drug molecules and still does not include additional diversity provided by other atoms, e.g. halogens. Consequently, additional constraints need to be used to identify regions of molecular space wherein particular drug candidates are likely to be located. Structure-based design can drastically reduce the volume of molecular space to be explored by identifying the types of molecules which have a higher probability of being good ligands. The inability to quantitatively predict which of these "focused" combinatorial library members will in fact be the tightest binding ligands (i.e. the quantitation problem) is then resolved by employing an efficient combinatorial synthesis and high-throughput testing of the library.

In the earlier peptide based serine and tyrosine kinase inhibitor design efforts, PKA was used as a convenient qualitative model for designing the protein kinase inhibitor module $M_1$ for interaction with the conserved catalytic residues. There is much more structural and kinetic information available for PKA than any other protein kinase.

Figure 2:
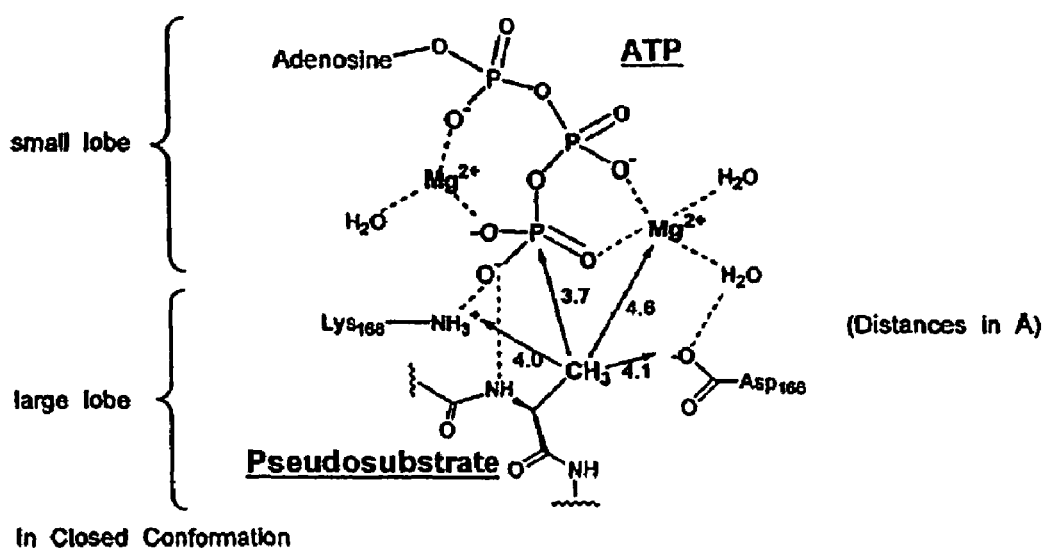
FIG. 2 provides a depiction of the x-ray structure of (PKA):$Mg_2$ATP:pseudosubstrate inhibitor.

The crystal structure of PKA complexed with $Mg_2ATP$ and a pseudosubstrate (i.e. OH replaced with H) peptide inhibitor (PKI 5-24 amide) has been solved (Zheng et al., 1993) and the active site interactions near the P 0 Ala of this inhibitor are shown in FIG. 2.

This crystal structure shows $Mg_2ATP$ bound to the small lobe of PKA and a 20-residue pseudosubstrate peptide inhibitor bound to the large lobe with the overall conformation of the enzyme in the closed (i.e. the two lobes are touching) and activated state. The distances between the P 0 Ala side chain carbon and the nearby heavy atoms in the complex are shown in Å in FIG. 2. These distances show that the Ala side chain is within van der Waals contact distance of the surrounding atoms and indicates that there is little space for appending bulky $M_1$ functional groups to the Ala side chain. However, PKA is a flexible enzyme with open, closed and intermediate conformations (Cox et al., 1994) and these more open conformations would result in a retraction back of the ATP γ-phosphate from the inhibitor Ala thereby creating a binding cavity for appended $M_1$ functional groups. Furthermore, PKA binds MgADP with the same affinity as MgATP (Whitehouse et al., 1983) and the ratio of ATP/ADP in cells is typically 10/1 (Alberts, et al. 1994). Therefore, at equilibrium, ca. 10% of the cellular protein kinase is in the MGADP bound state and this form of the enzyme can also be targeted with an inhibitor to drain all of the enzyme from the catalytic cycle into a PKA:MgADP:inhibitor inactive complex.

Since the PKA catalytic residues Asp-166 and Lys-168 are completely conserved in all serine kinases, and the tyrosine kinases only differ by the substitution of Arg for Lys-168 (Taylor et al., 1993), this region of the active site was chosen, along with the adjoining MgATP or MgADP, to target a selection of inhibitor functional groups which could serve as $M_1$ and be broadly useful for developing inhibitors for the entire protein kinase family. By targeting $M_1$ to the region of the active site adjacent to the nucleotide, an orientation point is provided for the non-peptide inhibitors which can extend into the peptide binding specificity sites without always competing with ATP/ADP binding.

A selection of functional groups which could be utilized as $M_1$ was identified first because, although this region of the active site is very highly conserved, it was expected that each particular protein kinase will still display some differing preferences across this selection due to small variations in the active site conformations and adjoining residues. Furthermore, the rank order preference among this selection of $M_1$'s may change somewhat as the $M_1$ module is appended to different non-peptide scaffolds. This expectation is based upon the potential for each non-peptide scaffold to bind in somewhat different orientations with each individual protein kinase and with each particular set of selectivity element ($S_n$) side chains. Pentapeptide scaffolds were chosen for the initial screening of functional groups for $M_1$ because the binding orientation of these larger peptide scaffolds is likely to be very consistent and predictable (i.e. closely resembling that observed by x-ray) throughout the series and could be more confidently assumed to position each tested $M_1$ functionality adjacent to the conserved catalytic residues as intended. Consequently, the goal of this earlier peptide-based work was to identify a collection of $M_1$ functional groups which can be used, not only for the initial screening of non-peptide scaffolds (Step 1), but also as an initial set of $M_1$ side chains which can be further expanded via close analogs and thereby optimized simultaneously with the other side chains in the final non-peptide combinatorial libraries (Step 3).

Figure 3:
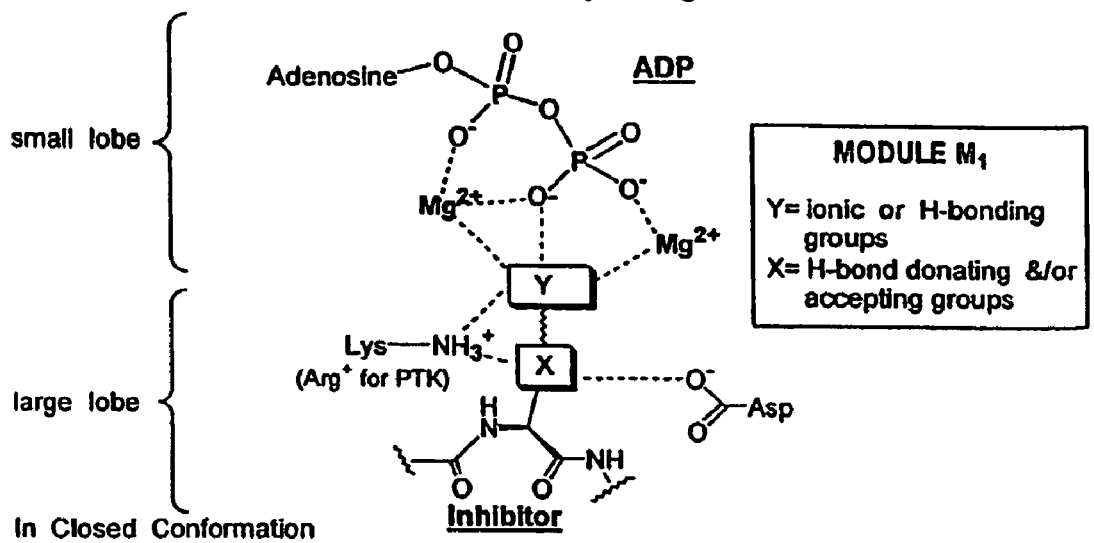
FIG. 3 provides a general module $M_1$ design features for binding to the conserved protein kinase catalytic region.

In order to model the candidate $M_1$ functional groups in this conserved catalytic region of the PKA active site, they were built onto the P 0 Ala position in the PKA ternary structure using the SYBYL molecular modeling package (Tripos) on a Silicone Graphics workstation as indicated in FIG. 3.

A crystal structure of PKA with MgATP and an inhibitor bound in a more "open" conformation was not available, so initial modeling studies were carried out on the MgADP bound form of PKA derived from the ternary complex illustrated in FIG. 2 by simply deleting the ATP γ-phosphate. Initial modeling studies were used to provide qualitative guidance for identifying interesting potential $M_1$ functional groups for the protein kinase family before synthesis and testing. The most advanced computational algorithms for quantitatively predicting the free energy of binding, such as Free Energy Perturbation methods, are computationally intensive methods which are not practical at this point in time for routine use by the non-specialist. Even the most advanced methods can be inaccurate due to difficulties in sampling, inadequacies in the molecular mechanics force fields/parameters, and an incomplete understanding of electrostatics in water (Ajay & Murcko, 1995). Less rigorous (and easier to use) computational methods tend to be unreliable in making quantitative predictions of binding affinities, especially when dealing with multiple polar and ionic interactions such as those involved in $M_1$ binding.

In order to allow molecular mechanics calculations to be done with the Silicone Graphics workstation in a reasonable amount of time, two layers of residues were carved out from the PKA ternary structure which are surrounding the PKA active site, along with the peptide inhibitor and $Mg_2ADP$. The $M_1$ functional groups were then appended to the P 0 Ala side chain and the entire PKA active site:$Mg_2ADP$:modified peptide inhibitor complex was then subjected to 300 iterations of molecular mechanics minimization using the Tripos force field with a distance dependent dielectric constant after assigning appropriate formal charges and calculating Gasteiger Marsili point charges using SYBYL. Setting the maximum number of iterations at 300 was sufficient to remove any serious strain in the complexes and yet not allow the overall structure to "drift" significantly from the starting x-ray structure if convergence is not reached. These minimized complexes were then visually evaluated to determine if the appended individual $M_1$ functional groups were able to engage in favorable interactions with the conserved catalytic residues and/or $Mg_2ADP$. This visual evaluation involved, among other standard interaction evaluations, measuring atom-atom distances to determine if hydrogen bonds and ionic interactions were being favorably formed.

Favorable intermolecular interactions between an individual $M_1$ functionality and the conserved catalytic residues or $Mg_2ADP$ does not necessarily mean enhanced binding affinity will be observed for the new inhibitor. Unfavorable desolvation of both the polar $M_1$ functionality and the polar PKA active site residues (as well as complex entropy effects) are not included in this analysis and may reduce the net binding affinity to the point that the modified inhibitor may even be less potent that the corresponding P 0 Ala inhibitor, even though the appended $M_1$ functionality is interacting with the conserved catalytic residues and/or MgADP (or MgATP) as intended. Even in cases where this desolvation penalty results in no net increase in binding affinity, these $M_1$ functional groups are still useful as an orienting groups for correctly positioning the non-peptide inhibitor analogs in the protein kinase active site. Positioning these polar functional groups elsewhere within the active site (assuming they are tethered so as not to be able to extend into bulk solvent while the scaffold is favorably bound in the active site) is likely to result in a reduced binding affinity because they were specifically designed and selected based upon their demonstrated ability (while appropriately tethered to pentapeptide scaffolds) to be accepted adjacent to the conserved catalytic residues and MgADP/MgATP. If a particular $M_1$ functionality does not correctly position a non-peptide scaffold in Step 1 then attempts to improve the potency by rationally appending initial specificity elements in Step 2 would likely fail.

None of the literature protein kinase assay procedures contain added ADP. A typical PKA literature assay procedure (Glass et al., 1989) was modified by adding 10% as much ADP as the ATP concentration used to reflect the natural 1/10 ratio in the cell. This protein kinase assay is hereinafter referred to as the "Literature Mimetic" assay. It has been used for PKA as well as the Src. An examination of the literature, and commercially available protein kinase assays, showed that there is poor consistency from lab to lab and company to company and that all of these assays use physical chemical conditions which differ considerably from those known to exist inside cells. Since inhibition of intracellular protein kinases is the ultimate goal for drug discovery, new protein kinase assays have been developed which come much closer to mimicking the overall cytosolic physical chemical conditions known to exist inside cells. The development of these "Cellular Mimetic" protein kinase assays, is described herein, along with a novel method for determining which form of a protein kinase a given inhibitor binds best to (the STAIRe method). Data was collected correlating the activity of the new non-peptide Src inhibitors in the Cellular Mimetic assay with that obtained in the LA25 Src transformed cell line (see below).

When these two assay conditions were applied to some of the pentapeptide-based PKA inhibitors, which were designed as illustrated in FIG. 3, the results shown in Table I were obtained. The same assay conditions were also applied to the analogously designed pentapeptide-based Src inhibitors and obtained the results shown in Table II.

TABLE I

INITIAL $M_1$ SCREENING RESULTS WHILE APPENDED TO THE PKA PENTAPEPTDE SCAFFOLD

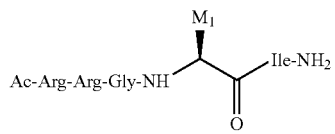

$K_i$ (μM), (Conditions*)

| | | |
|---|---|---|
| 1 $M_1$ = (End Product Inhibitor) | 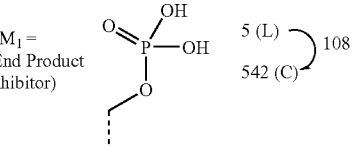 | 5 (L) ⎫ 108 X<br>542 (C) ⎭ |
| 2 $M_1$ = | | 76 (L)<br>NT (C) |
| 3 $M_1$ = | 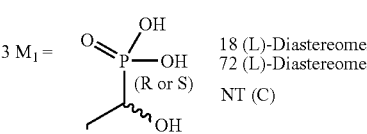 | 18 (L)-Diastereomer A<br>72 (L)-Diastereomer B<br>NT (C) |

TABLE I-continued

INITIAL $M_1$ SCREENING RESULTS WHILE APPENDED TO THE PKA PENTAPEPTDE SCAFFOLD

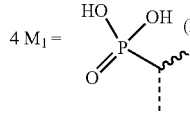

Ac-Arg-Arg-Gly-NH—C(M₁)(H)—C(O)—Ile-NH₂

$K_i$ (μM), (Conditions*)

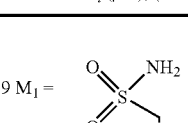

4 $M_1$ = [phosphonate with HO, OH, OH groups] (R or S)
 4 (L)-Diastereomer A ⎫
 20 (L)-Diastereomer B ⎬ 43 X
 171 (C)-Diastereomer A
 1510 (C)-Diastereomer B $M_1$ = HO₂C—CH(X)—O—CH₂—

5 X = H    28 (L) / 780 (C)    29 X

6 X = CO₂H    6 (L) / 450 (C)    75 X

7 $M_1$ = —CH₂CH₂—S(O)₂—NH₂    300 (L) / 2400 (C)    8 X

8 $M_1$ = —CH₂—NH—S(O)₂—OH    0.16 (L) / 5 (C)    31 X

9 $M_1$ = —CH₂—S(O)₂—NH₂    250 (L) / 2100 (C)    8 X

10 $M_1$ = —CH₂—CH₂—NH₂    38 (L) / 115 (C)    3 X

11 $M_1$ = —CH₂—CH(NH—)—CH(CO₂H)—CH₂—CO₂H

11 $M_1$ = [structure with two CO₂H groups and NH attachment]    45 (L), NT (C)

- - - - - = Attachment Point

*L = Literature Mimetic
C = Cellular Mimetic

The structure identified in Table I as Ac-Arg-Arg-Gly-Ala bonded to $M_1$-Ile-NH₂ is SEQ. ID. No. 2.

TABLE II

INITIAL $M_1$ SCREENING RESULTS WHILE APPENDED TO THE SRC PENTAPEPTIDE SCAFFOLD

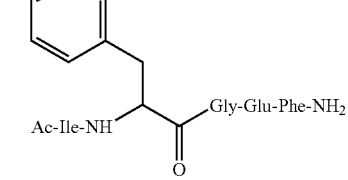

Ac-Ile-NH—CH(CH₂-C₆H₄-$M_1$)—C(O)—Gly-Glu-Phe-NH₂

% Inhibition of 2 mM RR-src phosphorylation by src Assay Conditions

| Inhibitor (1 mM) | Literature Mimetic | Cellular Mimetic | Inhibitor (1 mM) | Literature Mimetic | Cellular Mimetic |
|---|---|---|---|---|---|
| 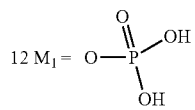 12 $M_1$ = O—P(O)(OH)(OH) | 36 | 0 |  16 $M_1$ = NH—C(O)—NH₂ | 60 | 8 |

TABLE II-continued

INITIAL $M_1$ SCREENING RESULTS WHILE APPENDED TO THE SRC PENTAPEPTIDE SCAFFOLD

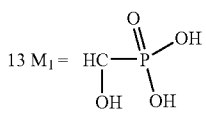

% Inhibition of 2 mM RR-src phosphorylation by src Assay Conditions

| Inhibitor (1 mM) | Literature Mimetic | Cellular Mimetic | Inhibitor (1 mM) | Literature Mimetic | Cellular Mimetic |
|---|---|---|---|---|---|
| 13 $M_1$ = 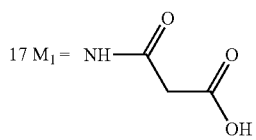 | 51 | 0 | 17 $M_1$ = 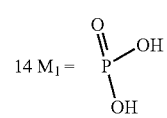 | 20 | 28 |
| 14 $M_1$ = 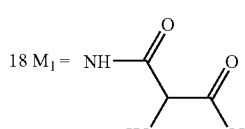 | 83 | 88 | 18 $M_1$ = 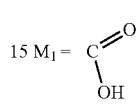 | 64 | 5 |
| 15 $M_1$ = 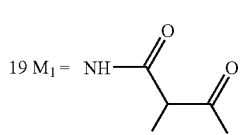 | 68 | 59 | 19 $M_1$ = | 24 | 0 |

The structure identified in Table II as Ac-Ile-Tyr bonded to $M_1$-Gly-Glu-Phe-$NH_2$ is SEQ. ID. No. 3.

The standard pentapeptide sequence chosen for the majority of PKA inhibitors in Table I was derived from the pseudosubstrate sequence of the peptide inhibitor which was bound to PKA, when the crystal structure illustrated in FIG. 1 was solved. The standard pentapeptide sequence used for Src in Table II, Ac-Ile-Xaa-Gly-Glu-Phe-$NH_2$ (SEQ. ID. No. 3), was described in Nair, Kim et al., 1995. Some of the chemistry used to prepare the PKA inhibitors is described in Nair, Lee & Hangauer 1995. The synthetic methodology used to develop a number of the Src inhibitors is described in Lai et al., 1998.

The collective results in Tables I and II show that both the serine kinase PKA and the PTK Src can accommodate a variety of large polar $M_1$ functional groups at the P 0 phosphorylation position. Furthermore, using the STAIRe methodology (see Choi et al. 1996), the sulfamic acid inhibitor 8, and related inhibitors, were shown to actually bind best when MgATP (not MgADP or no nucleotide) is also bound. This was a somewhat surprising result since these inhibitors are analogs of the "end product inhibitors" 1 and 12 which must bind simultaneously with MgADP just following phosphate transfer in the generally accepted reaction mechanism for protein kinases.

These results also demonstrate that both PKA and Src can show a large difference in binding affinity for structurally very similar inhibitors. For example, the sulfamic acid PKA inhibitor 8 (Table I) has a $K_i$ of 0.16 μM under Literature Mimetic assay conditions (L) whereas the isosteric sulfonamide 7 is 1,875× less potent ($K_i$=300 μM). The sulfamic acid inhibitor 8 is also isosteric with the end product phosphate inhibitor 1 yet it binds much more tightly under both Literature Mimetic assay conditions (31×) and Cellular Mimetic (C) assay conditions (108×). The beneficial effect of an oxygen atom positioned analogously to that in the substrate Ser is illustrated by comparison of phosphonate 2 to phosphate 1 and also ether 6 to phosphate 1. This oxygen atom can also be positioned as a serine-like OH side chain and enhance binding (compare 2 to 3A and 4A) wherein the closer serine mimic 4A is the more active. The difference in activity of the diastereomeric inhibitors 3A or B and 4A or B suggests a specific interaction with the active site catalytic residue Asp-166 may in fact be occurring as intended in the $M_1$ design (FIG. 3).

The Src inhibition results (Table II) show that the end product inhibitor 12 drops in activity upon going from Literature Mimetic assay conditions to the higher ionic strength Cellular Mimetic assay conditions, analogous to the PKA end product inhibitor 1. However, whereas all of the PKA inhibitors with polar $M_1$ functional groups were less active under Cellular Mimetic assay conditions, three of the Src inhibitors 14, 15, and 17 held their activity under these higher ionic strength assay conditions. Also, the hydroxyphosphonate Src inhibitor 13 (a mixture of the R and S diastereomers) is analogous to the PKA inhibitor 3A and both are roughly in the same activity range as their corresponding end product inhibitors, 12 and 1 respectively, under Literature Mimetic assay conditions. Shortening the side chain length in the phosphonate Src inhibitor 13 by one carbon atom (and necessarily removing the attached OH at the same time) to give 14 improved the activity (analogous to the PKA inhibitor comparison 3 to 4) and, more importantly, resulted in equivalent activity under Cellular Mimetic assay conditions. The Src results with 16-19 (particularly 17, see later for an analogous α-tricarbonyl acid $M_1$ analog appended to non-peptide Src inhibitors) also suggests that similar amides may be useful $M_1$ functional groups to explore with non-peptide Src inhibitors.

Non-peptide Src inhibitors are preferred to peptide scaffold based compounds, partly because some of these inhibitors have a dual effect on Src. For example, phosphonate inhibitor 14 not only inhibits Src by competitively binding in the active site but it also activates Src by binding to the $SH_2$ site thereby releasing the intramolecular autoinhibition mechanism (Xu et al., 1997). This opposing effect gives an unusual $IC_{50}$ curve for 14, wherein at low inhibitor concentrations Src is stimulated (to a maximum of 70%) in a smooth dose-response fashion (due to initial tighter SH2 binding) followed by a typical $IC_{50}$ inhibition curve at higher inhibitor concentrations (due to lower affinity blockade of the active site). This opposing activation effect of the pentapeptide inhibitors makes them appear to be less potent active site inhibitors than they in fact are, and makes it difficult to accurately rank $M_1$ groups while appended to this pentapeptide scaffold. However, the better $M_1$ groups identified with the Src pentapeptide scaffold must still be accommodated in the catalytic region of the active site and hence are useful orienting groups for the ongoing non-peptide Src inhibitor studies as intended. Since PKA does not have an SH2 domain, this complication is not a factor in interpreting the PKA pentapeptide inhibitor $M_1$ testing data.

The results in Tables I and II also show how much effect the assay conditions can have on both inhibitor potencies and the rank order of activity. For example, as shown in Table I, switching from the Literature Mimetic (L) assay conditions to the Cellular Mimetic (C) assay conditions can change the potency from as little as 3-fold (inhibitor 10) to as much as 108-fold (inhibitor 1). Also, whereas inhibitor 10 is less potent than 1 under Literature Mimetic conditions, it is more potent under Cellular Mimetic conditions. The Src inhibitor data presented in Table II show that many of the inhibitors lose their potency upon going from Literature Mimetic assay conditions to Cellular Mimetic assay conditions. The rank order of potency against Src is also sensitive to the assay conditions. Whereas inhibitor 18 is more potent than inhibitor 17 under Literature Mimetic conditions, the opposite is true under Cellular Mimetic conditions. Since activity within cells is the goal, the Cellular Mimetic Src assay was selected as the standard assay for testing potential non-peptide Src inhibitors. Activity within the Cellular Mimetic assay is a necessary, but not sufficient, condition for activity within cells. As will be described later, the Cellular Mimetic Src assay will be followed up with cell culture assays wherein cell penetration, metabolism, and binding to other cellular components are also factors in the measured potency.

The next class of $M_1$ functionality which was explored was the boronic acid group. This functional group is an intriguing candidate for $M_1$ for a number of reasons: 1) It can exist in a non-ionic state so that it should not prevent passive absorption of non-peptide inhibitors across cell membranes. 2) The planar, trigonal, boron acids might form reversible tetrahedral covalent borate complexes (a well known property of boronic acids, see Loomis & Durst, 1992) through their vacant 2p orbitals with anions present in the protein kinase active site, such as the catalytic Asp carboxyl group, or the ATP/ADP terminal phosphate oxygens. This ability to form borate complexes with active site nucleophiles has been extensively utilized to develop slow binding inhibitors of serine proteases (e.g. see Kettner & Shenvi, 1984), wherein the nucleophilic serine OH forms a covalent bond with the vacant 2p orbital in the boronic acid resulting in a tetrahedral borate complex (e.g. see Skordalakes et al., 1997). Also, an intramolecular complex of a boronic acid with a urea $NH_2$ was used to prepare transition state analogs inhibitors of dihydroorotase (Kinder et al., 1990). 3) Boronic acids act as Lewis acids and are converted to tetrahedral hydrates in water by forming borate complexes with water or hydroxide ions. Therefore, it is also possible that these boronic acid hydrates may function as phosphate mimics and $M_1$ modules as proposed in FIG. 2. This hydration property was utilized by Baggio et al. (1997) wherein a hydrated boronic acid functioned as a transition state analog inhibitor functionality for arginase. These researchers evaluated the inhibited complex by x-ray and showed that the hydrated boronic acid functionality formed two hydrogen bonds with the active site catalytic Glu-277 carboxyl side chain and one of the other hydrated boronic acid OH's interacted with two catalytic $Mn^{2+}$'s in the active site. These binding interactions are closely analogous to those proposed in protein kinase active sites, i.e. H-bonds to the catalytic Asp side chain carboxyl group and interactions with the active site $Mg^{2+}$'s (see FIGS. 2 and 4). The use of boronic acids for protein kinase inhibitors has not been explored previously.

In the area of pentapeptide-based PKA inhibitors, the boronic acid functionality has been prepared and tested as a potential $M_1$ module utilizing the four inhibitors 21-24 shown in Table III (see Hsiao & Hangauer, 1998, for some of the chemistry used to prepare these compounds).

TABLE III

PKA INHIBITION RESULTS WITH BORONIC ACID-CONTAINING PEPTIDE INHIBITORS

| Ac-RRGXI-NH$_2$, X = | IC$_{50}$ μM (cond. L, 0 h preincubation) | IC$_{50}$ μM (cond. L, 4 h preincubation) | IC$_{50}$ μM (cond. C, 0 h preincubation) | IC$_{50}$ μM (cond. C, 4 h preincubation) |
|---|---|---|---|---|
| 20 Ala | 278 (K$_i$ = 9 μM) | 417 | 41 (K$_i$ = 25 μM) | 50 |
| 21 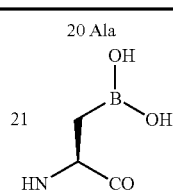 | 249 | *500 μM 34% inh | 764 | *2000 μM 19% sti |

TABLE III-continued

PKA INHIBITION RESULTS WITH BORONIC ACID-CONTAINING PEPTIDE INHIBITORS

| Ac-RRGXI-NH$_2$, X = | IC$_{50}$ μM (cond. L, 0 h preincubation) | IC$_{50}$ μM (cond. L, 4 h preincubation) | IC$_{50}$ μM (cond. C, 0 h preincubation) | IC$_{50}$ μM (cond. C, 4 h preincubation) |
|---|---|---|---|---|
| 22 (structure with B(OH)$_2$, HN, CO) | 81 | *65 | *1753 | *2000 μM 71% sti |
| 23 (structure with B(OH)$_2$, HN, CO, longer chain) | 398 | 133 | 2000 μM 16% inh | *2000 μM 5% inh |
| 24 (structure with B(OH)$_2$, HN, CO, longest chain) | 1000 μM 33% inh | 1000 μM 44% inh | 2000 μM 6% sti | 1734 μM |

*Very distorted IC$_{50}$ curve: Suggests Inhibitor is also a substrate.
L = Literature Mimetic Assay Conditions.
C = Cellular Mimetic Assay Conditions.
Inh = Inhibition.
Sti = Stimulation.

The structure identified in Table III as Ac-RRGXI-NH$_2$ is SEQ. ID. No. 4.

While testing these boronic acid-containing PKA inhibitors, the corresponding pentapeptide pseudosubstrate inhibitor 20 was included as an internal control while investigating time-dependent inhibition as shown in Table III. Under Literature Mimetic assay conditions, and no preincubation, the initial results suggested that the shortest chain L-amino acid 21 was binding with the same affinity as the pseudosubstrate inhibitor 20 (i.e. K$_i$ ca. 9 μM). As this side chain was increased in length (to 23 and then 24) binding affinity appeared to decrease. When the stereochemistry of the unnatural amino acid was inverted from L in 21 to D in 22, binding affinity appeared to increase 3-fold. This improvement in binding may occur as a result that the boronic acid OH in 21 is positioned at the same chain length as L-homoserine whereas the natural substrate, L-serine, has a one carbon shorter side chain. Modeling results with the PKA ternary structure indicated that the boronic acid OH can be retracted back somewhat by inverting the α-carbon stereochemistry from L in 21 to D in 22 and then repositioning the side chain to more closely mimic the positioning of the natural substrate L-serine OH adjacent to the catalytic residues (Asp-166 and Arg-168). The modeling results were subsequently supported by the finding that, upon incubation of PKA with these inhibitors for up to four hours without adding the competing peptide substrate (Kemptamide: LRRASLG-NH$_2$ (SEQ. ID. No. 5)), both 21 and 22 function as substrates with the D-diastereomer 22 being phosphorylated faster.

The fact that these boronic acid inhibitors are also substrates, became much more obvious by the greatly distorted IC$_{50}$ curves obtained under the Cellular Mimetic conditions, both with and without preincubation (both PKA and Src are more active enzymes under the Cellular Mimetic conditions than under Literature Mimetic conditions). In the assay used to obtain these results, the P$^{32}$ phosphorylated Kemptamide product (25 generated from γ-P$^{32}$ ATP) was isolated at the end of the substrate incubation period by binding to phosphocellulose filter paper via the three cationic groups (two Arg's and the N-terminus) and the level of phosphorylated product isolated on the paper is then measured by liquid scintillation counting (cpm's). The boronic acid inhibitors 21-24 have two Arg's in their sequence also and therefore will bind to the phosphocellulose paper in addition to Kemptamide (although not as consistently or completely due to one less positive charge). Consequently, when analyzed as inhibitors, the amount of phosphorylated Kemptamide produced was not only counted, but also the amount of phosphorylated inhibitor simultaneously produced (e.g. see 26 below). The net result is that distorted IC$_{50}$ curves are obtained which show net "stimulation" at higher inhibitor concentrations in some cases. The D diastereomer 22 gives the greatest apparent "stimulation" (71%) when preincubated with PKA for four hours under Cellular Mimetic conditions followed by the L diastereomer 21 (19%) and then the one carbon homolog 23 (5%), indicating all three are substrates for PKA (Table III). The underlying substrate behavior of these "inhibitors" makes an accurate measurement of their inhibition potency impossible with the current assay. However, it does appear from the data that homologating the boronic acid functionality out with only CH$_2$ groups (homologations with boronic acid non-peptide Src inhibitors may also be carried out) decreases the binding affinity and ability to function as a substrate.

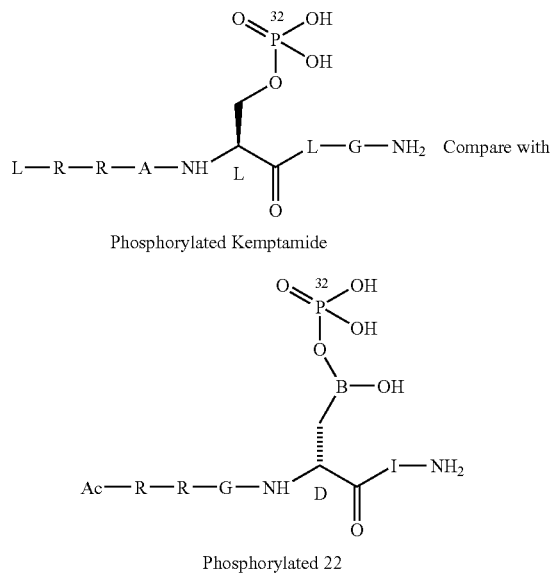

Phosphorylated Kemptamide

Phosphorylated 22

Figure 4:
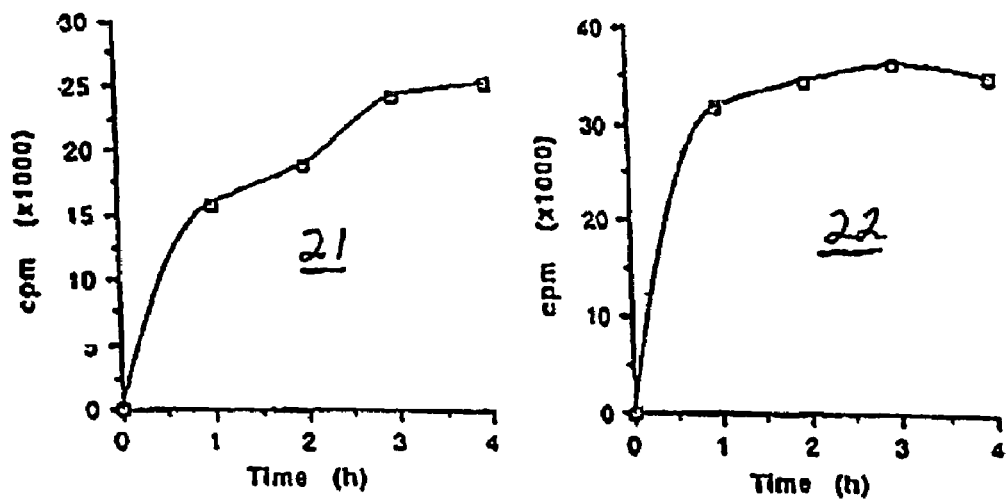
FIG. 4 shows that the boronic acid "inhibitors" 21 and 22 were shown to be substrates for PKA.

Phosphorylated Kemptamide is SEQ. ID. No. 6. Phosphorylated 22 is SEQ. ID. No. 4. The boronic acid "inhibitors" 21 and 22 were shown to be substrates for PKA by running the same assay, but without adding Kemptamide, and stopping the reaction at various time points as shown in FIG. 4. The graphs show their respective rates and levels of phosphorylation with the typical loss of initial velocity kinetics with time (due to substrate depletion and end product inhibition), analogous to a standard L-Ser substrate such as Kemptamide. The comparison of 21 to 22 shown was done in the same assay run, at identical boronic acid substrate concentrations, and with identical Cellular Mimetic assay solutions so that the cpm's could be directly compared. The graphs show that initial velocity conditions were lost within one hour for D isomer 22 whereas the linearity appears to have been lost somewhat slower with the L isomer 21 suggesting a slower consumption of starting material. That the boronic acid moiety would be phosphorylated by PKA was surprising, but it is even more surprising that the phosphonic-boronic acid mixed anhydride produced (e.g. 26) was stable enough to survive the pH 7.2/ 37° C. assay incubation and then be isolated by binding to phosphocellulose paper after acid quenching of the reaction with 10% TCA and washing the phosphocellulose paper with 25 mM phosphoric acid (3×). An STN substructure search was run on mixed anhydrides of phosphoric and boronic acids and found only three references to experiments and theoretical calculations for the analogous putative (but not proven) anhydride formed from boric acid and phosphoric acid as a solid surface impregnated catalyst for the partial oxidation of ethane to acetaldehyde at 823° K. (Zhanpeisov & Otsuka, 1992, Otsuka et al., 1992, Murakami et al., 1990). However, this highly unusual anhydride has never before been synthesized free of a solid surface, isolated, or characterized. Thus, this is a novel enzymatic reaction and chemical entity with interesting possibilities for protein kinase inhibitor designs.

The next class of $M_1$ functionality which was explored was the halogen group. This functional group is an intriguing candidate for $M_1$ for a number of reasons: 1) it is a good hydrogen bond acceptor; and 2) it reduces the rate of metabolism, leading to in vivo benefits.

The halogen functionality has been prepared and tested as a potential $M_1$ module utilizing the inhibitor shown below (see Example 1, for the chemistry used to prepare this compound).

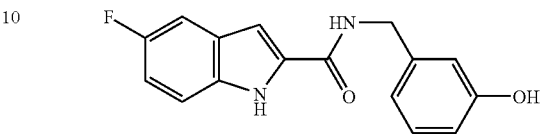

This inhibitor was tested for Src inhibition using the assay procedure set forth in Example 1. The results obtained are shown in Table VII, which indicates an $IC_{50}$ of 40 μM for the above inhibitor (1a in Table VII). This inhibitor includes a non-peptide scaffold (indole) which was chosen based on the screening method described below.

The Src and PKA pentapeptide scaffold tethered $M_1$ evaluations described above have resulted in identifying a variety of orienting $M_1$ groups which could be used for screening potential non-peptide scaffolds as indicated in Step 1 (FIG. 1). The boronic acid (from 22), the phosphonate (from 14), and the sulfamic acid (from 8) were chosen from the menu of potential $M_1$'s for the Src non-peptide scaffold screening. Among these choices, the boronic acid $M_1$ group has proven effective for Step 1 screening of non-peptide scaffolds.

The most useful crystal structures available for the design of non-peptide Src inhibitors, which do not compete with ATP, are the native Src structure and the IRTK:peptide:AMP-PNP ternary structure. For all of the modeling studies discussed below, the SYBYL molecular modeling software package is used on a Silicone Graphics Workstation.

Since the Src and IRTK structures are only used as qualitative guides in designing the non-peptide scaffolds and combinatorial libraries, the active sites along with two layers of surrounding residues were carved out from the native Src and IRTK ternary structures, analogous to the previous PKA modeling studies. The IRTK:peptide:AMP-PNP ternary structure active site region was used as the template structure to guide the building of the Src residue sequence 424-418 back onto the Src structure using the comparative homology modeling technique (see Hutchins & Greer, 1991). These residues were disordered in the native Src crystal structure and therefore not visible by x-ray. They were reintroduced because they help form the P+1 to P+3 binding sites for peptide substrates which are important for some of the modeling studies. The analogous residues in the IRTK ternary structure are seen by x-ray and directly interact with the bound peptide substrate. In fact, it is probably the presence of the bound peptide substrate which induces order in the positioning of this sequence so that it is visible by x-ray. The Src pentapeptide substrate Ac-Ile-Tyr-Gly-Glu-Phe-$NH_2$ (SEQ. ID. No. 1) (Nair et al., 1995) was then docked into the Src active site again using the IRTK ternary structure as a template. Small adjustments were then manually made to partially clean up this complex, all of the hydrogen atoms were added, appropriate formal and partial charges (calculated via the Gasteiger Marsili method) were added, and then the entire complex was subjected to 300 iterations of molecular mechanics minimization using the Tripos force field, analogous to the previous PKA modeling procedure. A schematic representation of this modeled complex is given in FIG. 5.

Any inaccuracies in this Src:peptide and the Src:inhibitor models are accommodated by experimentally evaluating a range of side chains, the number and diversity of which is scaled roughly to the level of uncertainty for the structure of their particular binding region in the Src model active site (see later), in a combinatorial fashion.

Figure 5:
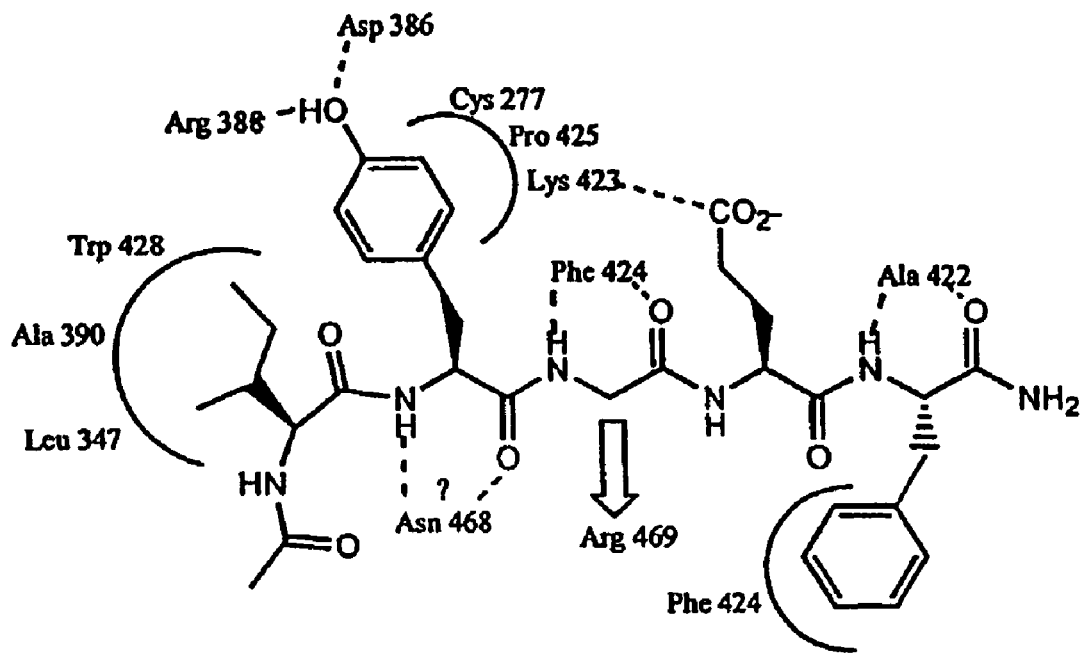
FIG. 5 demonstrates the binding interactions of Src substrate Ac-Ile-Tyr-Gly-Glu-Phe-$NH_2$ (SEQ. ID. No. 1) in model Src active site.

As shown in FIG. 5 the residues 424-418 built back into the Src interact with the P+1 to P+3 substrate residues, Gly-Glu-Phe-NH$_2$ respectively, through beta sheet type hydrogen bonding interactions with the substrate main chain (analogous to the IRTK peptide substrate). Lys 423 engages in two important interactions: 1) the β and γ CH$_2$'s fold over the top of the P 0 Tyr phenyl ring engaging in a hydrophobic binding interaction and then 2) the remaining CH$_2$—CH$_2$—NH$_3^+$ of this side chain extends away to form a salt bridge with the P+2 Glu side chain as indicated. The rest of the P 0 Tyr hydrophobic binding pocket is formed by Pro 425 under the phenyl ring and part of the Cys 277 side chain above the phenyl ring. Using a large combinatorial peptide Src substrate library, Songyang et al. (1995) found that the most commonly chosen side chain for the P+1 position was Gly followed by Glu. The present model indicates that a P+1 Glu side chain may form a salt bridge with nearby Arg 469 as indicated in FIG. 5. Previously, researchers found that only Glu was chosen for the P+2 position and the present model indicates that this side chain forms a salt bridge with the Lys 423 side chain. At the P+3 position Phe was very strongly preferred and the model indicates that this side chain forms a stacking interaction with the Phe 424 side chain. At the P−1 position Songyang et al. found that Ile was the most preferred residue followed by Val and then Leu. The model shows a hydrophobic pocket for binding the P−1 side chain formed mainly by Trp 428, Ala 390 and Leu 347. One might expect that the P 0 Tyr side main chain will strongly interact (though hydrogen bonding) with the active site in a catalytically competent complex because enzymes often form more critical interactions in this region close to where the reaction will be occurring. The IRTK ternary complex does not show a good hydrogen bond to either the P 0 Tyr NH or carbonyl. The nearest candidate residue for this interaction in the IRTK structure is Asn 1215 wherein the side chain NH$_2$ is 3.71 Å from the Tyr carbonyl oxygen. When the IRTK ternary structure is overlayed onto the Src native structure, using the four residues mentioned in the Background and Significance section, Asn 468 from the Src structure was found to be positioned very close to the analogous IRTK Asn 1215. This suggests that this conserved residue is performing an important role and might move a little closer (i.e. about 1 Å) to the substrate P 0 NH and carbonyl in a catalytically active complex and form the hydrogen bonding interactions indicated in FIG. 5. Finally, the catalytic Arg 388 and Asp 386 are correctly positioned in the Src model to catalyze the transfer of the γ-phosphate from ATP to the Tyr OH.

The Src:peptide substrate complex can now be used to model potential non-peptide scaffolds and determine preferred substitution positions for the specificity elements, all with an appropriately attached M$_1$ functionality, before choosing new scaffolds to experimentally evaluate. The IRTK:peptide:AMP-PNP ternary structure can also be used to model these potential scaffolds and preferred substitution positions. These scaffolds have broad utility for the development of selective PTK inhibitors by further developing them with appropriate specificity elements following the strategy outlined in FIG. 1.

Figure 6:
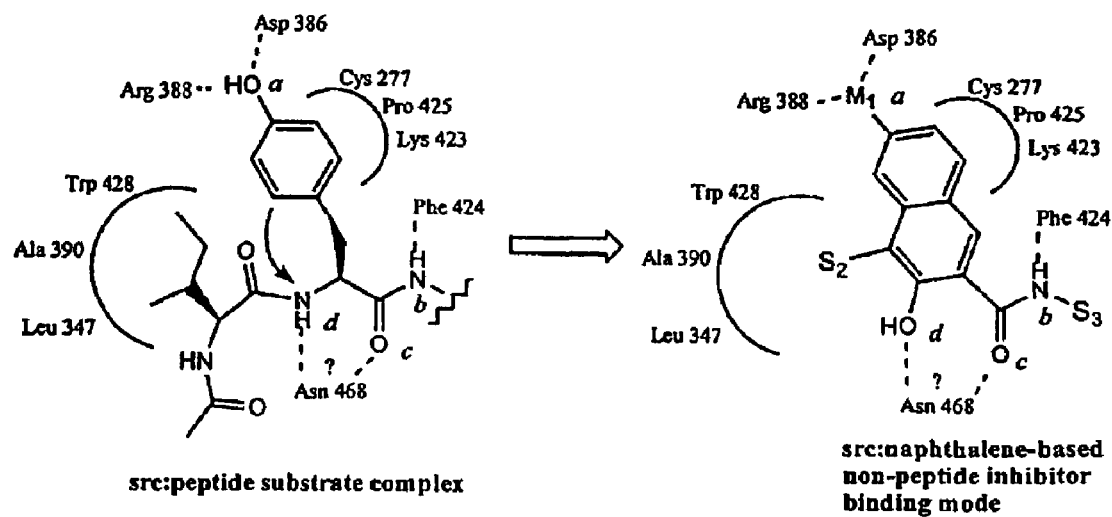
FIG. 6 shows the design of naphthalene-based Src inhibitor scaffolds.
Figure 7:
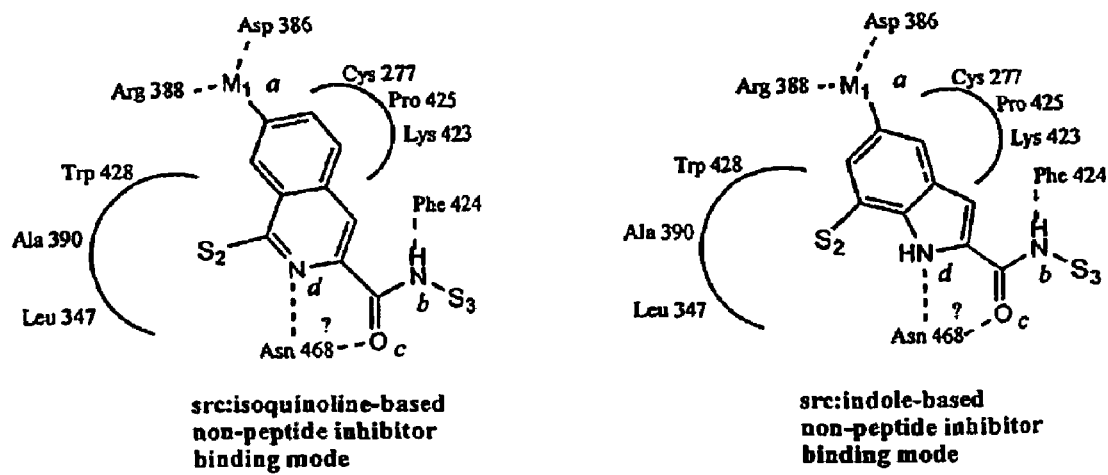
FIG. 7 shows the design of isoquinoline and indole-based Src inhibitor scaffolds.

The first non-peptide scaffold evaluated with this Src:peptide substrate model was the naphthalene scaffold. This is the first use of bicyclic aromatic scaffolds for non-peptide PTK inhibitors, which do not compete with ATP. The naphthalene scaffold's utility for this purpose was demonstrated by developing a non-peptide inhibitor of the IRTK and EGF receptor PTK (Saperstein et al., 1989). The IRTK ternary complexes were subsequently used to adapt this scaffold for Src inhibition (see Marsilje et al., 2000). The naphthalene scaffold was docked into the Src active site by first carrying out a least squares fitting of atoms a-d onto the peptide substrate as indicated in FIG. 6. In this way the naphthalene scaffold is related to the peptide substrate by the cyclization shown by the arrow in FIG. 6 and an appended OH as a substitute for the substrate Tyr NH. This is essentially the same process used to dock this scaffold into the IRTK structure as described in Marsilje 2000. The peptide substrate was then deleted from the active site, various M$_1$ functional groups and specificity elements S$_2$ and S$_3$ were then added to the scaffold as indicated and the complexes were then individually minimized for 300 iterations. This same process was also used to design the isoquinoline and indole scaffolds whose binding modes are indicated in FIG. 7.

In all of these modeled complexes, selectivity element S$_2$ consists of various hydrophobic side chains which can bind in the same pocket as the substrate P−1 Ile side chain and selectivity element S$_3$ consists of various molecular fragments which can bind in the P+1 to P+3 region of the peptide substrate binding sites (FIG. 5). Since the active site region where M$_1$ binds is highly conserved among all of the protein kinases, the small menu of M$_1$ functional groups previously identified using peptide scaffolds served as the initial M$_1$ groups for attachment to the scaffolds at the indicated positions. Of the two selectivity elements binding sites, the structure of the hydrophobic binding cavity for S$_2$ is known with greater confidence in the Src model than is the P+1 to P+3 binding region for S$_3$. This is because the S$_3$ binding site was constructed partially by comparative homology modeling whereas the S$_2$ site is largely unchanged from the structure determined by x-ray for native Src. In view of these varied levels of confidence in the modeled binding sites for M$_1$, S$_2$ and S$_3$, the combinatorial library diversity is scaled such that the greatest variety and number of side chains in the combinatorial libraries are at the S$_3$ site followed by the S$_2$ site and then M$_1$.

The Src results using M$_1$ functional groups to experimentally identify promising non-peptide scaffolds are listed in Table IV.

TABLE IV

INITIAL STEP 1 RESULTS
% SRC INHIBITION IN CELLULAR MIMETIC ASSAY

| Inhibitor | % Inhibition of 2 mM RR-src at Inhibitor Concentration ( ) |
|---|---|
| 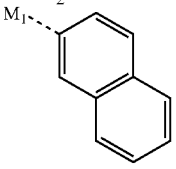 2 | ----- = Attaching bond. |
| 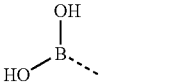 27 | 59 (1 mM) NON-ATP<br>13 (100 μM) COMPET-<br>IC$_{50}$ = 950 μM  ITIVE<br>K$_i$ = 554 μM |

TABLE IV-continued

INITIAL STEP 1 RESULTS
% SRC INHIBITION IN CELLULAR MIMETIC ASSAY

| Inhibitor | Structure | % Inhibition of 2 mM RR-src at Inhibitor Concentration ( ) |
|---|---|---|
| 28 | HO-S(=O)(=O)-NH- | 31 (1 mM); $IC_{50}$ = 1.6 mM; $K_i$ = 963 μM — NON-ATP COMPETITIVE |
| 29 | HO-S(=O)(=O)-(methanesulfonate) | 0 (1 mM) |
| 30 | HO-P(=O)(OH)- | 14 (1 mM) |
| 31 | H$_2$N-S(=O)(=O)- | 0 (100 μM) |

$M_1$ = 1-naphthyl

| 32 | HO-B(OH)- (on $M_1$) | 0 (100 μM) |
| 33 | HO-P(=O)(OH)- (on $M_1$) | 1 (1 mM) |
| 34 | H$_2$N-S(=O)(=O)- (on $M_1$) | 0 (100 μM) |

2-(dihydroxyboryl)benzo[b]furan/thiophene:

| 35 | X = O | 10 (100 μM) |
| 36 | X = S | 12 (100 μM) |

| 37 | 7-(dihydroxyboryl)isoquinoline-3-carboxylic acid methyl ester | 13 (500 μM) |

$M_1$ = 5-(methyl 1H-indole-2-carboxylate)

| 38 | HO-B(OH)- (on $M_1$) | 62 (500 μM) NON-ATP COMPETITIVE |
| 39 | HO-P(=O)(OH)- (on $M_1$) | 11 (500 μM) |

| 40 | 4-biphenylboronic acid | 13 (100 μM) |
| 41 | 3-biphenylboronic acid | 14 (100 μM) |

The data in Table IV allows a number of conclusions to be drawn: 1) Low, but measurable, inhibition potency can be obtained with an appropriate $M_1$ group attached to a scaffold (e.g. 27 and 28). 2) 1 mM inhibitor concentrations for this type of screening is higher than desirable but 100 μM is too low. Screening of scaffolds bearing an $M_1$ group would optimally be conducted at 500 μM. 3) The boronic acid, sulfamic acid, and phosphonic acid $M_1$ functional groups, which had been identified using the PKA pentapeptide scaffold (22, Table III and 8, Table I) or the Src pentapeptide scaffold (14, Table II), respectively, give measurable activity when placed at the 2 position of the naphthalene ring (27, 28, and 30, respectively), the preferred position for $M_1$ identified in the model naphthalene inhibitor:Src complex (FIG. 6). Moving the boronic acid or phosphonic acid $M_1$ groups to the 1 position (32 or 33) reduced activity. 4) The related $M_1$ sulfonamide functionality, which was poor on the PKA pentapeptide scaffold (7 & 9, Table I) is also poor when appended to the 2 (31) or 1 (34) position of the naphthalene scaffold. The sulfonic acid analog at the naphthalene 2 position (29) is completely inactive, even at 1 mM. 5) The naphthalene scaffold can be replaced with a benzofuran (35) or a benzothiophene (36) scaffold without a noticeable reduction in activity when the boronic acid $M_1$ group is positioned analogous to the 2 position on a naphthalene. 6) The boronic acid $M_1$ group also provides active compounds when appended to the isoquinoline (37) or indole (38) scaffolds at the positions indicated by modeling results (FIG. 7). However, the indole scaffold is clearly favored over the isoquinoline scaffold suggesting that a hydrogen bond donating ability to Asn 468 (see FIG. 7) is important for higher activity (this would require the protonated isoquinoline which is disfavored by the adjacent electron withdrawing ester group). This conclusion is also supported by considering that a peptide substrate may position a hydrogen bond donating peptide bond NH at a similar position (FIG. 6) and by finding that an equivalently positioned phenolic OH (FIG. 6) improves potency (phenolic OH's are much better H-bond donors than acceptors). 8) When directly compared to other $M_1$ groups, the boronic acid group is superior (e.g. 27 vs. 28-31, 38 vs. 39). 9) A biphenyl scaffold modeled into the Src and IRTK active sites and found promising binding modes for this scaffold. Combinatorial libraries were developed with the biphenyl scaffold (see Pavia et al., 1996), and the modeling results were encouraging. Therefore, the para (40) and meta (41) isomers were evaluated with the boronic acid $M_1$ group. Both biphenyl compounds showed potency equivalent to the best naphthalene boronic acid (27) and therefore provide another scaffold geometry (the two phenyl rings are not planar) for further evaluation and development.

Since the bare scaffolds, with only an $M_1$ group appended, often have low binding affinity, the $IC_{50}$'s and $K_i$'s for the 2-naphthalene boronic acid and sulfamic acid inhibitors were determined to ensure that a typical dose/response $IC_{50}$ curve is obtained. This analysis provided the typical shape dose/response curves seen with more potent inhibitors. The $IC_{50}$'s and $K_i$'s of these simple inhibitors also confirmed that the boronic acid inhibitor 27 is more potent than the sulfamic acid analog 28 and has a $K_i$ of about 554 μM.

The next issue addressed with these simple inhibitors before proceeding to elaborate them further was their mode of inhibition, specifically whether they are ATP-competitive inhibitors. In the case of the naphthalene inhibitors 27 and 28, their $IC_{50}$'s were monitored as the ATP concentration was increased in three steps up to 1 mM. As a comparison, the $IC_{50}$ of the pentapeptide phosphonic acid Src inhibitor 14 (Table II) was also monitored. If any of these inhibitors were competing with ATP, then their $IC_{50}$'s should have increased proportionally with the ATP concentration (i.e. the dashed line). As shown, the $IC_{50}$'s for all three inhibitors remained essentially constant as the ATP concentration was increased demonstrating that they are not ATP-competitive inhibitors. A very similar, but much less costly (commercial Src is expensive), analysis was conducted with the indole boronic acid inhibitor 38. In this case, the % inhibition was monitored with 38 at a constant 500 μM inhibitor concentration but with increasing ATP concentrations of 200, 500 and 1,000 μM. Once again the inhibitor potency was not reduced by the increasing ATP concentration demonstrating that 38 is also non-ATP competitive.

The initial results obtained in Step 1 suggests that it is possible to identify promising scaffolds for further elaboration with this procedure. The biggest uncertainty with Step 1 is that some of the scaffolds identified in this way might not be binding in the fashion suggested by the prior modeling evaluations. This is essentially a "false positive" problem. These "false positives" will likely fail in Step 2, when they are evaluated for improved binding using the modeled complexes as a guide. Some false positive results can be accepted in Step 1 because the bare scaffolds with only the $M_1$ group attached are easily obtained. For further inhibitor development, one may return to Step 1 each time new scaffolds are needed to carry through Steps 2 and 3. The best $M_1$ generated can be used each time Step 1 is repeated. Currently, the boronic acid $M_1$ group has been used since it has a proven ability to give measurable activity with bare scaffolds. Also the boronic acid $M_1$ group offers multiple interesting possibilities for covalent and non-covalent interactions with the conserved catalytic residues since it can: 1) hydrate, 2) form borate complexes with electron rich active site atoms, and/or 3) be phosphorylated and then react with active site nucleophiles or engage in additional non-covalent interactions. From the data in Table IV, the naphthalene and indole scaffolds were chosen as $M_2$ for the first efforts in Step 2 (the biphenyl scaffold is also a preferred scaffold). It is also worth mentioning that naphthylalanine and analogs can be successfully substituted for the P 0 tyrosine in Src peptide substrates (e.g. see Alfaro-Lopez et al., 1998) further supporting the notion that naphthalene and related scaffolds can bind at the P 0 site.

In comparing the naphthalene vs. indole scaffold results with a boronic acid $M_1$ group (i.e. 27 vs. 38, Table IV) the indole hydrogen bond donating NH and/or the adjacent ester group appeared to be the reason for the enhanced potency. Consequently, for Step 2 one of the first attempts was to add a hydroxyl group and an amide (with $S_2$) to the naphthalene scaffold at the adjacent positions suggested by the modeling results (FIG. 6). For the indole scaffold one priority was to prepare some amide analogs to see if potency can be increased with the $S_2$ specificity element (FIG. 7). In order to facilitate the synthesis of these initial analogs, an OH was temporarily substituted for the boronic acid $M_1$ group. The OH group is also known to interact with the catalytic residues, as required for an $M_1$ group, because it is the natural substrate $M_1$ whose phosphorylation rate is accelerated by interactions with the catalytic residues. The results obtained for some of the initial analogs are given in Table V along with a side by side comparison, in the Cellular Mimetic Src assay, to two literature Src inhibitors 50 and 51 which are reported be non-ATP competitive. Some of these results and additional analogs are described in Marsilje 2000.

TABLE V

INITIAL STEP 2 RESULTS
% SRC INHIBITION IN CELLULAR MIMETIC ASSAY

| Inhibitor | | % Inhibition of 2 mM RR-src at Inhibitor Concentration ( ) |
|---|---|---|
| 42 | [structure: 6-hydroxy-3-hydroxy-2-naphthoic acid methyl ester] | 47 (100 μM) |
| 43 | (M₁) [structure: 6,3-dihydroxy-2-naphthamide linked to hydroxyphenyl] NON-ATP COMPETITIVE | Ortho: 39 (100 μM)<br>Meta: 89 (100 μM)<br>IC₅₀ = 18 μM, K₁ = 10 μM<br>Para: 23 (100 μM) |
| 44 | (M₁) [structure: 6-hydroxy-2-naphthamide linked to 3-hydroxyphenyl] | 45 (100 μM) |
| 45 | (M₁) [structure: 5,3-dihydroxy-2-naphthamide linked to 3-hydroxyphenyl] NON-ATP COMPETITIVE | 51 (100 μM)<br>IC₅₀ = 170 μM |

TABLE V-continued

INITIAL STEP 2 RESULTS
% SRC INHIBITION IN CELLULAR MIMETIC ASSAY

| Inhibitor | % Inhibition of 2 mM RR-src at Inhibitor Concentration ( ) |
|---|---|
| (M$_1$) 46 [Structure: 3,6-dihydroxynaphthalene-2-carboxamide with N-benzyl-OH] | Ortho: 42 (100 μM)<br>Meta: In progress<br>Para: 42 (100 μM) |
| (M$_1$) 47 [Structure: methyl 5-hydroxy-1H-indole-2-carboxylate] | 40 (500 μM) |
| (M$_1$) 48 [Structure: 5-hydroxy-1H-indole-2-carboxamide with N-phenyl-OH] | Ortho: 43 (100 μM)<br>Meta: 30 (100 μM)<br>Para: 45 (100 μM) |
| (M$_1$) 49 [Structure: 5-hydroxy-1H-indole-2-carboxamide with N-benzyl-OH] | Ortho: 24 (100 μM)<br>Meta: 74 (100 μM)<br>Para: 54 (100 μM) |
| Huang et al 50 [Structure: 8-hydroxy-2-imino-2H-chromene-3-carboxamide with N-(3-hydroxyphenyl)] | 30 (100 μM)<br>Lit. IC$_{50}$ = 118 nm |

TABLE V-continued

INITIAL STEP 2 RESULTS
% SRC INHIBITION IN CELLULAR MIMETIC ASSAY

| Inhibitor | % Inhibition of 2 mM RR-src at Inhibitor Concentration ( ) |
|---|---|
| ($M_1$?) 51 ST 638 | 37 (100 μM)<br>Lit. $IC_{50}$ = 18 μM |
| ($M_1$?) 52 Piceatannol | 41 (100 μM)<br>Lit. $IC_{50}$ = 66 μM for p56[lck] |

Inhibitor 50, and analogs (Huang et al., 1995), were of particular interest because the iminochromene scaffold is closely related to the naphthalene scaffold and it's binding mode would be expected to be very similar based upon the model (FIG. 6). Partly because of this close analogy, the amides of hydroxyanilines with the naphthalene and indole scaffolds were examined as shown in Table V. Also, the modeling studies with these hydroxyaniline amide derivatives in the Src active site indicated that the hydroxyl group may be able to engage in hydrogen bonding interactions with the Src Phe 424-Ala 422 backbone peptide bonds analogous to peptide substrates (see FIG. 5). These modeling studies also indicated that the homologous hydroxybenzylamides should be active and, more importantly, provide a substitution position (i.e. the benzylic carbon) for appending side chains to bind in the P–1 side chain pocket (e.g. to Arg 469, FIG. 5).

The data in Table V allow the following conclusions to be drawn: 1) Adding an amide extension onto both the naphthalene and indole scaffolds can increase potency as predicted by the models for these scaffolds bound in the Src active site (ca. 5-fold in the cases of 42 vs. 43-meta & 47 vs 48). 2) Adding a hydroxyl group to the naphthalene scaffold adjacent to the amide increases potency (about 5-fold, 43-meta vs. 44) as predicted by the Src model, and also suggests Asn 468 does hydrogen bond with this OH. 3) Moving the $M_1$ OH group from the position predicted to be best in the Src model to the adjacent position reduces potency by one order of magnitude (43-meta to 45). 4) The indole scaffold is less responsive than the naphthalene scaffold to regiochemistry of the hydroxyaniline extension (48 vs. 43). 5) The naphthalene and the indole scaffolds accept the one carbon homologation provided by using hydroxybenzylamides (46 vs. 43 & 49 vs. 48). 6) The two $M_1$ hydroxy regioisomers of the naphthalene scaffold are both non-ATP competitive (see Marsilje 2000). 7) All of the methyl hydroxyaniline and hydroxybenzylamide inhibitors were found to be less active suggesting that the hydroxyl group in the amide extension is functioning as a hydrogen bond donor. In this regard it is worth mentioning that in another Src peptide substrate combinatorial library study, Ser and Thr were identified as two of the most preferred residues at the P+2 position (Alfaro-Lopez et al., 1998), suggesting that there are other binding opportunities for an amide extension OH other than to the Phe 424-Ala 422 peptide bonds suggested by the modeling studies. 8) The most potent non-ATP competitive, non-peptide, Src inhibitor previously disclosed in the literature (50) is not nearly as potent as reported when tested under the Cellular Mimetic assay conditions ($IC_{50}$=118 nM reported by Huang et al., 1995 vs only 30% inhibition at 100 μM) and is less potent than a number of the current inhibitors (especially 43-meta) including the most analogous inhibitor (50 vs. 45). The structure-activity-relationship (SAR) reported for hydroxy regioisomers of 50 in their assay (Huang et al., 1995) also does not correspond with the SAR which was obtained for the related naphthalene inhibitors. For example, their iminochromene analog of the most potent naphthalene inhibitor 43-meta is 230-fold less potent than 50 in their Src assay. An important advantage of the naphthalene scaffold over the iminochromene scaffold is that it allows a highly desirable $S_2$ specificity element to be added for accessing the P–1 hydrophobic site (see FIG. 6)

whereas the analogous position can not be substituted on the iminochromene scaffold because it is occupied by the ring oxygen atom.

The inhibitor potencies in the Src Cellular Mimetic assay can be further calibrated against other literature non-ATP, non-peptide Src inhibitors. Two additional examples are 51 (ST 638, Shiraishi et al., 1989) which is a member of the "tyrphostin" family of erbstatin analogs (see Lawrence & Niu, 1998) and the natural product PTK inhibitor piceatannol 52 (Thakkar et al., 1993). In the Cellular Mimetic assay all of these known inhibitors are less potent than had been reported suggesting that the assay is particularly demanding in terms of achieving high potency. The initial testing of Src inhibitors is carried out using a single concentration (in triplicate) because commercial Src is too expensive to do full $IC_{50}$ curves on every inhibitor. It should be mentioned, however, that an $IC_{50}$ dose response curve is not linear and the difference between ca. 50% inhibition at 100 μM and a ca. 90% inhibition at 100 μM is actually a factor of 10 and not a factor of 2 (e.g. 45 vs. 43-meta). Consequently, the literature Src inhibitors 50-52 are greater than an order-of-magnitude less active than the currently most potent inhibitor 43-meta.

The discrepancies found within the literature reporting the potency of these inhibitors, the sensitivity to assay conditions described earlier with the PKA inhibitors, and the lack of consistency among numerous labs and commercial protein kinase assay kits highlights this overlooked, but crucial, problem in the field. Although the inhibitors produced by the present invention may be more potent under other assay conditions, the Cellular Mimetic assay should be used, which mimics the intracellular physical chemical conditions as closely as possible, as the primary potency and rank order guide for evaluating the inhibitors before choosing compounds to proceed to whole cell or tissue assays. As will be discussed in more detail later, the most potent naphthalene-based inhibitor thus far from the Cellular Mimetic assay (i.e. 43-meta, $IC_{50}=18$ μM and $K_i=10$ μM) is also effective in specifically blocking $pp60^{v-src}$ stimulated cell proliferation with a similar $IC_{50}$ of ca. 25 μM. This suggests that not only is the Cellular Mimetic Src assay predictive, but also that this class of naphthalene-based inhibitors can readily pass through cell membranes and inhibit intracellular Src.

Analogs of a number of the naphthalene and indole inhibitors above can be prepared with the boronic acid or halogen $M_1$ group in place of the $M_1$ OH and/or with a $S_2$ hydrophobic specificity element attached for binding in the Src P–1 site as illustrated in FIGS. 6 and 7. The naphthalene and indole scaffolds can then be taken through to Step 3 as described below. Each time Step 2 is repeated with new scaffolds from Step 1, the best selectivity elements $S_2$ and/or $S_3$ which have discovered with previous scaffolds will be used in the combinatorial libraries of Step 3. Even though the optimal combination of $M_1$, $S_2$, and $S_3$ is likely to be different for each scaffold, those found optimal with the previous related scaffold (e.g. going from the naphthalene to the indole scaffold) should be suitable for utilization as better initial specificity elements in Step 2 with the new scaffold. The same process will be repeated each time there is a need to try another scaffold until sufficient potency, selectivity, and suitable pharmaceutical properties are achieved for the Src inhibitors or, subsequently, for inhibitors of additional therapeutically important PTK's.

Some of the chemistry used to prepare the naphthalene inhibitors is described in Marsilje 2000. For attaching a boronic acid functionality in place of a $M_1$ hydroxyl group in the Src inhibitors from Table V, the Pd (0)-catalyzed cross-coupling methodology was used wherein either an aryl triflate (Ishiyama et al., 1997) or an aryl halide (Ishiyama, 1995) can be coupled with the commercially available pinacol ester of diboron. An illustrative example recently completed is given in FIG. 8.

Figure 8:
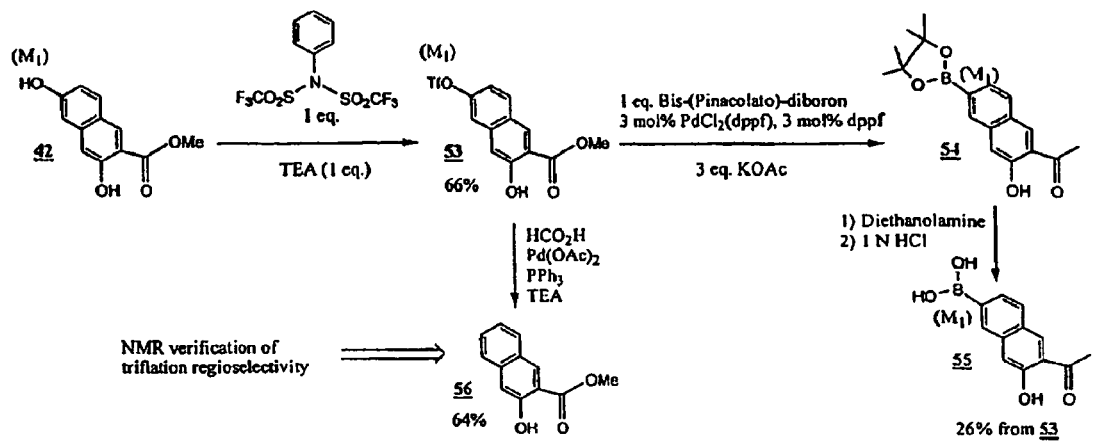
FIG. 8 provides an example of the chemistry used to prepare the naphthalene inhibitors, which is described in Marsilje 2000. A boronic acid functionality can be put in place of a $M_1$ hydroxyl groups in the Src inhibitors from Table V using the Pd (0)-catalyzed cross-coupling methodology wherein either an aryl triflate (Ishiyama et al, 1997) or an aryl halide (Ishiyama, 1995) can be coupled with the commercially available pinacol ester of diboron.
Figure 9:
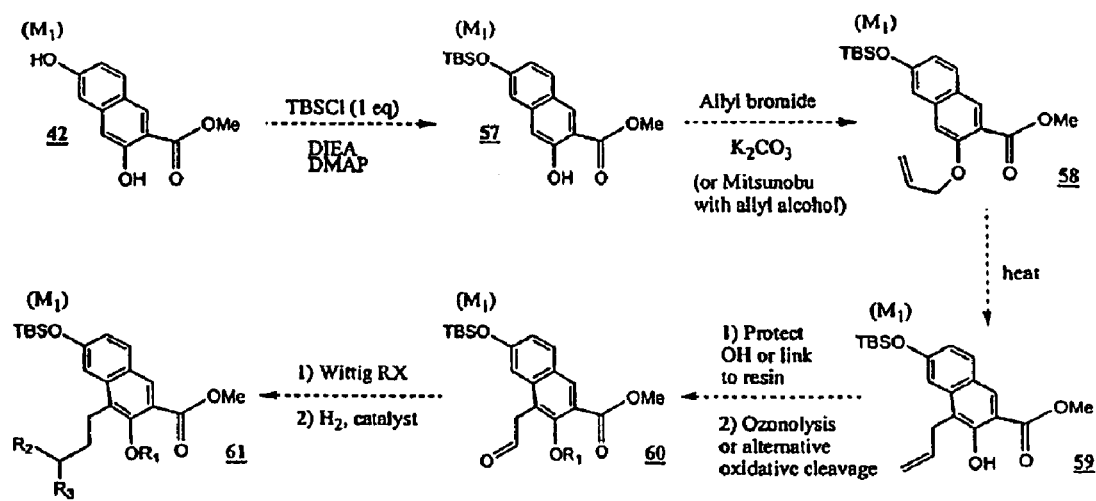
FIG. 9 shows a synthetic scheme that can be followed, in order to attach hydrophobic $S_2$ selectivity elements to the naphthalene scaffold.

The example shown in FIG. 8 demonstrates that it is possible to selectively triflate the less hindered OH at the $M_1$ position and this has been proven by its removal to 56 with subsequent $^1$H NMR verification of the substitution pattern. The monotriflate 53 was then taken on to the desired boronic acid 55 as indicated. The same reaction sequence also works well for the regioisomer of 42 which corresponds to inhibitor 45 from Table V. The synthetic scheme shown in FIG. 9 can be followed, in order to attach hydrophobic $S_2$ selectivity elements to the naphthalene scaffold.

Figure 10:
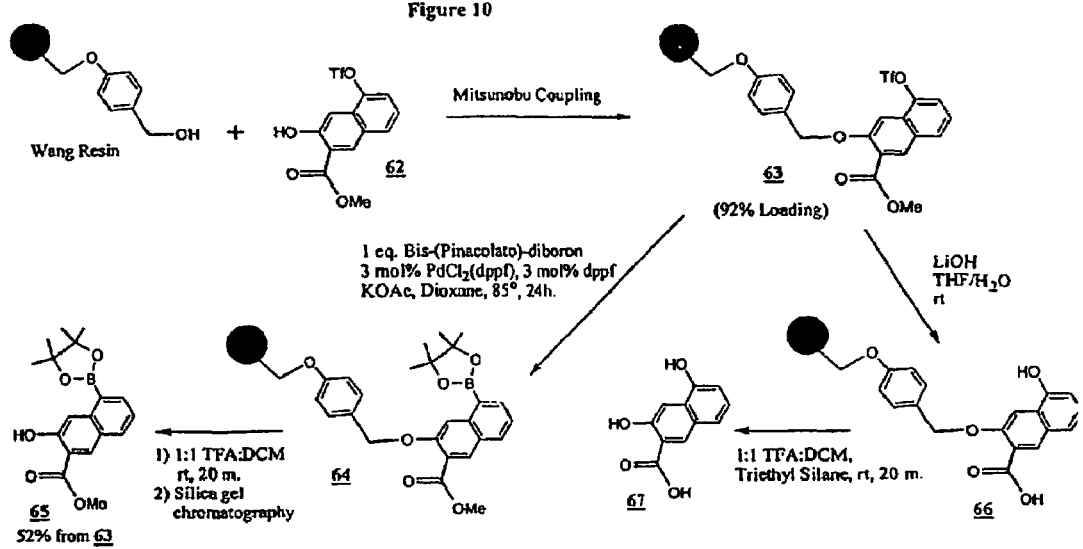
FIG. 10 shows successful model reactions with naphthalene chemistry, which can be converted to the solid phase in preparation for synthesizing combinatorial libraries of this scaffold in a 96-well plate format. The chemistry has been carried out on the less active naphthalene regioisomer represented by 44 because this compound is readily obtained from commercially available 3,5-dihydroxy-2-naphthoic acid, as described in Marsilje 2000.

The naphthalene chemistry can be converted to the solid phase in preparation for synthesizing combinatorial libraries of this scaffold in a 96-well plate format. Thus far, model chemistry has been carried out on the less active naphthalene regioisomer represented by 44 because this compound is readily obtained from commercially available 3,5-dihydroxy-2-naphthoic acid as described in Marsilje 2000. The successful model reactions to date are shown in FIG. 10.

These model reactions demonstrate that it is possible to couple the naphthalene scaffold to the Wang resin (63) and then carry out chemistry on the triflate [in this case the Pd (0)-catalyzed cross-coupling to the boronic ester 64] followed by cleavage under mild conditions (65). The ester in 63 can also be saponified for subsequent coupling reactions to form amides containing the $S_3$ selectivity elements.

Figure 11:
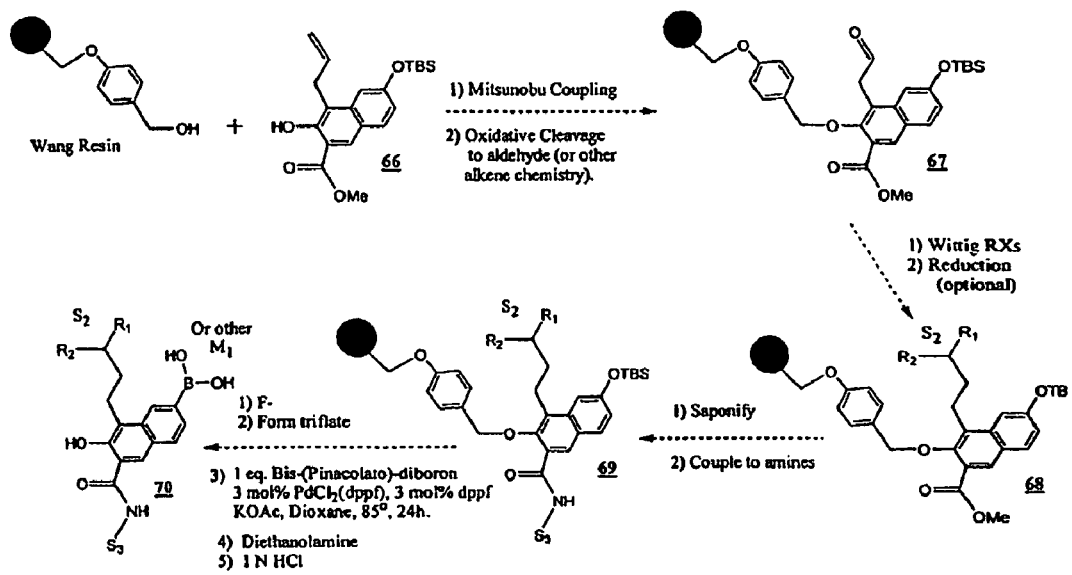
FIG. 11 provides a possible strategy for modifying the naphthalene scaffold in combinatorial libraries.

The naphthalene scaffold currently provides three diversity sites to be explored in the combinatorial libraries, $M_1$, $S_2$, and $S_3$. Solid phase combinatorial chemistry with 96-well plate reactors similar to that used in previous studies may be used (Pavia et al., 1996). The greatest number and diversity of side chains will be used for $S_3$ followed by $S_2$ and then $M_1$ for the reasons discussed earlier. One possible overall synthetic strategy, based upon the synthetic model studies above, for preparing these libraries is shown in FIG. 11.

Of course if problems arise with this route there are many other possibilities. For example, if the Mitsunobu coupling to give 67 proceeds in too low a yield (due to the increased steric congestion of the added adjacent allyl group—but perhaps not a problem given the 92% loading obtained in FIG. 10), then the scaffold could be tethered to a resin through the carboxyl group, rather than the OH, using the acylsulfonamide "safety catch" linker (Backes et al., 1996) and form the amides last (the excess amines can be removed after cleavage by filtering through an acidic resin). Likewise, other linkers and/or resins can be used if the reduction of the alkene in the presence of benzylic ethers (67 to 68) is desired but problematic. The first use of the chemistry proposed in FIG. 11 will be to simply prepare a library of 96 amides, containing the boronic acid $M_1$ group, without having the allyl side chain in place so that these two potential complications will not be a problem initially and the most promising $S_3$ elements can be quickly identified.

At least 14 $S_2$ hydrophobic side chains (includes linear, branched and cyclic) are identified for further study (28 if the corresponding alkenes are also explored) based upon the modeling of candidate side chains into the P–1 site of the Src model (FIG. 6) and on the commercial availability of the needed halides to prepare the corresponding Wittig reagents. At least 96 commercially available amines are available which will provide potential $S_3$ specificity elements including: 1) hydrocarbons (4), 2) alkyl groups containing hydrogen bond acceptors (4), 3) alkyl groups containing both hydrogen bond acceptors and donors (19), 4) alkyl/aryl groups containing hydrogen bond acceptors and donors (25), 5) aryl hydrogen bond acceptors and donors (10), 6) heterocyclic hydrogen bond acceptors and donors (20), 7) side chains containing cationic groups (4), 8) side chains containing anionic groups (9), and the 3-amino phenol side chain from inhibitor 43-meta as an internal control for Src activity. A broad range of amines were included for $S_3$, in order not to overly bias the library here due to the higher level of uncertainty for this binding site in the Src model.

The indole scaffold can be developed into a combinatorial library in much the same fashion. In this case, the indole NH would be used as the tether point for attachment to the Wang (or other) resin since the analogous Mitsunobu reaction is known (Bhagwat & Gude, 1994). A large amount of synthetic methodology has been developed for the synthesis of substituted indoles and have designed a route to include the $S_2$ hydrophobic side chain (see FIG. 7) (Ezquerra et al., 1996).

Figure 12:
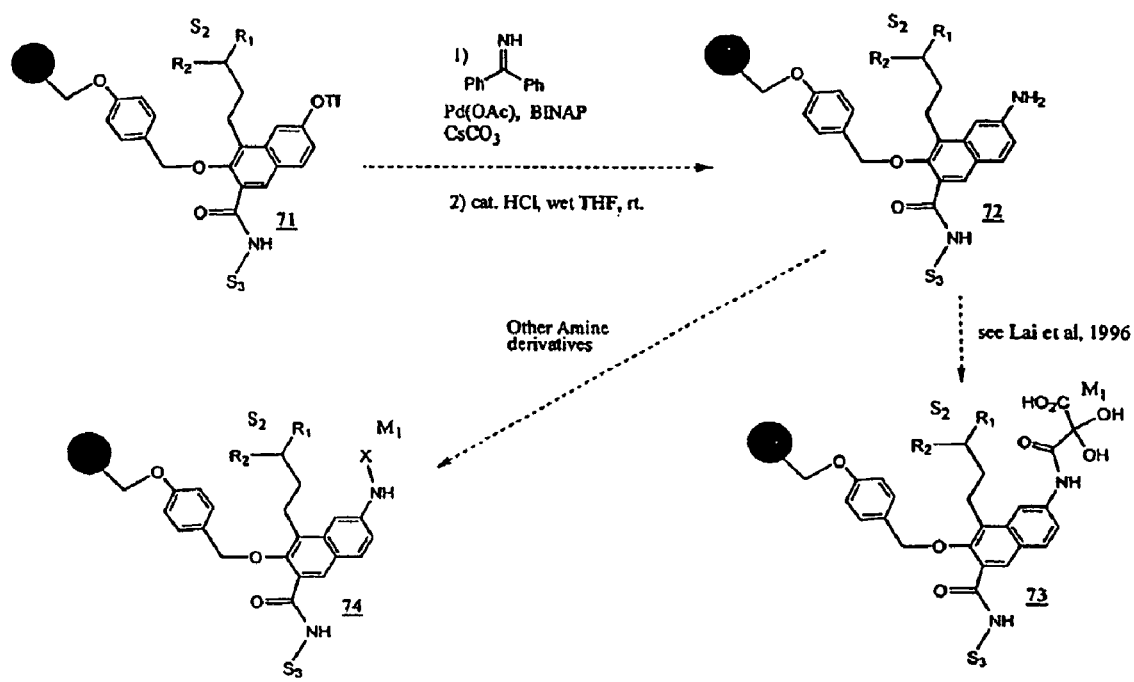
FIG. 12 shows the conversion of the triflate functionality formed in reaction 2 from intermediate 69 (FIG. 11) to an amine (Wolfe et al, 1997) and then a series of amides or other amine derivatives.

The triflate functionality formed in reaction 2 from intermediate 69 (FIG. 11) can be converted to an amine (Wolfe et al., 1997) and then a series of amides or other amine derivatives following the reaction sequence shown in FIG. 12. In fact, the triflate is a versatile synthetic handle and could be converted into other functional groups as well.

When the amine 72 is available, the known $M_1$'s (e.g. the sulfamic acid from Src inhibitor 28 Table V and amide-acid 17 Table III) can be evaluated with this more developed scaffold and evaluate some new amine derivatives as potential $M_1$'s. For example the hydrated tricarbonyl amide $M_1$ group shown in structure 73 (and it's non-hydrated precursor) is accessible via the synthetic methodology (see Lai et al., 1996) and could form a variety of interesting interactions with the conserved catalytic residues.

Figure 13:
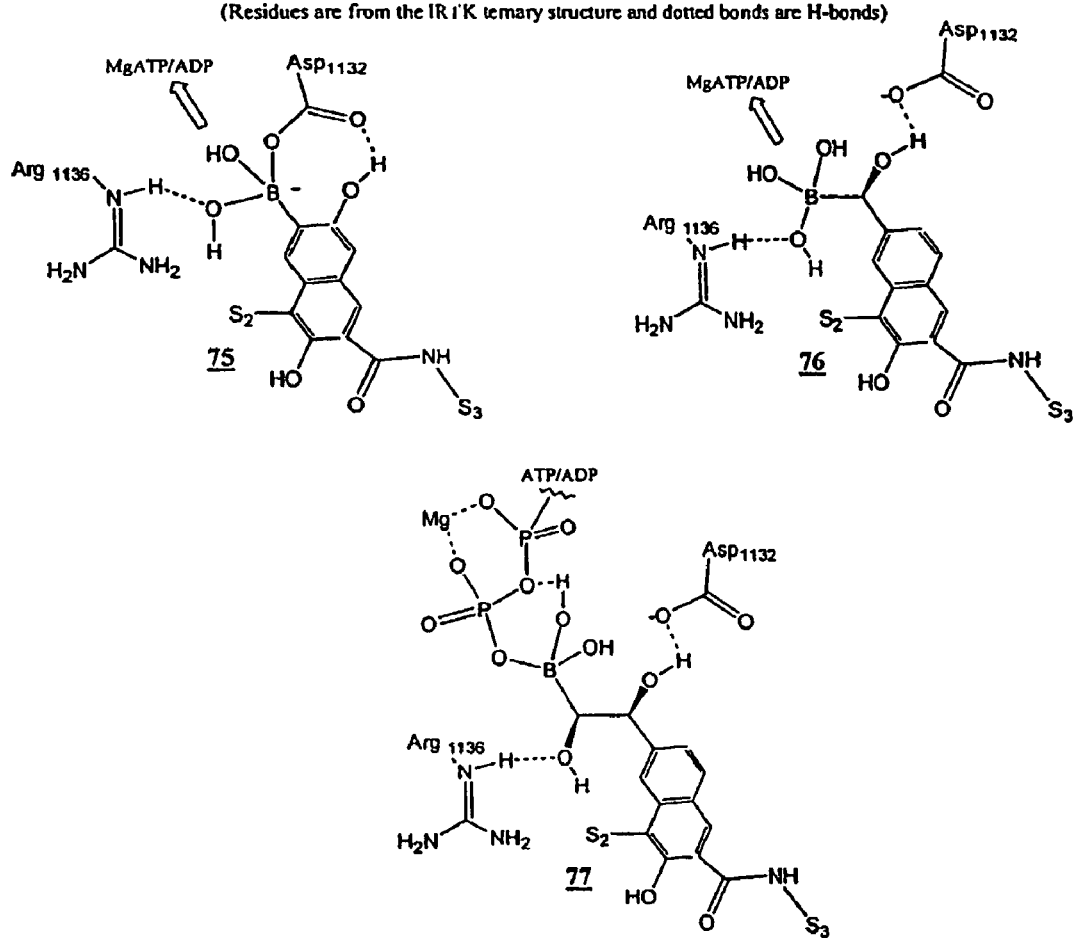
FIG. 13 shows modeling a series of hydroxy-containing analogs of the boronic acid $M_1$ group shown in the Src and IRTK (insulin receptor protein tyrosine kinase) active sites.

Following the modeling procedure described above, a series of hydroxy-containing analogs of the boronic acid $M_1$ group shown in FIG. 13 were modeled in the Src and IRTK active sites and the illustrated interactions/binding modes were found as some of the interesting possibilities. By phosphorylating the boronic acid, additional interesting possibilities are available (e.g. suicide type inhibition via reaction of the resulting mixed anhydride with an active site nucleophile). The presence of additional hydroxyl groups on the Tyr-mimetic phenyl ring is necessary and common among many PTK inhibitors (e.g. Piceatannol 52, Table V) and was shown to be beneficial on the side chain with the PKA phosphonate inhibitors (e.g. 2 vs. 3 and 4, Table I). Consequently, adding one or more OH's to the boronic acid inhibitor $M_1$ design as illustrated in FIG. 13 may considerably enhance potency. These OH groups would also extend the boronic acid side chain past the catalytic Asp and Arg residues without suffering a penalty for covering them with hydrocarbon as was probably the case with the PKA boronic acid homologs (23 and 24, Table III). One possible route to the hydroxyboronic acids 76 and 77 utilizes the chiral boronic ester homologation methodology of Matteson (e.g. see Matteson et al., 1987, 1988 & 1990).

Thus, in a preferred embodiment of the invention, the first module is produced by attaching the first module to a peptide scaffold. One or more functional groups are identified which preferentially bind to catalytic residues of the protein kinase, wherein at least one of the one or more functional groups is a halogen. Further, the first module is combined with the second module so that the second module substitutes for the peptide scaffold.

Preferred first modules have a two or more functional groups, including a halogen and one or more additional functional groups such as a boronic acid group, a hydroxyl group, phosphonic acid, sulfamic acid, a guanidino group, carboxylic acid, an aldehyde, an amide, and hydroxymethylphosphonic acid. More preferred additional functional groups are boronic acid groups, a hydroxyl group, or an amide group. An even more preferred amide group is a vicinal tricarbonyl amide.

Preferred second modules include indole, naphthalene, biphenyl, isoquinoline, benzofuran, and benzothiophene. More preferred second modules are an indole or naphthalene. In some embodiments of the invention more than one first module may be bound to the second module. In addition, the first module may have a linear chain comprising between one and three carbon atoms which links the first module to the second module. In alternative embodiments, one of the carbon atoms in the linear chain is substituted with a nitrogen, oxygen or sulfur atom.

The methods and compounds of the invention are broadly applicable to any protein kinase. Preferred protein kinases are protein tyrosine kinases and protein serine kinases (a.k.a. serine-threonine kinases). Preferred protein tyrosine kinases are $pp60^{c-src}$, $p56^{lck}$, $p55^{fyn}$, ZAP kinase, platelet derived growth factor receptor tyrosine kinase, Bcr-Abl, VEGF (vascular endothelial growth factor) receptor tyrosine kinase, epidermal growth factor receptor tyrosine kinase, and epidermal growth factor receptor-like tyrosine kinases. A more preferred protein tyrosine kinase is $pp60^{c-src}$. Preferred serine protein kinases include MAP (mitogen activated protein) kinase, protein kinase C, and CDK (cyclin dependent protein kinase).

The method of the present invention may further consist of adding one or more specificity side chain elements to the combination of the first and second modules, as described above. Specificity side chains can increase potency and specificity of the inhibitor. Suitable specificity side chains are described above (R groups for above structures) and in the Examples, which follow.

Once a promising second module is identified it is not necessary to repeat all the steps of the method. Rather, the first module, specificity side chains, or a combination the two may be modified to improve the original inhibitor, i.e an inhibitor which has an increased ability to inhibit protein kinase activity when compared to the unmodified first inhibitor.

The present method is designed to preferentially provide protein kinase inhibitors which do not act by inhibiting ATP binding to the protein kinase. Inhibitors of protein kinases which act by inhibiting ATP binding may be potent but often lack specificity and are therefore often not good drug candidates. Therefore, protein kinase inhibitors which inhibit protein kinase activity but do not inhibit or only weakly inhibit ATP binding to the protein kinase are preferred.

In another embodiment, the present invention provides a method of inhibiting a protein kinase. The protein kinase is contacted with a compound having at least one first module which has one or more functional groups capable of covalently or non-covalently binding to catalytic residues of the protein kinase, wherein the one or more functional groups comprise a halogen, and a second module which provides a non-peptide scaffold. The combination of the at least one first module and second module inhibits the protein kinase activity.

The present invention further provides a method of treating a condition, responsive to a protein kinase inhibitor, in a subject. An effective dose of a protein kinase inhibitor is administered to a subject. The protein kinase inhibitor has at least one first module having one or more functional groups each capable of covalently or non-covalently binding to catalytic residues of the protein kinase, wherein the one or more functional groups comprise a halogen, and a second module which provides a non-peptide scaffold, where the combination of the at least one first module and second module inhibits protein kinase activity.

Another aspect of the present invention is a method for identifying inhibitors of protein phosphatases. The method involves providing at least one first module having one or more functional groups each capable of covalently or non-covalently binding to catalytic residues of the protein phosphatase, combining at least one first module with at least one second module which provides a non-peptide scaffold to form one or more combinations of the first and second modules, screening the one or more combinations of the first and second modules for protein phosphatase inhibition, and selecting combinations of the first and second modules which inhibit protein phosphatase activity.

Suitable first and second modules and functional groups are described above. In a preferred embodiment, the at least one first module comprises a halogen, most preferably, fluorine. Examples of suitable non-peptide protein phosphatase inhibitors are shown in Table VIII, below.

Suitable protein phosphatases include, but are not limited to, PTP-1B. Other suitable protein phosphatases are described, for example, in Zhang, 2002; McCluskey et al., 2002a; Zhang 2001; McCluskey et al., 2001; Pestell et al., 2000; Moller et al., 2000; Ripka, 2000; Kennedy, 1999; Johnson et al., 2002; McCluskey 2002b.

As described above, this method is designed to preferentially provide phosphatase inhibitors which bind to the substrate peptide binding site.

The present invention also relates to a method of inhibiting a protein phosphatase. The protein phosphatase is contacted by a compound comprising at least one first module having one or more functional groups each capable of covalently or non-covalently binding to catalytic residues of the protein phosphatase, and a second module which provides a non-peptide scaffold. The combination of at least one first module and second module inhibits the protein phosphatase activity.

In one embodiment, the compound has the following formula:

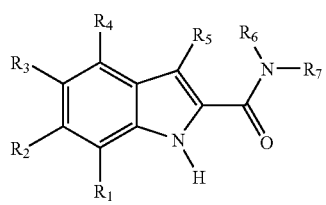

wherein $R_1$ through $R_7$ may be the same or different, and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond or optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl, or $R_5$ and $R_6$ together form a heterocyclic compound. $R_a$, $R_b$, and $R_c$, can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_1$ through $R_7$ and $R_a$ through $R_c$ may be substituted or unsubstituted. In a preferred embodiment, $R_3$ is a halogen, most preferably, fluorine.

In another embodiment, at least one of $R_6$ or $R_7$ is

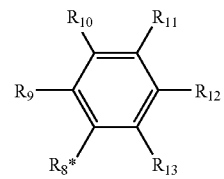

wherein $R_8$* is the point of attachment and is $(CH_2)_x$, wherein X is from 0 to 10, $CH_2CHOH$, $CH(CH_3)$(R-isomer), or $CH(CH_3)$(S-isomer), and each of $R_9$ through $R_{13}$ may be the same or different and are selected from the group consisting of H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. $R_a$, $R_b$, and $R_c$, can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that any of $R_9$ through $R_{13}$ and $R_a$ through $R_c$ may be substituted or unsubstituted. In a preferred embodiment, each of $R_9$ through $R_{13}$ may be selected from the group consisting of $OCH_3$, $OCH_2CH_3$, H, $CH_3$, OH, $CH_2OH$, $CF_3$, $OCF_3$, CFO, $C_6H_5$, $OC_6H_5$, $OCH_2C_6H_5$, $OCH_2CH_2CH_3$, CHO, $CO_2H$, $CO_2CH_3$, $CH_2CO_2H$, $CH_2CO_2CH_3$, $NO_2$, and halogen.

In a further embodiment, at least one of $R_6$ or $R_7$ is

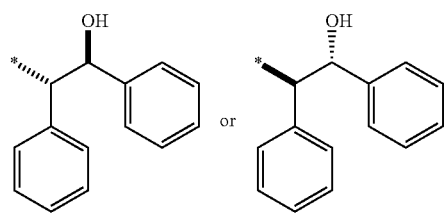

wherein the asterisk indicates the point of attachment to the nitrogen.

In yet a further embodiment, the compound has the formula:

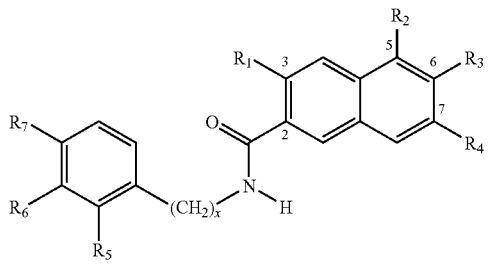

wherein R₁ through R₇ are each the same or different and are selected from the group consisting of H, C(O)R$_a$, C(O)NR$_a$R$_b$, C(O)OR$_a$, C(O)SR$_a$, OH, OR$_a$, OC(O)R$_a$, OC(O)OR$_a$, NH₂, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)₂R$_b$, NR$_a$S(O)OR$_b$, NR$_a$S(O)₂OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)₂R$_a$, S(O)OR$_a$, S(O)₂OR$_a$, S(O)NR$_a$R$_b$, S(O)₂NR$_a$R$_b$, P(O)OR$_a$OR$_b$, B(OH)₂, halogen, aryl, heteroaryl, biaryl, heterobiaryl, heterocyclic compound, and alkyl (branched, cyclic, or unbranched), preferably having from 1 to 20 carbon atoms, optionally containing a double or triple bond and optionally substituted with a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic, or unbranched), optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

Another aspect of the present invention relates to a method of treating a condition, responsive to a protein phosphatase inhibitor, in a subject. A protein phosphatase inhibitor is administered to a subject. The protein phosphatase inhibitor has at least one first module having one or more functional groups each capable of covalently or non-covalently binding to catalytic residues of the protein phosphatase, and a second module which provides a non-peptide scaffold. The combination of at least one first module and second module inhibits protein phosphatase activity in the subject.

Protein phosphatase inhibitors may be used in various therapeutic techniques, including, but not limited to, treatment of Type II diabetes, obesity, and cancer (Zhang, 2002; McCluskey et al., 2002a; Zhang 2001; McCluskey et al., 2001; Pestell et al., 2000; Moller et al., 2000; Ripka, 2000; Kennedy, 1999; Johnson et al., 2002; McCluskey 2002b).

Examples of other suitable compounds for the above-described methods include:

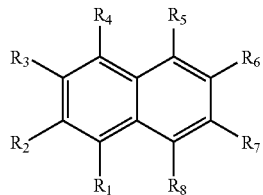

wherein any of the individual R's can be a halogen-containing M₁, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH₂, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)₂R$_b$, NR$_a$S(O)OR$_b$, NR$_a$S(O)₂OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)₂R$_a$, S(O)OR$_a$, S(O)₂OR$_a$, S(O)NR$_a$R$_b$, S(O)₂NR$_a$R$_b$, P(O)OR$_a$OR$_b$, B(OH)₂, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

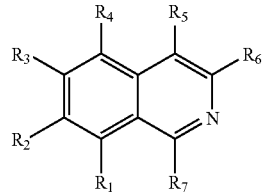

wherein any of the individual R's can be M₁, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH₂, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)₂R$_b$, NR$_a$S(O)OR$_b$, NR$_a$S(O)₂OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)₂R$_a$, S(O)OR$_a$, S(O)₂OR$_a$, S(O)NR$_a$R$_b$, S(O)₂NR$_a$R$_b$, P(O)OR$_a$OR$_b$, B(OH)₂, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

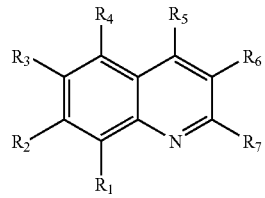

wherein any of the individual R's can be M₁, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH₂, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

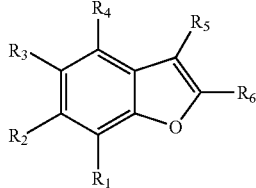

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

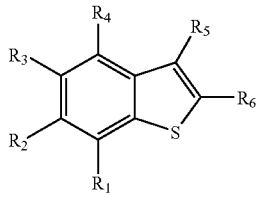

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

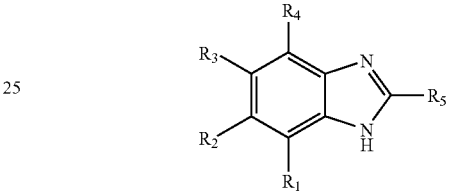

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

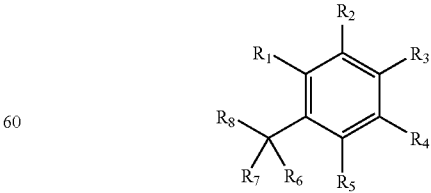

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C (O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

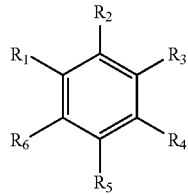

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_a$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions;

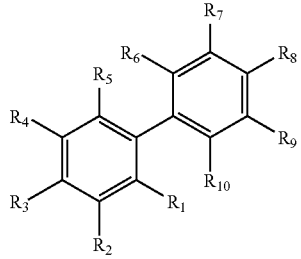

wherein any of the individual R's can be M$_1$, and the remaining R groups can be H, C(O)R$_a$, C(O)NR$_a$R$_b$, C(O)OR$_a$, C(O)SR$_a$, OH, OR$_a$, OC(O)R$_a$, OC(O)OR$_a$, NH$_2$, NR$_a$R$_b$, NR$_a$C(O)R$_b$, NR$_a$C(O)NR$_b$R$_c$, NR$_a$C(O)OR$_b$, NR$_a$C(O)SR$_b$, NR$_a$S(O)R$_b$, NR$_a$S(O)$_2$R$_b$, NR$_a$S(O)OR$_b$, NR$_a$S(O)$_2$OR$_b$, NR$_a$P(O)OR$_b$OR$_c$, NR$_a$P(O)OR$_b$R$_c$, NR$_a$P(O)OR$_b$OR$_c$, SR$_a$, S(O)R$_a$, S(O)$_2$R$_a$, S(O)OR$_a$, S(O)$_2$OR$_a$, S(O)NR$_a$R$_b$, S(O)$_2$NR$_a$R$_b$, P(O)OR$_a$OR$_b$, B(OH)$_2$, halogen, aryl, heteroaryl, biaryl, and alkyl group (branched, cyclic or unbranched) optionally containing a double or triple bond and/or a heteroatom or other functional groups, such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. R$_a$, R$_b$, and R$_c$ can be the same or different and are selected from the group consisting of H, aryl, heteroaryl, biaryl, heterobiaryl, and alkyl (branched, cyclic or unbranched) optionally substituted with a heteroatom or other functional groups such as a carboxylic acid, carboxylic ester, alcohol, ether, thioether, amide, thioamide, urea, urethane, sulfoxide, sulfone, phosphonic acid, phosphonic ester, phosphinic acid, phosphinic ester, boronic acid, aryl, heteroaryl, biaryl, and heterobiaryl. It is understood that all open substitution positions in the above side chains can contain further substitutions.

The present invention also provides a method for testing compounds for an ability to inhibit protein kinase or protein phosphatase activity. Compounds are produced as described above. The activity of the protein kinase or protein phosphatase is measured in the presence of the inhibitor at the same temperature, pH, ionic strength, osmolarity, and free magnesium concentration as found in a cell which expresses the protein kinase or protein phosphatase. The level of protein kinase or protein phosphatase activity is compared to the level of activity from the protein kinase or protein phosphatase without the presence of the inhibitor. Such an assay system which mimics physiological conditions provides the most relevant inhibition data. The assay may be conducted in an automated assay system. Furthermore, the assay may be combined with a combinatorial chemistry method to rapidly screen numerous candidates.

The Pierce 96-well plate non-radioactive ELISA PTK assay method may be adapted to the Cellular Mimetic assay conditions for initial Src screening of the 96-well plate combinatorial libraries. This high throughput assay utilizes the same RR-SRC peptide substrate, except that it is biotinylated so that it can be attached to the NeutrAvidin-coated wells in their commercial 96-well plates. This high throughput inhibition assay can be run by incubating Src with the RR-SRC substrate prebound to the wells followed by adding their anti-phosphotyrosine antibody (PY20)-horseradish peroxidase (HRP) conjugate and their HRP substrate to quantitate the level of phospho-RR-SRC produced via measuring the level of HRP product with a 96-well plate UV reader. Standard low throughput P$^{32}$-ATP radioactive assays have been used, but a 96-well plate format is preferred, especially with a non-radioactive assay if possible. As very potent Src inhibitors are developed, a panel of protein kinase assays could be set up with commercially available protein kinases, using the Cellular Mimetic protein kinase assay conditions, and test these inhibitors across the panel to obtain an initial assessment of specificity. A more complete specificity assessment, involving the full ca. 2,000 protein kinases, will need to be conducted in cell culture and in vivo.

Figure 14:
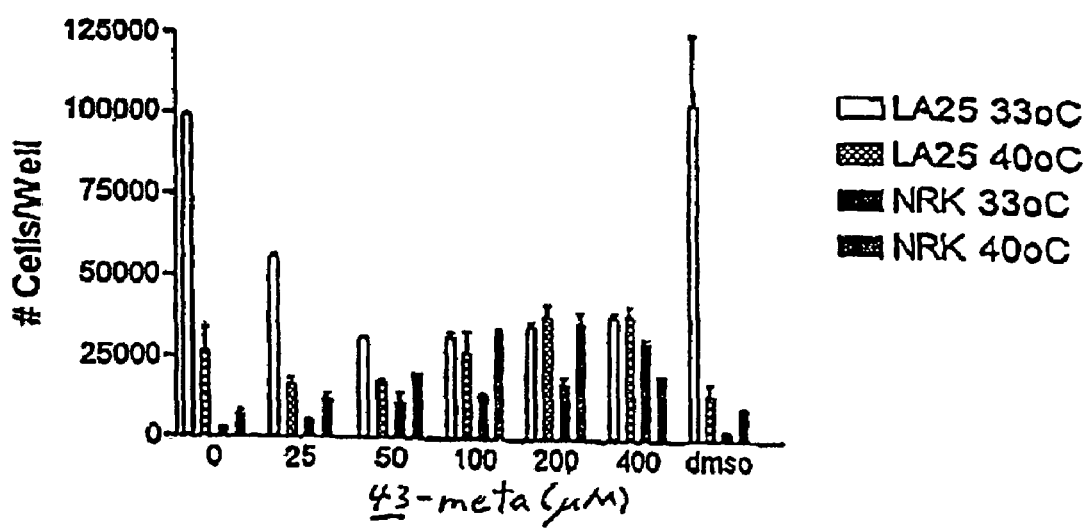
FIG. 14 shows results from testing of the non-peptide Src inhibitor 43-meta (Table V) in the LA25 and NRK cell lines.

Active Src inhibitors can be studied in a set of side-by-side cell-based assays using normal rat kidney (NRK) cells and a temperature-sensitive pp60$^{v\text{-}Src}$ transformant of this cell line (LA25). The LA25 transformant engages in anchorage- and serum-independent growth at the "permissive" temperature of 33° C. due to activation of pp60$^{v\text{-}src}$ but not at the "non-permissive" temperature of 40° C. at which pp60$^{v\text{-}src}$ is not activated (Li et al., 1996). The use of this pair of closely related cell lines for testing the Src inhibitors at both the permissive and non-permissive temperatures allows one to determine if a given Src inhibitor is blocking cell growth due to specific blockade of the Src signaling pathway, by a different mechanism or by a general cytotoxic effect. Results from initial testing of the non-peptide Src inhibitor 43-meta (Table V) in this pair of cell lines are shown in FIG. 14.

As shown in this graph the growth of the LA25 cells at the permissive temperature of 33° C. is inhibited by ca. 50% at a 25 μM concentration of 43-meta relative to the LA25 cell growth at the non-permissive 40° C. as a control. The lack of cell toxicity of 43-meta is evidenced by the fact that as its concentration is increased up to 400 μM, the basal growth of the NRK non-transformed cells, the LA25 cells at the non-permissive 40° C., and the LA25 cells at the permissive temperature of 33° C. (but with pp60$^{v-src}$ fully inhibited by 43-meta) not only does not decrease but actually increases somewhat (presumably due to a non-Src related activity of this compound). Since the 43-meta solutions were prepared with a low concentration of DMSO for solubilization, a DMSO control was also run at the same concentration.

Moreover, promising Src inhibitors can be screened in primary human tumor tissue assays, particularly to look for synergy with other known anti-cancer drugs.

EXAMPLES

Example 1

Synthesis and Activity of Indole Derivative Protein Kinase and/or Protein Phosphatase Inhibitors The following results show the solution phase synthesis of 5-fluoroindole-2-carbaxamide libraries and testing of indole derived protein kinase and/or protein phosphatase inhibitors. These final products are examples of indole-based inhibitors wherein synthesis with a 5-fluoro group is illustrated.

A. Synthesis of Intermediates and Sample Reagents:

5-fluoro-3-phenylindole-2-carboxylic acid

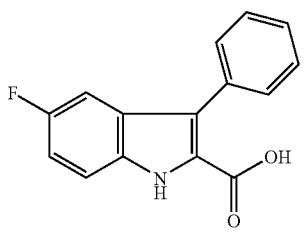

(a) Preparation of Methyl Ester

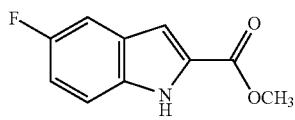

A mixture of 5-fluoroindole-2-carboxylic acid (6 g, 33.5 mmol) and a freshly prepared methanolic HCl (100 mL) was stirred overnight at room temperature. The precipitated ester was collected by filtration, washed with NaHCO$_3$ saturated solution, water, and MeOH. The filtrate was treated with saturated NaHCO$_3$ and extracted with EtOAc. The organic layer was washed with brine, dried (MgSO$_4$), and evaporated in vacuo. The product ester (6 g) was an off white solid and it was used for the next step without further purification: MP 200-201° C.; $^1$H NMR (CDCl$_3$, 500 MHz) δ 8.94 (br, 1H), 7.33 (dd, 1H, J=9.2 and 4.3 Hz), 7.30 (dd, 1H, J=2.2 and 9.2), 7.15 (d, 1H, J=2.1 Hz), 7.07 (ddd, 1H, J=2.5, 8.9 and 9.1 Hz), 3.92 (s, 3H)

(b) Preparation of the 3-iodo Derivative

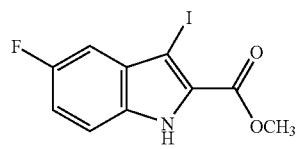

4.22 g (21.8 mmol) of the methyl ester was dissolved in DMF (25 mL). In another flask, a solution of iodine (6.09 g, 24 mmol) and KOH (4.65 g, 82.9 mmol) in DMF (25 mL) was stirred for 30 minutes and added dropwise to the ester solution over 5 minutes. After stirring for 10 minutes at room temperature, the reaction was quenched by pouring into a solution of NaHSO$_3$ (2.2 g), NH$_4$OH (25% solution in H$_2$O) in 300 mL water. The mixture was stirred for 30 minutes then the precipitated solid product was collected by filtration and washed with H$_2$O: $^1$H NMR (CDCl$_3$, 500 MHz) δ 9.17 (br, 1H), 7.33 (dd, 1H, J=9.0 and 4.2 Hz) 7.21 (dd, 1H J=9.0 and 2.0 Hz), 7.12 (dt, 1H, J=9.0 and 2.0 Hz), 3.81 (s, 3H).

(c) Suzuki Coupling

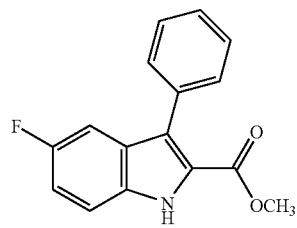

The Iodo derivative was mixed with benzeneboronic acid (2.76 g, 22 mmol), PdCl$_2$(PPh$_3$)$_2$ (0.7 g, 1 mmol), and 50 mL of 2M Na$_2$CO$_3$ in dioxane (200 mL). The mixture was stirred at 90° C. overnight. The solvent was evaporated under vacuum. The product was extracted with EtOAc (3×200 mL). The combined extract was washed with brine, dried with MgSO$_4$, and purified by crystallization (CH$_2$Cl$_2$-hexane) and silica gel chromatography (Hexane-EtOAc 4:1): MP 189° C.; $^1$H NMR (CDCl$_3$, 500 MHz) δ 8.94 (br, 1H), 7.51 (dd, 2H, J=1.5 and 7.9 Hz), 7.45 (ddd, 2H, J=1.8, 7.3 and 7.8), 7.39-7.34 (complex, 2H), 7.25 (dd, 1H, J=2.5 and 8.7 Hz), 7.10 (ddd, 1H, J=2.5, 8.9 and 9.1 Hz), 3.80 (s, 3H).

(d) Saponification of Methyl Ester

The ester described above (2.5 g, 9.28 mmol) was dissolved in THF (30 mL).

A solution of LiOH (2.4 g, 100 mmol) in water (20 mL) was added and the mixture was heated at reflux for 1 hour. The mixture was cooled to room temperature and THF was removed by vacuum evaporation. The mixture was treated with 2M HCl until it became acidic. The product was extracted with EtOAc. The organic layer was washed, dried (brine, Na$_2$SO$_4$), and concentrated under vacuum. The crude solid product was redissolved in NaHCO$_3$ (saturated solution) and washed several times with CH$_2$Cl$_2$. The aqueous layer was acidified with ice and 2M HCl and extracted with EtOAc. After washing, drying, and rotavaping, the product was collected as white solid (yield 2.3 g, 97%): MP 195-196° C.; $^1$H NMR (CDCl$_3$, 500 MHz) δ 8.94 (br, 1H), 7.52 (dd, 2H, J=1.8 and 7.9 Hz), 7.46 (ddd, 2H, J=1.8, 7.3 and 7.6), 7.40 (ddd, 1H, J=1.8, 7.4 and 7.8 Hz), 7.37 (dd, 1H, J=9.0 and 4.2 Hz), 7.25 (dd, 1H, J=2.5 and 8.7 Hz), 7.12 (ddd, 1H, J=2.4, 8.8 and 8.9. Hz).

3-benzyloxy-5-hydroxybenzonitrile

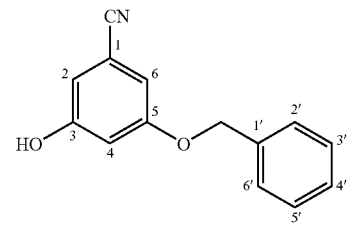

To a mixture of 3,5-dihydroxybenzonitrile (1.08 g, 8 mmol) and K$_2$CO$_3$ (1.104 g, 8 mmol) in CH$_3$CN (50 mL), benzyl bromide (1.438 g, 8 mmol) was added. The mixture was heated to reflux for 2 hours. Solvent was evaporated under vacuum. The residue was treated with EtOAc (200 mL) and 1M HCl (200 mL). The organic layer was washed, dried, and evaporated in vacuo. The residue was chromatographed (gradient, Hexanes-CH$_2$Cl$_2$-MeOH) to give 3-benzyloxy-5-hydroxybenzonitrile (529 mg, 29%), 3,5-dibenzyloxybenzonitryl (784 mg, 31%) and 256 mg (23.7 mg, 24%) of the starting material. The product 3-benzyloxy-5-hydroxybenzonitrile had: MP 144-145° C.; $^1$H NMR δ 9.15 (s, 1H, OH), 7.47 (d, 2H, J=7.0 Hz, 2' and 6'), 7.40 (ddd, 2H, J=7.0, 7.0, 2.0 Hz, 3' and 5'), 7.34 (dd, 1H, J=7.7 and 2.1 Hz, 4'), 6.89 (dd, 1H, J=1.5 Hz, 4), 6.78 (d, 2H, J=1.8 Hz), 5.16 (s, 2H).

3,5-dibenzyloxybenzonitryl

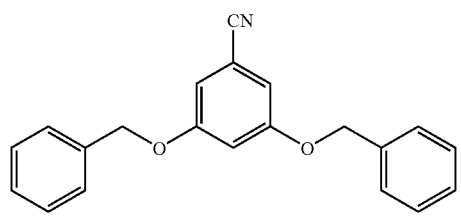

This compound had MP 106° C.; $^1$H NMR (CDCl$_3$, 500 MHz) δ 7.38 (complex, 10H), 6.83 (d, 2H, J=2.1 Hz), 6.79 (d, 1H, J=2.1 Hz).

4-benzyloxy-3-hydroxybenzonitrile

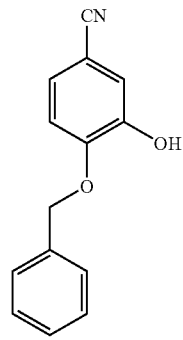

A mixture of 3,4-dihydroxybenzonitrile (540 mg, 4 mmol), K$_2$CO$_3$ (552 mg, 4 mmol) and benzyl bromide (476 mg, 4 mmol) in acetone (20 mL) was stirred at room temperature for 3 days. The mixture was evaporated under vacuum and subjected to flash column chromatography (2% MeOH in toluene-hexane, 2:1) to give the desired product (224 mg, 25%): MP 101° C.; $^1$H NMR (Acetone-d$_6$, 500 MHz) δ 8.55 (s, 1H), 7.50 (d, 2H, J=7.3 Hz), 7.39 (dd, 2H, J=7.0 and 7.3), 7.34 (dd, 1H, J=7.0 and 7.3), 7.2 (m, complex, 3H). 5.25 (s, 2H).

3-hydroxy-4-propyloxybenzonitrile

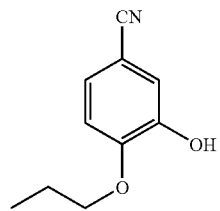

This compound was prepared following a similar procedure used to prepare 4-benzyloxy-3-hydroxybenzonitrile in 27% yield: MP 99° C.; $^1$H NMR (Acetone-d$_6$, 500 MHz) δ 8.33 (s, 1H), 7.21 (dd, 1H, J=8.2 and 1.8 Hz), 7.13 (d, 1H, J=1.8 Hz), 7.08 (d, 1H, J=8.3 Hz), 4.07 (t, 2H, J=6.4 Hz), 1.80 (m, 2H), 1.01 (t, 3H, J=7.3 Hz).

3-benzyloxy-5-hydroxybenzylamine 3-benzyloxy-5-hydroxybenzonitrile (225 mg, 1 mmol) was dissolved in 2 mL THF 2 mL of BH$_3$-THF (1.5 M in THF and ether) was added dropwise, then the mixture was heated at reflux temperature for 3 hours. After cooling, the mixture was carefully poured to 3M HCl (ice cooled) and allowed to stir for 20 hours at room temperature. The mixture was neutralized with solid NaHCO$_3$, thus the product precipitated as a white solid. The product was collected by filtration, washed with water, and dried (140 mg, 61%): MP 164-166° C. (dec); $^1$H NMR (DMSO-d$_6$, 400 MHz) δ 9.28 (br, 1H), 7.41 (d, 2H, J=6.9 Hz), 7.36 (dd, 2H, J=7.0 and 7.6 Hz), 7.30 (dd, 1H, J=7.0 and 6.6 Hz), 6.43 (s, 1H), 6.32 (s, 1H), 6.21 (dd, 1H, J=2.2 and 2.0 Hz), 4.99 (S, 2H), 3.57 (S, 2H).

3,5-dibenzyloxybenzylamine

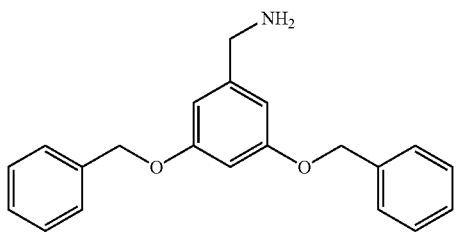

This compound was prepared according to the procedure used in preparation of 3-benzyloxy-5-hydroxybenzylamine. The reaction was quenched via addition of MeOH and the mixture was left to stir overnight. The solvent was removed and the product was obtained by flash column chromatography (CH$_2$Cl$_2$-Hexanes containing 5% MeOH) as clear thick oil (90%): $^1$H NMR (Acetone-d$_6$, 500 MHz) δ 7.46 (d, 4H, J=7.6), 7.37 (dd, 4H, J=7.3 and 7.6), 7.31 (dd, 2H, J=7.3 and 7.0), 6.65 (d, 1H, J=2.1 Hz), 6.64 (d, 1H, J=2.0 Hz), 6.52 (dd, 1H, J=2.0 and 2.2 Hz), 5.07 (s, 4H), 4.35 (s, 2H), 1.97 (br, 1H), 1.85 (br, 1H).

4-benzyloxy-3-hydroxybenzylamine

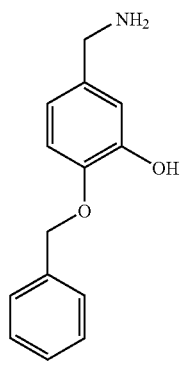

This compound was prepared according to procedure used in preparation of 3,5-dibenzyloxybenzylamine, starting from 4-benzyloxy-3-hydroxybenzonitrile. Yield was 33%. MP 122-125° C.; $^1$H NMR (DMSO-d$_6$, 400 MHz) δ 8.9 (br, 1H), 7.44 (d, 2H, J=7.4 Hz), 7.35 (dd, 2H, J=7.0 and 7.7 Hz), 7.28 (dd, 1H, J=7.0 and 7.3), 6.85 (d, 1H, J=7.6 Hz), 6.77 (d, 1H, J=2.1 Hz), 6.61 (dd, 1H, J=7.4 and 2.2 Hz), 5.05 (s, 2H), 3.55 (s, 1H), 2.50 (br, 2H).

3-hydroxy-4-propyloxybenzylamine

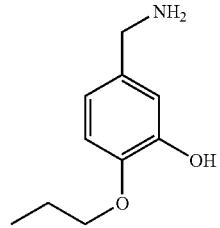

This compound was prepared by reduction of 3-hydroxy-4-propyloxybenzonitrile according to procedure described in preparation of 3,5-dibenzyloxybenzylamine. Yield was 48%: MP 110-113° C. (dec.); $^1$H NMR (CDCl$_3$, 400 MHz) δ 6.86 (s, 1H), 6.77 (d, 1H, J=8.4 Hz), 6.74 (d, 1H, J=8.1 Hz), 3.95 (t, 1H, J=6.6 Hz), 3.74 (s, 2H), 2.01 (br, 2H), 1.82 (m, 2H), 1.02 (t, 3H, J=7.4 Hz).

4-hydroxymethylbenzylamine

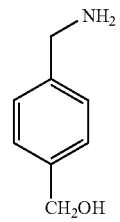

This compound was prepared by reduction of 4-cyanobenzaldehyde according to the procedure described in preparation of 3,5-dibenzyloxybenzylamine. Yield was 46%: MP 102-123° C.; $^1$H NMR (Acetone-d$_6$, 500 MHz) 7.27 (m, complex 4H), 4.58 (s, 2H), 3.72 (s, 2H), 3.69 (s, 1H) 2.77 (br, 1H), 2.45 (br, 1H).

3-hydroxymethylbenzylamine

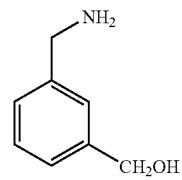

This compound was prepared by reduction of 3-cyanobenzaldehyde according to the procedure described in preparation of 3,5-dibenzyloxybenzylamine. Yield was 66%; $^1$H NMR (Acetone-d$_6$, 500 MHz) δ 7.32 (s, 1H), 7.23 (dd, 1H, J=7.6 and 7.0), 7.19, complex, 2H), 4.59 (s, 2H), 4.40 (s, 2H), 4.10 (br, 1H), 1.96 (br, 1H), 1.88 (br, 1H).

2-methoxy-5-nitrobenzaldehyde methyl hemiacetal

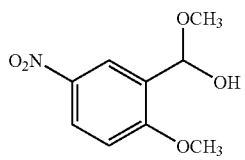

2-hydroxy-5-nitrobenzaldehyde (3.34 g, 20 mmol) was dissolved in acetone (70 mL); $k_2CO_3$ (5.53 g, 40 mmol) and iodomethane (14.19 g, 100 mmol) was added and the solution heated to reflux overnight. Solvent was removed in vacuo and residue was dissolved in EtOAc. The resulting product was washed with 2M NaOH, water, and brine and dried. Removal of solvent resulted in a solid product (2.5 g, 69%) of 2-methoxy-5-nitrobenzaldehyde methyl hemiacetal: MP 147-148° C. (89° C. reported for the aldehyde); $^1$H NMR (CDCl$_3$, 400 MHz) δ 8.43 (d, 1H, J=2.9 Hz), 8.24 (dd, 1H, J=2.6 and 9.1 Hz), 7.78 (d, 1H, 16.5 Hz), 6.99 (d, 1H, J=9.1 Hz), 6.83 (d, 1H, J=16.4 Hz). NOTE: This NMR was taken after about 10 months and the hemiacetal was still existing and pure.

5-nitro-2-propyloxybenzaldehyde

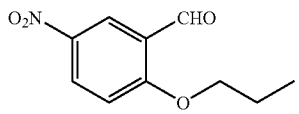

This compound was prepared by the reaction of 2-hydroxy-5-nitrobenzaldehyde and 1-iodopropane using a similar procedure as described in the preparation of 2-methoxy-5-nitrobenzaldehyde methyl hemiacetal. Yield was 72%: MP (51-52° C.); $^1$H NMR (500 MHz, CDCl$_3$) δ 10.46 (s, 1H), 8.68 (d, 1H, J=2.9 Hz), 8.39 (dd, 1H, J=2.7 and 9.1 Hz), 7.08 (d, 1H, J=9.1 Hz), 4.16 (t, 2H, J=6.2), 1.93 (m, 2H), 1.98 (t, 3H, J=7.37).

2-hydroxymethyl-4-nitrophenol

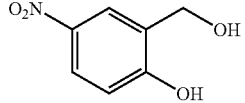

A solution of 2-hydroxy-5-nitrobenzaldehyde (5.01 g, 30 mmol) in a mixture of 60 mL 1M NaOH and 30 mL MeOH was cooled to 0° C. NaBH$_4$ (1.13 g, 30 mmol) solution in 15 mL 1M NaOH and 5 mL MeOH was added slowly. The reaction mixture was stirred for 24 hours at room temperature. The mixture was poured into ice cooled 2M HCl and extracted with EtOAc. The organic layer was washed, dried, and evaporated in vacuo to give the alcohol as a yellow solid (5.1 g, 100%): MP (112-114° C.); $^1$H NMR (DMSO-d$_6$, 400 MHz) δ 11.08 (s, 1H), 8.18 (d, 1H, J=2.5 Hz), 8.00 (dd, 1H, J=2.5 and 8.7 Hz), 6.92 (d, 1H, J=8.8 Hz), 5.20 (br, 1H), 4.49 (s, 2H).

2-methoxy-5-nitrobenzylalcohol

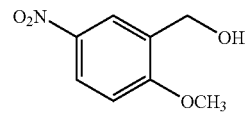

This compound was prepared by reduction of 2-methoxy-5-nitrobenzaldehyde methyl hemiacetal using a method similar to that described for preparing 2-hydroxymethyl-4-nitrophenol in 76% yield: MP 121-122° C.; $^1$H NMR (DMSO-d$_6$, 500 MHz) δ 8.22 (d, 1H, J=1.22 Hz), 8.16 (dd, 1H, J=2.7 and 9.1), 7.16 (d, 1H, J=8.9 Hz), 4.50 (s, 2H), 3.90 (s, 3H).

5-nitro-2-propyloxy-benzylalcohol

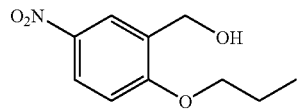

This compound was prepared by reduction of 5-nitro-2-propyloxybenzaldehyde using a method similar to that described for preparing 2-hydroxymethyl-4-nitrophenol in 93% yield: MP (No Sample left for MP); $^1$H NMR (400 MHz, DMSO-d$_6$) 8.22 (d, 1H, J=2.6 Hz), 8.13 (dd, 1H, J=2.9 and 9.2 Hz), 7.14 (d, 1H, J=9.2 Hz), 5.41 (t, 1H, J=5.5 Hz), 4.52 (d, 2H, J=5.8 Hz), 4.08 (t, 2H, J=6.2), 1.75 (m, 2H), 0.98 (t, 3H, J=7.6 Hz).

2-benzyloxy-5-nitrobenzylalcohol

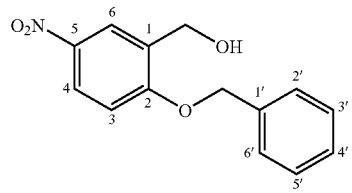

This intermediate was prepared by alkylation of 2-hydroxymethyl-4-nitrophenol with benzyl bromide following the method described for preparation of 2-methoxy-5-nitrobenzaldehyde methyl hemiacetal in a yield of 84%: MP 81-83° C.; $^1$H NMR δ (DMSO-d$_6$, 500 MHz) 8.26 (d, 1H, J=2.9 Hz <u>H-6</u>), 8.15 (dd, 1H, J=2.9 and 9.1 Hz, H-4), 7.46 (d, 2H, J=7.0, <u>2',6'-Hs</u>)7.41 (dd, 2H, J=7.0 and 7.7, <u>3',5'-Hs</u>), 7.34 (d, 1H, J=7 Hz, <u>4'-H</u>), 7.25 (d, 1H, J=9.1 Hz, <u>3-H</u>), 5.4 (br, 1H, <u>OH</u>), 5.29 (s, 2H, <u>CH$_2$</u>), 4.57 (s, 2H, <u>CH$_2$</u>).

3-hydroxymethyl-4-methoxyaniline

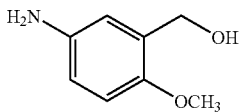

A mixture of 2-methoxy-5-nitrobenzylalcohol (1.02 g, 6.03 mmol) and SnCl$_2$.H$_2$O (6.8 g, 30.15 mmol) in EtOH (20 mL) was heated at 70° C. for 1 hour. After cooling, the mixture was treated with 2M NaOH and extracted with ether. The organic layer was washed with water, dried, and evaporated under vacuum to provide 2.18 g (84%) of the aniline 3-hydroxymethyl-4-methoxyaniline: $^1$H NMR (DMSO-d$_6$, 500 MHz) δ 6.66 (d, 1H, J=2.2 Hz), 6.61 (d, 1H, J=8.6 Hz), 6.38 (dd, 1H, J=2.4 and 8.2 Hz), 4.81 (t, 1H, J=5.5 Hz), 4.54 (br, 2H), 4.37 (d, 2H, J=5.8 Hz), 3.61 (s, 3H).

3-hydroxymethyl-4-propyloxyaniline

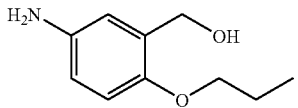

This compound was prepared by reduction of 5-nitro-2-propyloxy-benzylalcohol using the method described for the preparation of 3-hydroxymethyl-4-methoxyaniline in 37% yield: $^1$H NMR (DMSO-d$_6$, 500 MHz) δ 6.66 (d, 1H, J=2.5 Hz), 6.60 (d, 1H, J=8.6 Hz), 6.35 (dd, 1H, J=2.7 and 8.5 Hz), 4.79 (t, 1H, J=5.8 Hz), 4.54 (br, 2H), 4.37 (d, 2H, J=6.1 Hz), 3.74 (t, 2H, J=6.4 Hz), 1.65 (m, 2H), 0.94 (t, 3H, J=7.4 Hz).

4-benzyloxy-3-hydroxymethylaniline

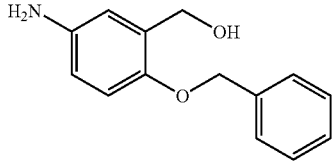

This compound was prepared by reduction of 2-benzyloxy-5-nitrobenzylalcohol using the method described for preparation of 3-hydroxymethyl-4-methoxyaniline in 86% yield: $^1$H NMR (DMSO-d$_6$, 500 MHz) δ 7.40 (d, 2H, J=7.3 Hz), 7.36 (dd, 2H, J=7.3 and 7.6 Hz), 7.28 (dd, 1H, J=7.0 and 7.4), 6.70 (d, 1H, J=8.5 Hz), 6.68 (d, 1H, J=2.4 Hz), 6.35 (dd, 1H, J=2.8 and 8.3 Hz), 4.92 (s, 2H), 4.84 (t, 1H, J=5.8 Hz), 4.59 (br, 2H), 4.44 (d, 2H, J=6.4 Hz).

B. Formation of Libraries

General Structure

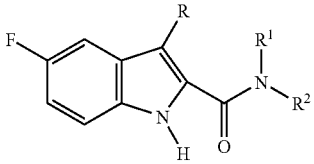

R = H, Ph
R$^1$, R$^2$ = H, alkyl, aryl, aralkyl, heterocyclic

1. General Procedures for Amide Coupling a. Method A

To a cold mixture (at 0° C.) of an amine (see Table VI below for amines) (0.15 mL of 1M solution in CH$_2$Cl$_2$, 0.15 mmol), an acid (5-fluoroindole-2-carboxylic acid or 5-fluoro-3-phenylindole-2-carboxylic acid) (0.15 mmol as 0.15 mL of 1M solution in THF) in CH$_2$Cl$_2$ (0.5 mL) was added and cooled to 0° C. Subsequently, a mixture of 1-(3-dimethylaminopropyl)-3-ethylcarbodiimide (EDCI) (0.15 mmol) and Et$_3$N (0.06 mmol) in CH$_2$Cl$_2$ (0.5 mL) was added and the reaction was shaken in a Bohdan orbital shaker (Mettler-Toledo Bohdan, Vernon Hills, Ill.) at 0° C. for 30 minutes then at room temperature for 18 hours. After adding 0.5 mL of CH$_2$Cl$_2$ and 0.5 mL MeOH, the mixture was passed through a cartridge charged with a cationic exchange resin (Dowex 50wX4-200, Aldrich Chemical Co., Milwaukee, Wis., pre-washed with 1M HCl, H$_2$O, H$_2$O MeOH, MeOH, MeOH—CH$_2$Cl$_2$). The eluent was directly passed through a chromatography cartridge containing silica gel mixed with 10% Na$_2$CO$_3$. The product was eluted with 2 mL CH$_2$Cl$_2$-MeOH (2 mL), CH$_2$Cl$_2$ (2 mL), and CH$_2$Cl$_2$-MeOH (2 mL). The fraction(s) containing pure product was identified by TLC (EtOAc-Hexane, 1:1). The compounds were characterized and their relative purity was estimated using $^1$H NMR.

b. Method B

A mixture of an amine (see Table VI below for amines) (0.1 mmol), an acid (5-fluoroindole-2-carboxylic acid or 5-fluoro-3-phenylindole-2-carboxylic acid) (0.1 mmol as 0.1 mL of 1M solution in DMF), and diisopropylethylamine (DIEA) (0.05 mL, 0.3 mmol) was cooled to 0° C. (benzotriazol-1-yloxy)tripyrrolidino-phosphonium-hexafluorophosphate (PyBOP) (0.1 mmol as 0.1 mL of 1M solution in DMF) was added. The reaction mixture was shaken using an orbital shaker at 0° C. for 30 minutes then at room temperature for 18 hours. EtOAc was added to the mixture and the organic solution was washed with 1M HCl (2×1 mL), brine (1 mL) NaHCO$_3$ (2×1 mL), and brine (1 mL). The organic layer was passed through a silica gel cartridge containing a top layer of anhydrous MgSO$_4$ and moistened with hexane. The product amide was eluted with hexane (1×1 mL), hexane-EtOAc 2:1 (3×1 mL), hexane-EtOAc 1:1 (2×2 mL), and hexane-EtOAc 1:2 (1×2 mL). The fraction(s) containing pure product was identified by TLC (EtOAc-hexane 1:1 and EtOAc-hexane 1:2 in the case of 5-fluoro-3-phenylindole-2-carboxylic acid amide derivatives). The compounds were characterized and their relative purity was estimated using $^1$H NMR.

c. Method C

A mixture of an amine (see Table VI below for amines) (0.1 mmol), an acid (5-fluoroindole-2-carboxylic acid or 5-fluoro-3-phenylindole-2-carboxylic acid) (0.1 mmol as 0.1 mL of 1M solution in THF), and DIEA (0.05 mL, 0.3 mmol) in 0.4 mL of CH$_2$Cl$_2$-THF (3:1) was cooled to 0° C. PyBrOP (0.1 mmol) was added. The reaction mixture was shaken using an orbital shaker at 0° C. for 30 minutes then at room temperature for 48 hours (0.1 mL THF and 0.2 mL CH$_2$Cl$_2$ were added after 24 hours). EtOAc was added to the mixture and the organic solution was washed with 1M HCl (2×1 mL), brine (1 mL) NaHCO$_3$ (2×1 mL), and brine (1 mL). The organic layer was passed through a silica gel cartridge containing a top layer of anhydrous MgSO$_4$ and moistened with hexane. The product amide was eluted with hexane (1×1 mL), hexane-EtOAc 2:1 (3×1 mL), hexane-EtOAc 1:1 (2×2 mL), and hexane-EtOAc 1:2 (1×2 mL). The fraction(s) containing pure product was identified by TLC (EtOAc-hexane 1:1 and EtOAc-hexane 1:2 in the case of 5-fluoro-3-phenylindole-2-carboxylic acid amide derivatives). The compounds were characterized by $^1$H NMR.

d. Method D

Preparation of 5-fluoroindole-2-carboxylic acid chloride 5-fluoroindole-2-carboxylic acid (537 mg, 3 mmol) was dissolved in DME (8 mL). 0.6 mL triethylamine was added and the mixture cooled to 0° C. Thionyl chloride (0.44 mL, 6 mmol) mixed with 4 mL DME was added cautiously using addition funnel over 10 minutes while stirring. The mixture was left to stir for 30 minutes. The formed precipitate was filtered off, and the solvent was evaporated under reduced pressure to give yellow solid of the acid chloride.

Reaction of Amines with 5-fluoroindole-2-carboxylic acid chloride

A mixture of an amine (see Table VI below for amines) (1 mmol) and pyridine (0.18 mL) in 1 mL DCM was cooled to 0° C. 5-fluoroindole-2-carboxylic acid chloride (19.8 mg, 1 mmol) was added, then reaction was stirred at room temperature for 1 hour. The resulting amide (in DCM) was washed with 1M HCl, then with Brine. The crude product was purified by silica gel chromatography.

e. Representative Examples of Amide Coupling Methods

Synthesis of Compound 1z

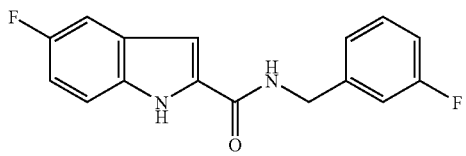

To a mixture of 3-fluorobenzylamine (2.03 g, 20 mmol) and 5-fluoroindole-2-carboxylic acid (3.58 g, 20 mmol) in DMF (50 mL), was added a solution of DIEA (6.98 mL, 40 mmol) in 15 mL $CH_2Cl_2$. The mixture was cooled to 0° C. and PyBOP (10.41 g, 20 mmol) was added portion wise. The reaction mixture was stirred at 0° C. for 30 minutes, then at room temperature for 4 hours. EtOAc (400 mL) was added to the mixture and the organic solution was washed with 2M HCl (4×200 mL), brine (200 mL), $NaHCO_3$ (4×200 mL), and brine (2×200 mL). The organic layer was dried ($MgSO_4$) and concentrated in vacuo to furnish the crude product as off-white solid. Recrystallization from MeOH and $CH_2Cl_2$ provided 5.36 g (93%) of 1z as white crystals: MP 239-241° C.; $^1$H NMR (DMSO-$d_6$, 500 MHz) δ 11.73 (s, 1H), 9.12 (t, 1H, J=6.1 Hz), 7.39 (complex, 3H), 7.17 (complex, 2H), 7.07 (dd, 1H, J=2.2 and 9.5 Hz), 7.07 (dd, 1H, J=2.2 and 9.0 Hz), 7.03 (ddd, 1H, J=2.4, 9.1 and 9.2 Hz), 4.52 (d, 2H, J=6.1 Hz); Anal. ($C_{16}H_{12}F_2N_2O$) C, 67.13; H, 4.23; N, 9.79; Found; C, 66.91; H, 4.31; N, 9.81.

Synthesis of Compound 1a

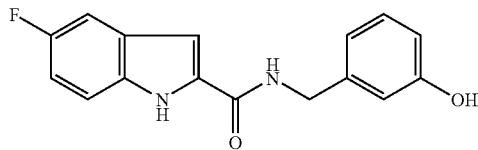

(a) Preparation of Methoxy Intermediate

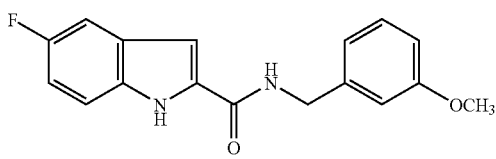

Following same procedure mentioned above for the synthesis of 1z, this compound was prepared starting from 20 mmol of amine and acid. Purification with flash column chromatography afforded 5.43 g (91%) of the methoxy intermediate as off-white crystalline solid: MP 192° C.

(b) Demethylation

A mixture of the methoxy intermediate (5 g, 16.7 mmol) and $CH_2Cl_2$ (80 mL) was placed in a multi neck flask equipped with a dropping funnel and a thermometer. The flask was cooled to 0° C. in an ice/salt bath. A solution of $BBr_3$ in $CH_2Cl_2$ (80 mL) was added dropwise while keeping the temperature less than 5° C. The mixture was stirred at room temperature for 3 hours. After addition of ice and 3M HCl (200 mL), the mixture was left to stir overnight. The precipitated solid product was collected by filtration, washed with water, and dried. Crystallization from $CH_2Cl_2$ and MeOH furnished 4.2 g (88%) of compound 1a: MP 213° C.; $^1$H NMR (DMSO-$d_6$, 400 MHz) δ 11.68 (br, 1H), 9.31 (br, 1H), 9.01 (t, 1H, J=6.0 Hz), 7.39 (complex, 2H), 7.14 (s, 1H), 7.09 (dd, 1H, J=8.0 and 7.7 Hz), 7.02 (ddd, 1H, J=9.2, 8.9 and 2.5 Hz), 6.72 (d, 2H, J=7.3 Hz), 6.61 (d, 1H, J=8.4 Hz), 4.41 (d, 2H, J=5.9 Hz), HRMS (EI): Required $M^+$ for $C_{16}H_{13}FN_2O_2$, 284.0956; Found, 284.0960. Anal. ($C_{16}H_{13}FN_2O_2$) C, 67.60; H, 4.61; F, N, 9.85; Found C, 67.50; H, 4.65; F, N, 9.76.

f. Other Representative Compounds Obtained and Relative Purity Data

The following are examples of compounds obtained using the above methods and their relative purity data. Table VI, below, lists all compounds obtained.

Compound 1bb

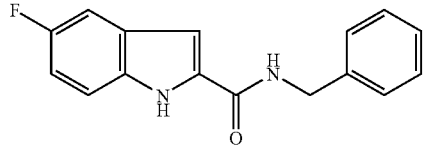

$^1$H NMR (acetone-$d_6$, 400 MHz) δ 10.85 (br, 1H), 8.29 (br, 1H), 7.53 (dd, 1H, J=9.9 and 4.6 Hz), 7.36 (d, 1H, J=7.4), 7.30 (complex, 3H), 7.22 (dd, 1H, J=7.3 and 7.0 Hz), 7.12 (s, 1H) 7.02 (ddd, 1H, J=2.6 and 9.2 and 9.1), 4.60 (d, 2H, J=6.3 Hz).

Compound 1cc

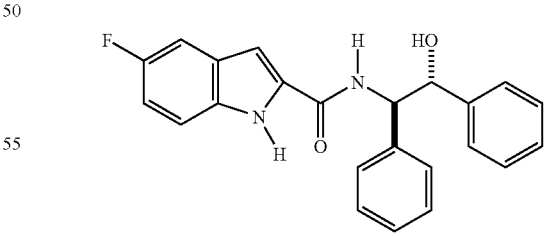

$^1$H NMR (Acetone-$d_6$, 500 MHz) δ 10.74 (br, 2H) 8.01 (d, br, 1H, J=9.0 Hz), 7.45 (dd, 1H, J=9.0 and 4.6 Hz), 7.37 (d, 2H, J=7.4 Hz), 7.34 (d, 2H, J=7.4 Hz), 7.28 (dd, 1H, J=9.5 and 2.5 Hz), 7.24 to 7.10 (complex. m, 7H), 6.99 (ddd, 1H, J=9.3, 9.2 and 2.6 Hz), 5.40 (dd, 1H, J=9.0 and 6.4 Hz), 5.20 (dd, 1H, J=6.2 and 4.6 Hz), 4.71 (d, 1H, J=4.6 Hz); LRMS (EI), m/z 356.1 ($M^+$-$H_2O$).

Compound 1dd

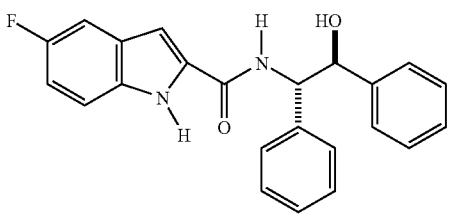

¹H NMR (Acetone-d₆, 500 MHz) δ 10.80 (br, 2H) 8.04 (d, br, 1H, J=8.7 Hz), 7.43 (dd, 1H, J=9.0 and 4.8 Hz), 7.38 (dd, 2H, J=8.0 and 1.4 Hz), 7.34 (dd, 2H, J=8.0 and 1.4 Hz), 7.28 (dd, 1H, J=9.6 and 2.4 Hz), 7.25 to 7.11 (complex. m, 7H), 6.98 (ddd, 1H, J=9.2, 9.1 and 2.5 Hz), 5.41 (dd, 1H, J=8.8d 6.6 Hz), 5.21 (dd, 1H, J=6.2 and 4.8 Hz), 4.71 (d, 1H, J=4.6 Hz).

Compound 1bbb

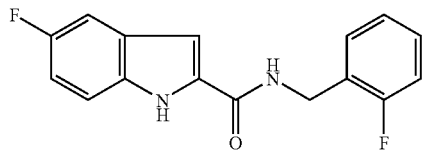

¹H NMR (acetone-d₆, 500 MHz) δ 10.89 (br, 1H), 8.31 (br, 1H), 7.54 (dd, 1H, J=9.1 and 4.6 Hz), 7.45 (dd, 1H, J=7.7 and 7.7 Hz), 7.29 (complex, 2H), 7.17-7.08 (complex, 3H), 7.03 (ddd, 1H, J=9.2, 9.1 and 2.6 Hz), 4.66 (d, 2H, J=5.8 Hz).

Compound 1yyy

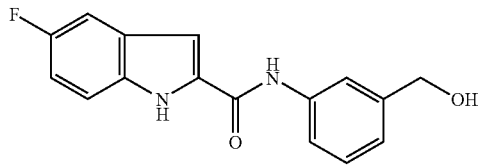

¹H NMR (Acetone-d₆, 500 MHz) δ 10.99 (br, 1H), 9.57 (br, 1H), 7.80 (s, 1H), 7.76 (d, 1H, J=8.3 MHz), 7.57 (dd, 1H, J=9.0 and 4.4 Hz), 7.35 (dd, 1H, 9.2 and 2.4 Hz), 3.34 (s, 1H), 7.29 (dd, 1H, J=7.7 and 7.8 Hz), 7.09 (d, 1H, J=8.8 Hz), 7.06 (ddd, 1H, J=9.2, 8.9 and 2.4 Hz), 4.63 (d, 2H, J=5.8 Hz), 4.24 (t, 1H, J=5.8 Hz); LRMS (EI) m/z 284.1 (74%, M⁺).

Compound 1ccc

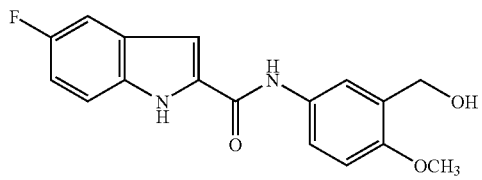

¹H NMR (acetone-d₆, 500 MHz) δ 10.96 (br, 1H), 9.49 (br, 1H), 7.79 (complex, 2H), 7.56 (dd, 1H, J=8.9 and 4.5 Hz), 7.34 (complex, 2H), 7.05 (ddd, 1H, J=9.2, 9.1 and 2.4 Hz), 6.92 (d, 1H, J=8.6 Hz), 4.65 (d, 1H, J=7.0 Hz), 4.06 (t, 1H, J=5.8), 3.81 (s, 1H); LRMS (EI) m/z 314.12 (51%, M⁺).

Compound 1oooo

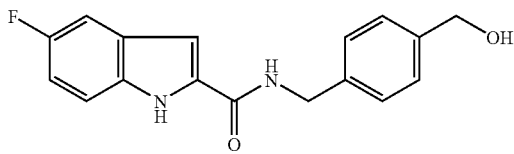

¹H NMR (acetone-d₆, 500 MHz) δ 10.94 (br, 1H), 8.31 (br, 1H), 7.52 (dd, 1H, J=8.9 and 4.6), 7.33 (d, 2H, J=8.9), 7.30 (d, 2H, J=8.5), 7.29 (dd, 1H, J=9.6 and 2.6 Hz), 7.13 (s, 1H), 7.02 (ddd, 1H, J=9.3, 9.1 and 2.4 Hz), 4.60 (d, 4H, J=5.8 Hz), 4.15 (t, 1H, J=5.8 Hz); LRMS (EI) m/z 298.12 (100%, M⁺).

Compound 2f

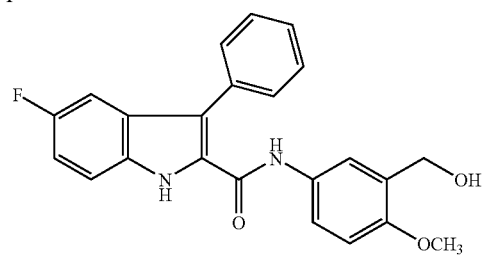

¹H NMR (acetone-d₆, 500 MHz) δ 11.12 (br, 1H), 8.07 (br, 1H), 7.66-77.60 (m, complex, 5H), 7.52 (m, 1H), 7.36 (d, 1H, J=2.2 Hz), 7.30 (dd, 1H, J=8.7 and 2.6), 7.15-7.09 (m, complex, 2H), 6.84 (d, 1H, J=8.8 Hz), 4.56 (d, 2H, J=6.1 Hz), 4.04 (t, 1 h, J=5.8 Hz), 3.77 (s, 3H).

Compound 2g

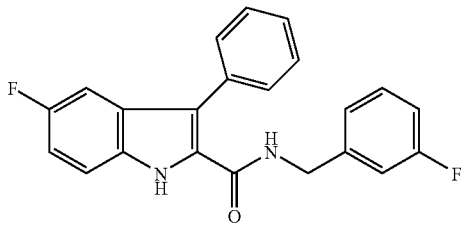

¹H NMR (Acetone-d₆, 500 MHz) δ 11.02 (br, 1H), 7.59 (dd, 1H, J=9.7 and 4.6 Hz), 7.53 (d, 1H, J=9.8 Hz), 7.47 (dd, 2H, J=7.9 and 7.4 Hz), 7.40 (m, 1H), 7.31 (dd, 1H. J=7.0 and 6.5 Hz), 7.08 (complex, 2H), 7.03 (d, 1H, J=7.7 Hz), 6.99 (complex, 2H), 6.91 (br, 1H), 4.48 (d, 2H, J=5.8 Hz); LRMS (EI) m/z 362.14 (85%, M⁺).

Compound 2s

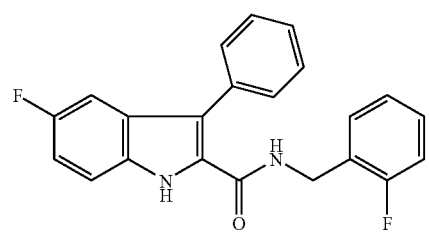

¹H NMR (Acetone-d₆, 500 MHz) δ 11.03 (br, 1H), 7.57-7.45 (complex, 4H), 7.544 (m, 1H), 7.31-7.24 (complex, 2H), 7.13-7.055 (complex, 4H), 6.76 (br, 1H), 4.50 (d, 2H, J=5.2 Hz); LRMS (EI) m/z 362.1 (95%, M⁺).

Compound 3q

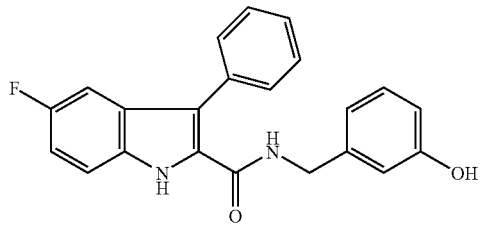

$^1$H NMR (Acetone-$d_6$, 500 MHz) δ 10.99 (br, 1H), 8.26 (s, 1H), 7.58 (dd, 1H, J=9.5 and 4.6 Hz), 7.51 (dd, 2H, J=8.2 and 1.4 Hz), 7.46 (dd, 2H, J=7.7 and 7.3 Hz), 7.38 (m, 1H), 7.10-7.05 (complex, 3H), 6.72 (br, 1H), 6.67 (complex, 2H), 6.62 (d, 1H, J=7.6 Hz), 4.38 (d, 2H, J=6.2 Hz); LRMS (EI) m/z 360.12 (100%, M$^+$).

2. General Procedure for Oxidation of Benzyl Alcohol Amide Derivatives to Benzaldehyde Preparation of Compounds 3b, 3d, 3e, 3f, 3g, and 3h The starting benzyl alcohol amide derivative was dissolved in a 1:1 mixture of $CH_2Cl_2$ and THF (5 mL/mmol), pyridinium chlorochromate (2 molar equivalent) was added, and the mixture was stirred at room temperature for 3.5 hours. EtOAc and water were added. The brown solid was removed by filtration. The organic phase was washed several times with $NaHCO_3$, brine, dried, and concentrated. Product aldehyde was purified by crystallization and confirmed by $^1$H NMR (disappearance of the methylene of benzyl alcohol and appearance of aldehyde peak).

The following table sets forth the structures made by the above methods:

TABLE VI

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1a | 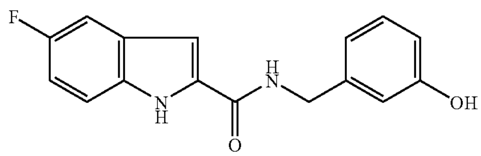 | 284.29 | See Example 1 |
| 1b | 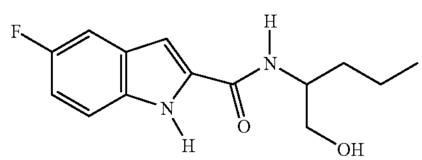 | 264.3 | Amide Coupling Method A |
| 1c | 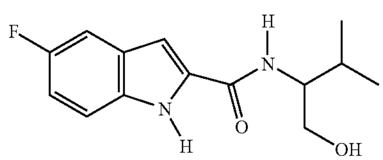 | 264.3 | Amide Coupling Method A |
| 1d | 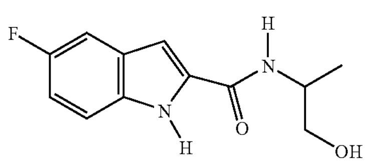 | 236.24 | Amide Coupling Method A |
| 1e | 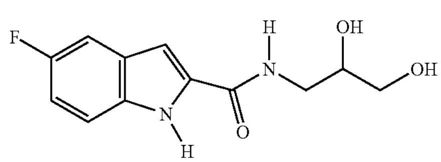 | 252.24 | Amide Coupling Method A |
| 1f | 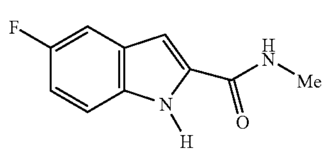 | 192.19 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1g | 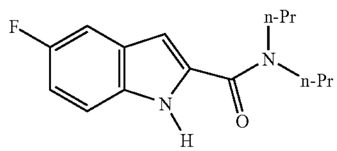 | 262.32 | Amide Coupling Method A |
| 1h | 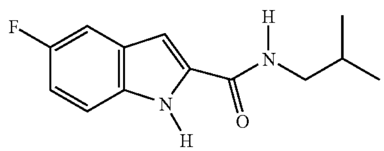 | 234.27 | Amide Coupling Method A |
| 1i | 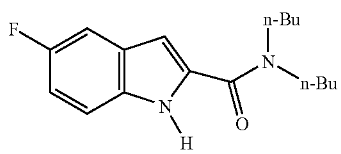 | 290.38 | Amide Coupling Method A |
| 1j | 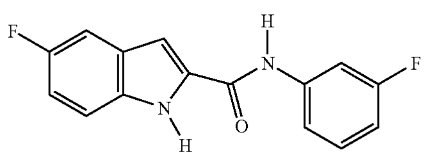 | 272.25 | Amide Coupling Method A |
| 1k | 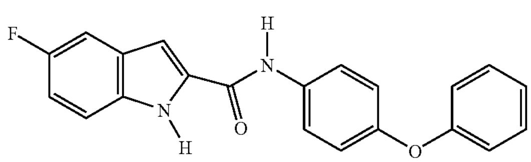 | 346.35 | Amide Coupling Method A |
| 1l | 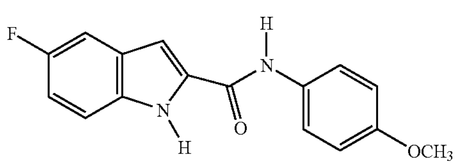 | 284.29 | Amide Coupling Method A |
| 1m | 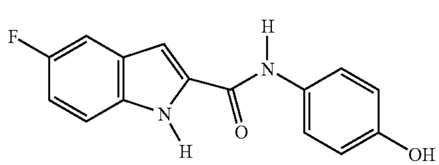 | 270.26 | Amide Coupling Method A |
| 1n | 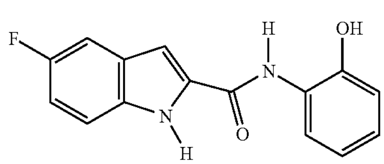 | 270.26 | Amide Coupling Method A |
| 1o | 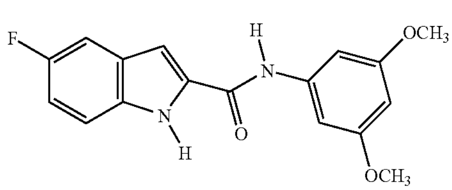 | 314.31 | Amide Coupling Method A |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1p | 5-fluoroindole-2-carboxamide, N-phenyl | 254.26 | Amide Coupling Method A |
| 1q | 5-fluoroindole-2-carboxamide, N-(2-naphthyl) | 304.32 | Amide Coupling Method A |
| 1r | 5-fluoroindole-2-carboxamide, N-(3,5-dihydroxyphenyl) | 286.26 | Amide Coupling Method A |
| 1s | 5-fluoroindole-2-carboxamide, N-(2-trifluoromethylphenyl) | 322.26 | Amide Coupling Method A |
| 1t | 5-fluoroindole-2-carboxamide, N-(3,5-dimethylphenyl) | 282.31 | Amide Coupling Method A |
| 1u | 5-fluoroindole-2-carboxamide, N-(2-(1H-indol-3-yl)ethyl) | 321.35 | Amide Coupling Method A |
| 1v | 5-fluoroindole-2-carboxamide, pyrrolidinyl | 232.25 | Amide Coupling Method A |
| 1w | 5-fluoroindole-2-carboxamide, morpholinyl | 248.25 | Amide Coupling Method A |

TABLE VI-continued
LIBRARY OF 5-FLUOROINDOLE-2-CARBAXAMIDE COMPOUNDS AND METHOD OF PREPARATION
| Cmpd Code | Structure | M. Wt. | Method of Preparation |
|---|---|---|---|
| 1x | 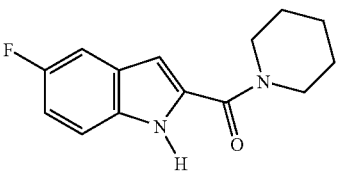 | 246.28 | Amide Coupling Method A |
| 1y | 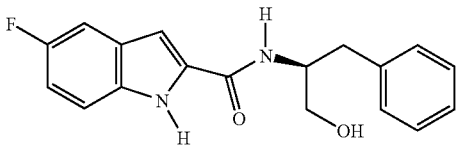 | 312.34 | Amide Coupling Method A |
| 1z | 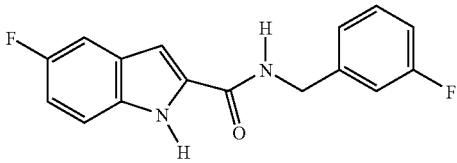 | 286.28 | Amide Coupling Method A |
| 1aa | 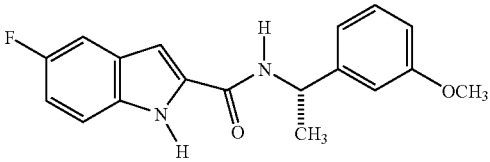 | 312.34 | Amide Coupling Method A |
| 1bb | 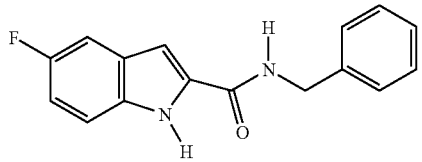 | 268.29 | Amide Coupling Method A |
| 1cc | 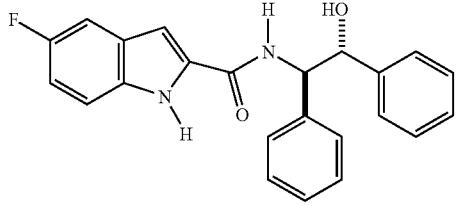 | 374.41 | Amide Coupling Method A |
| 1dd | 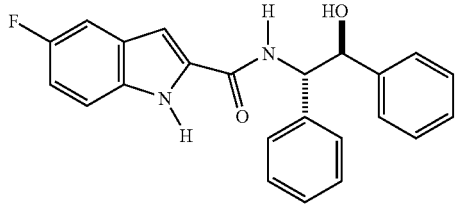 | 374.41 | Amide Coupling Method A |
| 1ee | 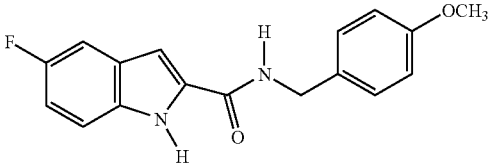 | 298.31 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1ff | 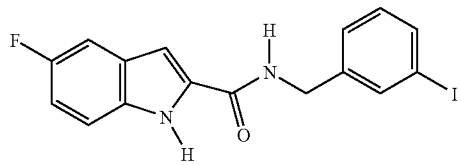 | 394.18 | Amide Coupling Method A |
| 1gg | 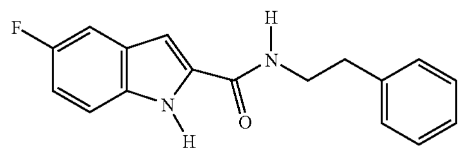 | 282.31 | Amide Coupling Method A |
| 1hh | 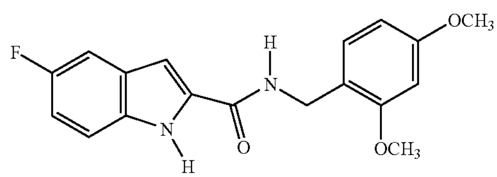 | 328.34 | Amide Coupling Method A |
| 1ii | 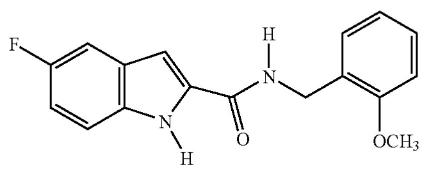 | 298.31 | Amide Coupling Method A |
| 1jj | 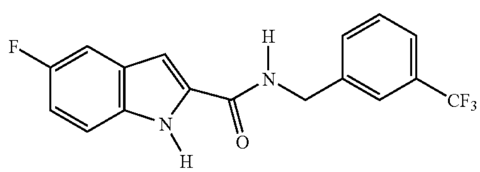 | 336.28 | Amide Coupling Method A |
| 1kk | 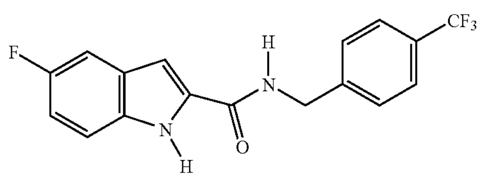 | 336.28 | Amide Coupling Method A |
| 1ll | 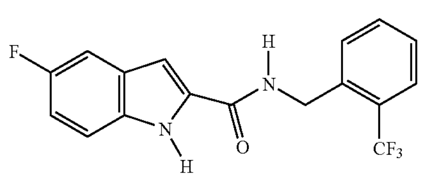 | 336.28 | Amide Coupling Method A |
| 1mm | 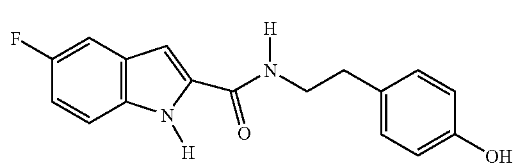 | 298.31 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1nn | 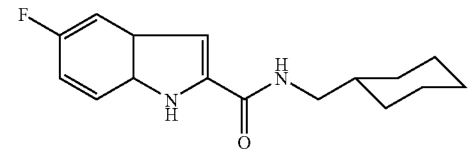 | 274.33 | Amide Coupling Method A |
| 1oo | 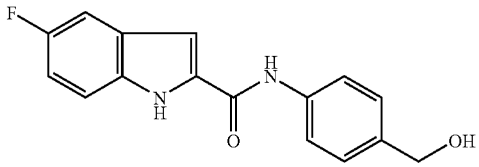 | 284.29 | Amide Coupling Method A |
| 1pp | 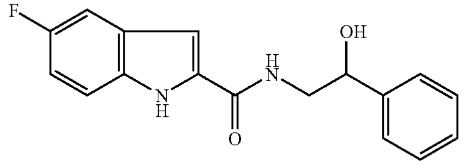 | 298.31 | Amide Coupling Method A |
| 1qq | 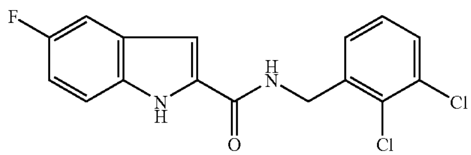 | 337.18 | Amide Coupling Method A |
| 1rr | 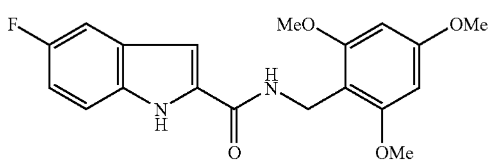 | 358.36 | Amide Coupling Method A |
| 1ss | 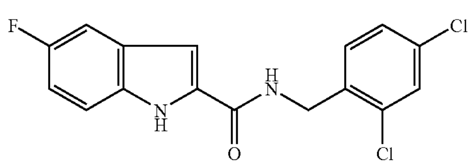 | 337.18 | Amide Coupling Method A |
| 1tt | 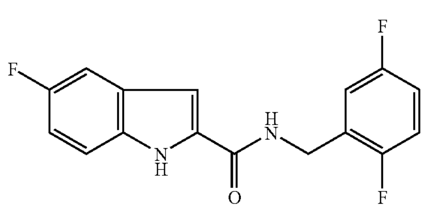 | 304.27 | Amide Coupling Method A |
| 1uu | 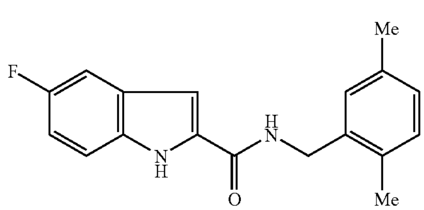 | 296.34 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1vv | 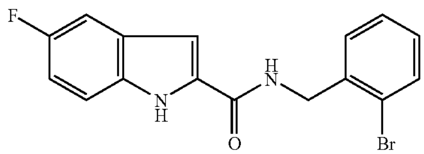 | 347.18 | Amide Coupling Method A |
| 1ww | 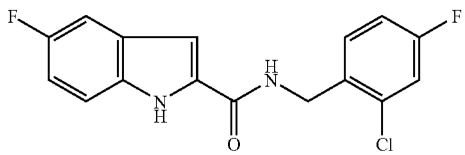 | 320.72 | Amide Coupling Method A |
| 1xx | 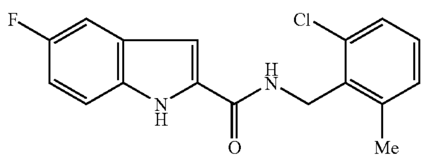 | 316.76 | Amide Coupling Method A |
| 1yy | 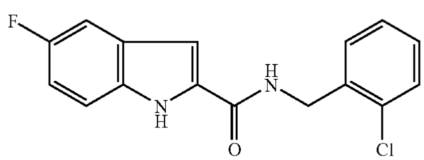 | 302.73 | Amide Coupling Method A |
| 1zz | 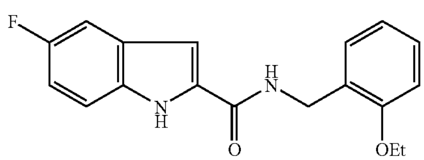 | 312.34 | Amide Coupling Method A |
| 1aaa | 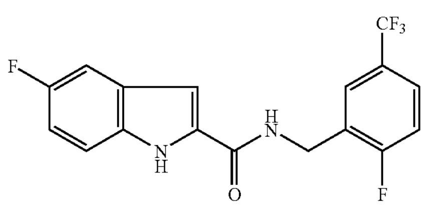 | 354.27 | Amide Coupling Method A |
| 1bbb | 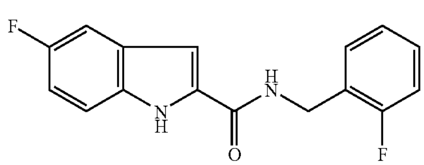 | 286.28 | Amide Coupling Method A |
| 1ccc | 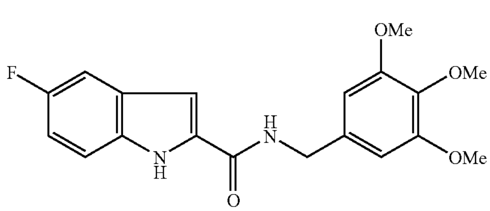 | 358.36 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1ddd | 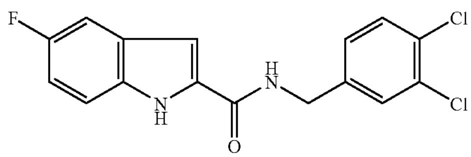 | 337.18 | Amide Coupling Method A |
| 1eee | 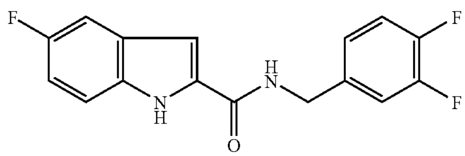 | 304.27 | Amide Coupling Method A |
| 1fff | 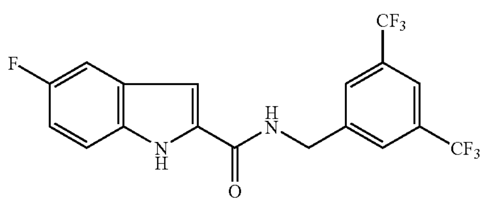 | 404.28 | Amide Coupling Method A |
| 1ggg | 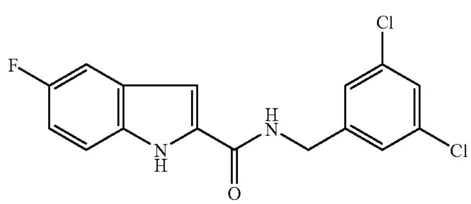 | 337.18 | Amide Coupling Method A |
| 1hhh | 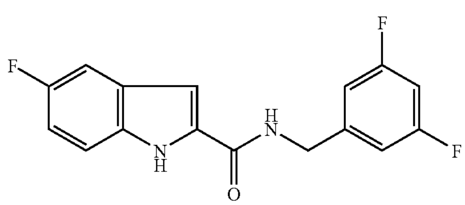 | 304.27 | Amide Coupling Method A |
| 1iii | 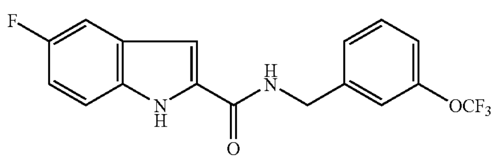 | 352.28 | Amide Coupling Method A |
| 1jjj | 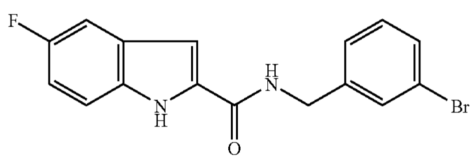 | 347.18 | Amide Coupling Method A |
| 1kkk | 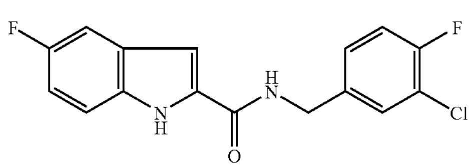 | 320.72 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1lll | 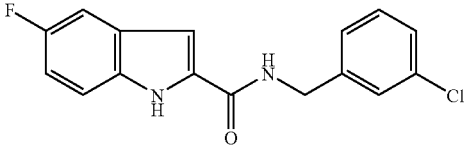 | 302.73 | Amide Coupling Method A |
| 1mmm | 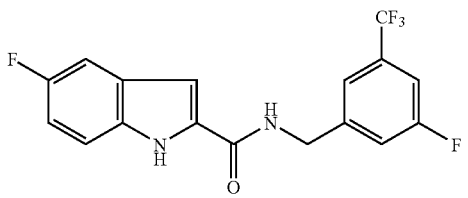 | 354.27 | Amide Coupling Method A |
| 1nnn | 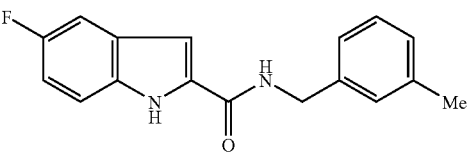 | 282.31 | Amide Coupling Method A |
| 1ooo | 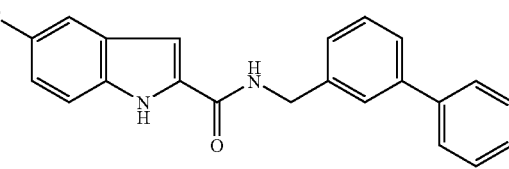 | 344.38 | Amide Coupling Method A |
| 1ppp | 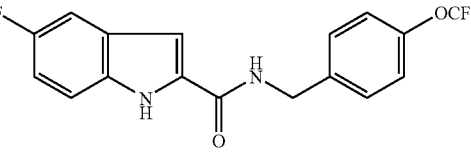 | 352.28 | Amide Coupling Method A |
| 1qqq | 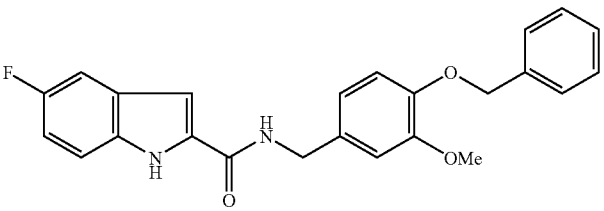 | 404.43 | Amide Coupling Method A |
| 1rrr | 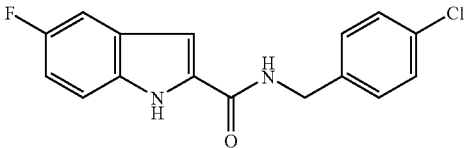 | 302.73 | Amide Coupling Method A |
| 1sss | 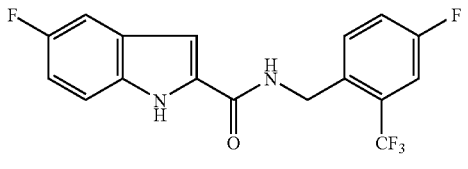 | 354.27 | Amide Coupling Method A |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1ttt | 5-F-indole-2-C(O)NH-CH2-(4-F,3-CF3-phenyl) | 354.27 | Amide Coupling Method A |
| 1uuu | 5-F-indole-2-C(O)NH-CH2-(4-F-phenyl) | 286.28 | Amide Coupling Method A |
| 1vvv | 5-F-indole-2-C(O)NH-CH2-(4-Me-phenyl) | 282.31 | Amide Coupling Method A |
| 1www | 5-F-indole-2-C(O)NH-CH2-(5-Br,2-F-phenyl) | 365.17 | Amide Coupling Method A |
| 1xxx | 5-F-indole-2-C(O)NH-(2-CH2OH-phenyl) | 284.29 | Amide Coupling Method C |
| 1yyy | 5-F-indole-2-C(O)NH-(3-CH2OH-phenyl) | 284.29 | Amide Coupling Method B |
| 1zzz | 5-F-indole-2-C(O)NH-(3-OH-phenyl) | 270.26 | Amide Coupling Method C |
| 1aaaa | 5-F-indole-2-C(O)NH-(3-CH2OH,4-OPr-phenyl) | 342.36 | Amide Coupling Method C |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 1bbbb | 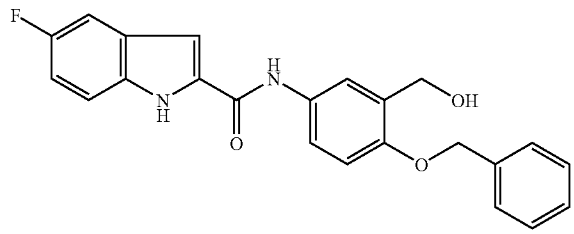 | 390.41 | Amide Coupling Method C |
| 1cccc | 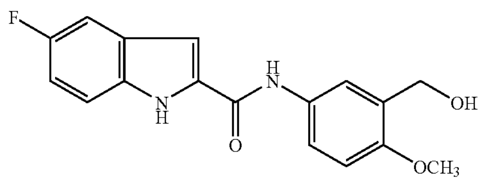 | 314.31 | Amide Coupling Method C |
| 1dddd | 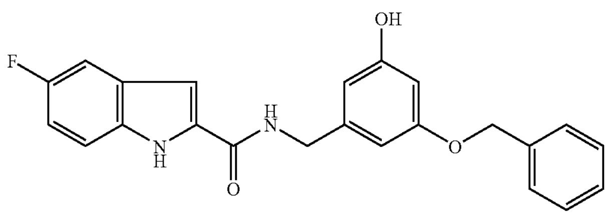 | 390.41 | Amide Coupling Method B |
| 1eeee | 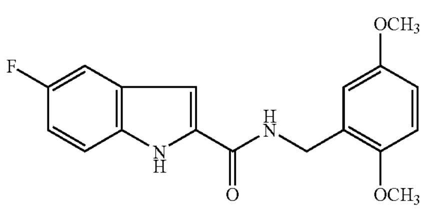 | 328.34 | Amide Coupling Method B |
| 1ffff | 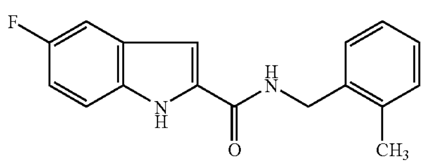 | 282.31 | Amide Coupling Method B |
| 1gggg | 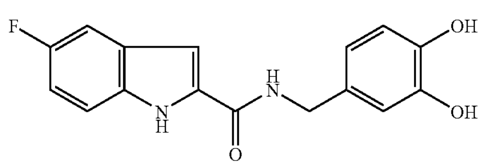 | 300.28 | Amide Coupling Method B |
| 1hhhh | 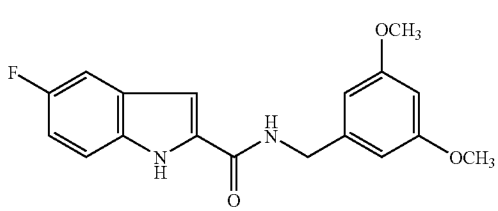 | 328.34 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 1iiii | 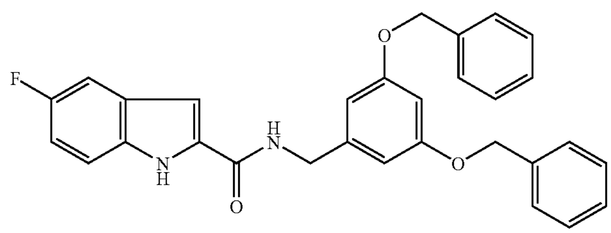 | 480.53 | Amide Coupling Method B |
| 1jjjj | 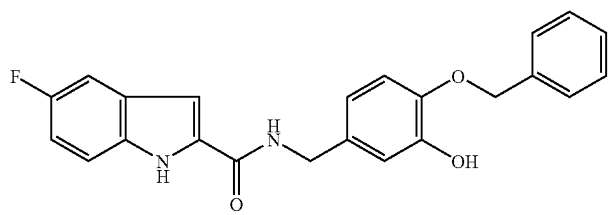 | 390.41 | Amide Coupling Method B |
| 1kkkk | 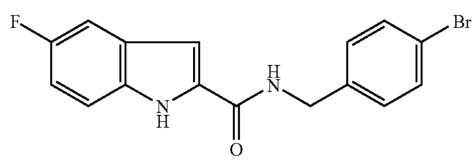 | 347.18 | Amide Coupling Method B |
| 1llll | 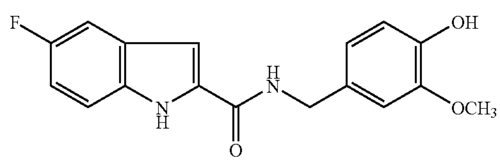 | 314.31 | Amide Coupling Method B |
| 1mmmm | 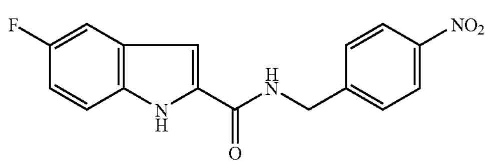 | 313.28 | Amide Coupling Method B |
| 1nnnn | 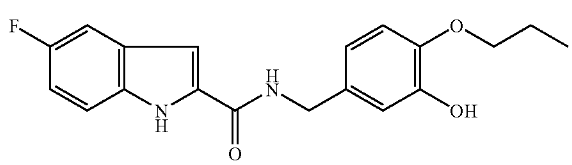 | 342.36 | Amide Coupling Method B |
| 1oooo | 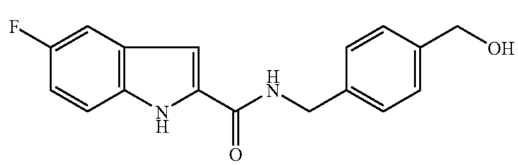 | 298.31 | Amide Coupling Method B |
| 1pppp | 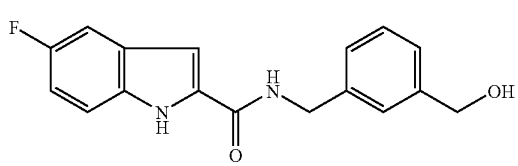 | 298.31 | Amide Coupling Method B |

TABLE VI-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 1qqqq | 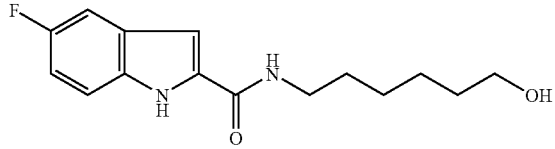 | 278.32 | Amide Coupling Method B |
| 2a | 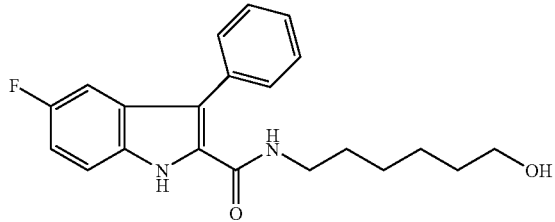 | 354.42 | Amide Coupling Method B |
| 2b | 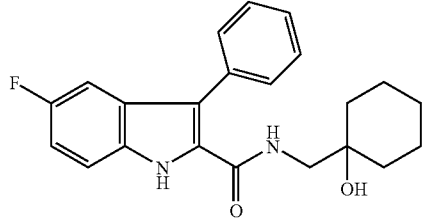 | 366.43 | Amide Coupling Method B |
| 2c | 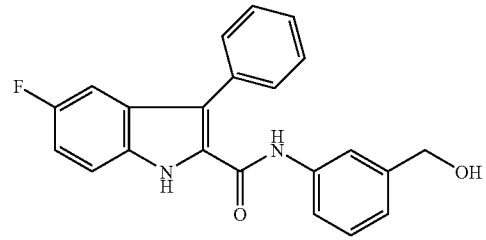 | 360.38 | Amide Coupling Method B |
| 2d | 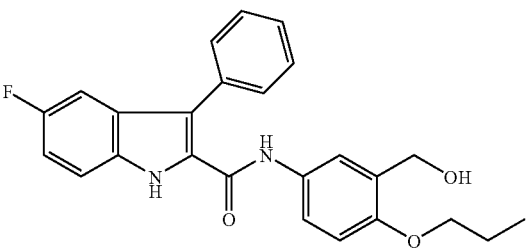 | 418.46 | Amide Coupling Method B |
| 2e | 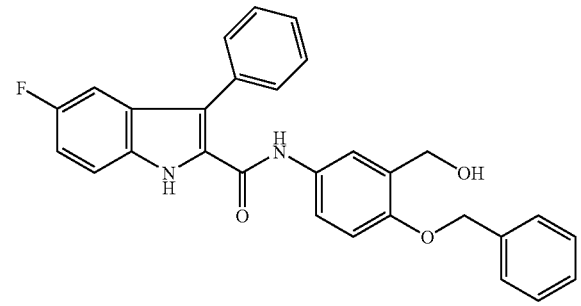 | 466.5 | Amide Coupling Method B |

TABLE VI-continued
LIBRARY OF 5-FLUOROINDOLE-2-CARBAXAMIDE
COMPOUNDS AND METHOD OF PREPARATION
| Cmpd Code | Structure | M. Wt. | Method of Preparation |
|---|---|---|---|
| 2f | 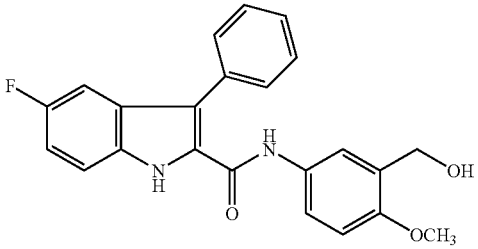 | 390.41 | Amide Coupling Method B |
| 2g | 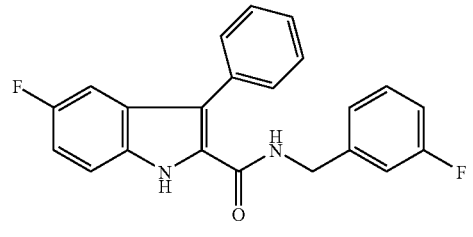 | 362.37 | Amide Coupling Method B |
| 2h | 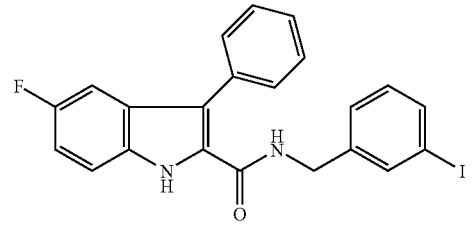 | 470.28 | Amide Coupling Method B |
| 2i | 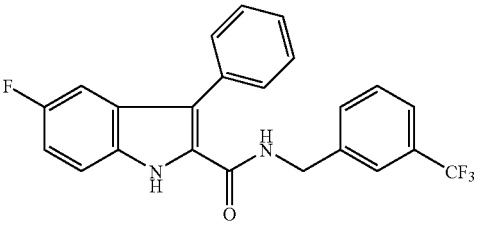 | 412.38 | Amide Coupling Method B |
| 2j | 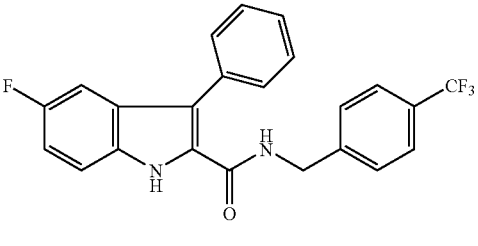 | 412.38 | Amide Coupling Method B |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2k | 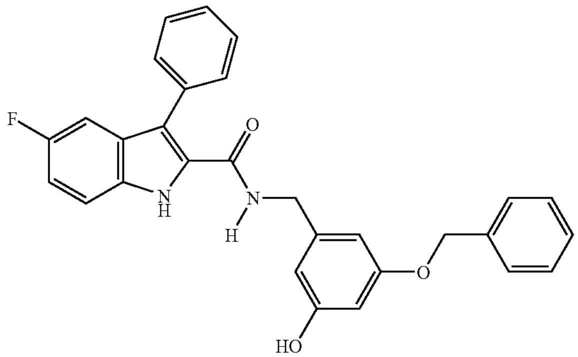 | 466.5 | Amide Coupling Method B |
| 2l | 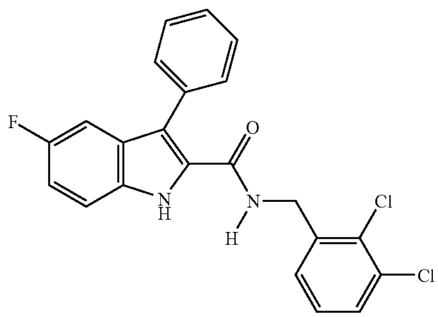 | 413.27 | Amide Coupling Method B |
| 2m | 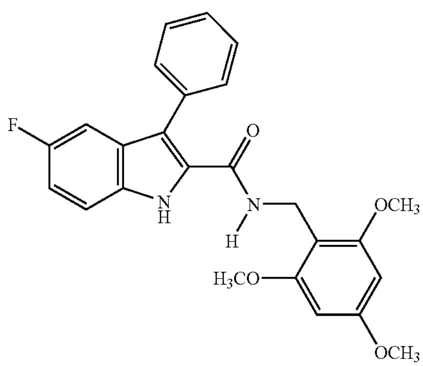 | 434.46 | Amide Coupling Method B |
| 2n | 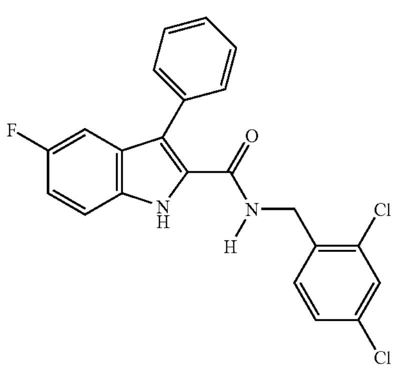 | 413.27 | Amide Coupling Method B |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2o | 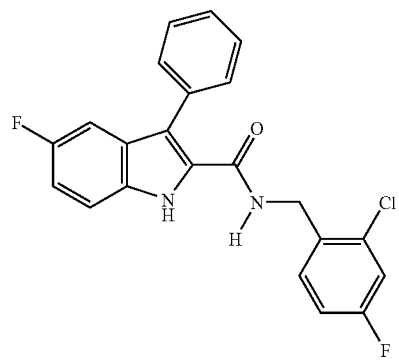 | 396.82 | Amide Coupling Method B |
| 2p | 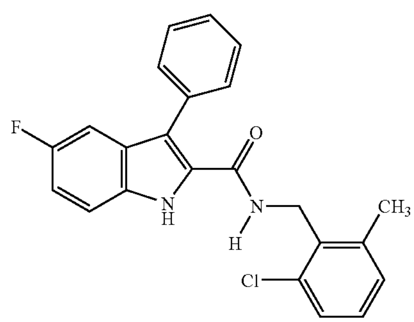 | 392.85 | Amide Coupling Method B |
| 2q | 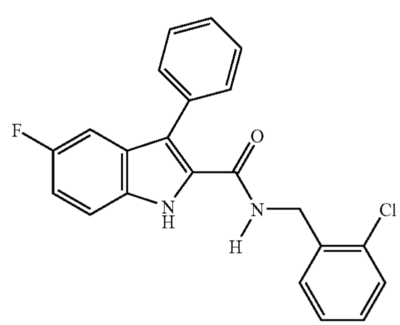 | 378.83 | Amide Coupling Method B |
| 2r | 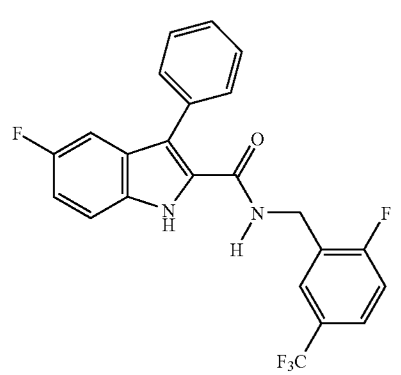 | 430.37 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 2s | 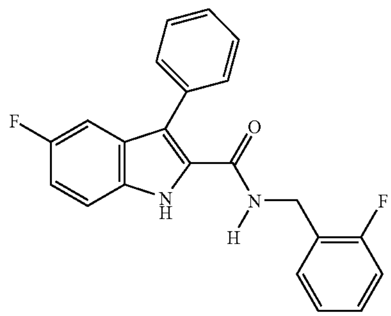 | 362.37 | Amide Coupling Method B |
| 2t | 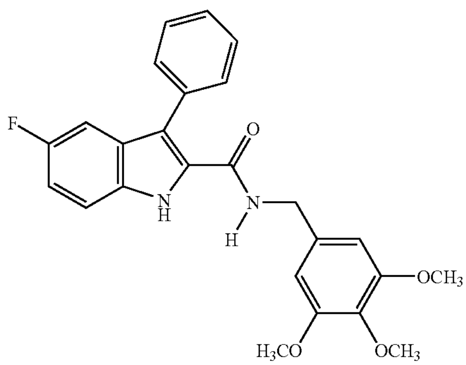 | 434.46 | Amide Coupling Method B |
| 2u | 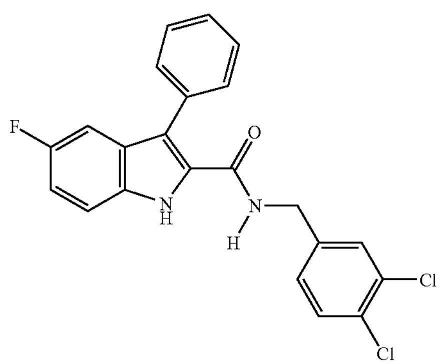 | 413.27 | Amide Coupling Method B |
| 2v | 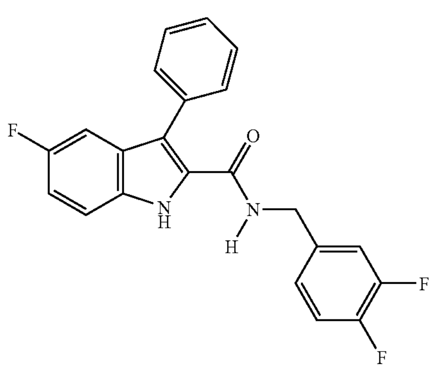 | 380.36 | Amide Coupling Method B |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2w | 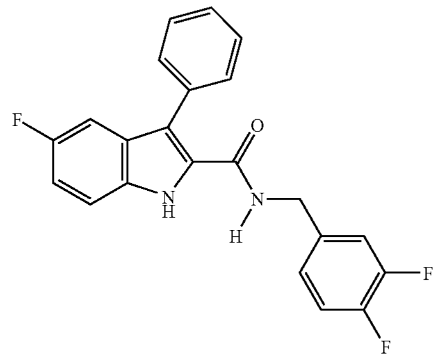 | 480.38 | Amide Coupling Method B |
| 2x | 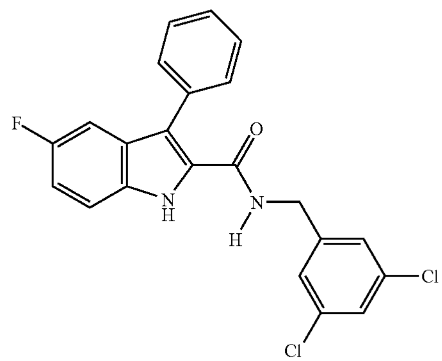 | 413.27 | Amide Coupling Method B |
| 2y | 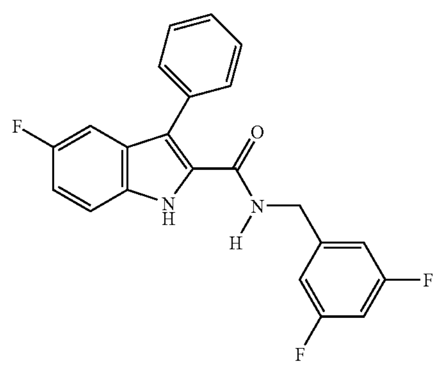 | 380.36 | Amide Coupling Method B |
| 2z | 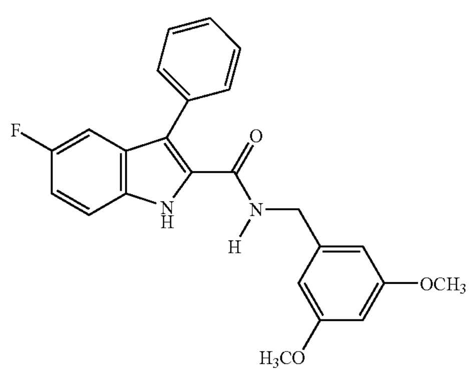 | 404.43 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 2aa | 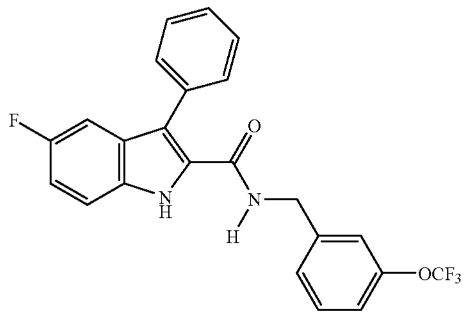 | 428.38 | Amide Coupling Method B |
| 2bb | 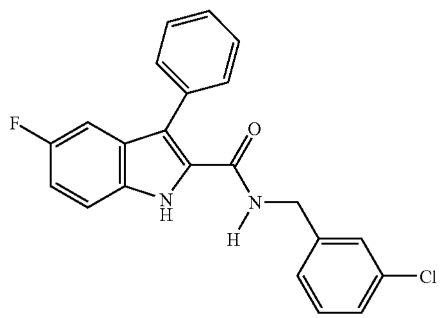 | 378.83 | Amide Coupling Method B |
| 2cc | 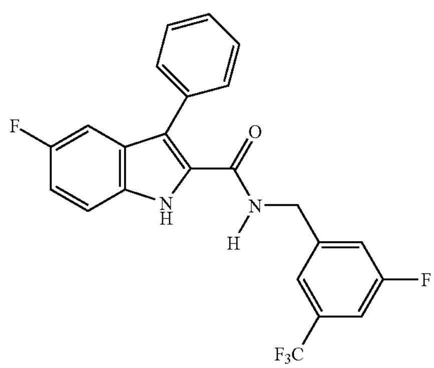 | 430.37 | Amide Coupling Method B |
| 2dd | 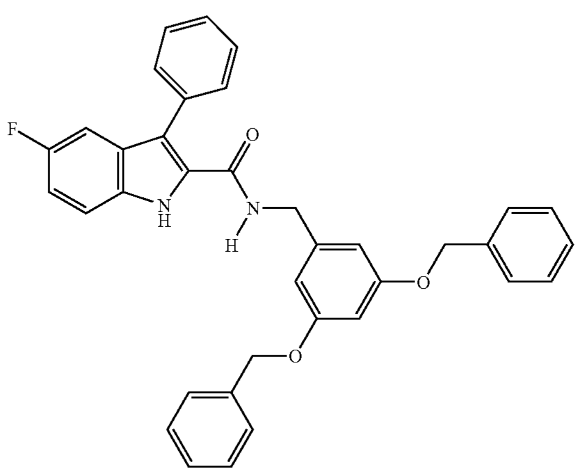 | 556.63 | Amide Coupling Method B |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 2ee | 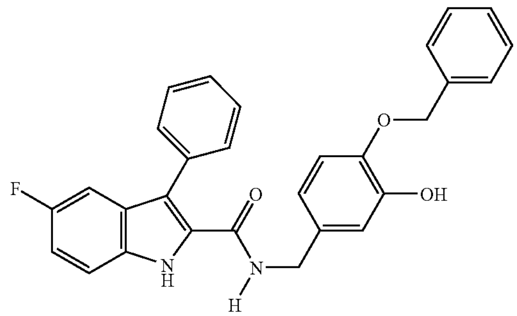 | 466.5 | Amide Coupling Method B |
| 2ff | 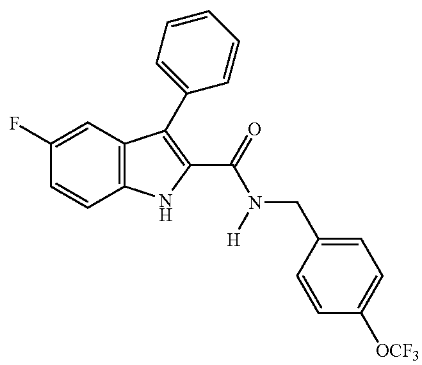 | 428.38 | Amide Coupling Method B |
| 2gg | 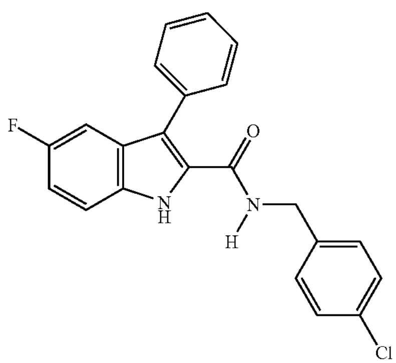 | 378.83 | Amide Coupling Method B |
| 2hh | 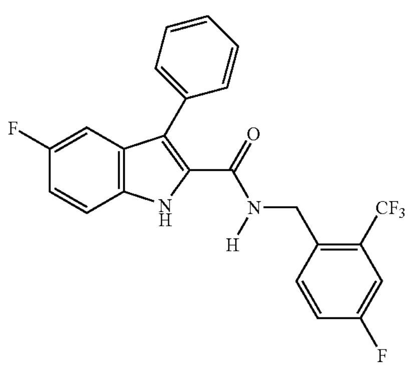 | 430.37 | Amide Coupling Method B |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 2ii | 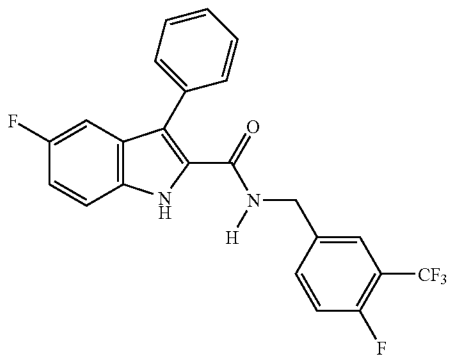 | 431.37 | Amide Coupling Method B |
| 2jj | 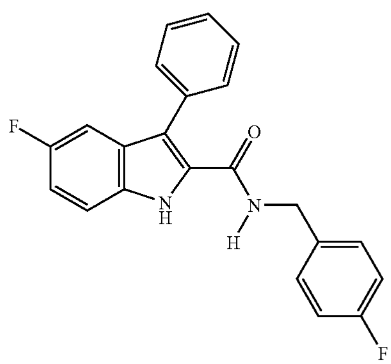 | 362.37 | Amide Coupling Method B |
| 2kk | 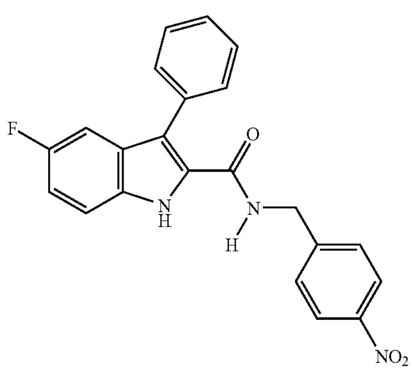 | 389.38 | Amide Coupling Method B |
| 2ll | 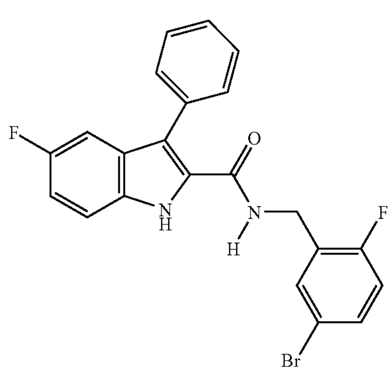 | 441.27 | Amide Coupling Method B |

TABLE VI-continued
LIBRARY OF 5-FLUOROINDOLE-2-CARBAXAMIDE COMPOUNDS AND METHOD OF PREPARATION
| Cmpd Code | Structure | M. Wt. | Method of Preparation |
|---|---|---|---|
| 2mm | 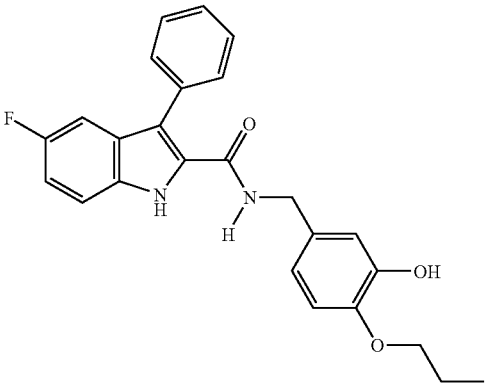 | 418.46 | Amide Coupling Method B |
| 2nn | 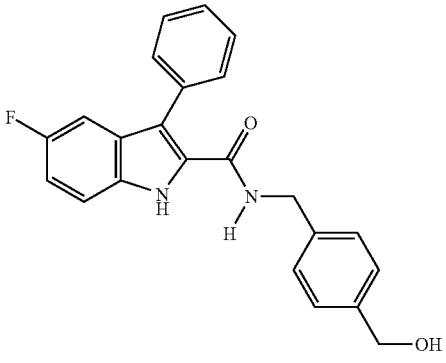 | 374.41 | Amide Coupling Method B |
| 2oo | 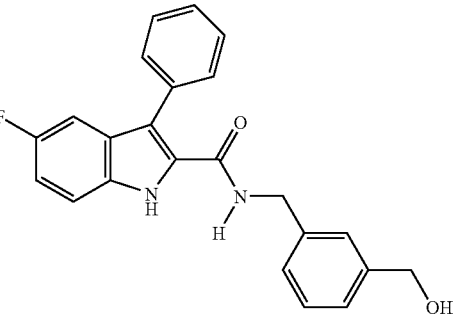 | 375.41 | Amide Coupling Method B |
| 3a | 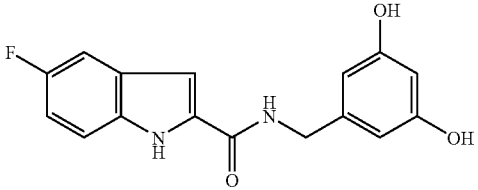 | 300.28 | Demethylation of compound 1hh using BBr$_3$ method in Example 1. |
| 3b | 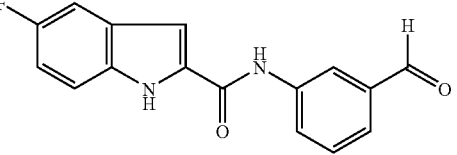 | 282.27 | Oxidation of 1yyy |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 3c | 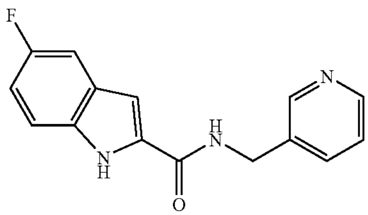 | 269.29 | Amide Coupling Method C |
| 3d | 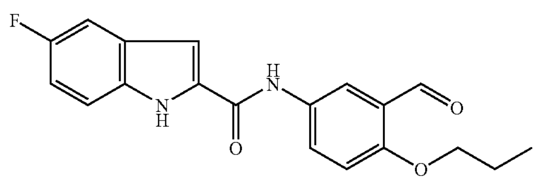 | 340.35 | Oxidation of 1aaaa |
| 3e | 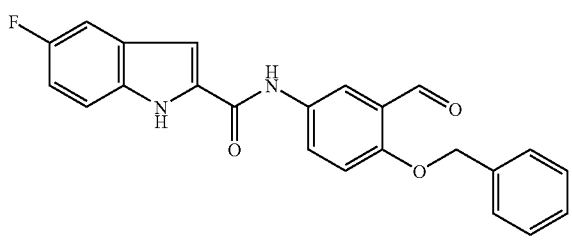 | 388.39 | Oxidation of 1bbbb |
| 3f | 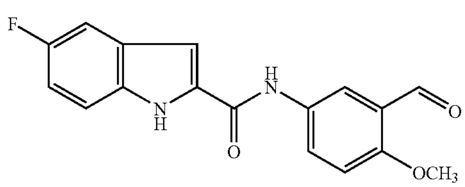 | 312.3 | Oxidation of 1cccc |
| 3g | 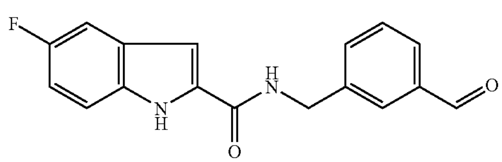 | 296.3 | Oxidation of 1pppp |
| 3h | 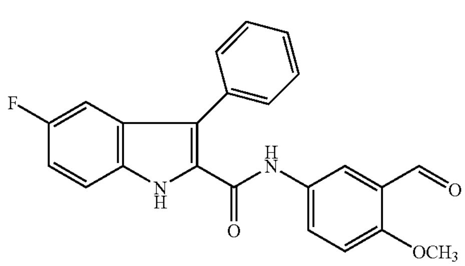 | 388.39 | Oxidation of 2f |

TABLE VI-continued
LIBRARY OF 5-FLUOROINDOLE-2-CARBAXAMIDE COMPOUNDS AND METHOD OF PREPARATION
| Cmpd Code | Structure | M. Wt. | Method of Preparation |
|---|---|---|---|
| 3i | 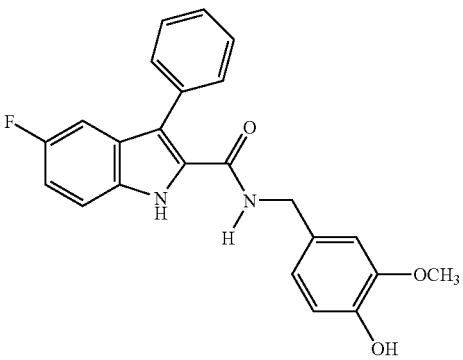 | 390.41 | Amide Coupling Method B |
| 3j | 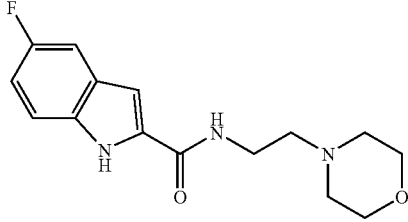 | 291.31 | Amide Coupling Method C |
| 3k | 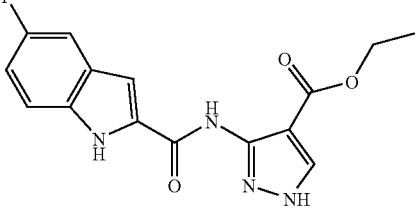 | 316.28 | Amide Coupling Method C |
| 3l | 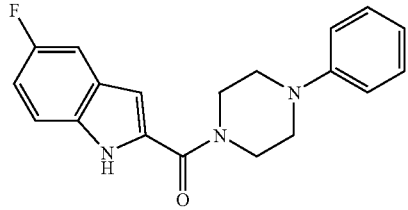 | 323.35 | Amide Coupling Method C |
| 3m | 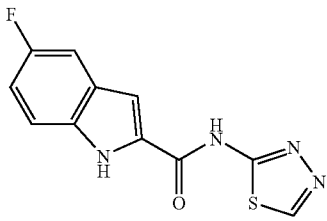 | 262.26 | Amide Coupling Method C |
| 3n | 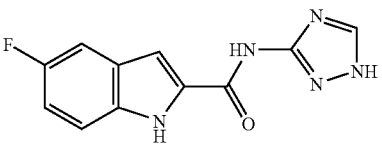 | 245.21 | Amide Coupling Method C |

TABLE VI-continued

LIBRARY OF 5-FLUOROINDOLE-2-CARBAXAMIDE
COMPOUNDS AND METHOD OF PREPARATION

| Cmpd Code | Structure | M. Wt. | Method of Preparation |
|---|---|---|---|
| 3o | | 450.5 | Amide Coupling Method B |
| 3p | | 374.41 | Amide Coupling Method B |
| 3q | | 360.38 | See synthesis of 1a in Example 1 |
| 3r | | 263.3 | Amide Coupling Method D |

TABLE VI-continued

LIBRARY OF 5-FLUOROINDOLE-2-CARBAXAMIDE COMPOUNDS AND METHOD OF PREPARATION

| Cmpd Code | Structure | M. Wt. | Method of Preparation |
|---|---|---|---|
| 3s | 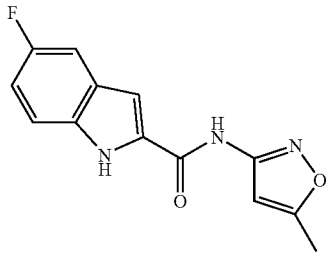 | 259.24 | Amide Coupling Method D |
| 3t | 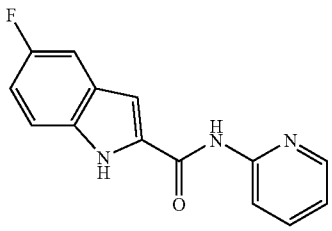 | 255.25 | Amide Coupling Method D |

C. Inhibition of Human Cancer Cell Line H460 and Isolated Src.

Subsequent to synthesis, several of the above compounds were tested for the inhibition of the growth of human lung cancer cell line H460 and the inhibition of isolated Src. To test for inhibition of H460, the cells were seeded at 600 cells/well in 96 well plates in complete medium-RPMI-1640 containing 5% FCS, 5% NuSerum IV, 2 mM L-glutamine, and 10 mM HEPES. Following an overnight incubation, compounds which were solubilized in DMSO and diluted in RPMI-1640, were added to cells plates. After 72 hours, cells were fixed, stained, and total protein/well was determined. Compound concentration which inhibited growth by 50% ($IC_{50}$) was determined and is reported below. To test for inhibition of isolated Src, the compounds were tested using the assay procedure described in Lai et al., 1998, with the following assay components, final concentrations, and conditions: 50.0 mM MOPS, 4.02 mM $MgCl_2$, 6.00 mM $K_3$ citrate (used as a $Mg^{2+}$ buffer to stabilize the free $Mg^{2+}$ at 0.5 mM), 99.0 mM KCl, 10.0 mM 2-mercaptoethanol, 198 μM ADP, 10 U full length human purified recombinant pp60$^{c-src}$ (Upstate Biotechnology Inc., Lake Placid, N.Y.), 2.00 mM RR-SRC, 4.0% DMSO, pH 7.2, 37° C. These overall assay conditions have been shown to reproduce the intracellular conditions of pH, temperature, free $M^{2+}$ (0.5 mM), ionic strength, osmolality, ATP/ADP, and reduction potential. The results are in Table VII, below.

TABLE VII

INHIBITION OF THE GROWTH OF HUMAN LUNG CANCER CELL LINE H460 AND THE INHIBITION OF ISOLATED SRC

| Compound | H460[a] $IC_{50}$ (μM)[b] | Src $IC_{50}$ (μM) |
|---|---|---|
| 1a | 35 ± 0.59 | $IC_{50}$ = 40 |
| 1z | 15 ± 1.6 | NT[c] |
| 1bb | 82 ± 3.5 | NT |

TABLE VII-continued

INHIBITION OF THE GROWTH OF HUMAN LUNG CANCER CELL LINE H460 AND THE INHIBITION OF ISOLATED SRC

| Compound | H460[a] $IC_{50}$ (μM)[b] | Src $IC_{50}$ (μM) |
|---|---|---|
| 1dd | 33 ± 0.78 | NT |
| 1yyy | 104 ± 10 | NT |
| 1cc | 30 ± 0.66 | NT |
| 1cccc | >100 | NT |
| 1oooo | 74 ± 2.7 | NT |
| 2f | 13 ± 0.46 | NT |
| 2s | 26 ± 0.34 | NT |
| 1bbb | >100 | NT |
| 2g | 13 ± 0.56 | NT |
| 3q | 30 ± 0.34 | NT |

[a]H460 - NSCLC cells.
[b]All compounds were solubilized in DMSO and further diluted in RPMI 1640 containing 5% FCS, 5% NuSerum IV, 2 mM L-glutamine, and 20 mM HEPES.
[c]NT = not tested.

These results show that the use of a phenyl group attached to the 3 position of the indole ring can significantly improve the activity of the inhibitor.

D. Inhibition of Epidermal Growth Factor Receptor Tyrosine Kinase (EGFRTK), p56 lck, p55 fyn, and PTP-1B The compounds listed in Table VIII below were tested for inhibition of EGFRTK, a transmembrane receptor tyrosine kinase, p56 lck, a member of the Src family of non-receptor tyrosine kinases, p55 fyn, another member of the Src family of non-receptor tyrosine kinases, and PTP-1B, a phosphotyrosine phosphatase, the opposite of a kinase and a target for type II diabetes and/or obesity. The data in the table are the % inhibition of the indicated enzyme by the compound at a concentration of 10 micromolar. Blanks for a particular enzyme indicate that inhibition was not found.

TABLE VIII

| | | | | | | |
|---|---|---|---|---|---|---|
| Structure | MW | Compound Code | PTP-1B @ 10 μm | EGFRTK @ 10 μm | p56 LcK @ 10 μm | p55fyn @ 10 μm |
| 5-fluoro-N-(1-hydroxypentan-2-yl)-1H-indole-2-carboxamide | 264.3 | 1b | | | | |
| 5-fluoro-N-(1-hydroxy-3-methylbutan-2-yl)-1H-indole-2-carboxamide | 264.3 | 1c | | | | |
| 5-fluoro-N-(1-hydroxypropan-2-yl)-1H-indole-2-carboxamide | 236.2 | 1d | | | | |
| 5-fluoro-N-(2,3-dihydroxypropyl)-1H-indole-2-carboxamide | 252.2 | 1e | | | | |
| 5-fluoro-N-methyl-1H-indole-2-carboxamide | 192.2 | 1f | | | | |
| 5-fluoro-N,N-di-n-propyl-1H-indole-2-carboxamide | 262.3 | 1g | | | | 19 |
| 5-fluoro-N-isobutyl-1H-indole-2-carboxamide | 234.3 | 1h | | | | |
| 5-fluoro-N,N-di-n-butyl-1H-indole-2-carboxamide | 290.4 | 1i | | | | |
| 5-fluoro-N-(3-fluorophenyl)-1H-indole-2-carboxamide | 272.3 | 1j | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 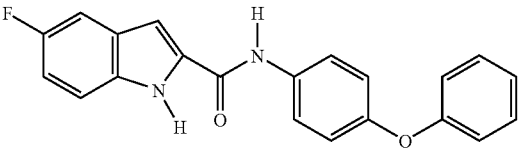 | 346.4 | 1k | | | | 13 |
| 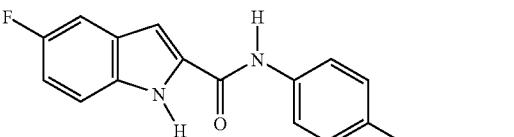 | 284.3 | 1l | | | | |
| 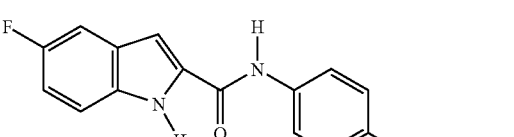 | 270.3 | 1m | | | | |
| 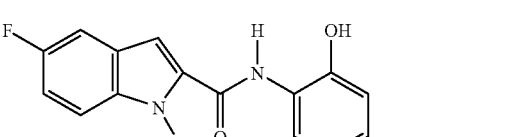 | 270.3 | 1n | | | | 12 |
| 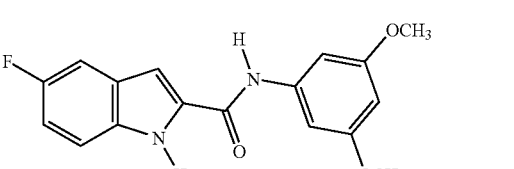 | 314.3 | 1o | | | | |
| 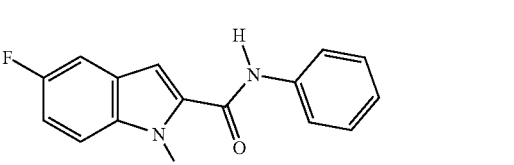 | 254.3 | 1p | | | | |
| 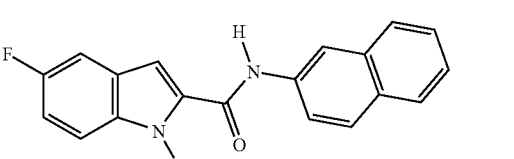 | 304.3 | 1q | | | | |
| 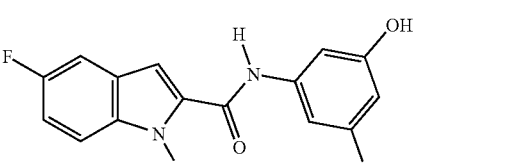 | 286.3 | 1r | | | | 11 |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 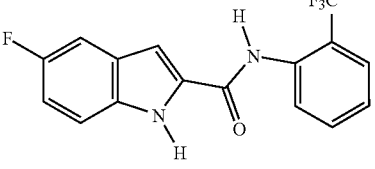 | 322.3 | 1s | | | | |
| 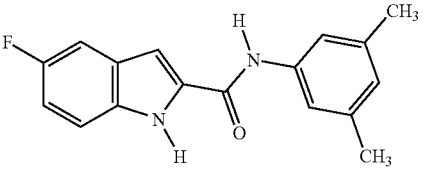 | 282.3 | 1t | | | | 11 |
| 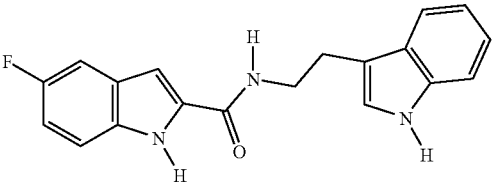 | 321.4 | 1u | | | | 10 |
| 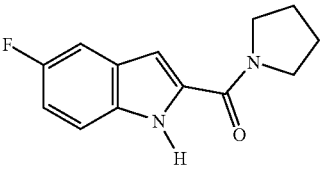 | 232.3 | 1v | | | | |
| 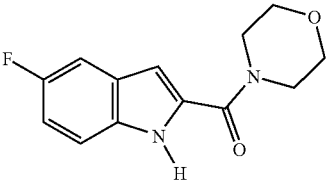 | 248.3 | 1w | | | | 10 |
| 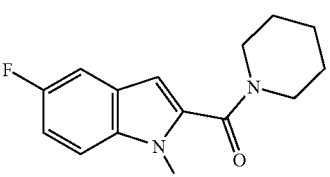 | 246.3 | 1x | | | | |
| 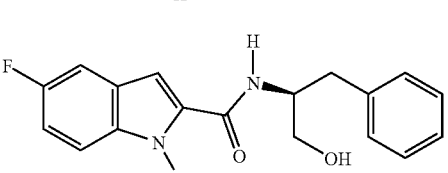 | 312.3 | 1y | | | | |
| 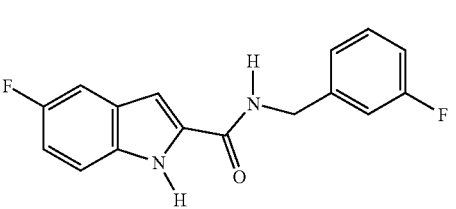 | 286.3 | 1z | | 26 | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| 5-fluoro-1H-indole-2-carboxamide, N-[(1R)-1-(3-methoxyphenyl)ethyl] | 312.3 | 1aa | | 12 | | 10 |
| 5-fluoro-N-benzyl-1H-indole-2-carboxamide | 268.3 | 1bb | | 19 | | |
| 5-fluoro-N-(2-hydroxy-1,2-diphenylethyl)-1H-indole-2-carboxamide | 374.4 | 1cc | | 19 | | |
| 5-fluoro-N-(2-hydroxy-1,2-diphenylethyl)-1H-indole-2-carboxamide (diastereomer) | 374.4 | 1dd | | 41 | | |
| 5-fluoro-N-(4-methoxybenzyl)-1H-indole-2-carboxamide | 298.3 | 1ee | | 16 | | |
| 5-fluoro-N-(3-iodobenzyl)-1H-indole-2-carboxamide | 394.2 | 1ff | | 24 | | |
| 5-fluoro-N-(2-phenylethyl)-1H-indole-2-carboxamide | 282.3 | 1gg | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 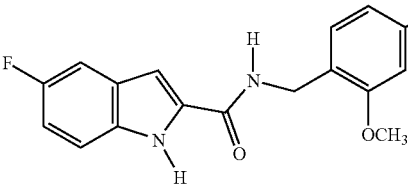 | 328.3 | 1hh | | | | |
| 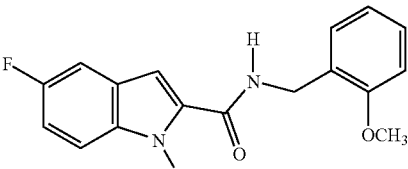 | 298.3 | 1ii | | | | |
| 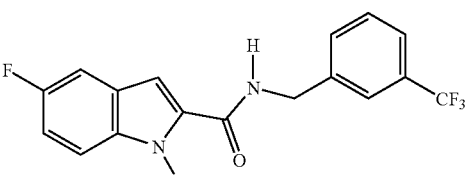 | 336.3 | 1jj | | | | 18 |
| 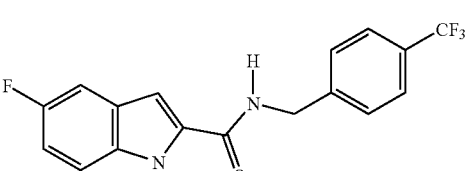 | 336.3 | 1kk | | | | |
| 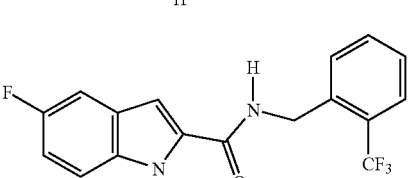 | 336.3 | 1ll | | | | |
| 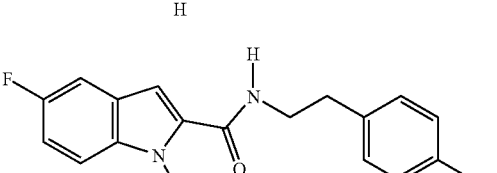 | 298.3 | 1mm | | | | |
| 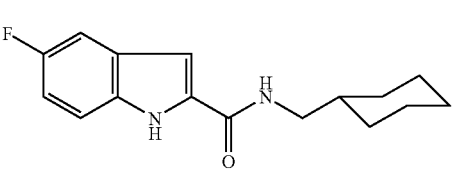 | 274.3 | 1nn | | | | |
| 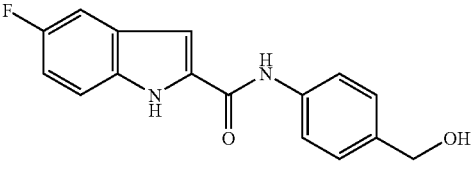 | 284.3 | 1oo | | | | 17 |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 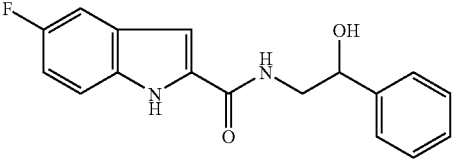 | 298.3 | 1pp | | | | |
| 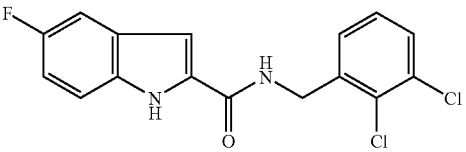 | 337.2 | 1qq | | | | |
| 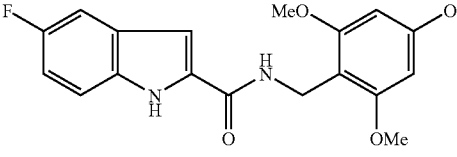 | 358.4 | 1rr | | | 12 | |
| 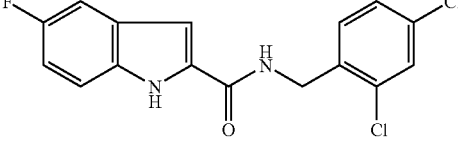 | 337.2 | 1ss | 12 | | | |
| 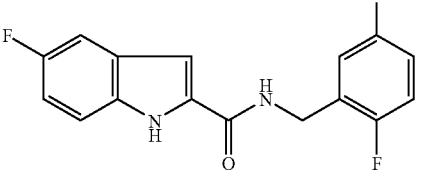 | 304.3 | 1tt | | | | |
| 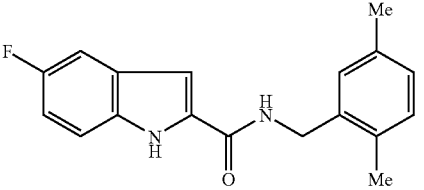 | 296.3 | 1uu | | | | |
| 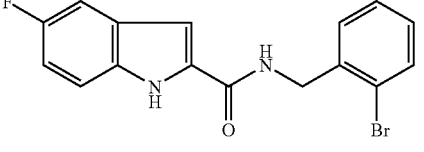 | 347.2 | 1vv | | | | |
| 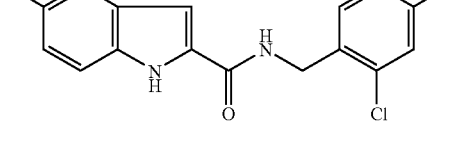 | 320.7 | 1ww | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 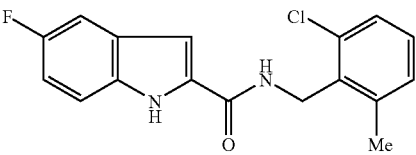 | 316.8 | 1xx | | | | 14 |
| 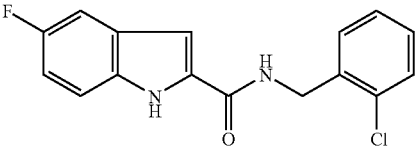 | 302.7 | 1yy | 10 | | | 12 |
| 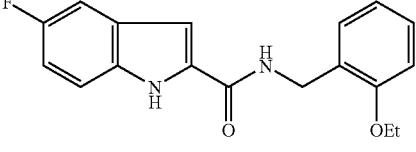 | 312.3 | 1zz | | | | |
| 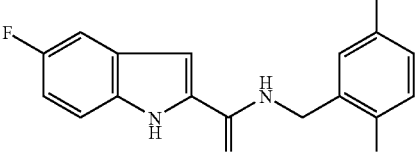 | 354.3 | 1aaa | 12 | | | |
| 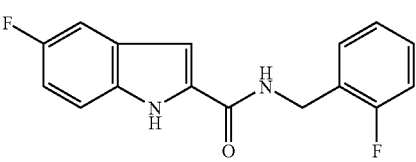 | 286.3 | 1bbb | | | | |
| 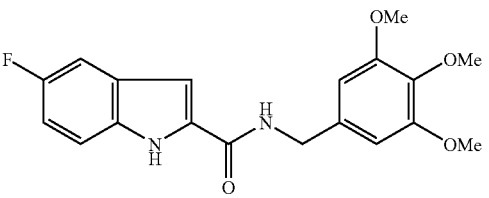 | 358.4 | 1ccc | | | | |
| 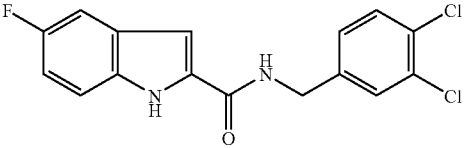 | 337.2 | 1ddd | | | | |
| 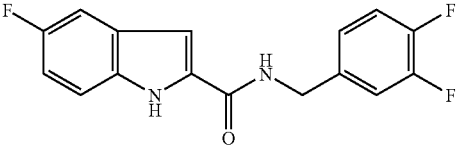 | 304.3 | 1eee | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 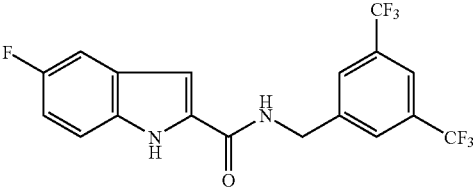 | 404.3 | 1fff | | | | |
| 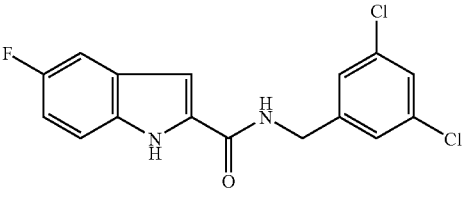 | 337.2 | 1ggg | | | | |
| 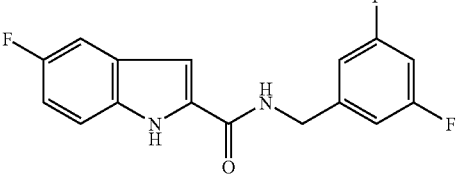 | 304.3 | 1hhh | | | | |
| 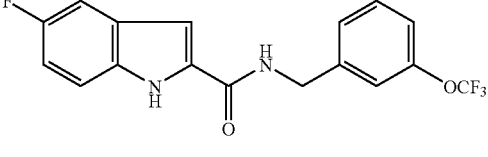 | 352.3 | 1iii | | | | |
| 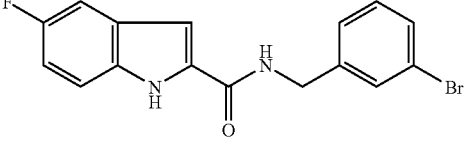 | 347.2 | 1jjj | | | | |
| 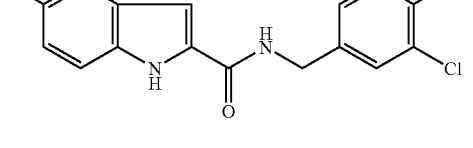 | 320.7 | 1kkk | | | | |
| 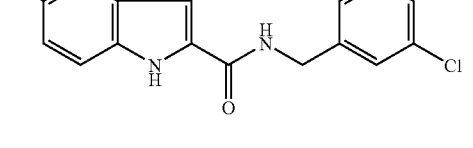 | 302.7 | 1lll | | | | |
| 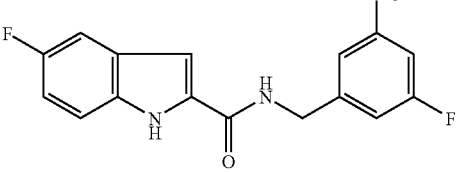 | 354.3 | 1mmm | | | | 14 |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 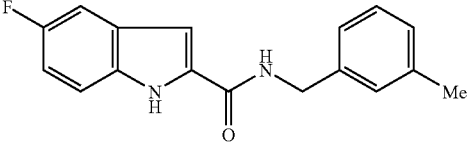 | 282.3 | 1nnn | | | | |
| 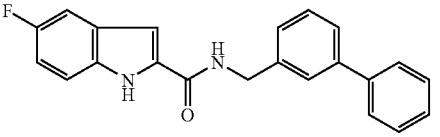 | 344.4 | 1ooo | | | | |
| 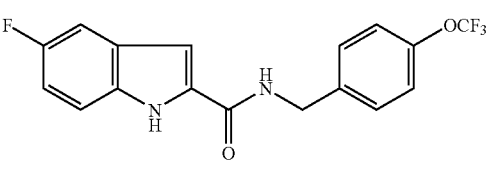 | 352.3 | 1ppp | | | | |
| 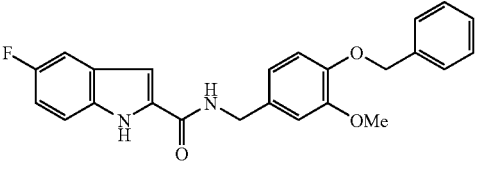 | 404.4 | 1qqq | | | | 11 |
| 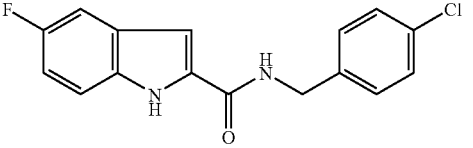 | 302.7 | 1rrr | | | | 15 |
| 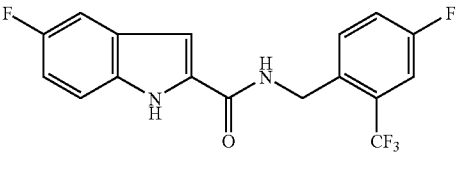 | 354.3 | 1sss | | | | |
| 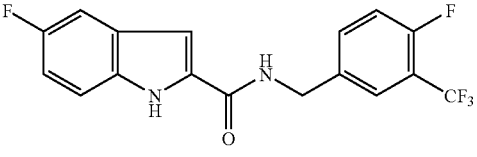 | 354.3 | 1ttt | | | | |
| 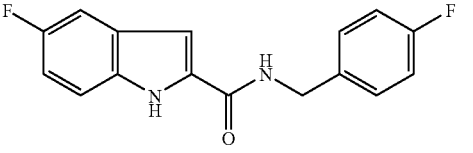 | 286.3 | 1uuu | 13 | | | 16 |
| 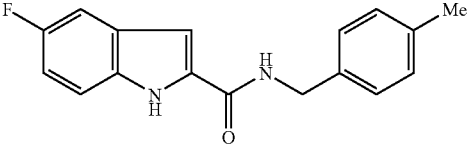 | 282.3 | 1vvv | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| 5-F-indole-2-carboxamide-N-CH2-(5-Br-2-F-phenyl) | 365.2 | 1www | | | | |
| 5-F-indole-2-carboxamide-NH-(2-CH2OH-phenyl) | 284.3 | 1xxx | 12 | | | |
| 5-F-indole-2-carboxamide-NH-(3-CH2OH-phenyl) | 284.3 | 1yyy | | 11 | | |
| 5-F-indole-2-carboxamide-NH-(3-OH-phenyl) | 270.3 | 1zzz | | | | |
| 5-F-indole-2-carboxamide-NH-(3-CH2OH-4-O-propyl-phenyl) | 342.4 | 1aaaa | | | | |
| 5-F-indole-2-carboxamide-NH-(3-CH2OH-4-OBn-phenyl) | 390.4 | 1bbbb | | | | |
| 5-F-indole-2-carboxamide-NH-(3-CH2OH-4-OCH3-phenyl) | 314.3 | 1cccc | 20 | 19 | | |
| 5-F-indole-2-carboxamide-NH-CH2-(3-OH-5-OBn-phenyl) | 390.4 | 1dddd | 16 | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| 5-F-indole-2-carboxamide-N-CH2-(2,5-dimethoxyphenyl) | 328.3 | 1eeee | | | | |
| 5-F-indole-2-carboxamide-N-CH2-(2-methylphenyl) | | 1ffff | | 12 | | |
| 5-F-indole-2-carboxamide-N-CH2-(3,4-dihydroxyphenyl) | 300.3 | 1gggg | | | 25 | |
| 5-F-indole-2-carboxamide-N-CH2-(3,5-dimethoxyphenyl) | 328.3 | 1hhhh | 17 | | | |
| 5-F-indole-2-carboxamide-N-CH2-(3,5-dibenzyloxyphenyl) | 480.5 | 1iiii | | 12 | | |
| 5-F-indole-2-carboxamide-N-CH2-(4-benzyloxy-3-hydroxyphenyl) | 390.4 | 1jjjj | 15 | | | |
| 5-F-indole-2-carboxamide-N-CH2-(4-bromophenyl) | 347.2 | 1kkkk | | | 30 | |
| 5-F-indole-2-carboxamide-N-CH2-(4-hydroxy-3-methoxyphenyl) | 314.3 | 1llll | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| F-indole-C(O)NH-CH2-C6H4-NO2 | 313.3 | 1mmmm | | | | 29 |
| F-indole-C(O)NH-CH2-C6H3(OH)(OPr) | 342.4 | 1nnnn | | 17 | | 11 |
| F-indole-C(O)NH-CH2-C6H4-OOH | 298.3 | 1oooo | | 33 | 10 | |
| F-indole-C(O)NH-CH2-C6H4-CH2OH | 298.3 | 1pppp | | | | |
| F-indole-C(O)NH-(CH2)5-OH | 278.3 | 1qqqq | | 18 | | |
| F-(3-Ph)indole-C(O)NH-(CH2)5-OH | 354.4 | 2a | | | | |
| F-(3-Ph)indole-C(O)NH-CH2-C6H10-OH | 366.4 | 2b | | 19 | | 13 |
| F-(3-Ph)indole-C(O)NH-C6H4-CH2OH | 360.4 | 2c | | | | |

… TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| 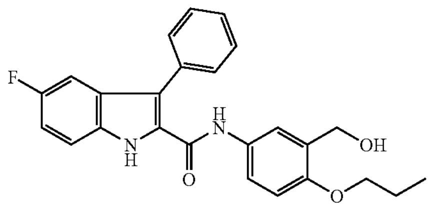 | 418.5 | 2d |  | 23 |  |  |
| 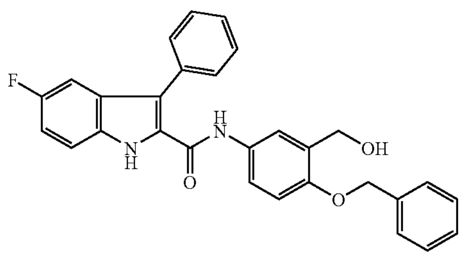 | 466.5 | 2e |  | 10 |  |  |
| 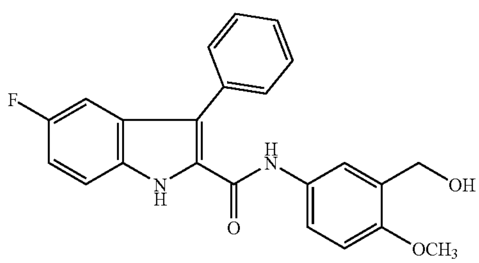 | 390.4 | 2f |  | 18 |  | 11 |
| 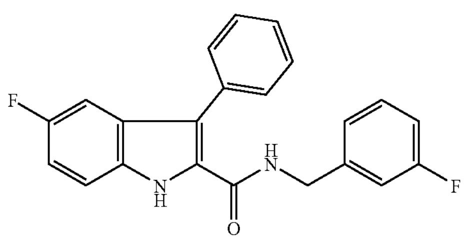 | 362.4 | 2g |  |  |  |  |
| 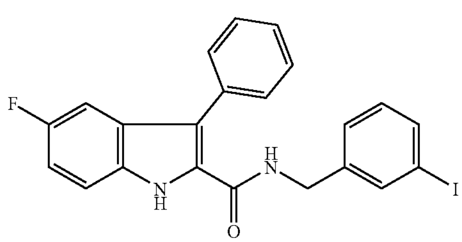 | 470.3 | 2h |  |  |  |  |
| 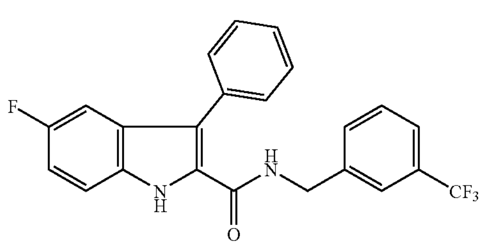 | 412.4 | 2i |  |  |  |  |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| [5-fluoro-3-phenyl-1H-indole-2-carboxamide, N-(4-trifluoromethylbenzyl)] | 412.4 | 2j | | 20 | | |
| [5-fluoro-3-phenyl-1H-indole-2-carboxamide, N-(3-benzyloxy-5-hydroxybenzyl)] | 466.5 | 2k | | | | |
| [5-fluoro-3-phenyl-1H-indole-2-carboxamide, N-(2,3-dichlorobenzyl)] | 413.3 | 2l | | | | |
| [5-fluoro-3-phenyl-1H-indole-2-carboxamide, N-(2,4,6-trimethoxybenzyl)] | 434.5 | 2m | | | | |

TABLE VIII-continued
INHIBITION OF EGFRPTK, p56 lck, p55 fyn, and PTP-1B
| Structure | MW | Compound Code | PTP-1B @ 10 μm | EGFRTK @ 10 μm | p56 LcK @ 10 μm | p55fyn @ 10 μm |
|---|---|---|---|---|---|---|
| 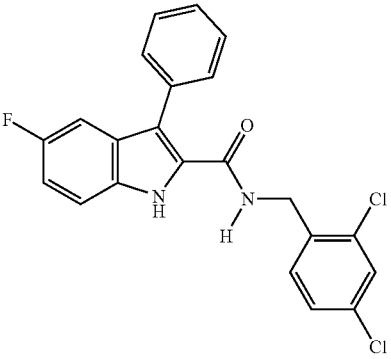 | 413.3 | 2n | | | | |
| 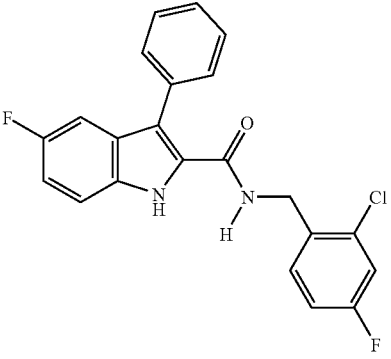 | 396.8 | 2o | | | | 12 |
| 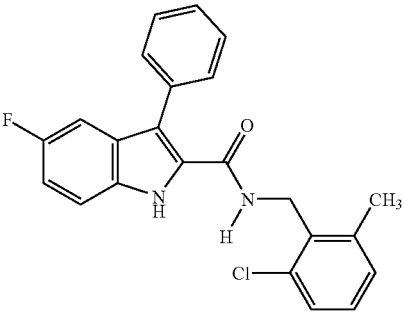 | 392.9 | 2p | | | | |
| 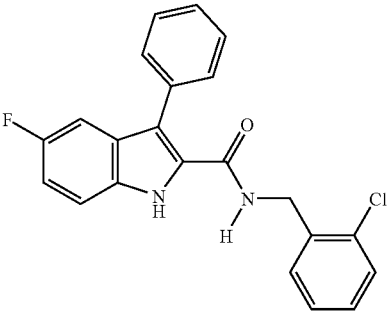 | 378.8 | 2q | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| (5-fluoro-3-phenyl-1H-indole-2-carboxylic acid (2-fluoro-5-trifluoromethyl-benzyl)amide) | 430.4 | 2r | | | | |
| (5-fluoro-3-phenyl-1H-indole-2-carboxylic acid 2-fluorobenzylamide) | 362.4 | 2s | 33 | 10 | 11 | |
| (5-fluoro-3-phenyl-1H-indole-2-carboxylic acid 3,4,5-trimethoxybenzylamide) | 434.5 | 2t | | | | |
| (5-fluoro-3-phenyl-1H-indole-2-carboxylic acid 3,4-dichlorobenzylamide) | 413.3 | 2u | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
|  | 380.4 | 2v |  |  |  |  |
| 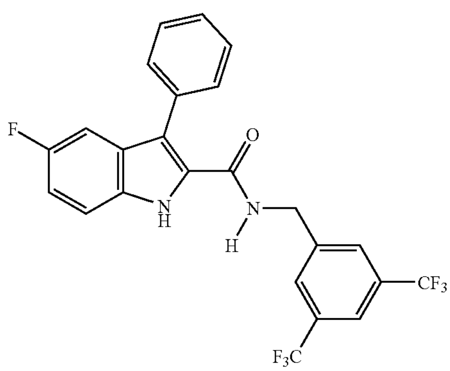 | 480.4 | 2w | 12 |  |  |  |
| 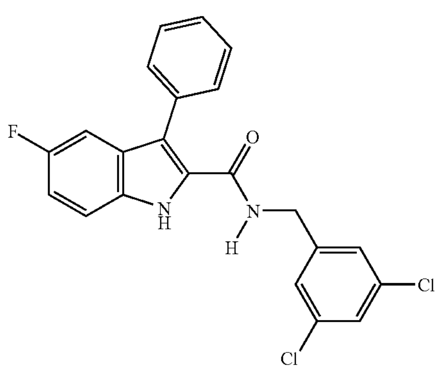 | 413.3 | 2x |  |  |  |  |
|  | 380.4 | 2y |  | 20 |  |  |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| (5-fluoro-3-phenyl-1H-indole-2-carboxamide, N-(3,5-dimethoxybenzyl)) | 404.4 | 2z | | | | |
| (5-fluoro-3-phenyl-1H-indole-2-carboxamide, N-(3-trifluoromethoxybenzyl)) | 428.4 | 2aa | | | | |
| (5-fluoro-3-phenyl-1H-indole-2-carboxamide, N-(3-chlorobenzyl)) | 378.8 | 2bb | | | | |
| (5-fluoro-3-phenyl-1H-indole-2-carboxamide, N-(3-fluoro-5-trifluoromethylbenzyl)) | 430.4 | 2cc | | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| 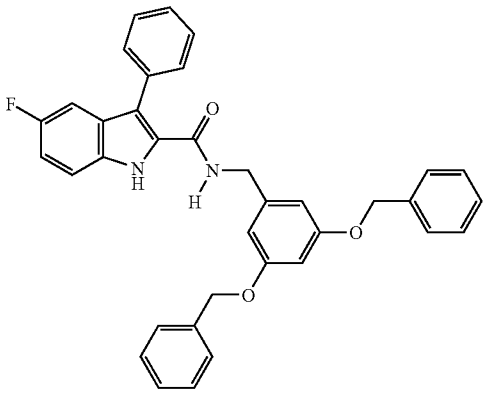 | 556.6 | 2dd | | | | |
| 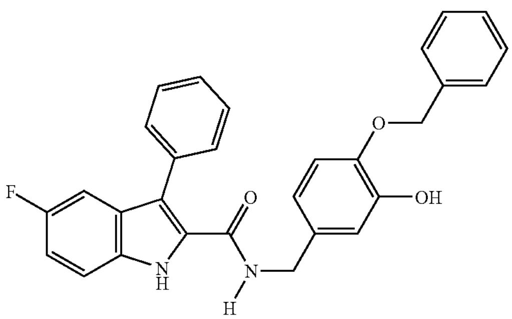 | 466.5 | 2ee | | | | |
| 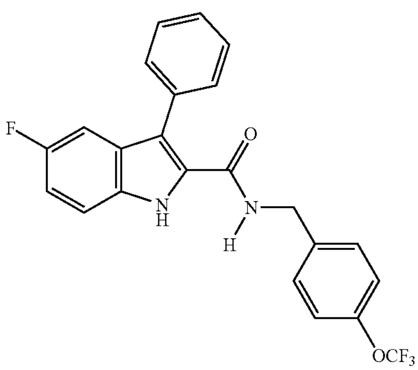 | 428.4 | 2ff | | | | |
| 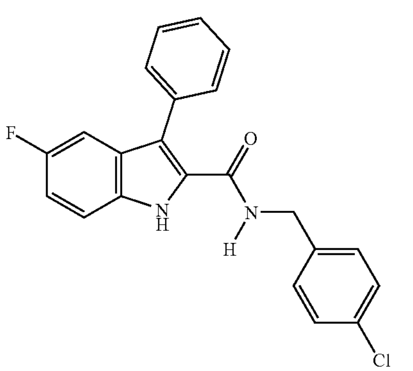 | 378.8 | 2gg | 12 | | | |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| | 430.4 | 2hh | | 12 | | |
| | 430.4 | 2ii | | | | |
| 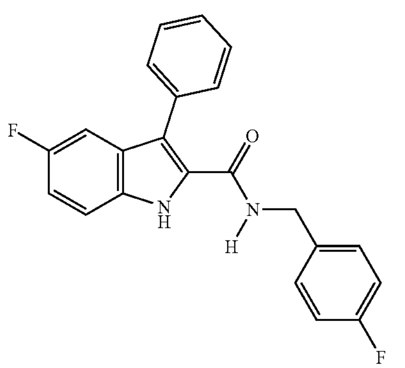 | 362.4 | 2jj | | | | |
| 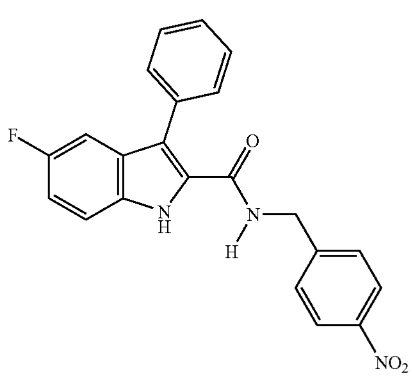 | 389.4 | 2kk | | | | 24 |

TABLE VIII-continued

INHIBITION OF EGFRPTK, p56 lck, p55 fyn, and PTP-1B

| Structure | MW | Compound Code | PTP-1B @ 10 μm | EGFRTK @ 10 μm | p56 LcK @ 10 μm | p55fyn @ 10 μm |
|---|---|---|---|---|---|---|
| 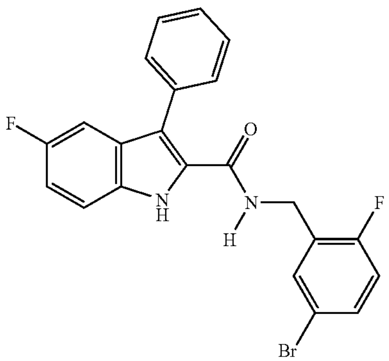 | 441.3 | 2ll | | 10 | | |
| 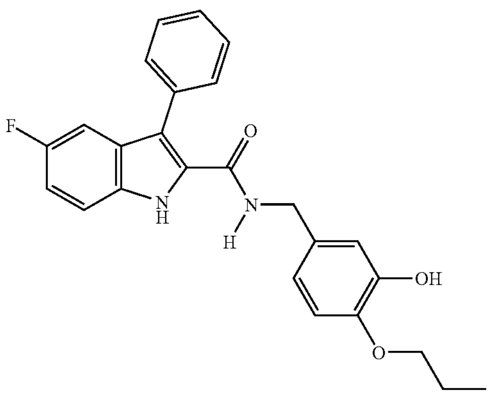 | 418.5 | 2mm | | | | |
| | 374.4 | 2nn | | | | |
| | 374.4 | 2oo | | | | |

E. Mice Toxicity Study

Figure 15:
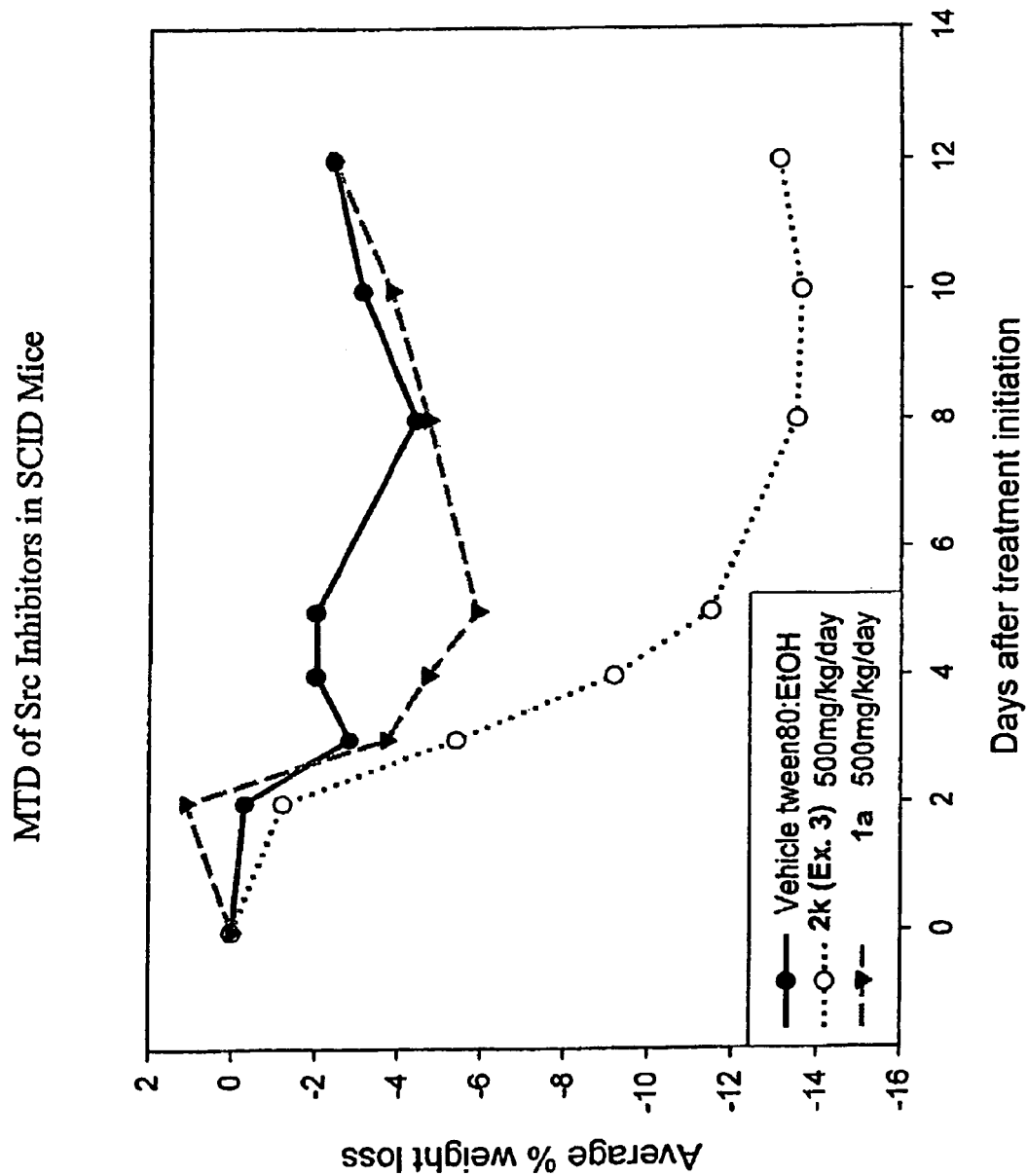
FIG. 15 is a graph showing the maximum tolerated dose (MTD) of two Src inhibitors (1a from Example 1 and 2k from Example 4) in SCID mice.

FIG. 15 shows the results of a maximum tolerated dose (MTD) study with two indole inhibitors:

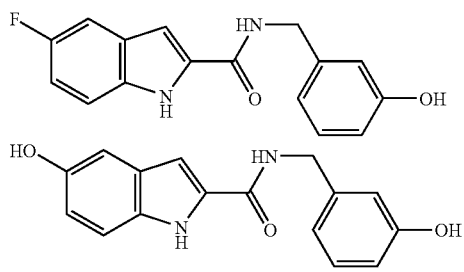

2k from Example 4

These compounds were administered to SCID mice by intraperitoneal administration in tween80:EtOH. The results in FIG. 17 show that compound 1a is less toxic in mice than compound 2k from Example 4, since the mice exhibited less weight loss when compound 1a was administered.

Example 2

Synthesis and Activity of 7-Substituted Indole Derivative Protein Kinase Inhibitors 7-substituted indole derivative protein kinase inhibitors were synthesized as set forth in Scheme 1, below:

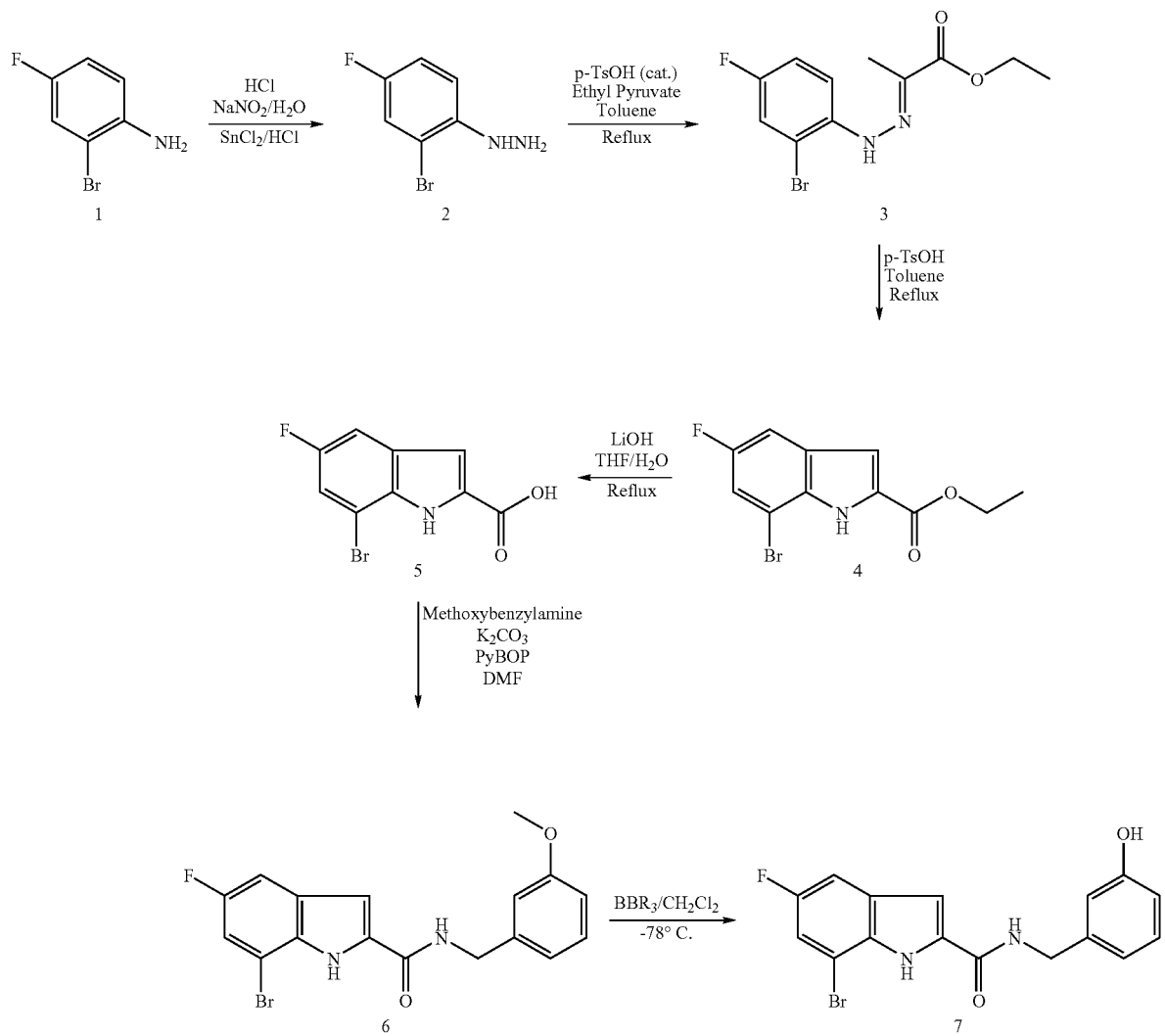

(2-bromo-4-fluoro-phenyl)-hydrazine (2)

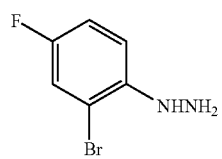

Commercially available 2-bromo-4-fluoroaniline 1 (2.36 ml, 20.75 mmol) was added to a stirring solution of concentrated hydrochloric acid (40 ml) that was cooled to −5° C. This solution was allowed to age while stirring for 10 minutes. An aqueous solution of $NaNO_2$ was added over 15 minutes. $SnCl_2$/HCl (10.40 g, 46.1 mmol, 10 ml HCl) was added over 15 minutes and aged for an additional 30 minutes to 1 hour. The mixture was filtered and washed with dichloromethane. The resulting solid was dissolved in 1.0M HCl and extracted 3 times with dichloromethane. The organic layer was vacuum dried overnight to give 3.53 g (83% yield). $^1$H NMR (400 MHz, $CDCl_3$): δ7.169 (dd, J=8 Hz, J=2.8 Hz 1H), δ 7.076 (dd, J=5.2 Hz, J=9.2 Hz, 1H), δ6.982 (td, J=8.4 Hz, J=2 Hz 1H), δ5.540 (bs, 1H), δ 3.590 (bs, 1H).

2-[(2-bromo-4-fluoro-phenyl)-hydrazono]-propionic acid ethyl ester (3)

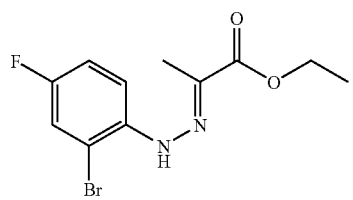

Commercially available p-toluensulfonic acid (38.37 mg, 0.217 mmol) was added to 60 ml of toluene in a round bottom flask and magnetic stir bean. The flask was then fitted with a Dean Stark trap and reflux condenser. The solution was then allowed to stir for 2 hours. After 2 hours, the solution was cooled and 2-(bromo-4-phenyl)hydrazine (4.135 g, 20.17 mmol) was added. The solution was then refluxed for an additional 1.5 hours using the same apparatus. After 1.5 hours, the solution was placed on the rotary evaporator to remove the toluene. A dark brown tar-like substance was left in the flask. An appropriate amount of hexanes were added to the flask and refluxed to dissolve the pure hydrazine. The hexanes took on a yellow color and were then decanted hot into another flask leaving the tar-like side product behind. This was repeated. The flask containing the hexane solution was refluxed so as to dissolve the precipitating hydrazine and placed in the freezer to form crystals. 3.6 g (11.9 mmol, 87% yield) of 3. $^1$H NMR (Acetone-$d_6$): δ 12.369 (bs, 1H), δ 7.646 (dd, J=9.2 Hz, J=5.6 Hz 1H), δ 7.449 (dd, J=8.2 Hz, J=2.8 Hz 1H), δ 7.22 (td, J=~8.6 Hz, J=2.8 Hz, 1H), δ 4.37 (q, J=7.2 Hz, 2H), δ 2.203 (s, 3H), δ 1.402 (t, J=7.2 Hz, 3H).

7-bromo-5-fluoro-1H-indole-2-carboxylic acid ethyl ester (4)

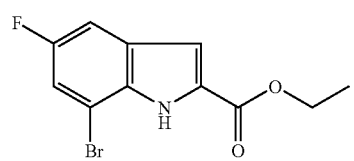

Commercially available p-toluensulfonic acid dihydrate (2.26 g, 11.9 mmol) was added to 120 ml of toluene and dried under reflux using a Dean Stark apparatus for 2 hours. 2-[(2-bromo-4-fluoro-phenyl)-hydrazono]-propionic acid ethyl ester (3.6 g, 11.9 mmol), was added to the cooled solution, and refluxed for an additional 1.5 hours. After 1.5 hours the solution was cooled. The toluene was removed under reduced pressure. Then the solid was refluxed with hexane to isolate the indole ester. The resulting hexane solution was refluxed to dissolve the precipitating indole, and placed in the freezer for crystallization. After removal of supernatant and drying of crystals gave 3.30 g, 11.543 mmol of 4 (97% yield). $^1$H NMR (400 MHz, Acetone-$d_6$): δ 10.85 (bs, 1H), δ 7.45 (dd, J=9.2 Hz, J=2.4 Hz, 1H), δ 7.39 (dd, J=9.2 Hz, J=2.0 Hz, 1H), δ 7.28 (d, J=2.0 Hz, 1H), δ 4.36 (q, J=6.8 Hz, 2H), δ 1.345 (t, J=6.8 Hz, 1H).

7-bromo-5-fluoro-1H-indole-2-carboxylic acid (5)

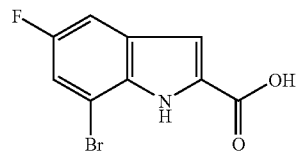

Tetrahydrofuran (35.2 ml), water (23.5 ml), lithium hydroxide (2.61 g, 10.9 mmol), and 7-bromo-5-fluoro-1H-indole-2-carboxylic acid ethyl ester (3.1 µg, 10.9 mmol) were added to a round bottom flask and mixed with a magnetic stirrer. This mixture was refluxed for 1 hour. The THF was removed via rotary evaporator, and the aqueous solution was acidified with 1M HCL, and extracted with ethyl acetate. $^1$H NMR (DMSO-$d_6$): δ 13.206 (bs, 1H), δ 11.876 (s, 1H), δ 7.498-7.445 (m, 2H), δ 7.19 (d, J=2.0 Hz, 1.0H).

7-bromo-5-fluoro-1H-indole-2-carboxylic acid 3-methoxy-benzylamide (6)

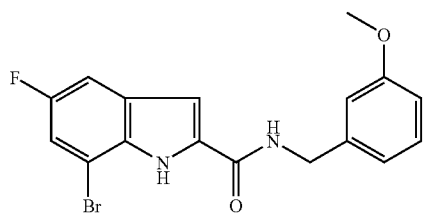

To a round bottom flask that has been fire dried, flushed with a continuous stream of argon, and equipped with a stir bean, DMF (4.8 ml) was added. To this stirring solution 5

(600 mg, 2.33 mmol), was combined with methoxybenzylamine (328 μL, 2.56 mmol), and PyBOP (1.33 g, 2.56 mmol). This solution was then cooled to a temperature of 0 degrees C. After 2 minutes diisopropylamine (1.7 ml, 9.67 mmol) was added and the entire solution was allowed to stir at room temperature overnight. The reaction was then diluted with roughly 60 ml of ethyl acetate and extracted 3× with saturated sodium bicarbonate, and 3× with 1M HCl in appropriate volumes to remove any unreacted starting materials. The ethyl acetate layer was isolated and dried over sodium sulfate. The ethyl acetate was removed using a rotary evaporator to yield a brownish film on the sides of the flask. Hexanes were added to the flask and refluxed. A solid then formed on the sides of the flask, and the hexanes were removed via rotary evaporator to give 709.0 mg of 6 (81% yield). $^1$H NMR (400 MHz, DMSO-$d_6$) δ 11.537 (bs, 1H), δ 9.092 (t, J=5.6 Hz, 1H), δ 7.49 (dd, J=9.4 Hz, J=2.4 Hz 1H), δ (dd, J=8.8 Hz, J=2 Hz 1H), δ 7.268-7.228 (m, 2H), δ 6.91 (d, J=6.8 Hz, 2H), δ 6.82 (d, J=8.2 Hz, 1H), δ 4.48 (d, J=6 Hz, 2H), δ 3.729 (s, 3H).

7-bromo-5-fluoro-1H-indole-2-carboxylic acid 3-hydroxy-benzylamide (7)

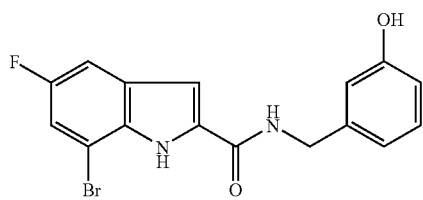

A stirring solution of methylene chloride (1 ml) was cooled to −78 degrees in a dry ice acetone bath and flushed with a stream of argon. To this cold stirring solution 6 (50 mg, 0.133 mmol) was added. 7 equivalents of BBr$_3$ was added and allowed to stir at −78 degrees for 1 hour, and then the solution was allowed to stir at room temperature overnight. The reaction was then quenched with excess water, then neutralized with saturated sodium bicarbonate, and extracted with methylene chloride. The methylene chloride layer was dried over sodium sulfate and removed under reduced pressure to yield 35.0 mg of 2 (70% yield). $^1$H NMR (400 MHz, Acetone-$d_6$) δ 10.633 (bs, 1H), δ 8.42 (d, J=15.6, 2H), 7.48 (dd, J=9.2 Hz, J=2.4 Hz, 1H), δ 7.42 (dd, J=9 Hz, J=2.4 Hz, 1H), δ 7.373 (d, J=2.4 Hz, 1H), δ 7.217 (t, J=7.6 Hz, 1H), δ 6.932-6.898 (m, 2H), δ 6.80 (dd, J=2 Hz, J=8 Hz, 1H), δ 4.634 (d, J=5.6 Hz, 2H). Disappearance of the characteristic methoxy peak at 3.7 ppm indicates a successful deprotection.

Example 3

Design, Synthesis and Activity of Non-ATP Competitive Hydroxynaphthalene Derivative Inhibitors of pp60$^{c-Src}$ Tyrosine Kinase The crystal structure of the autoinhibited human IRTK catalytic domain (Hubbard et al., 1994) was used to carry out qualitative molecular modeling studies (SYBYL™, 6.4, Tripos Inc., St. Louis) wherein a naphthalene ring was superimposed upon the IRTK Tyr 1,162. The IRTK region containing Tyr 1,162 folds back into the active site, with Tyr 1,162 positioned analogous to a phosphorylatable Tyr in a peptide substrate, thereby autoinhibiting the tyrosine kinase. This superimposition indicated that an amide carbonyl should be placed at the 2-position (Scheme 1) of the

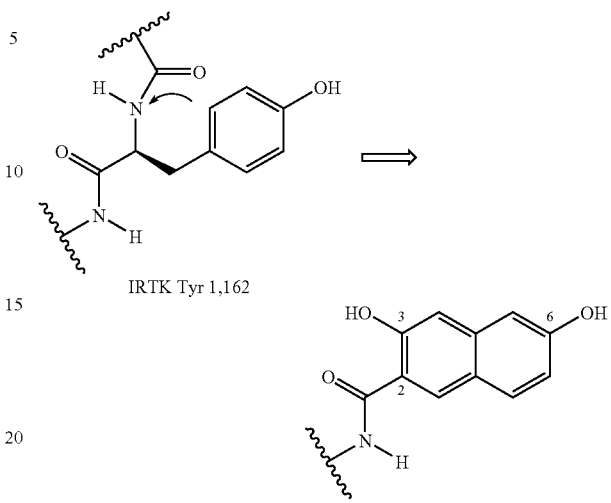

Scheme 1 naphthalene ring to mimic the Tyr 1,162 carbonyl and a hydroxyl group should be positioned at the 6-position to mimic the Tyr 1,162 hydroxyl group. These modeling studies also indicated that a hydroxyl group at the 3-position could mimic the Tyr 1,162 NH.

In order to test these design concepts experimentally, the 2-position carbonyl group was appended as either a methyl ester or as a series of amides (Table IX). The hydroxy N-phenyl (X=0) and N-benzyl (X=1) amides were chosen based upon the increase in pp60$^{c-src}$ inhibitor potency observed with iminochromene analogs containing appended hydroxy N-phenyl amide side-chains (Huang et al., 1995). Analogs wherein the 6-hydroxyl group was either deleted or moved were also prepared to determine if a drop in potency occurs as predicted from the modeling studies.

The series of 2-carbonyl-3,5-dihydroxy naphthalene inhibitors (1a, 2a-2d, 2i-2l, 2o-2p) and 2-carbonyl-3,7-dihydroxy naphthalene inhibitors (1c, 2t-2u) were synthesized from commercially available (Aldrich) 3,5-dihydroxy-2-naphthoic acid and 3,7-dihydroxy-2-naphthoic acid, respectively. The methyl esters 1a and 1c were obtained by refluxing the respective acid starting materials for 48 h in methanol pre-saturated with HCl gas. The amides (2a-2d, 2i-2l, 2o-2p, 2t-2u) were synthesized by coupling the respective carboxylic acid with commercially available (Aldrich or Lancaster) amines using one of two methods. The first method utilized the NBS/PPh$_3$ methodology as described by Froyen (Froyen, 1997). The second method utilized IIDQ (Aldrich) as the coupling reagent. The carboxylic acid was first reacted with 1.0 eq. IIDQ in anhydrous DMF at room temperature for 24 hours. The respective amine (2.0 eq.) was then added neat and the reaction was heated to 80° C. for 2-6 hours. After aqueous workup, purification was achieved by silica gel chromatography and precipitation from CH$_2$Cl$_2$/hexane, followed by preparative C-18 RP-HPLC (CH$_3$CN/H$_2$O), if necessary. The benzyl amines were commercially available only as their corresponding hydroxyl protected methyl ethers. Consequently, after amide formation, the hydroxyl groups were deprotected by treatment with 6 eq. BBr$_3$ in DCM for 1 minute at −78° C. followed by 1 hour at room temperature.

TABLE IX pp60[c-src] INHIBITORY ACTIVITY OF HYDROXYNAPHTHALENE
DERIVATIVES AND SELECT PUBLISHED INHIBITORS.[a,b,c]

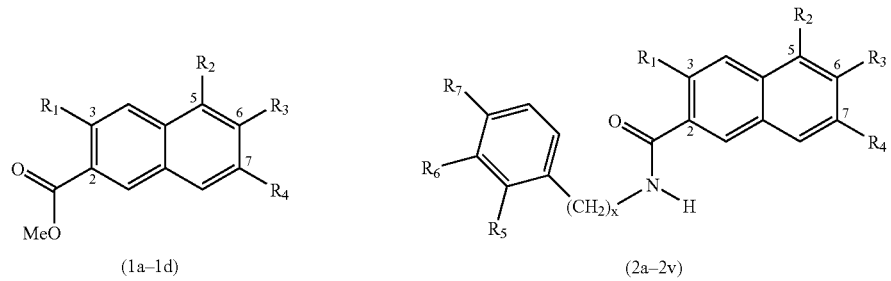

(1a–1d)    (2a–2v)

| Cmpd | $R_1$ | $R_2$ | $R_3$ | $R_4$ | $R_5$ | $R_6$ | $R_7$ | $R_8$ | % Inhibition at 100 μM (std. dev.) | $IC_{50}$ (μM) |
|---|---|---|---|---|---|---|---|---|---|---|
| 1a | OH | OH | H | H | N/A | N/A | N/A | N/A | 5 (+/−2) | n.t. |
| 1b | OH | H | OH | H | N/A | N/A | N/A | N/A | 47 (+/−3) | n.t. |
| 1c | OH | H | H | OH | N/A | N/A | N/A | N/A | 19 (+/−6) | n.t. |
| 1d | $NH_2$ | H | H | H | N/A | N/A | N/A | N/A | Inactive | n.t. |
| 2a | OH | OH | H | H | OH | H | H | 0 | 12 (+/−4) | n.t. |
| 2b | OH | OH | H | H | H | OH | H | 0 | 51 (+/−1) | 150 |
| 2c | OH | OH | H | H | H | H | OH | 0 | 60 (+/−7) | n.t. |
| 2d | OH | OH | H | H | OH | H | OH | 0 | 14 (+/−2) | n.t. |
| 2e | OH | H | OH | H | OH | H | H | 0 | 39 (+/−5) | n.t. |
| 2f | OH | H | OH | H | H | OH | H | 0 | 89 (+/−1) | 16 |
| 2g | OH | H | OH | H | H | H | OH | 0 | 23 (+/−5) | n.t. |
| 2h | OH | H | OH | H | OH | H | OH | 0 | 56 (+/−1) | n.t. |
| 2i | OH | OH | H | H | H | OMe | H | 0 | 33 (+/−5) | n.t. |
| 2j | OH | OH | H | H | H | H | OMe | 0 | 35 (+/−8) | n.t. |
| 2k | OH | OH | H | H | OMe | H | H | 1 | 13 (+/−3) | n.t. |
| 2l | OH | OH | H | H | H | H | OMe | 1 | 14 (+/−2) | n.t. |
| 2m | OH | H | OH | H | OMe | H | H | 1 | inactive | n.t. |
| 2n | OH | H | OH | H | H | H | OMe | 1 | 4 (+/−7) | n.t. |
| 2o | OH | OH | H | H | OH | H | H | 1 | 41 (+/−2) | n.t. |
| 2p | OH | OH | H | H | H | H | OH | 1 | 49 (+/−4) | n.t. |
| 2q | OH | H | OH | H | OH | H | H | 1 | 42 (+/−2) | n.t. |
| 2r | OH | H | OH | H | H | OH | H | 1 | 55 (+/−3) | n.t. |
| 2s | OH | H | OH | H | H | H | OH | 1 | 42 (+/−3) | n.t. |
| 2t | OH | H | H | OH | H | OH | H | 0 | 68 (+/−5) | n.t. |
| 2u | OH | H | H | OH | H | OH | H | 1 | 40 (+/−3) | n.t. |
| 2v | H | H | OH | H | H | OH | H | 0 | 45 (+/−5) | n.t. |
| Iminochromene 9TA | | | | | | | | | 30 (+/−15) | Lit[8]: 0.118 |
| Piceatannol | | | | | | | | | 41 (+/−2) | Lit[13]: 66 (lck) |
| ST-638 | | | | | | | | | 37 (+/−5) | Lit[14]: 18 |
| Emodin[d] | | | | | | | | | 22 (+/−3) | Lit[15]: 38 |
| Tyrophostin A47 | | | | | | | | | 43 (+/−3) | |

Table IX Footnotes:

[a]The previously described assay procedure (Lai et al., 1998) was used with the following assay components, final concentrations and conditions: 50.0 mM MOPS, 4.02 mM $MgCl_2$, 6.00 mM $K_3$citrate (used as a $Mg^{2+}$ buffer to stabilize the free $Mg^{2+}$ at 0.5 mM), 99.0 mM KCl, 10.0 mM 2-mercaptoethanol, 198 μM ATP, 19.8 μM ADP, 10 U full length human purified recombinant pp60[c-src] (Upstate Biotechnology Inc.), 2.00 mM RR-SRC, 4.0% DMSO, pH 7.2, 37° C. These overall assay conditions have been shown (Choi, 1999) to reproduce the intracellular conditions of pH, temp., free $Mg^{2+}$ (0.5 mM), ionic strength, osmolality, ATP/ADP and reduction potential.

[b]All new compounds were characterized by proton NMR, EI or FAB(+) MS and are pure by TLC.

[c]N/A = Not applicable, n.t. = Not tested.

[d]ATP-competitive.

The series of 2-carbonyl, 3,6-dihydroxy naphthalene inhibitors (1b, 2e-2h, 2m-2n, 2q-2s) were synthesized from 3,6-dihydroxy-2-naphthoic acid 6 using the methods described above. The synthesis of intermediate 6 that was developed is shown in Scheme 2 beginning with commercially available 2,7-dihydroxynaphthalene 3 (Aldrich).

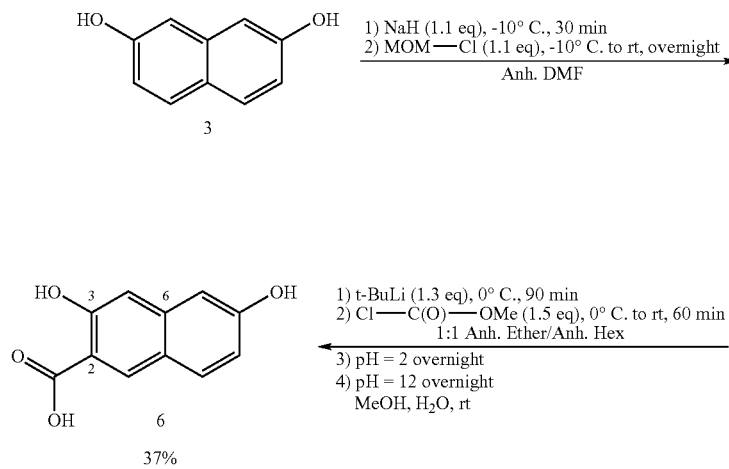

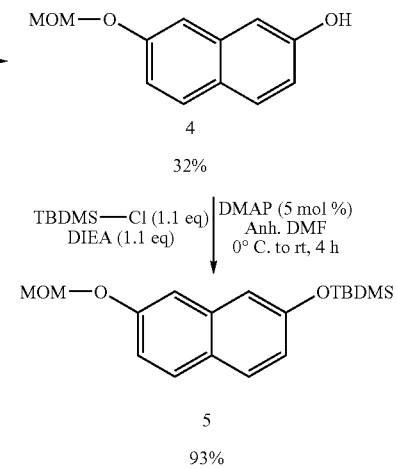

Compound 1d was synthesized from 3-amino-2-naphthoic acid (Aldrich) by reaction with TMS-diazomethane in DCM at room temperature. Compound 2v was synthesized from 6-hydroxy-2-naphthoic acid (Aldrich) using the amidation method described by Froyen (Froyen, 1997).

Kinase assay conditions have been shown to influence the measured inhibitory activity (Lawrence et al., 1998). Consequently, in order to accurately determine the relative potency of the newly designed class of pp60$^{c-src}$ inhibitors, the inhibitory activity of four previously published, non-ATP competitive PTK inhibitors, was also tested. Piceatannol, ST-638, and Tyrphostin A47 were chosen because they are commercially available (Sigma or Calbiochem), and are representative of the spectrum of known non-ATP competitive PTK inhibitors. Emodin (Calbiochem) is ATP-competitive when analyzed with the tyrosine kinase p56$^{lck}$. Previously, iminochromene 9TA was the most potent non-ATP competitive pp60$^{c-src}$ inhibitor reported (Huang et al., 1995). Since iminochromene 9TA was not commercially available, it was synthesized using a novel route by converting 3-Aminophenol to the corresponding TBDMS ether (1.1 eq. TBDMS-Cl, 1.1 eq. DIEA, 5 mol % DMAP, DMF, 24 h, rt, 71%). The resulting aniline was coupled using 2.0 eq. of cyanoacetic acid (1.1 eq. EDCI, 1.1 eq. TEA, DMF, 18 h, 75° C., 70%). Condensation of the resulting amide with 1.2 eq. of 2,3-dihydroxybenzaldehyde (cat. piperidine, abs. EtOH, 2 h, 60° C.) followed by deprotection (1.1 eq. TBAF, THF, 15 m, 43% overall) gave iminochromene 9TA with satisfactory elemental, FAB(+)MS and $^1$H NMR analysis after purification by flash chromatography (10:1, DCM:MeOH).

The inhibitory activities shown in Table IX for compounds 1a-d and 2a-2v were determined using purified, full length, human recombinant pp60$^{c-src}$. Due to the number of compounds tested, and the associated cost, their rank order potencies were first determined at a constant inhibitor concentration (100 µM). As predicted by the modeling studies, based upon analogy to the IRTK Tyr 1,162 hydroxyl group, a preference for positioning the naphthalene hydroxyl group on carbon 6 vs. 5 or 7 was observed in both the ester (1b, 47% vs. 1a, 5% & 1c, 19%) and amide (e.g. 2f, 89% vs. 2b, 51% & 2t, 68%) series. The prediction that attaching a hydroxyl group at naphthalene carbon 3 (mimicking the Tyr 1,162 NH) would improve potency was also confirmed (2f, 89% vs. 2v, 45%). Finally, the prediction that extending the inhibitor as an amide at the 2 position (mimicking the peptide bond) could further improve potency was confirmed as well (e.g. 2f, 89% vs. 1b, 47%).

The data provided in Table IX demonstrate that moving the hydroxyl group from the optimal 6 position to the adjacent naphthalene carbon 5 results in a different structure activity profile with regard to the optimal concurrent positioning of the hydroxyl group(s) in the amide side chain (e.g. 2f/2g vs. 2b/2c). Also of note is the replacement of the amide side chain hydroxyl group with a corresponding methoxy group in compounds 2i-2n. In the case of the N-phenyl amides (2i-2j), their activity, relative to the corresponding hydroxy amides (2b-2c), was not reduced as significantly as in the case of the N-benzyl amides (2k-2n vs. 2o-2q, 2s). This suggests that in the benzyl derivatives, the amide side chain hydroxyl groups either interact with the enzyme as hydrogen bond donors, or the methoxy groups are too large to fit in the binding site.

A more quantitative analysis of the selectivity for positioning a hydroxyl group on carbon 6 vs. 5 is provided by comparing the IC$_{50}$'s of 2f (16 µM) vs. 2b (150 µM), respectively. These results also confirm that a drop in % inhibition from ca. 90% to ca. 50% represents an order of magnitude difference in potency, as expected. Similarly, a drop in % inhibition from ca. 50% to 10% would represent another order of magnitude difference in potency.

A direct comparison of the most potent inhibitor from this series, compound 2f, with the five previously reported PTK inhibitors shown in Table IX demonstrates that, under these assay conditions, 2f is more potent by one to two orders of magnitude. Interestingly, iminochromene 9TA was previously reported (Huang et al., 1995) to have an IC$_{50}$ of 118 nM against pp60$^{c-src}$, and was the most potent known non-ATP competitive pp60$^{c-src}$ inhibitor, but under the current assay conditions only a 30% inhibition at 100 µM was observed. These results re-emphasize (Lawrence et al., 1998) the importance of comparing protein kinase inhibitors under identical assay conditions.

A goal of these studies was to obtain non-peptide pp60$^{c-src}$ inhibitors which do not compete with ATP. Consequently the % inhibition of pp60$^{c-src}$ by 2f and 2b at constant inhibitor concentrations was monitored as a function of increasing [ATP] up to a cellular mimetic 1 mM level. Since the [ATP] had little effect on the % inhibition, both 2f and 2b are non-competitive inhibitors with respect to ATP. The % inhibition was measured using ATP concentrations of 200, 500 & 1,000 µM while holding the inhibitor concentration constant. If the inhibitor is directly competing with ATP, then this 5-fold overall increase in [ATP] is equivalent to decreasing the inhibitor concentration 5-fold in terms of the effect on % inhibition. Consequently the % inhibition should decrease to the value observed in the IC$_{50}$ dose-response curve (obtained with 200 μM ATP) for ⅕ of the set inhibitor concentration used in this experiment if direct competition with ATP is occurring. For inhibitor 2f (set at 25 M) a 62% (+/−5), 54% (+/−3) and 50% (+/−1) inhibition at 200 μM, 500 μM and 1,000 μM ATP, respectively, was obtained whereas the level of inhibition should have dropped to ca. 20% at 1,000 μM ATP if direct competition with ATP were occurring. Similarly, for inhibitor 2b (set at 300 μM) an 84% (+/−1), 81% (+/−1) and 77% (+/−2) inhibition at 200 μM, 500 μM and 1,000 μM ATP, respectively, was obtained. The high cost of many kinases has stimulated other researchers to monitor inhibitor potency as a function of increasing [ATP] for the same purpose (Saperstein et al., 1989; Burke et al., 1993; Davis et al., 1989; Davis et al., 1992; Faltynek et al., 1995; and Sawutz et al., 1996).

In summary, structure-based design has produced a series of hydroxynaphthalene pp60$^{c\text{-}src}$ non-peptide inhibitors that do not compete with ATP. Results with compounds from this series in cell-based assays, as well as detailed kinetic studies under various assay conditions, will be reported in due course. An extension of these design concepts from the naphthalene scaffold to an indole scaffold is reported in the following Example.

Example 4

Design, Synthesis and Activity of Non-ATP Competitive Hydroxyindole Derivative Inhibitors of pp60$^{c\text{-}Src}$ Tyrosine Kinase In the preceding example, the structure-based design of a series of pp60$^{c\text{-}src}$ inhibitors utilizing a naphthalene scaffold is described. These compounds were designed to bind in the peptide substrate site because of the potential for greater selectivity and efficacy in a cellular environment relative to the alternative ATP substrate site. This example presents an extension of these design concepts to a series of pp60$^{c\text{-}src}$ inhibitors based upon an indole scaffold. Once again the crystal structure of the autoinhibited insulin receptor PTK (IRTK) was used to carry out qualitative molecular modeling studies, except in this case an indole ring was superimposed upon the IRTK Tyr 1,162. This superimposition indicated that the indole NH can mimic the Tyr 1,162 NH, that a carbonyl should be placed at the 2-position, and a hydroxyl group at the 5 position to mimic the Tyr 1,162 carbonyl and OH, respectively (Scheme 1).

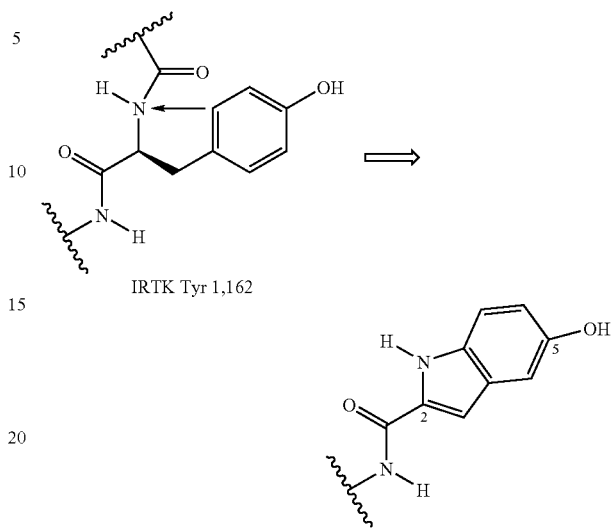

IRTK Tyr 1,162

The conceptual cyclization of Tyr 1,162 to the smaller 5-membered ring of an indole illustrated in Scheme 1, relative to a 6-membered ring in the case of the naphthalene scaffold (Karni et al., 1999), results in a movement of the optimal positioning of the OH from carbon 6 in the naphthalene scaffold to carbon 5 in the indole scaffold.

The indole amide derivatives containing hydroxy phenyl/benzyl side chains 2d-f, 2j-l (Table X), respectively, were selected based upon the increase in pp60$^{c\text{-}src}$ inhibitor potency observed for the analogous naphthalene-based hydroxy phenyl amides reported in the previous example. The corresponding methyl ethers 2a-c, g-i, v are precursors in the synthesis. The additional analogs shown in Table X were prepared to begin expanding the range of side chains beyond the hydroxy/methoxy groups that have now been extensively probed with both the indole and naphthalene scaffolds.

The indole amides containing only hydroxy or methoxy side chains were synthesized as illustrated:

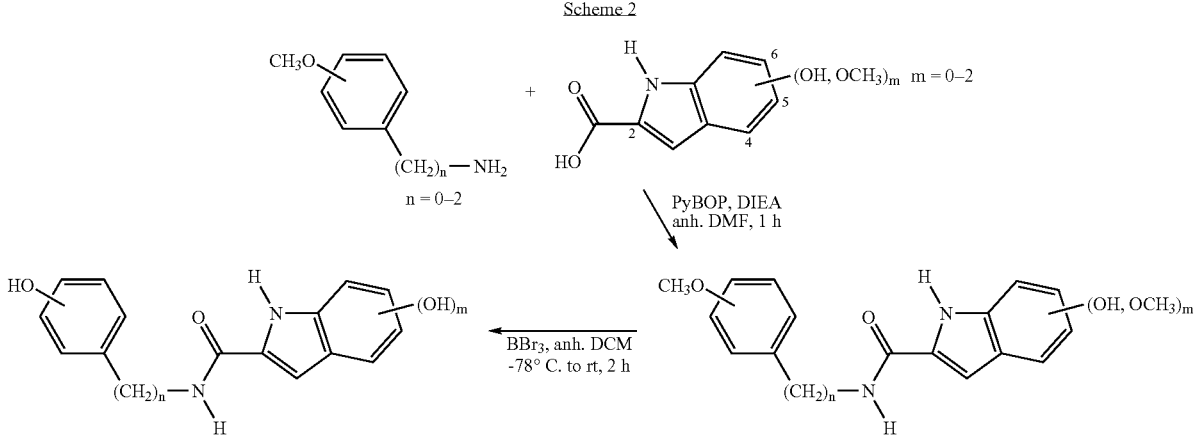

The 2-indolecarboxylic acid derivative, the methoxyphenyl amine (1.1 eq, Aldrich, Lancaster or Fluka), and the coupling reagent PyBOP (benzotriazol-1-yloxy)tripyrrolidino-phosphonium-hexafluorophosphate) (1 eq. Fluka) were dissolved in anhydrous DMF. The solution was cooled to 0° C. under argon and then diisopropylethylamine (DIEA, 3 eq) was added. The reaction was stirred at 0° C. for 1 m followed by 1 hour at room temperature. After workup the residue was purified by silica gel chromatography.

The methyl ethers were cleaved with boron tribromide (1 M in DCM, Aldrich) when desired. The indole amide methyl ether was suspended in dry DCM and cooled to –78° C. under argon. One equivalent of $BBr_3$ was added for each heteroatom in the starting material plus one excess equivalent. The resulting dark red solution was stirred at –78° for 30 m and then at room temperature for 1-2 hours. The reaction was quenched with water (10 minutes) before workup.

Using this synthetic route, the series of 5-hydroxyindole amide inhibitors 2a-m,y,z were prepared from 5-hydroxy-2-indolecarboxylic acid. The 4- and 6-hydroxyindole amides (2x,u, respectively) were synthesized from methyl 4-methoxy-2-indolecarboxylate and methyl 6-methoxy-2-indolecarboxylate, respectively. The 5,6-dihydroxyindole amide 2t was prepared from ethyl 5,6-dimethoxyindole-2-carboxylate. Sonication of the esters in 1 N NaOH for 1 hour provided the corresponding carboxylic acids for coupling. The des-hydroxy indole amides 2v,w were synthesized from indole-2-carboxylic acid. All of the indole starting materials were commercially available (Aldrich or Lancaster).

The fluoro inhibitors 2r,s were likewise prepared from the corresponding fluorophenyl amines (Aldrich). The inhibitors containing esters or carboxylic acids on the amide side chain, 2n-q, were prepared from the corresponding amino carboxylic acids (Aldrich). The side chain carboxylic acid was first protected as a methyl ester (anh. MeOH pre-saturated with

TABLE X pp60$^{c-src}$ INHIBITORY ACTIVITY OF HYDROXYINDOLE DERIVATIVES.[a,b,c]

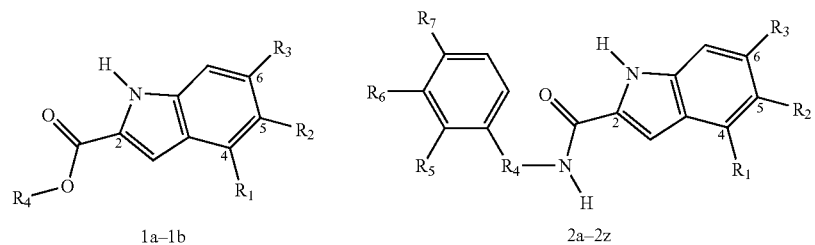

1a–1b     2a–2z

| Cmpd | $R_1$ | $R_2$ | $R_3$ | $R_4$ | $R_5$ | $R_6$ | $R_7$ | % Inhibition at 100 μM (std. dev.) |
|---|---|---|---|---|---|---|---|---|
| 1a | H | OH | H | $CH_3$ | N/A | N/A | N/A | 40 (+/–5) [at 500 μM] |
| 1b | H | OH | OH | $CH_2CH_2$ | N/A | N/A | N/A | 28 (+/–3) |
| 2a | H | OH | H | | $OCH_3$ | H | H | 3 (+/–1) |
| 2b | H | OH | H | | H | $OCH_3$ | H | 21 (+/–2) |
| 2c | H | OH | H | | H | H | $OCH_3$ | 39 (+/–9) |
| 2d | H | OH | H | | OH | H | H | 43 (+/–1) |
| 2e | H | OH | H | | H | OH | H | 30 (+/–6) |
| 2f | H | OH | H | | H | H | OH | 45 (+/–3) |
| 2g | H | OH | H | $CH_2$ | $OCH_3$ | H | H | 21 (+/–5) |
| 2h | H | OH | H | $CH_2$ | H | $OCH_3$ | H | 7 (+/–6) |
| 2i | H | OH | H | $CH_2$ | H | H | $OCH_3$ | 18 (+/–4) |
| 2j | H | OH | H | $CH_2$ | OH | H | H | 24 (+/–3) |
| 2k | H | OH | H | $CH_2$ | H | OH | H | 74 (+/–2) [$IC_{50}$ = 38 μM] |
| 2l | H | OH | H | $CH_2$ | H | H | OH | 54 (+/–2) |
| 2m | H | OH | H | $CH_2CH_2$ | H | H | OH | 21 (+/–7) |
| 2n | H | OH | H | $CH_2$ | H | H | $CO_2H$ | not active |
| 2o | H | OH | H | $CH_2$ | H | H | $CO_2CH_3$ | 11 (+/–4) |
| 2p | H | OH | H | | H | H | $CH_2CO_2H$ | 7 (+/–6) |
| 2q | H | OH | H | | H | H | $CH_2CO_2CH_3$ | 32 (+/–7) |
| 2r | H | OH | H | | H | F | H | 21 (+/–7) |
| 2s | H | OH | H | $CH_2$ | H | F | H | 57 (+/–31 6) |
| 2t | H | OH | OH | $CH_2$ | H | OH | H | 26 (+/–2) |
| 2u | H | H | OH | $CH_2$ | H | OH | H | 56 (+/–6) |
| 2v | H | H | H | $CH_2$ | H | H | $OCH_3$ | 4 (+/–4) |
| 2w | H | H | H | $CH_2$ | H | H | OH | 36 (+/–4) |
| 2x | OH | H | H | $CH_2$ | H | OH | H | 60 (+/–3) |
| 2y | H | OH | H | $CH(CH_3)$ R | H | OH | H | 15 (+/–3) |
| 2z | H | OH | H | $CH(CH_3)$ S | H | OH | H | 13 (+/–7) |

[1] All compounds were tested as described in the preceding Example.[5]
[b] All compounds were characterized by proton NMR, FAB(+) MS and are pure by TLC.
[c] N/A = Not applicable.

HCl, reflux, 1d), followed by PyBOP coupling (as above), then saponification back to the carboxylic acid when desired.

The methyl ester 1a was prepared by refluxing a solution of the carboxylic acid overnight in anhydrous methanol presaturated with HCl gas. The ethyl ester 1b was prepared by BBr$_3$ deprotection of ethyl 5,6-dimethoxyindole-2-carboxylate as above. All of the inhibitors listed in Table X were purified by silica gel chromatography.

As in Marsilje 2000, the rank order activity of this series of pp60$^{c\text{-}src}$ inhibitors was first determined at a constant inhibitor concentration (Table X). The same inhibitor concentration (100 μM) was used for the current indole series of inhibitors, the previous naphthalene series of inhibitors, and five non-ATP competitive literature PTK inhibitors (see preceding example). This allowed an efficient rank order comparison of 59 compounds in total under identical assay conditions.

The modeling studies predicted that a hydroxy group at carbon 5 of the indole scaffold would be optimal. Comparison of the 5-hydroxy indole inhibitor 2k (74%) with the analogous 6-hydroxy indole inhibitor 2u (56%) and 4-hydroxy indole inhibitor 2x (60%) confirms this prediction, although the preference is not strong. The prediction that a hydroxy group at carbon 5 will improve the activity (relative to no hydroxy group) is confirmed by comparing the 5-hydroxy indole inhibitor 2l (54%) with the corresponding des-hydroxy inhibitor 2w (36%).

Extending the indole inhibitors as aryl amides at carbon 2 improved potency, as expected based upon the previous naphthalene inhibitors. For example, the meta-hydroxybenzyl amide indole 2k gives 74% inhibition at 100 μM whereas the analogous methyl ester 1a gives only 40% inhibition at 500 μM. Interestingly, comparing the 5,6-dihydroxy ethyl ester 1b (28%) to the corresponding aryl amide 2t (26%) shows that the simultaneous presence of the second hydroxy at carbon 6 prevents the potency enhancement normally provided by the otherwise preferred meta-hydroxybenzyl amide side chain. This amide side chain was the best of the current series when the 5-hydroxyl group is present alone (2k, 74%) and still gave good inhibition when a 6-hydroxy group was present alone (2u, 56%). Also, the simultaneous presence of two hydroxy groups at carbons 5 and 6 seems well tolerated in the absence of an amide side chain (1b vs. 1a and 2e). This data suggests that a change in the binding orientation of the indole scaffold may have occurred due to the presence of the second hydroxy group and that a different amide side chain may now be preferred. The optimal combination of side chains at carbons 4-7 (including functional group replacements for hydroxy groups (Lai et al., 1999)) and amide side chains is currently under investigation.

In general, the indole scaffold structure-activity-relationships ("SARs") revealed by the data in Table X parallels that reported in the preceding example for the naphthalene scaffold. In both cases positioning a hydroxy group on the scaffold analogous to the Tyr 1,162 OH, as identified by modeling studies, provided the highest potency. Moving this hydroxy group to one of the adjacent carbons reduced the potency, but not dramatically, in both cases. Extending both scaffolds with aryl amides at the position identified by the modeling studies to mimic the Tyr 1,162 peptide bond improved the potency. With both scaffolds, substitution of a methoxy group for the hydroxy groups on the amide side chain usually reduced potency, and did so to a greater extent with the longer benzylamide side chain (e.g. 2k, 74% vs. 2h, 7% compared to 2e, 30% vs. 2b, 21%). The major difference in the SARs for these two scaffolds is that the 5-hydroxyindole scaffold prefers the longer m-hydroxybenzyl amide side chain (2k, 74% vs. 2e, 30%) whereas the analogous 3,6-dihydroxynaphthalene scaffold prefers the shorter amide side chain derived from m-hydroxyaniline. The 5-hydroxyindole scaffold showed essentially no preference for the position of the hydroxyl group on the shorter amide side chain (2d-f) whereas with the longer hydroxybenzyl amide side chain a significant preference for the meta position was observed (2j-l). In the case of the 3,6-dihydroxynaphthalene scaffold the opposite was observed.

Additional molecular modeling studies were carried out to further probe the preference for a longer amide side chain with the indole scaffold. The most active naphthalene inhibitor 3 from the previous report was used as a template upon which the analogous indole inhibitor 2e and the homologated indole inhibitor 2k were superimposed. The three most important side chain functional groups in naphthalene inhibitor 3 are considered to be the 6-hydroxy group (H-bond donor and acceptor), the hydrogen from the 3-hydroxy group (H-bond donor), and the side chain hydroxy group (H-bond acceptor) based upon the rational design and SAR for both series of inhibitors. This three point pharmacophore model is identified in both series by asterisks in Scheme 3.

Scheme 3

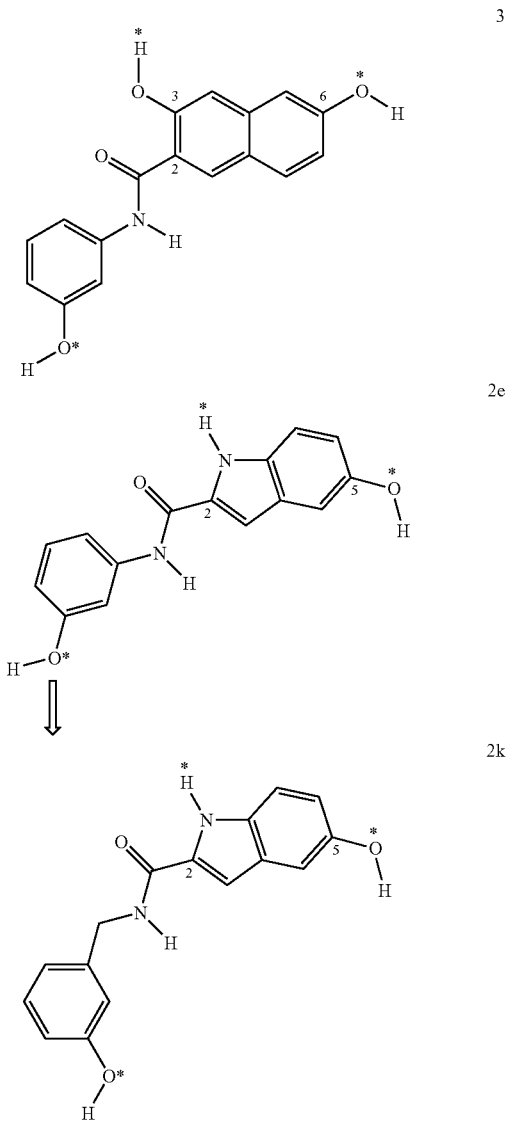

The "multifit" energy minimization and "fit atoms" facilities within SYBYL™ (6.4, Tripos, St. Louis) were used in sequence to superimpose 2e and 2k onto 3. This overall fitting process was carried out with spring constants (multifit) and weights (fit atoms) chosen such that the highest emphasis was on optimally superimposing the scaffold pharmacophore O's and H's (100), followed by the side chain O's (10) and then the intervening amide bond (1). The "multifit" process adjusted the conformations for maximum pharmacophore fit, the subsequent minimization produced the nearest local minimum energy conformations and finally the "fit atoms" process produced the best pharmacophore superimposition of these minimized conformations. As expected, the scaffold pharmacophore O's and H's of both 2e and 2k superimposed closely and similarly upon the corresponding atoms in 3 (all within ca. 0.50 Å). However, the side chain pharmacophore O's of 2e and 2k differed significantly in their superimposition on the corresponding O of 3, with displacements of 1.8 Å vs. only 0.08 Å respectively. This close fit of the three key pharmacophore sites between 2k and 3 provides a rationalization for their potency differing by only a factor of 2.4 ($IC_{50}$'s 38 µM vs. 16 µM, respectively).

Extending the amide side chain by another carbon atom reduced the activity (2m, 21% vs. 21, 54%). Adding a methyl group to the benzylic carbon of 2k, in either stereochemistry, greatly reduced the activity (2y, 15% & 2z, 13% vs. 2k, 74%). Replacing the side chain hydroxy group (in the para position) with a carboxylate anion (2n, 0% vs. 21, 54% and 2p, 7% vs. 2f, 45%) reduced the activity whereas the corresponding methyl esters (2o, 11% & 2q, 32%, respectively) showed a smaller loss of potency. Importantly, replacing the side chain hydroxy group with a fluorine maintained much of the potency (2s, 57% vs. 2k, 74% and 2r, 21% vs. 2e, 30%). Consequently, the fluoro analog 2s has only one hydroxy group left for potential Phase II metabolism (e.g. glucuronide formation), and this remaining hydroxy group is a current target for replacement (Lai et al., 1998).

Using the same method as in the preceding example (Marsilje, 2000), the most potent inhibitor from the current indole series (2k) was analyzed for ATP competition by monitoring the % inhibition at increasing [ATP] while holding the inhibitor concentration constant. Since the [ATP] had little effect on the % inhibition (The % inhibition was 46% and 41% with 2k at 45 µM and [ATP] at 200 µM or 1,000 µM, respectively.), 2k is non-competitive with respect to ATP under these assay conditions.

In summary, an indole scaffold has been designed, and an initial SAR carried out, for the development of non-ATP competitive $pp60^{c-src}$ inhibitors. The potency of the best indole-based inhibitor from the current series was found to be close to that of the best naphthalene-based inhibitor. The % inhibition was 46% and 41% with 2k at 45 µM and [ATP] at 200 µM or 1,000 µM, respectively.

Example 5

Synthesis of Additional Indole Derivative Protein Kinase Inhibitors

The following results show the synthesis and testing of indole derived protein kinase inhibitors. Four reaction schemes are provided and separately followed by experimental details for the preparation of the final product of each of these reaction schemes. These final products are examples of indole-base tyrosine kinase inhibitors wherein the synthesis with preferred R groups is illustrated (boronic acid, Scheme 1; OH, Scheme 2; an aliphatic amide extension, Scheme 3; and a phosphonic acid Scheme 4).

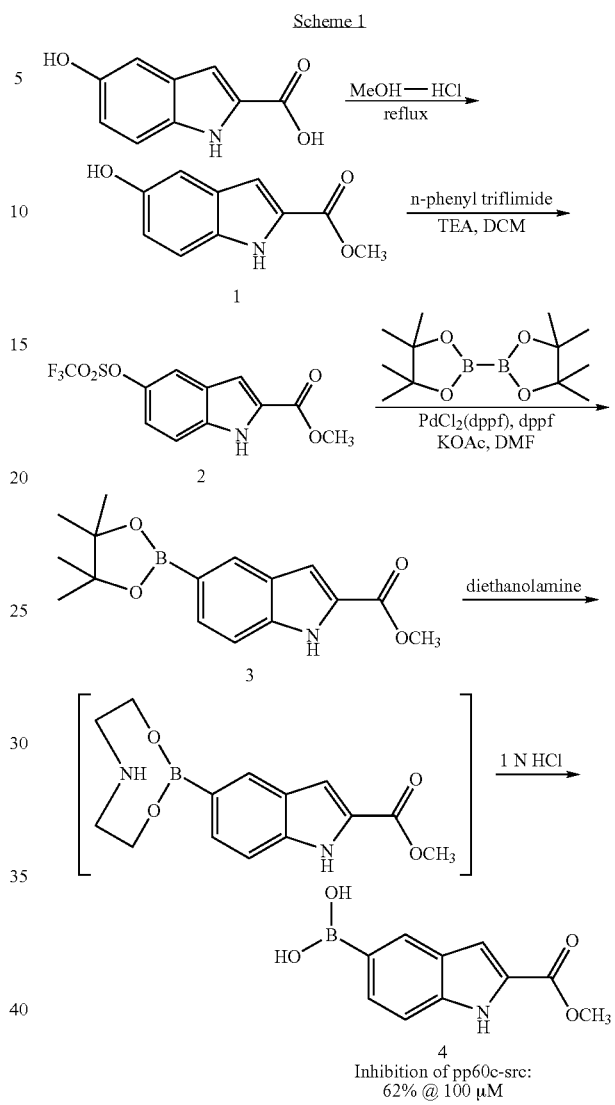

Methyl 5-hydroxy-2-indolecarboxylate (1)

Dissolved 3.50 g 5-hydroxy-2-indolecarboxylic acid in anh. MeOH presaturated with HCl gas. Refluxed for 48 hours. Concentrated in vacuo and triturated with AcCN x3 to remove residual acid. Filtered through silica plug with EtOAc to remove baseline contamination. Recovered 4.32 g (quant. yield) TLC $R_f$=0.78 (EtOAc) 1H NMR (DMSO-$d_6$): 3.82 (s, 3H), 6.78 (d, J=8.8 Hz, 1H), 6.88 (s, 1H), 6.93 (s, 1H), 7.23 (d, J=8.8 Hz, 1H), 8.90 (s, 1H) 11.62 (s, 1H) FAB(+) MS m/e 191.9 (M+1)

Methyl 5-[(trifluoromethyl)sulfonyloxy]indole-2-carboxylate (2)

Added 150 ml anh. DCM to 3.24 g (17 mmol) methyl 5-hydroxy-2-indolecarboxylate (1) and 6.67 g (18.7 mm) n-phenyl trifluoromethane sulfonamide at 0° C. Added 2.6 ml triethylamine dropwise at which point clear yellow solution formed. Stirred at 0° C. for 1 hour. Warmed to room temperature and stirred for 2 hours. Concentrated in vacuo and purified through silica gel column (1/1 EtOAc/hexanes). Recovered 4.69 g (86%). TLC $R_f$=0.63 (1/1 EtOAc/hexanes). HPLC $R_f$=20.879 1H NMR (DMSO-$d_6$): 3.87 (s, 3H), 7.25 (s, 1H), 7.31 (d, J=9.2 Hz, 1H), 7.55 (d, J=9.2 Hz, 1H), 7.80 (s, 1H), 12.34 s, 1H) FAB(+) MS m/e 323.1 (M+1).

Methyl 5-methylindole-2-carboxylate, 4,4,5,5-tetramethyl-1,3,2-dioxaborolanemethyl (3)

500 mg 1.55 mmol methyl 5-[(trifluoromethyl)sulfonyloxy]indole-2-carboxylate (2), 37.9 mg (0.05 mmol) $PdCl_2$ (dppf), 432 mg (1.7 mmol) bispinacolatodiboron, 454.8 mg (4.65 mmol) potassium acetate, and 25.7 mg (0.05 mmol) dppf were added to a flask and vacuum dried at 40° C. for 2 hours. Added 20 ml anh dioxane and heated to 80° C. overnight. Reaction turned black as Pd black precipitated out. Filtered off catalyst and ran silica plug to remove baseline impurities. TLC $R_f$=0.51 (1/4 EtOAc/Hexane) Crude product was taken through to next reaction.

Methyl 5-boronyl indole-2-carboxylate (4)

391.2 mg (1.3 mmol) methyl 5-methylindole-2-carboxylate, 4,4,5,5-tetramethyl-1,3,2-dioxaborolanemethyl (3) was dissolved in EtOAc. 0.25 ml (2.6 mmol) diethanolamine was added, and the reaction was stirred at room temperature overnight. The white ppt which formed was filtered and sonicated in 1 N HCl. The resulting white ppt was filtered, dissolved in MeOH, and concentrated in vacuo. Recovered 36.6 mg (13%). HPLC $R_f$=13.912, 1H NMR (DMSO-$d_6$): 3.85 (s, 3H), 7.15 s, (1H), 7.36 (d, J=8.4 Hz, 1H), 7.67 (d, J=8.4 Hz, 1H), 7.87 (s, 1H), 8.14 (s, 1H), 11.91 (s, 1H).

(5-hydroxyindol-2-yl)-N-[(3-methoxyphenyl)methyl]carboxyamide (5)

Dissolved 2.00 g (11.3 mmol) 5-hydroxy-2-indolecarboxylic acid, 1.6 ml (12.4 mmol) 3 methoxybenzylamine, and 5.87 g (11.3 mmol) PyBOP in 10 ml anh. DMF. Cooled to 0° C. and added 5.9 ml (33.9 mmol) DIEA. Stirred for 5 minutes at 0° C. and allowed to warm to room temperature for 1 hour. Recovered 2.83 g (85% yield) TLC $R_f$=0.34 (1/1 EtOAc/hexanes) $^1$H NMR (DMSO-$d_6$): 3.70 (s, 3H), 4.43 (d, J=4.4 Hz, 2H) 6.69 (d, J=8.8 Hz, 1H), 6.78 (d, J=7.7 Hz, 1H), 6.83 (s, 1H), 6.86 (s, 1H), 6.94 (s, 1H), 7.20 (m, 3H), 8.92 (t, J=4.4 Hz, 1H), 11.36 (s, 1H) FAB(+) MS m/e 297.3 (M+1)

(5-hydroxyindol-2-yl)-N-[(3-hydroxyphenyl)methyl]carboxyamide (6)

Added 20 ml anh. DCM to 200 mg (0.67 mmol) (5-hydroxyindol-2-yl)-N-[(3-methoxyphenyl)methyl]carboxyamide(5) and cooled to −78° C. under argon. Added 4.0 ml (4.0 mmol, 6 eq) $BBr_3$. Held at −78° C. for 5 minutes and warmed to rt. After 90 minutes at room temperature, quenched with $H_2O$ and stirred for 10 minutes. Diluted reaction mix with EtOAc and washed with $NaHCO_3$ and brine. Dried organic layer over $MgSO_4$ and concentrated in vacuo. Ran through silica plug to remove baseline contamination. Recovered X mg. (80% yield.) TLC $R_f$=0.21 (1/1 EtOAc/hexanes). $^1$H NMR (DMSO-$d_6$): 4.38 (d, J=4.8 Hz, 2H), 6.59 (d, J=8.8 Hz, 1H), 6.71 (m, 3H) 6.83 (d, J=1.8 Hz, 1H), 6.94 (s, 1H), 7.08 (dd, J=7.7 Hz, 1H), 7.19 (d, J=8.8 Hz, 1H), 8.84 (t, J=5.9 Hz), 11.28, (s, 1H). FAB(+) MS m/e 283.2 (M+1)

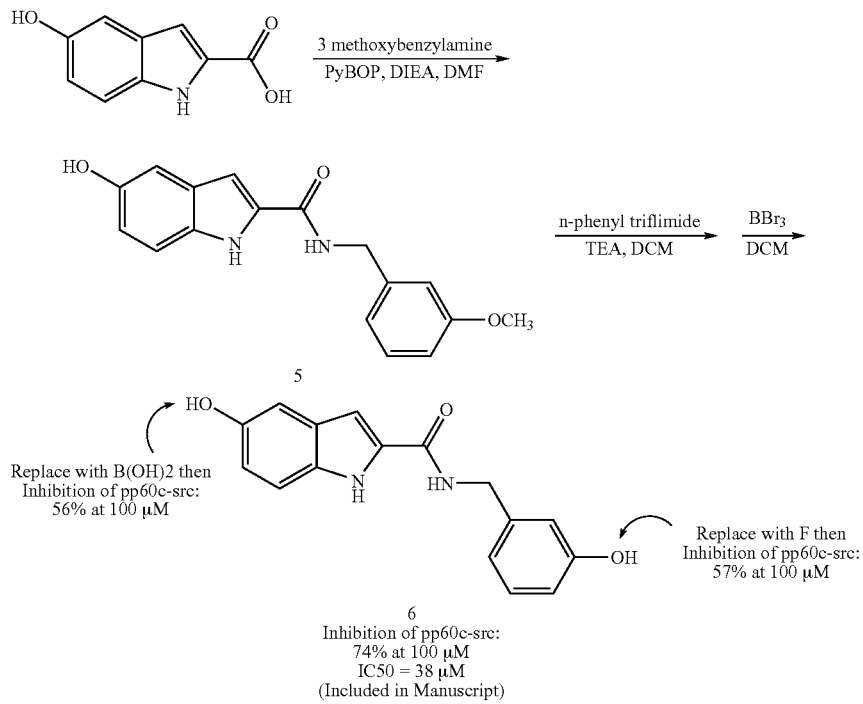

Scheme 2

Scheme 3

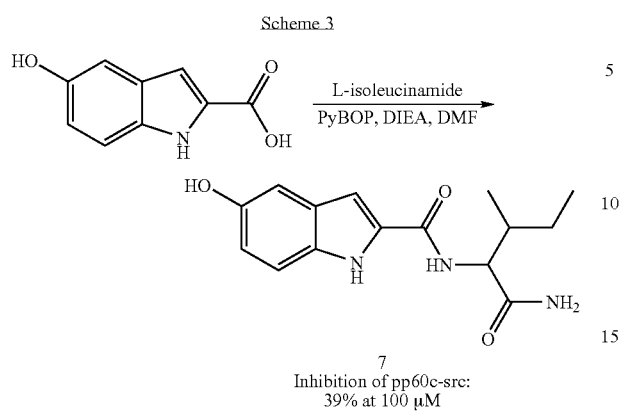

7
Inhibition of pp60c-src:
39% at 100 µM

N-(1-carbamoyl-2-methylbutyl)(5-hydroxyindol-2-yl)carboxyamide (7)

100 mg (0.56 mmol) 5-hydroxy-2-indolecarboxylic acid, 103.4 mg (0.62 mmol, 1.1 eq) L-isoleucinamide, and 291 mg (0.56 mmol, 1 eq) PyBOP were all dissolved in 1 ml anh DMF. The solution was cooled to 0° C. and 0.3 ml (1.68 mmol, 3 eq) DIEA was added. The reaction mixture was stirred for 1 minute at 0° C. and at room temperature for 1 hour. The reaction was then diluted with EtOAc and washed with 1 N HCl×3 and sated NaHCO3×3. The organic layer was dried over MgSO4, and concentrated in vacuo to give 166.7 mg (91% yield.) TLC $R_f$=0.08 (1/1 EtOAc/hexanes). $^1$H NMR (DMSO-d$_6$): 0.83 (m, 6H), 1.15 (m, 2H), 1.68 (m, 1H), 1.83 (m, 1H), 4.29 (t, J=8.8 Hz, 1H), 6.69 (d, J=8.5 Hz, 1H), 6.83 (s, 1H), 7.01, (s, 1H), 7.06 (s, 1H), 7.19 (d, J=8.4 Hz, 1H), 7.48, (s, 1H), 8.00 (d, 9.2 Hz, 1H), 8.76 (s, 1H), 11.3, (s, 1H). FAB(+) MS m/e 290.1 (M+1)

Scheme 4

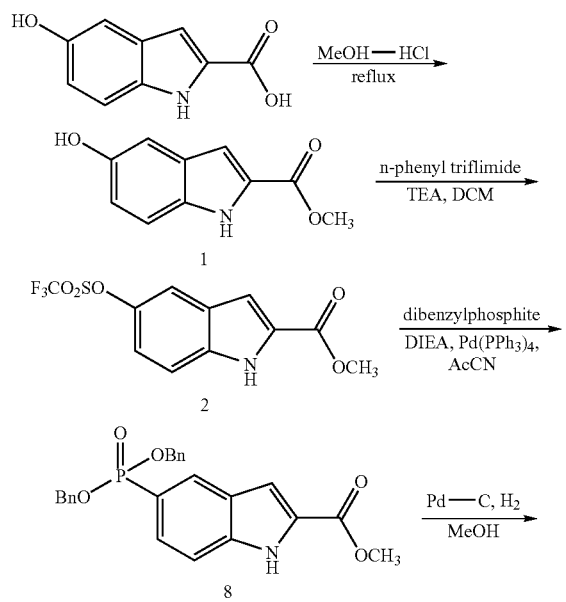

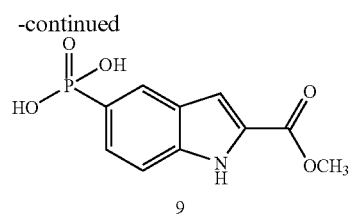

9
Inhibition of pp60c-src:
11% at 500 µM

Methyl 5-dibenzylphosphorylindole-2-carboxylate (8)

200 mg (0.62 mmol) methyl 5-[(trifluoromethyl)sulfonyloxy]indole-2-carboxylate (2), 195.8 mg (0.74 mmol, 1.2 eq) dibenzylphosphite, 0.14 ml (0.81 mmol, 1.3 eq) DIEA, and 35.7 mg (0.03 mmol, 5 mol %) Pd(PPh$_3$)$_4$ were all dissolved in anh AcCN under argon. The reaction mix was heated to 80° C. overnight. The solvent was removed under reduced pressure, and the title compound was isolated by silica gel chromatography. 130 mg (50% yield). TLC $R_f$=0.28 (1/1 EtOAc/hexanes) $^1$H NMR (DMSO-d$_6$): 3.85 (s, 3H), 4.98-5.01 (m, 4H), 7.28-7.32 (m, 11H), 7.53-7.55 (m, 2H), 8.17 (d, J=14.6 Hz, 1H) $^{31}$P NMR (DMSO-d$_6$): 23.89.

Methyl 5-phosphonolindole-2-carboxylate

Methyl 5-dibenzylphosphorylindole-2-carboxylate (8) (125 mg) was dissolved in 10 ml MeOH. 20 mg Pd—C was added and the mixture was hydrogenated in a Parr apparatus overnight. Filtered off catalyst and removed solvent under reduced pressure. Obtained 72.5 mg (73% yield). TLC $R_f$=baseline in EtOAc. $^1$H NMR (DMSO-d$_6$): 3.84 (s, 3H), 7.24 (s, 1H), 7.44-7.49 (m, 2H), 8.01 (d, J=14.3 Hz, 1H) 12.11 (s, 1H) $^{31}$PNMR (DMSO-d$_6$): 17.22.

The ester compounds in this example could be increased in potency by converting the ester to an amide and/or adding additional specificity elements.

Example 6

Synthesis of Further Indole Derivative Protein Kinase Inhibitors

The synthesis of some further elaborated indole inhibitors is illustrated in below. These syntheses could result in compounds with greater potency against pp60c-src and other tyrosine kinases. The methyl ester group can be subsequently converted into various amide derivatives to increase potency.

Scheme 1:

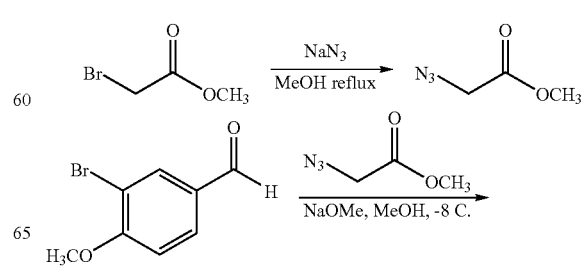

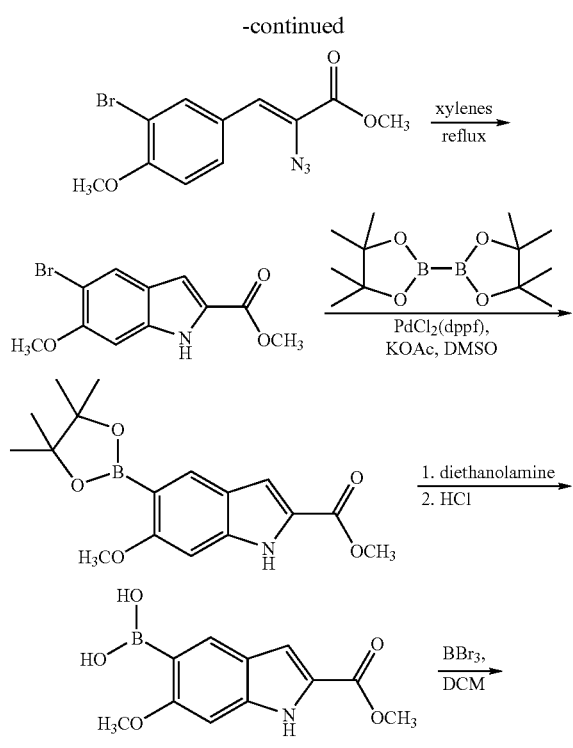

Scheme 2:

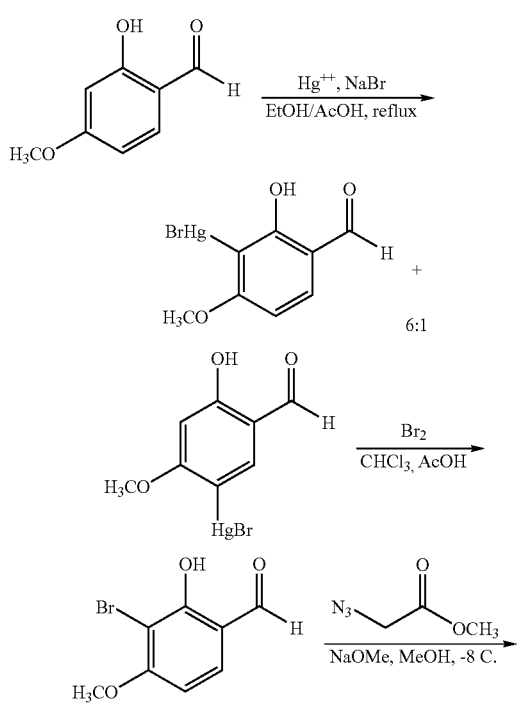

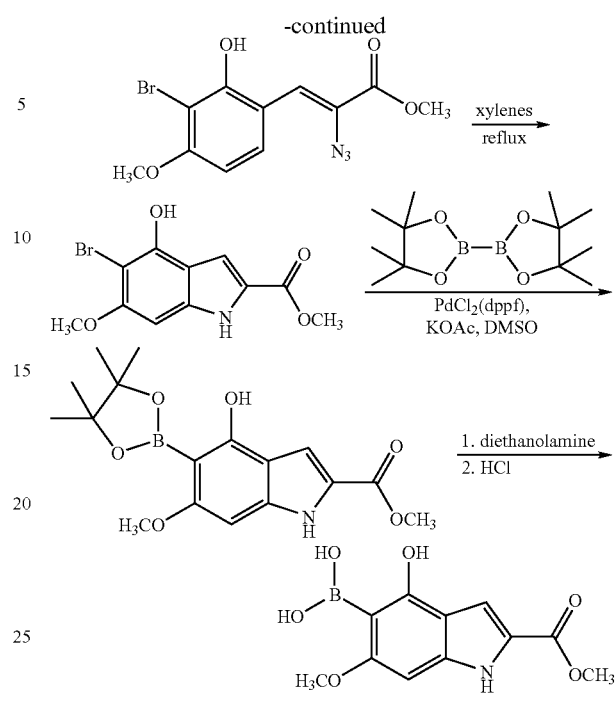

Scheme 3:

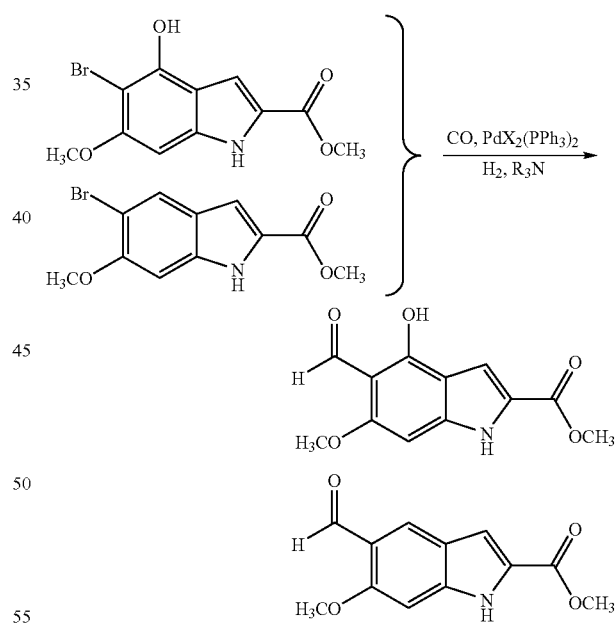

Example 7

Toxicity of Src Inhibitors

There is considerable recent literature support for targeting pp60[c-src] (Src) as a broadly useful approach to cancer therapy without resulting in serious toxicity. For example, tumors that display enhanced EGF receptor PTK signaling, or overexpress the related Her-2/neu receptor, have constitutively activated Src and enhanced tumor invasiveness. Inhibition of Src in these cells induces growth arrest, triggers apoptosis, and reverses the transformed phenotype (Karni et al., 1999). It is known that abnormally elevated Src activity allows transformed cells to grow in an anchorage-independent fashion. This is apparently caused by the fact that extracellular matrix signaling elevates Src activity in the FAK/Src pathway, in a coordinated fashion with mitogenic signaling, and thereby blocks an apoptotic mechanism which would normally have been activated. Consequently FAK/Src inhibition in tumor cells may induce apoptosis because the apoptotic mechanism which would have normally become activated upon breaking free from the extracellular matrix would be induced (Hisano et al., 1997). Additionally, reduced VEGF mRNA expression was noted upon Src inhibition and tumors derived from these Src-inhibited cell lines showed reduced angiogenic development (Ellis et al., 1998).

The issue of potential toxicity of Src inhibition has been addressed with very promising results. For example, a knockout of the Src gene in mice led to only one defect, namely osteoclasts that fail to form ruffled borders and consequently do not resorb bone. However, the osteoclast bone resorb function was rescued in these mice by inserting a kinase defective Src gene (Schwartzberg et al., 1997). This suggested that Src kinase activity can be inhibited in vivo without triggering the only known toxicity because the presence of the Src protein is apparently sufficient to recruit and activate other PTKs (which are essential for maintaining osteoclast function) in an osteoclast essential signaling complex.

Src has been proposed to be a "universal" target for cancer therapy since it has been found to be overactivated in a growing number of human tumors, in addition to those noted above (Levitzki, 1996). The potential benefits of Src inhibition for cancer therapy appear to be four-fold based upon the cited, and additional, literature. They are: 1) Inhibition of uncontrolled cell growth caused by autocrine growth factor loop effects, etc. 2) Inhibition of metastasis due to triggering apoptosis upon breaking free from the cell matrix. 3) Inhibition of tumor angiogenesis via reduced VEGF levels. 4) Low toxicity.

Figure 16E:
FIG. 16E provides the structures of the Src inhibitors 45, 43-meta, and 49-meta.

The initial non-peptide Src inhibitors have also shown very encouraging results in four different series of cell culture assays. 1) In the NIH 60-tumor cell panel assay, broad activity (as one would expect for a Src inhibitor) was seen against the tumor cell lines, including the prostate lines. For example, three of the inhibitors gave the following growth inhibition $IC_{50}$'s against the NIH prostate cancer cell lines: 45 (PC-3, 15 μM; DU-145, 38 μM), 43-meta (PC-3, 19 μM), 49-meta (PC-3, 39 μM; DU-145, >100 μM). 2) In the v-Src transformed normal rat kidney cell line (LA25) 43-meta and 45 specifically blocked the v-Src induced cell growth without inhibiting the normal growth of the parent non-transformed cells. This result showed that the inhibitors do not affect normal cells but are effective in blocking Src induced cell transformation. 3) The Src inhibitors were compared to the cancer drugs etoposide, taxol, doxorubicin and cisplatin in ovarian tumors from three different patients and an abdominal carcinoma from another patient. In all cases, the Src inhibitors were at least as effective, and typically more effective, than the known cancer drugs, with full efficacy seen at the lowest dose tested (3 μM). As a representative example, a comparison of taxol and doxorubicin (they were more effective than etoposide & cisplatin in this particular tumor cell culture) with the three Src inhibitors mentioned above (structures shown in FIG. 16E) utilizing ovarian tumor cells from tumor N015 is shown in FIG. 16A. 4) The Src inhibitors were also tested for inhibition of normal human fibroblast cell growth and found no inhibition of normal cell growth (both subconfluent and confluent; some enhanced growth was observed instead), indicating that these inhibitors are not toxic to normal cells even at a 10-fold higher concentration. An example of his data is given in FIG. 16B. 5) Two of the Src inhibitors were also tested for inhibition of ts v-Src stimulated LA25 cell growth. The results are shown in FIG. 16C. These results show that the tested compounds inhibit Src stimulated cell growth. 6) Two of the Src inhibitors were also tested for inhibition of normal rat kidney cell growth. The results are shown in FIG. 16D and illustrate that the inhibitors are cytoprotective for normal cells.

Overall, the cell data obtained thus far shows what one might expect for Src inhibitors, i.e. broad activity against many cancer cell lines with little or no normal cell toxicity.

The preliminary Src inhibitors are lead structures from which it is possible to design more potent and selective inhibitors. In addition to utilizing the tyrosine kinase crystal structures, molecular modeling studies can be carried out with the natural product tyrosine kinase inhibitor damnacanthal (Faltynek et al., 1995) to investigate its peptide-competitive binding mode. These additional modeling studies are enable one to design further analogs of Src inhibitors wherein the key pharmacophore elements of damnacanthal are incorporated into the new inhibitors. Their syntheses will be undertaken and the isolated Src testing done as reported (Marsilje 2000).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

LITERATURE CITED

The following references which were cited herein, are hereby incorporated by reference in their entirety into this application:

Abram, C. L.; Courtneidge, S. A. (2000) *Src family tyrosine kinases and growth factor signaling.* Experimental Cell Research 254, 1-13.

Ajay, Murcko, M. A. (1995) *Computational Methods to Predict Binding Free Energy in Ligand-Receptor Complexes.* J. Med. Chem., 38, 4953-4967.

Alberts, B., Bray, D., Lewis, J., Raff, M., Roberts, K. & Watson, J. D. (1994) Molecular Biology Of The Cell, 3rd ed., Garland Publishing, Inc., New York, pp. 97, 508 & 667.

Alfaro-Lopez, J., Yuan, W., Phan, B. C., Kamath, J., Lou, Q., Lam, K. S., Hruby, V. J. (1998) *Discovery of a Novel Series of Potent and Selective Substrate-Based Inhibitors of p60c-src Protein Tyrosine Kinase: Conformational and Topographical Constraints in Peptide Design.* J. Med. Chem., 41, 2252-2260.

Backes, B. J., Virgilo, A. A., Ellman, J. A. (1996) *Activation Method to Prepare a Highly Reactive Acylsulfonamide "Safety-Catch" Linker for Solid-Phase Synthesis.* J. Am. Chem. Soc., 118, 3055-3056.

Baggio, R., Elbaum, D., Kanyo, Z. F., Carroll, P. J., Cavalli, C., Ash, D. E., Christianson, D. W. (1997) *Inhibition of Mn2+-Arginase by Borate Leads to the Design of a Transition State Analog Inhibitor, 2(S)-Amino-6-boronohexanoic acid.* J. Am. Chem. Soc., 119, 8107-8108.

Barnekow, A.; Paul, E.; Schartl, M. (1987) *Expression of the c-src protooncogene in human skin tumors.* Cancer Res., 47, 235-240.

Benson, W. H., Birge, W. J., Dorough, H. W. (1984) Environ. Toxicol. Chem., 3, 209. Chem. Abstr. 101:124626g.

Bhagwat, S. S., Gude, C. (1994) *N-Alkylation of indole ring using Mitsunobu reaction*. Tet. Lett., 35, 1847-1850.

Biscardi, J. S., Tice, D. A.; Parsons, S. J. (1999) *c-Src, Receptor Tyrosine Kinases and Human Cancer*. Advances in Cancer Research, 61-119.

Biscardi, K. S., Ishizawar, R. C.; Silva, C. M.; Parsons, S. J. (2000) *Tyrosine kinase signaling in breast cancer: Epidermal growth factor receptor and c-Src interactions in breast cancer*. Breast Cancer Res. 2, 203-210.

Bjorge, J. D., O'Connor, T. J., Fujita, D. J. (1996) *Activation of human pp60$^{c\text{-}src}$*. Biochemistry & Cell Biology, 74, 477-484.

Bjelfman, C.; Hedborg, F.; Johansson, I.; Nordenskjold, M.; Pahlman, S. (1990) *Expression of the neuronal for of pp60c-src in neuroblastoma in relation to clinical stage and prognosis*. Cancer Res, 50, 6908-6914.

Blume-Jensen, P.; Hunter, T. (2001) *Oncogenic kinase signaling*. Nature 411, 355-365.

Bohacek, R. S., McMartin, C., Guida, W. C. (1996) *The Art and Practice of Structure-Based Drug Design: A Molecular Modeling Perspective*. Medicinal Research Reviews, 16, 3-50 (see p. 43).

Boyd, M. R., Paull, K. D. (1995) *Some practical considerations and applications for the National Cancer Institute in vitro anticancer drug discovery screen*. Drug Development Research, 34, 91-109.

Bridges, A. J. (2001) *Chemical Inhibitors of Protein Kinases*. Chemical Reviews 101(8), 2541-2572.

Brooks, S. P. J. & Storey, K. B. (1992) *Bound and Determined: A Computer Program for Making Buffers of Defined Ion Concentrations*. Analytical Biochemistry, 201, 119-126.

Brown, D. (1997) *Future Pathways for Combinatorial Chemistry*. Molecular Diversity, 2(4), 217-222.

Budde, R. J. A., McMurray, J. S., Saya, H., Gallick, G. E. & Levin, V. A. (1995) *Discovery, Development, and Testing of Substrates and Inhibitors of pp60$^{c\text{-}src}$*. International Journal of Pharmacognosy, 33, 27-34.

Budde, R. J. A., Ke, S., Levin, V. A. (1994) *Activity of pp60c-src in 60 different cell lines derived from human tumors*. Cancer Biochem. Biophys., 14, 171-175.

Burger, A. M., Kaur, G., Alley, M. C., Supko, J. G., Malspeis, L., Grever, M. R. & Sausville, E. A. (1995) *Tyrphostin AG17, [(3,5-Di-tert-butyl-4-hydroxybenzylidene)-malonitrile], inhibits cell growth by disrupting mitochondria*. Cancer Research, 55, 2794-2799.

Burke, T. R.; Lim, B.; Marquez, V. E.; Li, Z-H.; Bolen, J. B.; Stefanova, I.; Horak, I. D. (1993) J. Med. Chem. 36, 425.

Choi, S. (1999), Ph.D. Thesis SUNY at Buffalo, Buffalo, N.Y.

Cooper, C. M. (1990) Oncogenes. Jones and Bartlett Publishers, Boston, Mass.

Coughlin, J. R. (1996) *Inorganic borates-chemistry, human exposure, and health and regulatory guidelines*. J. Trace Elements in Experimental Medicine, 9, 137-151.

Courtneidge, S. A. (1994) *Protein tyrosine kinases, with emphasis on the Src family*. Seminars in Cancer Biology, 5, 239-246.

Cox, S., Radzio-Andzelm, E. & Taylor, S. S. (1994) *Domain movements in protein kinases*. Current Opinion in Structural Biology, 4(6), 893-901.

Culver, B. D., Hubbard, S. A. (1996) *Inorganic boron health effects in humans-and aid to risk assessment and clinical judgment*. J. Trace Elements in Experimental Medicine, 9, 175-184.

Davis, P. D.; Hill, C. H.; Keech, E.; Lawton, G.; Nixon, J. S.; Sedgwick, A. D.; Wadsworth, J.; Westmacott, D.; Wilkinson, S. E. (1989) FEBS Lett. 259(1), 61.

Davis, P. D.; Elliott, L. H.; Harris, W.; Hill, C. H.; Hurst, S. A.; Keech, E.; Kumar, M. K. H.; Lawton, G.; Nixon, J. S.; Wilkinson, S. E. (1992) J. Med. Chem. 35, 994.

Ellis, L. M., Staley, C.A., Liu, W., Fleming, R. Y., Parikh, N. U., Bucana, C. D., & Gallick, G. E. (1998) *Down-regulation of vascular endothelial growth factor in a human colon carcinoma cell line transfected with an antisense expression vector specific for c-src*. Journal of Biological Chemistry 273 (2):1052-1057.

Ezquerra, J., Pedregal, C., Lamas, C., Barluenga, J., Perez, M., Garcia-Martin, M. A., Gonzalez, J. M. (1996) *Efficient reagents for the synthesis of 5-, 7-, and 5,7-substituted indoles starting from aromatic amines: scope and limitations*. J. Org. Chem., 61, 5804-5812.

Faltynek, C., et al. (1995) *Damnacanthal is a highly potent, selective inhibitor of p56lck tyrosine kinase activity*. Biochemistry 34, 12404-12410.

Faltynek, C. R.; Wang, S.; Miller, D.; Mauvais, P.; Gauvin, B.; Reid, J.; Xie, W.; Hoekstra, S.; Juniewicz, P.; Sarup, J.; Lehr, R.; Sawutz, D. G.; Murphy, D. J. (1995) Enzyme Inhibition 9, 111.

Fanning, P.; Bulovas, K.; Saini, K. S.; Libertino, J. A.; Joyce, A. D.; Summerhayes, I. C. (1992) *Elevated expression of pp60$^{c\text{-}src}$ in low grade human bladder carcinoma*. Cancer Research, 52, 1457-1462.

Frame, M. C. (2002) *Src in cancer: deregulation and consequences for cell behavior*. Biochemica et Biophysica Acta, 1602, 114-130.

Fredenhagen, A.; Mett, H.; Meyer, T.; Buchdunger, E.; Regenass, U.; Roggo, B. E.; Petersen, F. J. (1995) Antibiotics 48, 1355.

Froyen, P. (1997) Tetrahedron Lett. 38(30), 5359.

Fry, D. W., Kraker, A. J., McMichael, A., Ambroso, L. A., Nelson, J. M. Leopold, W. R., Connors, R. W. & Bridges, A. J. (1994) *A Specific Inhibitor of the Epidermal Growth Factor Receptor Tyrosine Kinase*. Science, 265, 1093-1095.

Garcia-Echeverria, C.; Traxier, P.; Evans, D. B. (2000) *ATP Site-directed competitive and irreversible inhibitors of protein kinases*. Med. Res. Rev. 20(1), 28-57.

Glass, D. B., Cheng, H.-C., Mende-Mueller, L., Reed. J. & Walsh, D. A. (1989) *Primary structure determinants essential for potent inhibition of cAMP-dependent protein kinase by inhibitory peptides corresponding to the active portion of the heat-stable inhibitor protein*. J. Biol. Chem., 264, 8802-8810.

Groundwater, P. W., Solomons, K. R. H., Drewe, J. A. & Munawar, M. A. (1996) *Protein Tyrosine Kinase Inhibitors*. Progress in Medicinal Chemistry, 33, 233-329.

Hanks, S. K. & Hunter, T. (1995) Protein kinases. 6. *The eukaryotic protein kinase superfamily: Kinase (catalytic) domain structure and classification*. FASEB J., 9, 576-596.

Hanke, J. H., Gardner, J. P., Dow, R. L., Changelian, P. S., Brissette, W. H., Weringer, E. J., Pollok, B. A. & Connelly, P. A. (1996) *Discovery of a novel, potent, and Src family-selective tyrosine kinase inhibitor*. J. Biol. Chem., 271, 695-701.

Haskell, M. D.; Slack, J. K.; Parsons, J.; Parsons, S. J. (2001) *c-Src tyrosine phosphorylation of epidermal growth factor receptor, p-190 RhoGAP, and focal adhesion kinase regulates diverse cellular processes*. Chemical Reviews 101 (8), 2425-2440.

Hisano, C., Nakano, S., Fujishima, H., Masumoto, N., Tatsumoto, T., & Niho. Y. (1997) *src oncogene inhibits detachment-induced apoptosis through constitutive activation of p125FAK in HAG-1 human epithelial cells*. Proc. Annu. Meet. Am. Assoc. Cancer Res. 38:A1925.

Hsiao, G. K., Hangauer, D. G. (1998) *A Facile Synthesis of tert-Butyl 2-[(Benzyloxycarbonyl)amino]-3-(4,4,5,5-tetramethyl-1,3,2-dioxaborolan-2-yl)propionate: An Orthogonally Protected Boronic acid Analog of Aspartic acid.* Synthesis, 1043-1046.

Hsu, C-Y., J., Jacoski, M. V., Maguire, M. P., Spada, A. P. & Zilberstein, A. (1992) *Inhibition Kinetics and Selectivity of the Tyrosine Kinase Inhibitor Erbstatin and a Pyridone-based Analog.* Biochemical Pharmacology, 43, 241-2477.

Huang, C-K., Wu, F-Y., Ai, Y-X. (1995) *Polyhydroxylated 3-(N-phenyl) carbamoyl-2-iminochromene derivatives as potent inhibitors of tyrosine kinase p60c-src.* Bioorg. & Med. Chem. Lett., 5, 2423-2428.

Hubbard, S. R., Wei, L, Ellis, L, & Hendrickson, W. A. (1994) *Crystal structure of the tyrosine kinase domain of the human insulin receptor*, Nature, 372, 746-754.

Hubbard, S. R. (1997) *Crystal structure of the activated insulin receptor tyrosine kinase in complex with peptide substrate and ATP analog.* The EMBO Journal, 16, 5572-5581.

Hughes, R. L., Smith, I. C., Lawless, E. W. (1967) Production of the Boranes and Related Research, Holtzman R. T., Ed., Academic Press, New York, pp. 291-294.

Hunter, T. (1987) *A thousand and one protein kinases.* Cell, 50, 823-829.

Hunter, T. (1994) *1001 protein kinases redux-towards 2000.* Seminars in Cell Biology, 5, 367-376.

Hunter, T. (1998) *The Croonian Lecture 1997. The phosphorylation of proteins on tyrosine: its role in cell growth and disease.* Philosophical Transactions of the Royal Society of London—Series B: Biological Sciences 353 (1368): 583-605.

Hutchins, C., Greer, J. (1991) *Comparative modeling of proteins in the design of novel renin inhibitors.* Critical Reviews in Biochemistry & Molecular Biology, 26, 77-127.

Irby, R. B.; Yeatman, T. J. (2000) *Role of Src expression and activation in human cancer.* Oncogene 19, 5536-5642.

Ishiyama, T., Murata, M., Miyaura, N. (1995) *Palladium(0)-catalyzed cross-coupling reaction of alkoxydboron with haloarenes: A direct procedure for arylboronic esters.* J. Org. Chem., 60, 7508-7510.

Ishiyama, T., Itoh, Y., Kitano, T., Miyaura, N. (1997) *Synthesis of arylboronates via the palladium(0)-catalyzed cross-coupling reaction of tetra(alkoxo)diborons with aryl triflates.* Tet. Lett., 38, 3447-3450.

Johnson, T. O., Ermolieff, J., Jirousek, M. R. (2002) *Protein tyrosine phosphatase 1B inhibitors for diabetes.* Nat. Rev. Drug Discov., 1(9), 696-709.

Karni, R., Jove R., & Levitzki A. (1999) *Inhibition of pp60c-src reduces Bcl-X expression and reverses the transformed phenotype of cells overexpressing EGF and HER-2 receptors.* Oncogene 18(33): 4654-4662.

Kelloff, G. J., Fay, J. R., Steele, V. E., Lubet, R. A., Boone, C. W., Crowell, J. A. (1996) *Epidermal growth factor receptor tyrosine kinase inhibitors as potential cancer chemopreventatives.* Cancer Epidemiology, Biomarkers & Prevention, 5, 657-666.

Kennedy, B. P. (1999) *Role of protein tyrosine phosphatase-1B in diabetes and obesity.* Biomedicine & Pharmacotherapy. 53(10), 466-470.

Kettner, C. A., Shenvi, A. B. (1984) *Inhibition of the Serine Proteases Leukocyte Elastase, Pancreatic Elastase, Cathepsin G, and Chymotrypsin by Peptide Boronic Acids.* J. Biol. Chem., 259, 15106-15114.

Kim. M. H., Lai, J. H. & Hangauer, D. G. (1994) *Tetrapeptide tyrosine kinase inhibitors: Enantioselective synthesis of p-hydroxymethyl-L-phenylalanine, incorporation into a tetrapeptide, and subsequent elaboration into p-(R,S-hydroxyphosphonomethyl)-L-phenylalanine.* Int. J. Peptide Protein Res., 44, 457-465.

Kinder, D. H., Frank, S. K., Ames, M. M. (1990) *Analogues of Carbamyl Aspartate as Inhibitors of Dihydroorotase: Preparation of Boronic acid Transition-State Analogues and a Zinc Chelator Carbamylhomocysteine.* J. Med. Chem., 33, 819-823.

Klein, G. (1990) *Multistep emancipation of tumors from growth control: can it be curbed in a single step?* BioEssays, 12, 347-350.

Knighton, D. R., Cadena, D. L., Zheng, J., Ten Eyck, L. F., Taylor, S. S. & Sowadski, J. M. (1993) *Structural features that specify tyrosine activity deduced from homology modeling of the epidermal growth factor receptor.* Proc. Natl. Acad. Sci. U.S.A., 90(11), 5001-5.

Kolibaba, K. S. & Druker, B. J. (1997) *Protein tyrosine kinases and cancer.* Biochimica et Biophysica Acta, 1333: F217-F248.

Lai, J. H., Marsilje, T. M., Choi, S., Nair, S. A., Hangauer, D. G. (1998) *The design, synthesis and activity of pentapeptide pp60c-src inhibitors containing L-phosphotyrosine mimics.* J. Peptide Res., 51, 271-281.

Lai, J. H., Pham, H. & Hangauer, D. G. (1996) *Synthesis of a Vicinal Tricarbonyl Amide Derivative of L-Phenylalanine.* J. Org. Chem., 61, 1872-1874.

Lam, K. S. (1997) *Application of Combinatorial Library Methods in Cancer Research an Drug Discovery.* Anti-Cancer Drug Design, 12(3), 145-167.

Lawrence, D. S. & Niu, J. (1998) *Protein Kinase Inhibitors: The Tyrosine-Specific Protein Kinases.* Pharmacol. Ther., 77(2), 81-114.

Levitzki, A. (1996a) *Targeting signal transduction for disease therapy.* Current Opinion in Cell Biology, 8, 239-244.

Levitzki, A. (1996b) *SRC as a target for anti-cancer drugs.* Anti-Cancer Drug Design, 11, 175-182.

Levitzki, A.; Gazit, A. (1995) *Tyrosine Kinase Inhibition: An Approach to Drug Development.* Science, 267, 1782-1788.

Li, H., Liu, T. F., Lazrak, A., Peracchia, C., Goldberg, G. S., Lampe, P. D., Johnson, R. G. (1996) *Properties and regulation of gap junctional hemichannels in the plasma membranes of cultured cells.* J. Cell. Biol., 134, 1019-1030.

Loonis, W. D. & Durst, R. W. (1992) *Chemistry and biology of boron.* BioFactors, 3, 229-239.

Lou, Q., Leftwich, M. E., McKay, T., Salmon, S. E., Rychetsky, L. & Lam, K. S. (1997) *Potent Pseudosubstrate-based Peptide Inhibitors for p60$^{c\text{-}src}$ Protein Tyrosine Kinase.* Cancer Research, 57(10), 1877-1881.

Lou, Q., Leftwich, M. E. & Lam, K. S. (1996) *Identification of GIYWHHY as a Novel Peptide Substrate for Human p60c-src Protein Tyrosine Kinase.* Biorganic & Medicinal Chemistry, 4, 677-682. (SEQ. ID. No. 7).

Luttrell, D. K.; Lee, A.; Lansing, T. J.; Crosby, R. M.; Jung, K. D.; Willard, D.; Luther, M.; Rodriguez, M.; Berman, J.; Gilmer, T. M. (1994) *Involvement of pp60$^{c\text{-}src}$ with two major signaling pathways in human breast cancer.* Proc. Natl. Acad. Sci. USA, 91, 83-87.

Lynch, S. A.; Brugge, J. S.; Fromowitz, F.; Glantz, L.; Wang, P.; Caruso, R.; Viola, M. V. (1993) *Increased expression of the src proto-oncogene in hairy cell leukemia and a subgroup of B-cell lymphomas.* Leukemia, 7, 1416-1422.

Madhusudan, Trafny, E. A., Xuong, N-H, Adams, J. A., Ten Eyck, L. F., Taylor, S. S. & Sowadski, J. M. (1994) *cAMP-dependent protein kinase: Crystallographic insights into substrate recognition and phosphotransfer.* Protein Science, 3, 176-187.

Mao, W. G., Irby, R., Coppola, D., Fu, L., Turner, J. (1997) *Activation of c-src by receptor tyrosine kinases in human colon cancer cells with high metastatic potential*. Oncogene, 15, 3083-3090.

Marsilje, T. H., Milkiewicz, K. L., & Hangauer, D. L. (2000) *The design, synthesis and activity of non-ATP competitive inhibitors of pp60c-src tyrosine kinase 1. Hydroxynaphthalene Derivatives*. Bioorganic and Medicinal Chemistry Letters, in press.

Martin, G. S. (2001) *TIMELINE: The hunting of the Src*. Nat. Rev. Mol. Cell. Biol., 2, 467-475.

Marx, J. (1990) *Oncogenes evoke new cancer therapies*. Science, 249, 1376-1378.

National Cancer Institute (1989) Survey of Compounds which have been tested for carcinogenic activity. NIH Publication No. 49-468, p. 16.

Matteson, D. S., Kandil, S. A., Soundararajan, R. (1990) *Synthesis of Asymmetrically. Deuterated Glycerol and Dibenzylglyceraldehyde via Boronic Esters*. J. Am. Chem. Soc., 112, 3964-3969.

Matteson, D. S. (1988) Acc. Chem. Res., 21, 294-300.

Matteson, D. S., Kandil, A. A. (1987) *Conversion of α-halo boronic esters to inverted α-(methylsulfonyl)oxy boronic esters*. J. Org. Chem., 52, 5121-5124.

Matteson, D. S., Soloway, A. H., Tomlinson, D. W., Campbell, J. D., Nixon, G. A. (1964) J. Med. Chem., 7, 640.

Mazurenko, N. N.; Kogen, E. A.; Zborovskaya, I. B.; Kisseljov, F. L. (1992) *Expression of pp60$^{c-src}$ in human small cell and non-small cell lung carcinomas*. European J. of Cancer, 28, 372-377.

McCluskey, A.; Sim A. T. R.; Sakoff, J. A. (2002a) *Serine-Threonine Protein Phosphatase, Inhibitors: Development of Potential Therapeutic Strategies*. J. Medicinal Chem. 45(6), 1151-1175.

McCluskey, A.; Sakoff, J. A. (2001) *Small molecule inhibitors of serine/threonine protein phosphatases*. Mini-Reviews in Medicinal Chemistry. 1(1), 43-55.

McCluskey, A.; Sim A. T. R.; Sakoff, J. A. (2002b) *Serine-threonine protein phosphatase inhibitors: development of potential therapeutic strategies*. Journal of Medicinal Chemistry. 45(6), 1151-75.

Milkiewicz, K.; Marsilje, T.; Woodward Jr, R.; Bifulco Jr, N.; Hangauer, M.; Hangauer, D. G. (2000) *The design, synthesis and activity of non-ATP competitive inhibitors of pp60c-src tyrosine kinase 2. Hydroxyindole Derivatives*. Bioorganic and Medicinal Chemistry Letters, in press.

Mohammadi, M., Schlessinger, J., Hubbard, S. R. (1996) *Structure of the FGF Receptor Tyrosine Kinase Domain Reveals a Novel Autoinhibitory Mechanism*. Cell, 86, 577-587.

Mohammadi, M., McMahon, G., Li, S., Tang, C., Hirth, P., Yeh, B. K., Hubbard, S. R., Schlessinger, J. (1997) *Structures of the Tyrosine Kinase Domain of Fibroblast Growth Factor Receptor in Complex with Inhibitors*. Science, 276, 955-960.

Moller, N. P. H.; Inversen, L. F.; Andersen, H. S.; McCormack, J. G. (2000) *Protein tyrosine phosphatases (PTPs) as drug targets: inhibitors of PTP-1B for treatment of diabetes*. Current Opinion in Drug Discovery & Development. 3(5), 527-540.

Morin, C. (1994) *The Chemistry of Boron Analogues of Biomolecules*. Tetrahedron, 50, 12521-12569.

Murakami, Y., Otsuka, K. Wada, Y., Morikawa, A. (1990) *The partial oxidation of ethane over a $B_2O_3$—$Al_2O_3$ catalyst*. Bull. Chem. Soc. Jpn., 63, 340-346.

Nair, S. A., Kim, M. K., Warren, S. D., Choi, S., Songyang, Z., Cantley, L. C. & Hangauer, D. G. (1995). *Identification of Efficient Pentapeptide Substrates for the Tyrosine Kinase pp60$^{c-src}$*. J. Med. Chem., 38, 4276-4283.

Nair, S. A., Lee, B. & Hangauer, D. G. (1995b). *Synthesis of Orthogonally Protected L-Homocysteine and L-2-Amino-4-phosphonobutanoic acid From L-Homoserine*. Synthesis, 7, 810-814.

Nielsen, F. H. (1997) *Boron in human and animal nutrition*. Plant & Soil, 193, 199-208.

Otsuka, K., Uragami, Y., Hatano, M. (1992) *The partial oxidation of ethane to acetaldehyde*. Catalysis Today, 13, 667-672.

Park, B. K, Kitteringham, N. R., O'Neill, P. M. (2001) *Metabolism of Fluorine-Containing Drugs*. Ann. Rev. Pharmacol. Toxicol., 41, 443-470.

Parsons, J. T. & Parsons, S. J. (1997) *Src family protein tyrosine kinases: cooperating with growth factor and adhesion signaling pathways*. Current Opinion in Cell Biology, 9, 187-192.

Patrick, D. R. & Heimbrook, D. C. (1996) *Protein Kinase Inhibitors For The Treatment of Cancer*. Drug Discovery Today, 1, 325-330.

Pavia, M. R., Cohen, M. P., Dilley, G. J., Dubuc, G. R., Durgin, T. L., Forman, F. W., Hediger, M. E., Milot, G., Powers, T. S., Sucholeiki, I., Zhou, S. & Hangauer, D. G. (1996) *The Design and Synthesis of Substituted Biphenyl Libraries*. Biorganic & Medicinal Chemistry, 4, 659-666.

Pestell, K. E.; Ducruet, A. P.; Wipf, P.; Lazo, J. S. (2000) *Small molecule inhibitors of dual specificity protein phosphatases*. Oncogene, 19(56), 6607-6612.

Posner, I., Engel, M., Gazit, A. & Levitzki, A. (1994) *Kinetics of Inhibition by Tyrphostins of the Tyrosine Kinase Activity of the Epidermal Growth Factor Receptor and Analysis by a New Computer Program*. Molecular Pharmacology, 45, 673-683.

Powis, G. (1991) *Signal targets for anticancer drug development*. TIPS, 188-194.

Ramdas, L., Obeyesekere, N. U., McMurray, J. S., Gallick, G. E., Seifert, W. E. Jr. & Budde, R. J. (1995) *A tyrphostin-derived inhibitor of protein tyrosine kinases: isolation and characterization*. Archives of Biochemistry & Biophysics, 323, 237-242.

Ramdas, L., McMurray, J. S. & Budde, R. J. (1994) *The degree of inhibition of protein tyrosine kinase activity by tyrphostin 23 and 25 is related to their instability*. Cancer Research, 54, 867-869.

Rewcastle, G. W., Palmer, B. D., Thompson, A. M., Bridges, A. J., Cody, D. R., Zhou, H. Fry, D. W., McMichael, A. & Denny, W. A. (1996) *Tyrosine Kinase Inhibitors. 10. Isomeric 4-[(3-Bromophenyl)amino]pyrido[d]-pyrimidines Are Potent ATP Binding Site Inhibitors of the Tyrosine Kinase Function of the Epidermal Growth Factor Receptor*. J. Med. Chem., 39, 1823-1835.

Ripka, W. C. (2000) *Protein tyrosine phosphatase inhibition*. Annual Reports in Medicinal Chemistry. 35, 231-250.

Rudd, C. E.; Janssen, O.; Prasad, K. V. S.; Raab, M.; da Silva, A.; Telfer, J. C.; Yamamoto, M. (1993) *src-related protein tyrosine kinases and their surface receptors*. Biochimica et Biophysica Acta, 1155, 239-266.

Saperstein, R., Vicario, P. P., Strout, H. V., Brady, E., Slater, E. E., Greenlee, W. J., Ondeyka, D. L., Patchett, A. A. & Hangauer, D. G. (1989) *Design of a selective insulin receptor tyrosine kinase inhibitor and its effect on glucose uptake and metabolism in intact cells*. Biochemistry, 28, 5694-5701.

Sawyer, T.; Boyce, B.; Dalgarno, D.; Iulicci, J. (2001) *Src inhibitors: genomics to therapeutics*. Expert Opin. Investg. Drugs 10(7), 1327-1344.

Sawutz, D. G.; Bode, D. C.; Briggs, G. M.; Reid, J. R.; Canniff, P.; Caldwell, L.; Faltynek, C. R.; Miller, D.; Dunn, J. A.; Garavilla, L.; Guiles, J. W.; Weigelt, C.; Michne, W.; Treasurywala, A. M.; Silver, P. J. (1996) Biochem. Pharmacol. 51, 1631.

Schlessinger, J. (2000) *New roles for Src kinases in control of cell survival and angiogenesis*. Cell 100, 293-296.

Schwartzberg, P. L., et al. (1997) *Rescue of osteoclast function by transgenic expression of kinase-deficient Src in src–/– mutant mice*. Genes & Development 11: 2835-2844.

Sedlacek, H. H. (2000) *Kinase inhibitors in cancer therapy*. Drug, 59(3), 435-476.

Shiraishi, T., Owada, M. K., Tatsuka, M., Yamashita, T., Watanabe, K., Kakunaga, T. (1989) *Specific Inhibitors of Tyrosine-specific Protein Kinases: Properties of 4-hydroxycinnamamide derivatives in vitro*. Cancer Research, 49, 2374-2378.

Showalter, H. H. & Kraker, A. J. (1997) *Small molecule inhibitors of the platelet-derived growth factor receptor, the fibroblast growth factor receptor, and src family tyrosine kinases*. Pharmacology & Therapeutics, 76, 55-71.

Sicheri, F., Moarefi, I. & Kuriyan, J. (1997) *Crystal structure of the Src family tyrosine kinase Hck*. Nature, 385, 602-609.

Skordalakes, E., Tyrell, R., Elgendy, S., Goodwin, C. A., Green, D., Dodson, G., Scully, M. F., Freyssinet, J-M. H., Kakkar, V. V., Deadman, J. J. (1997) *Crystallographic Structures of Human α-Thrombin Complexed to Peptide Boronic Acids Lacking a Positive Charge at $P_1$. Evidence of Novel Interactions*. J. Am. Chem. Soc., 119, 9935-9936.

Snyder, H. R., Kuck, J. A., Johnson, J. R. (1938) J. Am. Chem. Soc., 60, 105.

Soloway, A. H., Whitman, B., Messer, J. R. (1962) J. Med. Pharm. Chem., 7, 640.

Soloway, A. H., Whitman, B., Messer, J. R. (1960) J. Pharmacology and Experimental Therapeutics, 129, 310-314.

Soloway, A. H. (1958) Science, 128, 1572.

Songyang, Z, Blechner, S., Hoagland, N., Hoekstra, M. F., Piwnica-Worms, H. & Cantley, L. C. (1994) *Use of an oriented peptide library to determine the optimal substrates of protein kinases*. Current Biology, 4, 973-982.

Songyang, Z., Carraway III, K. L., Eck, M. J., Harrison, S. C., Feldman, R. A., Mohammadl, M., Schlessinger, J., Hubbard, S. R., Smith, D. P., Eng. C., Lorenzo, J. J., Ponder, B. A. J., Mayer, B. J. & Cantley, L. C. (1995) *Protein tyrosine kinases and SH2 domains have overlapping specificities*. Nature, 373, 536-539.

Sridhar, R.; Hanson-Painton, O.; Cooper, D. R. (2000) *Protein kinases as therapeutic targets*. Pharmaceutical Research 17(11), 1345-1353.

Staley, C. A.; Parikh, N. U.; Gailick, G. E. (1997) Cell Growth & Differentiation 8(3), 269.

Stanwell, C., Burke, T. R. & Yuspa, S. H. (1995) *Erbstatin Analogue Methyl 2,5-dihydrocinnamate Cross-links Proteins and is Cytotoxic to Normal and Neoplastic Epithelial Cells by a Mechanism Independent of Tyrosine Kinase Inhibition*. Cancer Research, 55, 4950-4956.

Stanwell, C., Ye, B. & Burke, T. R. (1996) *Cell Protein Cross-linking by Erbstatin and Related Compounds*. Biochemical Pharmacology, 52, 475-480.

Susa, M., Teti, A. (2000) *Tyrosine kinase Src inhibitors: Potential Therapeutic Applications*. Drug News Perspect. 13(3), 169-175.

Susa, M., Missbach, M.; Green, J. (2000) *Src inhibitors: drugs for the treatment of osteoporosis, cancer of both?* TIPS 21, 489-495.

Takeshima, E.; Hamaguchi, M.; Watanbe, T.; Akiyama, S.; Kataoka, M.; Ohnishi, Y.; Xiao, H.; Hagai, Y., Taka, H. (1991) *Aberrant elevation of tyrosine-specific phosphorylation in human gastric cancer cells*. Japan J. Cancer Res., 82, 1428-1435.

Talamonti, M. S.; Roh, M. S.; Curley, S. A.; Gallick, G. E. (1993) *Increase in activity and level of $pp60^{c\text{-}src}$ in progressive stages of human colorectal cancer*. J. of Clinical Investigation, 91, 53-60.

Taniyama, K., Fujiwara, H., Kuno, T., Saito, N., Shuntoh, H., Sakaue, M. (1989) *Acute and subacute toxicity of 10B-paraboronophenylalanine*. Pigment Cell Research, 2, 291-296.

Taylor, S. J., Shalloway, D. (1996) *Src and the control of cell division*. Bioessays, 18, 9-11.

Taylor, S. S., Knighton, D. R., Zheng, J., Sowadski, J. M., Gibbs, C. S. & Zoller, M. J. (1993) *A template for the protein kinase family*. Trends in Biochemical Sciences, 18(3), 84-9.

Taylor, S. S., Radzio-Andzelm, E. (1994) *Three protein kinase structures define a common motif*. Structure, 2, 345-355.

Thakkar, K., Geahlen, R. L., Cushman, M. (1993) *Synthesis and protein-tyrosine kinase inhibitory activity of polyhydroxylated stilbene analogs of piceatannol*. J. Med. Chem., 36, 2950-2955.

Weinberg, R. A. (1989) *Oncogenes, antioncogenes, and the molecular basis of multistep carcinogenesis*. Cancer Research, 49, 3713-3721.

Wolfe, J. P., Ahman, J., Sadighi, J. P., Singer, R. A., Buchwald, S. L. (1997) *An ammonia equivalent for the palladium-catalyzed amination of aryl halides and triflates*. Tet. Lett., 38, 6367-6370.

Wong, T. W. & Goldberg, A. R. (1984) *Kinetics and mechanism of angiotensin phosphorylation by the transforming gene product of Rous Sarcoma Virus*. J. Biol. Chem., 259, 3127-3131.

Xu, W., Harrison, S.C. & Eck, M. J. (1997) *Three-dimensional structure of the tyrosine kinase c-Src*. Nature, 385, 595-602.

Yamaguchi, H. & Hendrickson, W. A. (1996) *Structural basis for activation of human lymphocyte kinase Lck upon tyrosine phosphorylation*. Nature, 384, 484-489.

Yamamoto, T. (1993) *Molecular Basis of Cancer: Oncogenes and Tumor Suppresor Genes*. Microbiol. Immunol. 37, 11-22.

Zhang, Z. Y. (2002a) *Protein tyrosine phosphatases: structure and function, substrate specificity, and inhibitor development*. Annual Review of Pharmacology and Toxicology, 42, 209-234.

Zhang, Z. Y. (2002b) *Protein tyrosine phosphatases: prospects for therapeutics*. Current Opinion in Chemical Biology. 5(4), 416-423.

Zhanpeisov, N. U., Otsuka, K. (1992) *Cluster quantum chemical study of the mechanism of selective oxidation of ethane to acetaldehyde on boron-phosphorous mixed oxide catalysts*. React. Kinet. Catal. Lett., 48, 301-308.

Zheng, J., Knighton, D. R., Ten Eyck, L. R., Karlsson, R., Xuong, N-H., Taylor, S. S. & Sowadski, J. M. (1993) *Crystal structure of the catalytic subunit of cAMP-dependent protein kinase complexed with MgATP and peptide inhibitor*. Biochemistry, 32, 2154-61.

Zhong-Yin, Shang (2002) *Protein tyrosine phosphatases: structure and function, substrate specificity, and inhibitor development*. Annual Review of Pharmacology and Toxicology 42, 209-234.

What is claimed is:

1. A compound having the formula:

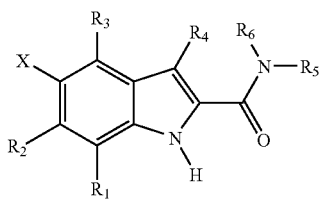

wherein $R_1$, $R_2$, $R_3$, and $R_4$ may be the same or different, and are selected from H, halogen, aryl, and branched or unbranched alkyl;
one of $R_5$ and $R_6$ is H, and the other of $R_5$ and $R_6$ is branched or unbranched alkyl substituted with phenyl wherein said phenyl is further substituted; and
wherein any of $R_1$ through $R_4$ is substituted or unsubstituted.

2. The compound of claim 1, wherein $R_4$ is H.

3. The compound of claim 1, wherein $R_4$ is aryl.

4. The compound of claim 3, wherein $R_4$ is phenyl.

5. The compound of claim 1, wherein $R_1$, $R_2$, $R_3$, and $R_4$ are each H.

6. The compound of claim 1, wherein $R_2$, $R_3$, and $R_4$ are each H.

7. The compound of claim 1, wherein $R_1$ is H.

8. The compound of claim 1, wherein one of $R_5$ and $R_6$ is substituted benzyl and the other of $R_5$ and $R_6$ is H.

9. The compound of claim 1, wherein one of $R_5$ or $R_6$

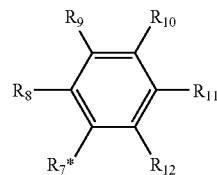

is wherein $R_7^*$ is the point of attachment and is $CH(CH_3)$ or $(CH_2)_x$, wherein X is from 1 to 10, and each of $R_8$ through $R_{12}$ may be the same or different and are selected from H, $C(O)R_a$, $C(O)NR_aR_b$, $C(O)OR_a$, $C(O)SR_a$, OH, $OR_a$, $OC(O)R_a$, $OC(O)OR_a$, $NH_2$, $NR_aR_b$, $NR_aC(O)R_b$, $NR_aC(O)NR_bR_c$, $NR_aC(O)OR_b$, $NR_aC(O)SR_b$, $NR_aS(O)R_b$, $NR_aS(O)_2R_b$, $NR_aS(O)OR_b$, $NR_aS(O)_2OR_b$, $NR_aP(O)OR_bOR_c$, $NR_aP(O)OR_bR_c$, $NR_aP(O)OR_bOR_c$, $SR_a$, $S(O)R_a$, $S(O)_2R_a$, $S(O)OR_a$, $S(O)_2OR_a$, $S(O)NR_aR_b$, $S(O)_2NR_aR_b$, $P(O)OR_aOR_b$, $B(OH)_2$, halogen, nitro, aryl, heteroaryl, biaryl, heterobiaryl, heterocyclic compound, and a branched, cyclic, or unbranched alkyl, wherein $R_a$, $R_b$, and $R_c$ may be the same or different and are selected from H, aryl, heteroaryl, biaryl, heterobiaryl, and branched, cyclic, or unbranched alkyl; and wherein any of $R_8$ through $R_{12}$ and $R_a$ through $R_c$ is substituted or unsubstituted.

10. The compound of claim 9, wherein X is from 1 to 3.
11. The compound of claim 9, wherein each of $R_8$ through $R_{12}$ may be the same or different and are selected from H, OH, halogen, $CF_3$, unbranched alkyl, nitro, $C(O)R_a$, and $OR_a$.
12. The compound of claim 11, wherein $R_a$ is selected from aryl, $CF_3$, and unbranched alkyl.
13. A compound selected from
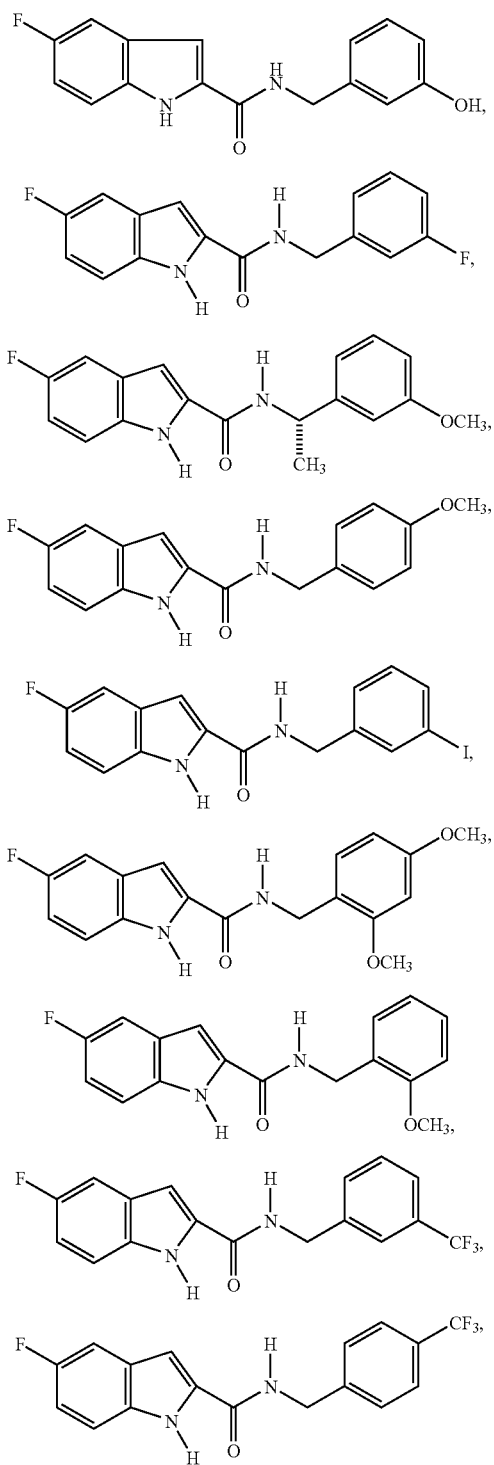
-continued
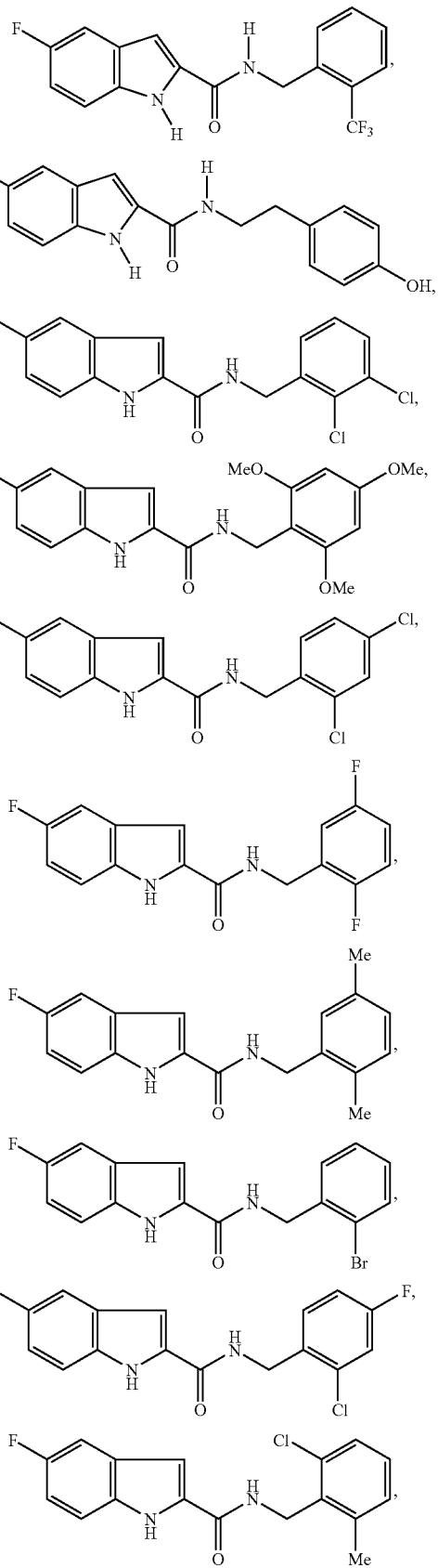

-continued
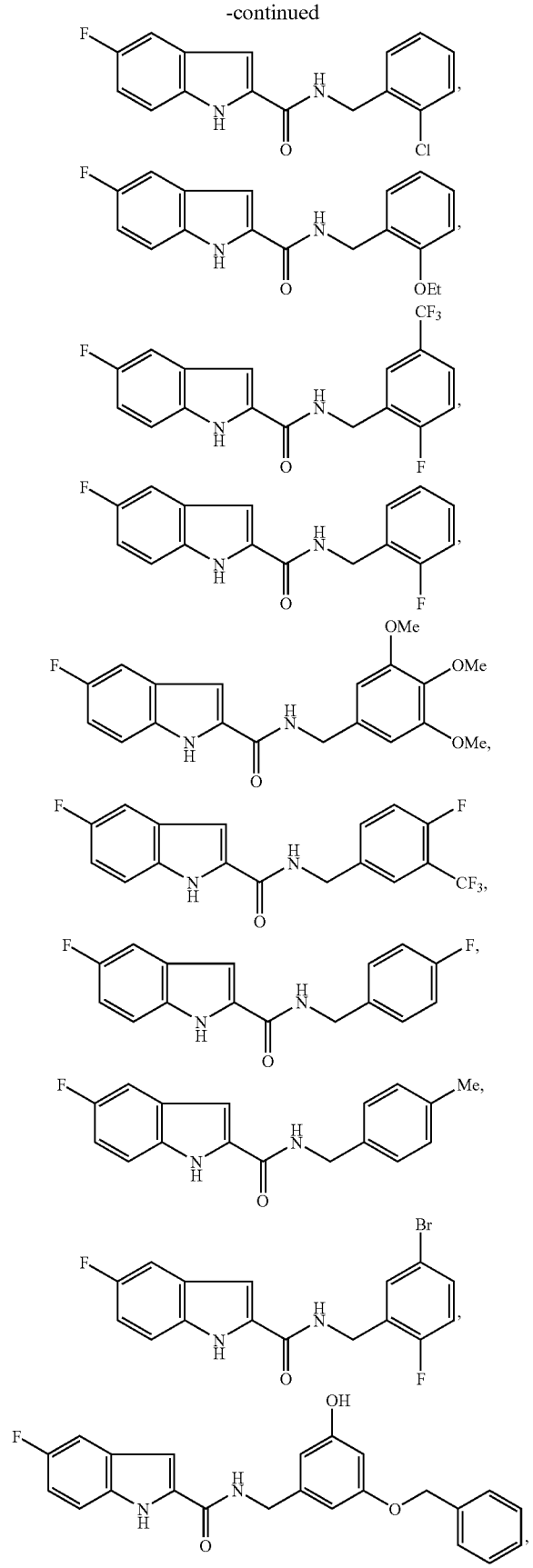
-continued
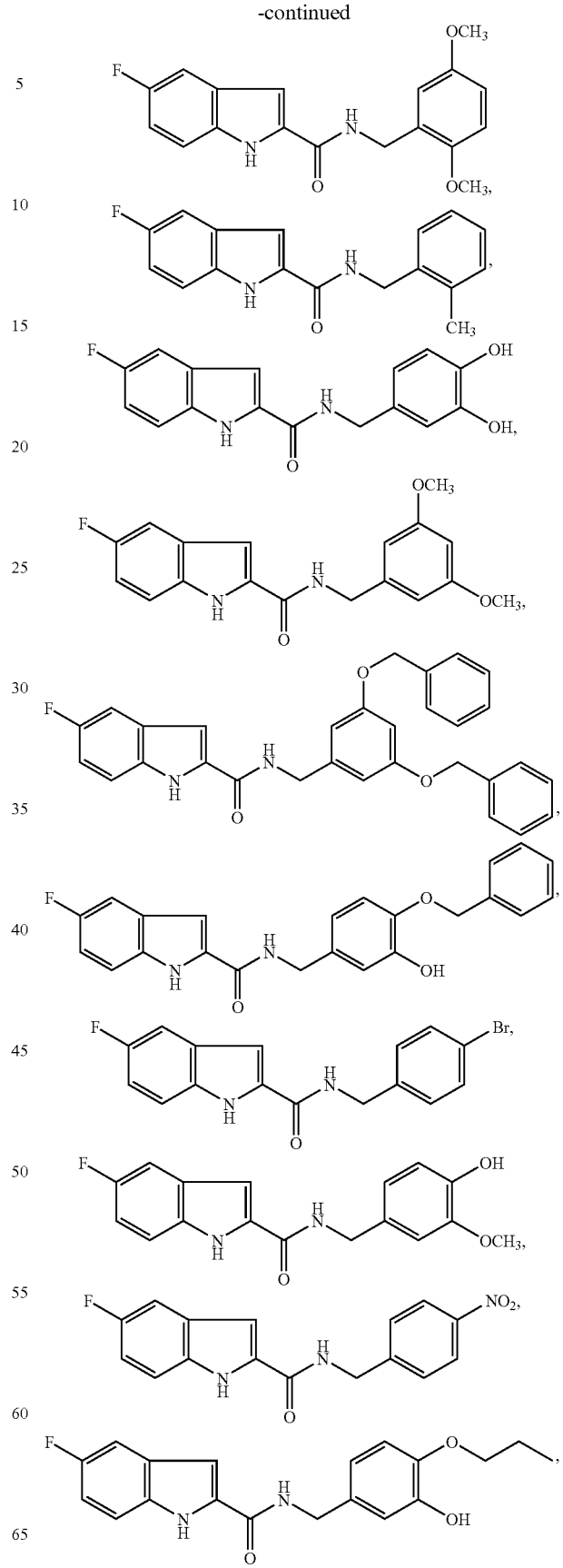

-continued
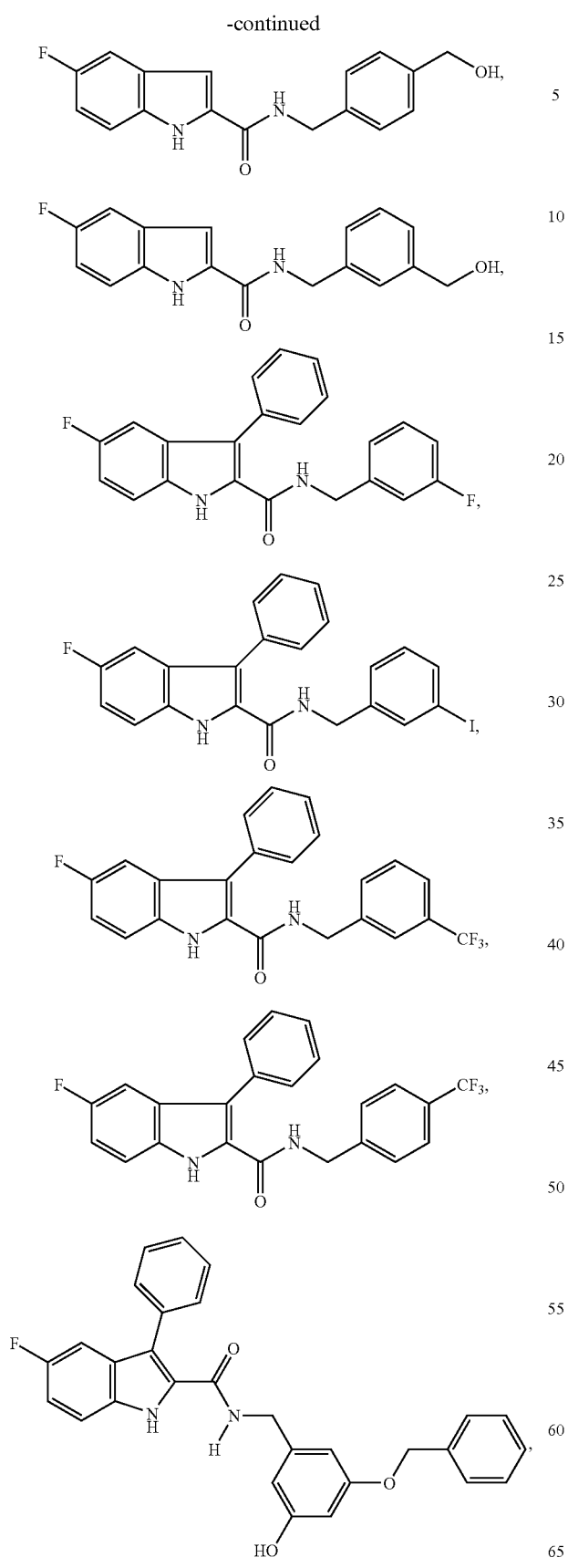
-continued
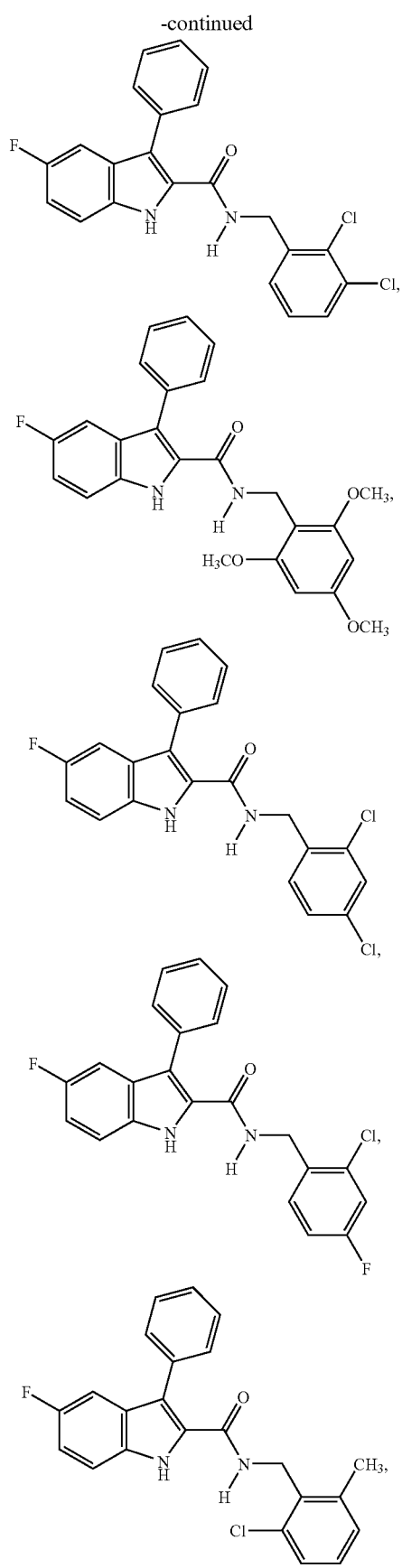

-continued
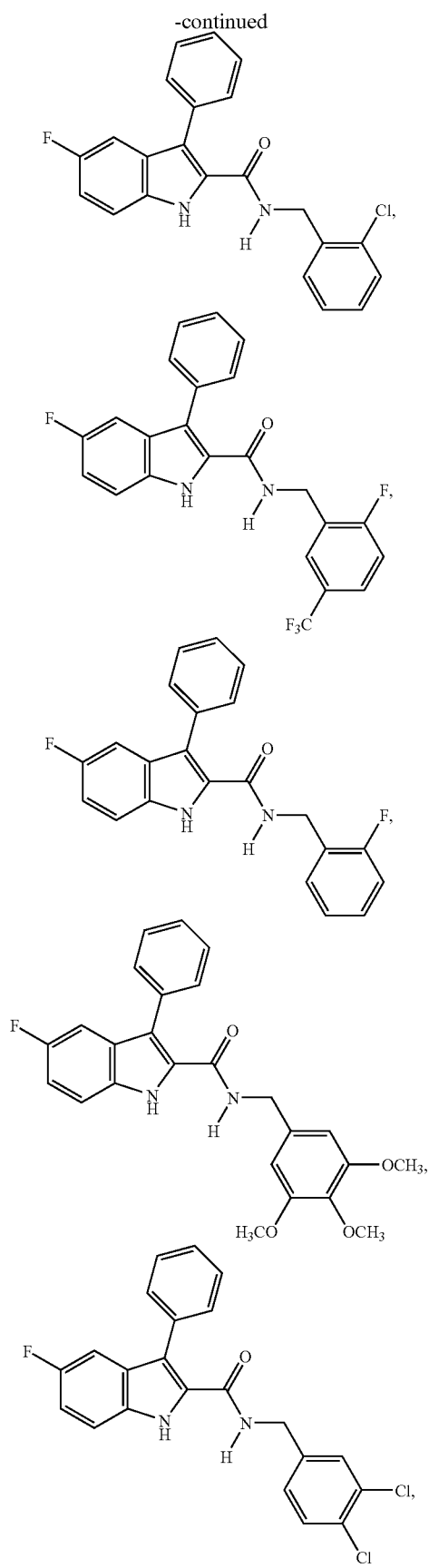
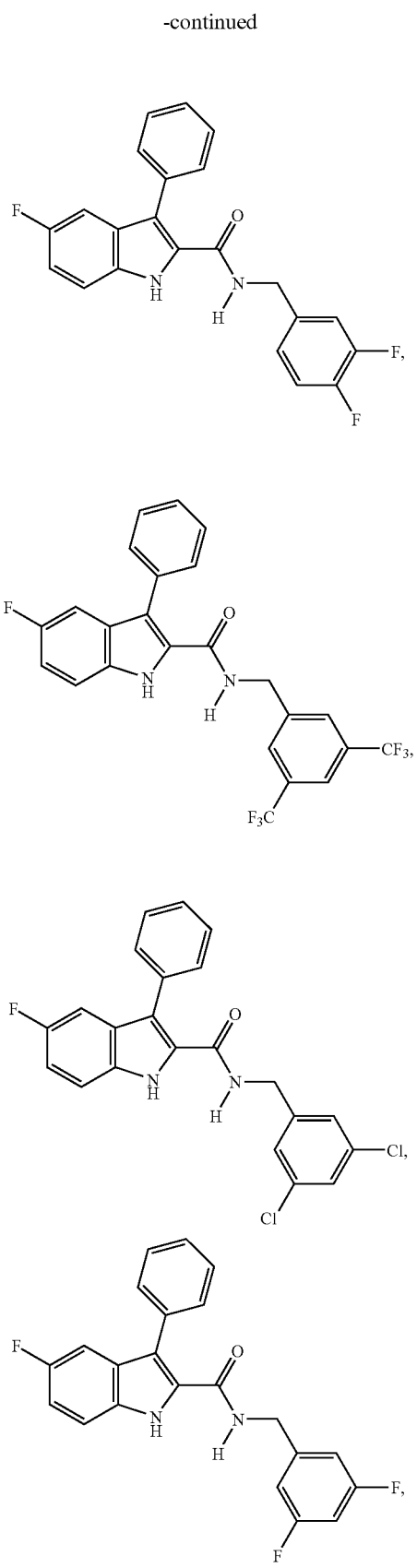

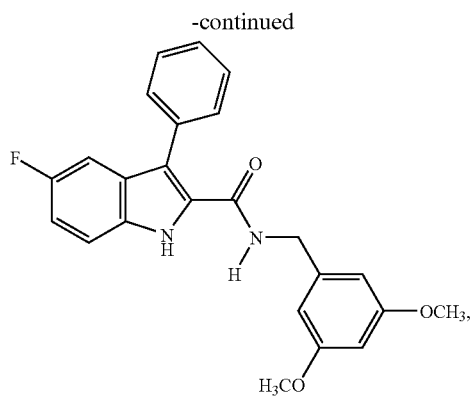
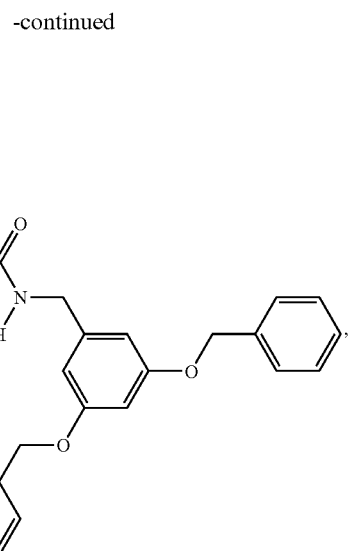
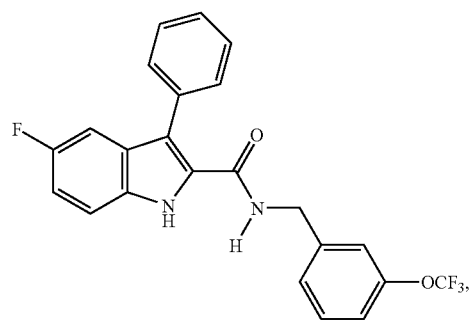
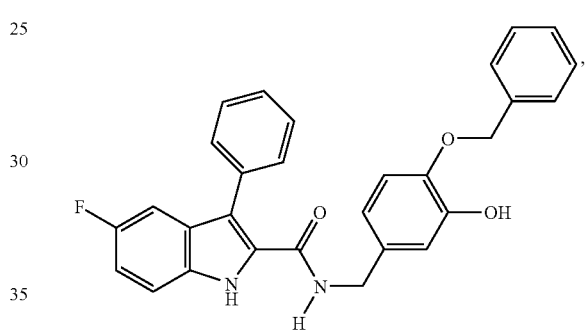
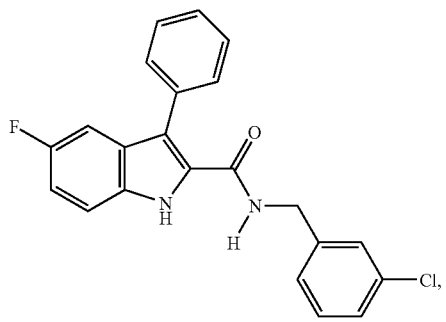
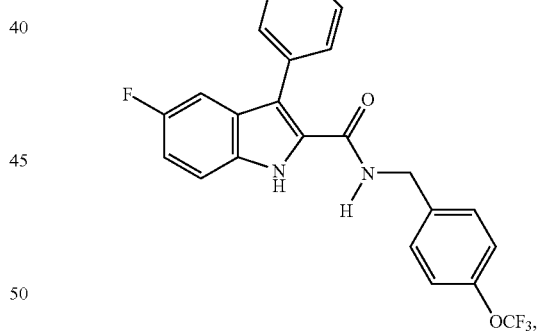
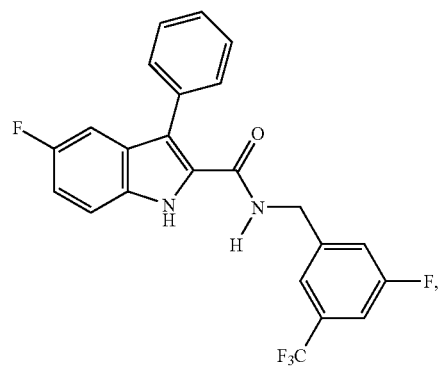
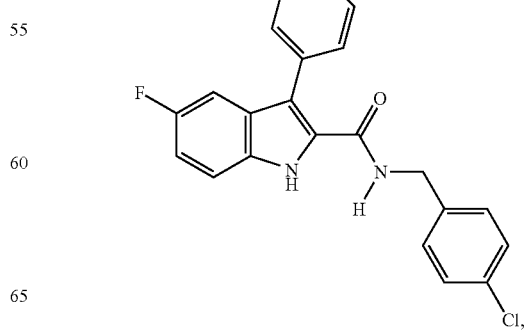

205
-continued
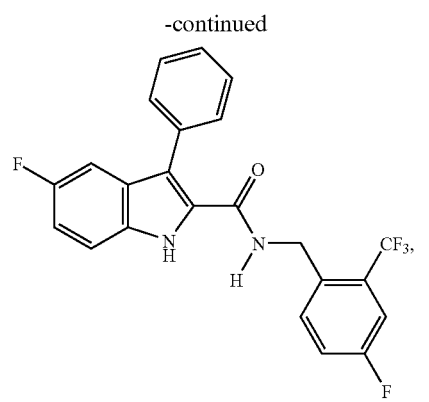
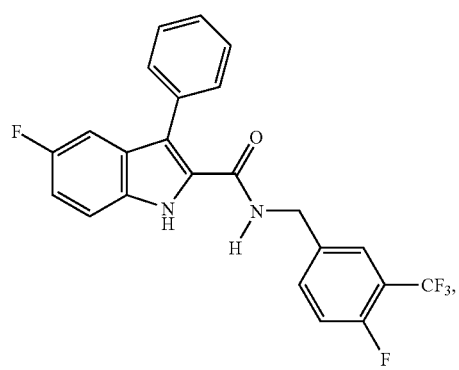
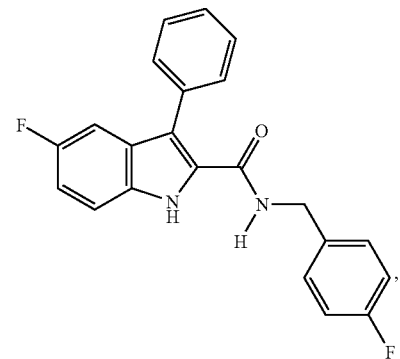
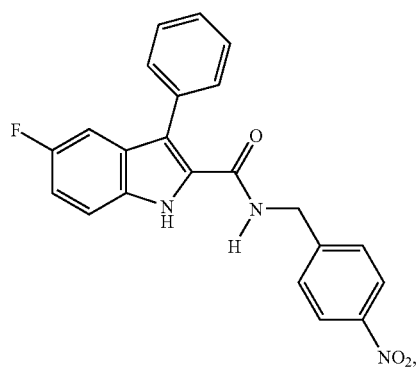
206
-continued
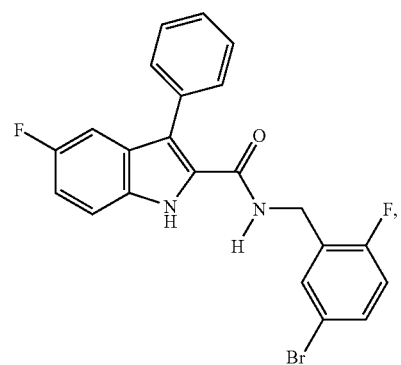

-continued
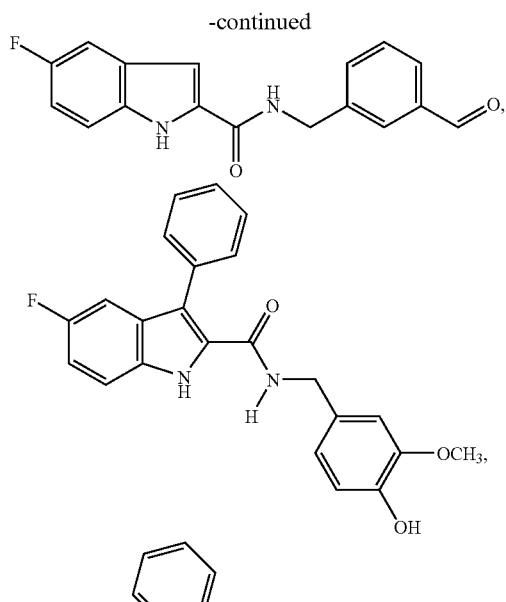
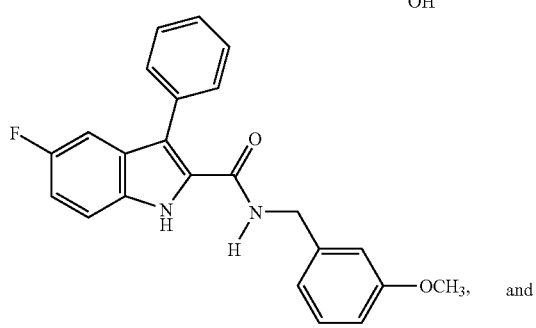
and
-continued
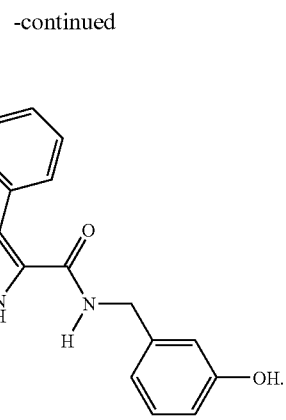
14. A compound having the formula:
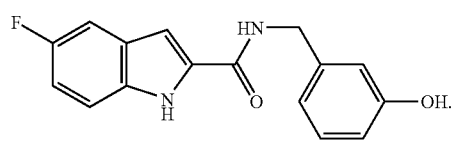
* * * * *